United States Patent
Rigamonti et al.

(10) Patent No.: US 12,331,090 B2
(45) Date of Patent: *Jun. 17, 2025

(54) MULTISPECIFIC PROTEINS

(71) Applicant: Molecular Partners AG, Zurich-Schlieren (CH)

(72) Inventors: Nicolo Rigamonti, Zurich (CH); Clara Domke, Dietikon (CH); Valérie Perrine Calabro, Bergdietikon (CH); Pamela Anna Trail Smith, Mystic, CT (US); Victor Levitsky, Birmensdorf (CH); Niina Elisabet Veitonmäki, Leuven (BE)

(73) Assignee: Molecular Partners AG, Zurich-Schlieren (CH)

( * ) Notice: Subject to any disclaimer, the term of this patent is extended or adjusted under 35 U.S.C. 154(b) by 22 days.

This patent is subject to a terminal disclaimer.

(21) Appl. No.: 17/302,898

(22) Filed: May 14, 2021

(65) Prior Publication Data

US 2021/0395318 A1    Dec. 23, 2021

(30) Foreign Application Priority Data

May 14, 2020  (EP) .................................. 20174847
Jun. 22, 2020  (EP) .................................. 20181498

(51) Int. Cl.
*C07K 14/47* (2006.01)
*A61K 38/00* (2006.01)
*A61P 35/00* (2006.01)

(52) U.S. Cl.
CPC .............. *C07K 14/47* (2013.01); *A61P 35/00* (2018.01); *A61K 38/00* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 7,338,660 B2 | 3/2008 | Bedian et al. |
| 7,417,130 B2 | 8/2008 | Stumpp et al. |
| 8,710,187 B2 | 4/2014 | Binz et al. |
| 8,722,618 B2 | 5/2014 | Jacobs et al. |
| 8,846,577 B2 | 9/2014 | Steiner et al. |
| 8,901,076 B2 | 12/2014 | Binz et al. |
| 9,163,070 B2 | 10/2015 | Baumann |
| 9,221,892 B2 | 12/2015 | Binz |
| 9,284,361 B2 | 3/2016 | Steiner et al. |
| 9,365,629 B2 | 6/2016 | Parmeggiani et al. |
| 9,458,211 B1 | 10/2016 | Bakker et al. |
| 10,370,414 B2 | 8/2019 | Fiedler et al. |
| 10,717,772 B2 | 7/2020 | Metz et al. |
| 11,453,708 B2 | 9/2022 | Tresch et al. |
| 2008/0206201 A1 | 8/2008 | Beier et al. |
| 2013/0296221 A1 | 11/2013 | Binz |
| 2015/0284463 A1 | 10/2015 | Tamaskovic et al. |
| 2020/0385488 A1 | 12/2020 | Reichen et al. |
| 2021/0347835 A1 | 11/2021 | Amstutz et al. |
| 2021/0380713 A1 | 12/2021 | Nakayama et al. |
| 2021/0395318 A1 | 12/2021 | Rigamonti et al. |
| 2022/0064234 A1 | 3/2022 | Binz et al. |
| 2022/0106707 A1 | 4/2022 | Levitsky et al. |
| 2022/0242973 A1 | 8/2022 | Fiedler et al. |
| 2022/0298212 A1 | 9/2022 | Reichen et al. |

FOREIGN PATENT DOCUMENTS

| | | |
|---|---|---|
| WO | WO 87/04462 | 7/1987 |
| WO | WO 02/20565 A2 | 3/2002 |
| WO | WO 2005/063815 A2 | 7/2005 |
| WO | WO 2009/040338 A1 | 4/2009 |
| WO | WO 2010/060748 A1 | 6/2010 |
| WO | WO 2011/040972 A1 | 4/2011 |
| WO | WO 2011/135067 A1 | 11/2011 |
| WO | WO 2012/069654 A1 | 5/2012 |
| WO | WO 2012/069655 A2 | 5/2012 |
| WO | WO 2014/001442 A1 | 1/2014 |
| WO | WO 2014/083208 A1 | 6/2014 |
| WO | WO 2014/191574 A1 | 12/2014 |
| WO | WO 2016/156596 A1 | 10/2016 |
| WO | WO 2018/054971 A1 | 3/2018 |
| WO | WO 2018/185045 A1 | 10/2018 |
| WO | WO 2019/093342 A1 | 5/2019 |

(Continued)

OTHER PUBLICATIONS

Steiner et al. "Efficient Selection of DARPins with Sub-nanomolar Affinities using SRP Phage Display" J. Mol. Biol. 382:1211-1227. (Year: 2008).*
Pluckthun A "Designed Ankyrin Repeat Proteins (DARPins): Binding Proteins for Research, Diagnostics, and Therapy" Annual Rev. Pharmacol. Toxicol. 55:489-511. (Year: 2015).*
Amstutz et al., "Intracellular Kinase Inhibitors Selected from Combinatorial Libraries of Designed Ankyrin Repeat Proteins," The Journal of Biological chemistry, vol. 280, No. 26, pp. 24715-24722 (2005).
Amstutz et al., "Rapid selection of specific MAP kinase-binders from designed ankyrin repeat protein libraries." Protein Engineering, Design & Selection, vol. 19, No. 5, pp. 219-229 (2006).
Bandeiras et al., "Structure of wild-type Plk-1 kinase domain in complex with a selective DARPin," Acta. Cryst., vol. D64, pp. 339-353 (2008).

(Continued)

*Primary Examiner* — Sudhakar Katakam
*Assistant Examiner* — Zachary J Miknis
(74) *Attorney, Agent, or Firm* — FINNEGAN, HENDERSON, FARABOW, GARRETT & DUNNER, LLP

(57) ABSTRACT

The present disclosure relates to multispecific proteins comprising designed ankyrin repeat domains with binding specificity for different targets, such as, e.g. CD40 and FAP. In addition, the present disclosure relates to nucleic acids encoding such multispecific proteins, pharmaceutical compositions comprising such multispecific proteins or nucleic acids, and the use of such binding proteins, nucleic acids or pharmaceutical compositions in methods for treating or diagnosing diseases, such as cancer, in a mammal, including a human.

19 Claims, 28 Drawing Sheets

Specification includes a Sequence Listing.

(56) References Cited

FOREIGN PATENT DOCUMENTS

| WO | WO 2020/070041 A1 | 4/2020 |
|---|---|---|
| WO | WO 2020/245171 A1 | 12/2020 |
| WO | WO 2021/116470 A2 | 6/2021 |
| WO | WO 2021/229076 A1 | 11/2021 |
| WO | WO 2022/101458 A1 | 5/2022 |
| WO | WO 2022/129428 A1 | 6/2022 |
| WO | WO 2022/130300 A1 | 6/2022 |
| WO | WO 2022/179562 A1 | 9/2022 |
| WO | WO 2022/190008 A1 | 9/2022 |
| WO | WO 2022/190010 A1 | 9/2022 |
| WO | WO 2022/190018 A1 | 9/2022 |
| WO | WO 2022/215032 A1 | 10/2022 |
| WO | WO 2023/110983 A1 | 6/2023 |

OTHER PUBLICATIONS

Binz et al., "Crystal Structure of a Consensus-Designed Ankyrin Repeat Protein: Implications for Stability," Proteins: Structure, Function, and Bioinformatics, vol. 65, pp. 280-284 (2006).
Binz et al., "Design and characterization of MP0250, a trispecific anti-HGF/anti-VEGF DARPin® drug candidate," MABS, vol. 9, No. 8, pp. 1262-1269 (2017).
Binz et al., "Designed Repeat Proteins—Molecules with Antibody-like Binding Properties," BIOforum Europe, vol. 4, pp. 34-36 (2005).
Binz et al., "Designing Repeat Proteins: Well-expressed, Soluble and Stable Proteins from Combinatorial Libraries of Consensus Ankyrin Repeat Proteins," J. Mol. Biol, vol. 332, pp. 489-503 (2003).
Binz et al., "Engineered proteins as specific binding reagents," Current Opinion in Biotechnology, vol. 16, pp. 459-469 (2005).
Binz et al., "Engineering novel binding proteins from nonimmunoglobulin domains," Nature Biotechnology, vol. 23, No. 10, pp. 1257-1268 (2005).
Binz et al., "High-affinity binders selected from designed ankyrin repeat protein libraries," Nature Biotechnology, vol. 22, No. 5, pp. 575-582 (2004).
Boersma et al., "DARPins and other repeat protein scaffolds: advances in engineering and applications," Current Opinion in Biotechnology, vol. 22, pp. 849-857 (2011).
Boersma, "Advances in the Application of Designed Ankyrin Repeat Proteins (DARPins) as Research Tools and Protein Therapeutics," Protein Scaffolds: Design, Synthesis, and Applications, Methods in Molecular Biology, vol. 1798, pp. 307-327 (2018).
Brennen et al., "Rationale Behind Targeting Fibroblast Activation Protein—Expressing Carcinoma-Associated Fibroblasts as a Novel Chemotherapeutic Strategy," Mol. Cancer Ther, vol. 11, No. 2, pp. 257-266 (2012).
Challa et al., "Epitope-dependent synergism and antagonism between CD40 antibodies and soluble CD40 ligand for the regulation of CD23 expression and IgE synthesis in human B cells," Allergy, vol. 54, pp. 576-583 (1999).
Chichili et al., "Linkers in the structural biology of protein-protein interactions," Protein Science, vol. 22, pp. 153-167 (2013).
Eggel et al., "DARPins as Bispecific Receptor Antagonists Analyzed for Immunoglobulin E Receptor Blockage," J. Mol. Biol., vol. 393, pp. 598-607 (2009).
Fiedler et al., "MP0250, a VEGF and HGF neutralizing DARPin® molecule shows high anti-tumor efficacy in mouse xenograft and patient-derived tumor models," Oncotarget, vol. 8, No. 58, pp. 98371-98383 (2017).
Fiedler et al., "MP0250, a VEGF and HGF neutralizing DARPin® molecule shows high anti-tumour efficacy in mouse xenograft and patient-derived tumour models"—Supplementary Materials, Oncotarget, vol. 8, No. 58, 2 pages (2017).
Forrer et al., "A novel strategy to design binding molecules harnessing the modular nature of repeat proteins," FEBS Letters, vol. 539, pp. 2-6 (2003).
Forrer et al., "Consensus Design of Repeat Proteins," ChemBioChem, vol. 5, pp. 183-189 (2004).
Garin-Chesa et al., "Cell surface glycoprotein of reactive stromal fibroblasts as a potential antibody target in human epithelial cancers," Proc Natl Acad Sci USA, vol. 87, pp. 7235-7239 (1990).
Hanes et al., "In vitro selection and evolution of functional proteins by using ribosome display," Proc Natl Acad Sci USA, vol. 94, pp. 4937-4942 (1997).
He et al., "Ribosome display: Cell-free protein display technology," Briefings in Functional Genomics and Proteomics, vol. 1, No. 2, pp. 204-212 (2001).
Interlandi et al., "Characterization and Further Stabilization of Designed Ankyrin Repeat Proteins by Combining Molecular Dynamics Simulations and Experiments," J Mol Biol, vol. 375, pp. 837-854 (2008).
International Search Report and Written Opinion of the International Search Authority for International Application No. PCT/EP2021/062860, Aug. 27, 2021, 15 pages.
Kawe et al., "Isolation of Intracellular Proteinase Inhibitors Derived from Designed Ankyrin Repeat Proteins by Genetic Screening," J Biol Chem, vol. 281, No. 52, pp. 40252-402563 (2006).
Kohl et al., "Designed to be stable: Crystal structure of a consensus ankyrin repeat protein," Proc Natl Acad Sci USA, vol. 100, No. 4, pp. 1700-1705 (2003).
Kornbluth et al., "Design of CD40 Agonists and their use in growing B cells for cancer immunotherapy," Int. Rev. Immunol, vol. 31, No. 4, 16 pages (2012).
Kramer et al., "Structural Determinants for Improved Stability of Designed Ankyrin Repeat Proteins with a Redesigned C-Capping Module," J Mol Biol, vol. 404, pp. 381-391 (2010).
Main et al., "Design of Stable α-Helical Arrays from an Idealized TPR Motif," Structure, vol. 11, pp. 497-508 (2003).
Nakamura et al., "Codon usage tabulated from International DNA sequence databased: status for the year 2020," Nucleic Acids Research, vol. 28, No. 1, p. 292 (2000).
Nguyen et al., "Surface Plasmon Resonance: A Versatile Technique for Biosensor Applications," Sensors, vol. 15, pp. 10481-10510 (2015).
Plückthun, "Designed Ankyrin Repeat Proteins (DARPins): Binding Proteins for Research, Diagnostics, and Therapy," Annu Rev Pharmacol Toxicol, vol. 55, pp. 489-511 (2015).
Pound et al., "Minimal cross-linking and epitope requirements for CD40-dependent suppression of apoptosis contrast with those for promotion of the cell cycle and homotypic adhesions in human B cells," International Immunology, vol. 11, No. 1, pp. 11-20 (1999).
Rettig et al., "Cell-surface glycoproteins of human sarcomas: Differential expression in normal and malignant tissues and cultured cells," Proc Natl Acad Sci USA, vol. 85, pp. 3110-3114 (1988).
Rettig et al., "Regulation and Heteromeric Structure of the Fibroblast Activation Protein in Normal and Transformed Cells of Mesenchymal and Neuroectodermal Origin," Cancer Research, vol. 43, pp. 3327-3335 (1993).
Rothenberger et al., "Ensovibep, a novel trispecific DARPin candidate that protects against SARS-CoV-2 variants," bioRxiv, 76 pages (2022).
Sennhauser et al., "Chaperone-Assisted Crystallography with DARPins," Structure, vol. 16, pp. 1443-1453 (2008).
Steiner et al., "Efficient Selection of DARPins with Sub-nanomolar Affinities using SRP Phage Display," J Mol Biol, vol. 382, pp. 1211-1227 (2008).
Steiner et al., "Efficient Selection of DARPins with Subnanomolar Affinity using SRP Phage Display"—Supplementary Material, J Mol Biol, vol. 382, 17 pages (2008).
Steiner et al., "Half-life extension using serum albumin-binding DARPin® domains," Protein Engineering, Design & Selection, pp. 1-9 (2017).
Stumpp et al., "DARPins: A new generation of protein therapeutics," Drug Discovery Today, vol. 13, No. 15-16, pp. 695-701 (2008).
Stumpp et al., "DARPins: A true alternative to antibodies," Current Opinion in Drug Discovery & Development, vol. 10, No. 2, pp. 153-159 (2007).

(56) References Cited

OTHER PUBLICATIONS

Stumpp et al., "Beyond Antibodies: The DARPin® Drug Platform," BioDrugs, 11 pages (2020).

Stumpp et al., "Designing Repeat Proteins: Modular Leucine-rich Repeat Protein Libraries Based on the Mammalian Ribonuclease Inhibitor Family," J Mol Biol, vol. 332, pp. 471-487 (2003).

Theurillat et al., "Designed ankyrin repeat proteins: a novel tool for testing epidermal growth factor receptor 2 expression in breast cancer," Modern Pathology, vol. 23, No. 9, pp. 1289-1297 (2010).

Veesler et al., "Crystal Structure and Function of a DARPin Neutralizing Inhibitor of Lactococcal Phage TP901-1 Comparison of DARPin and Camelid VHH Binding Mode," J Biol Chem, vol. 284, No. 44, pp. 30718-30726 (2009).

Walser et al., "Highly potent anti-SARS-CoV-2 multivalent DARPin therapeutic candidates," bioRxiv, 48 pages (2021).

Yu et al., "Complex Interplay between Epitope Specificity and Isotype Dictates the Biological Activity of Antihuman CD40 Antibodies," Cancer Cell, vol. 33, pp. 664-675 (2018).

Zahnd et al., "Efficient Tumor Targeting with High-Affinity Designed Ankyrin Repeat Proteins: Effects of Affinity and Molecular Size," Cancer Research, vol. 70, No. 4, pp. 1595-1605 (2010).

Zahnd et al., "Efficient tumor targeting with high-affinity Designed Ankyrin Repeat Proteins (DARPins): Effects of affinity and molecular size"—Supplementary Information, Cancer Research, vol. 70, No. 4, 23 pages (2010).

Zahnd et al., "Ribosome display: selecting and evolving proteins in vitro that specifically bind to a target," Nature Methods, vol. 4, No. 3, pp. 269-279 (2007).

Zahnd et al., "Selection and Characterization of Her2 Binding-designed Ankyrin Repeat Proteins," J Biol Chem, vol. 281, No. 46, pp. 35167-35175 (2006).

\* cited by examiner

Early time point termination for FACS analysis

Study PD1033

Study PD1038

Tumor efficacy studies+ termination FACS

Study PD1032

Study PD1035

MULTISPECIFIC PROTEINS

CROSS-REFERENCE TO RELATED APPLICATION

The present application claims the benefit of and priority from European patent application EP20174847 filed on 14 May 2020 with the European Patent Office and from European patent application EP20181498 filed on 22 Jun. 2020 with the European Patent Office. The contents of European patent applications EP20174847 and EP20181498 are incorporated herein by reference in their entirety, including all tables, figures, and claims.

FIELD OF THE INVENTION

The present disclosure relates to multispecific proteins comprising designed ankyrin repeat domains with binding specificity for different targets, such as, e.g. CD40 and FAP. In addition, the disclosure relates to nucleic acids encoding such multispecific proteins, pharmaceutical compositions comprising such multispecific proteins or nucleic acids, and the use of such binding proteins, nucleic acids or pharmaceutical compositions in methods for treating or diagnosing diseases, such as cancer, in a mammal, including a human.

BACKGROUND OF THE INVENTION

Tumor necrosis factor receptor (TNFR) superfamily member CD40 is a key co-stimulatory receptor, and when engaged by its ligand (CD40L) or by agonistic antibodies, it is involved in the regulation of a wide spectrum of molecular and cellular processes, including the initiation and progression of cellular and humoral adaptive immunity. For example, it has been demonstrated that CD40 engagement on the surface of dendritic cells promotes their cytokine production, induces the expression of costimulatory molecules on their surface, and facilitates the presentation of antigen. Overall, the impact of CD40 signaling 'licenses' dendritic cells to mature and achieve all of the necessary characteristics to effectively trigger T-cell activation and differentiation. CD40 signaling in B cells promotes germinal center formation, immunoglobulin (Ig) isotype switching, somatic hypermutation of the Ig to enhance affinity for antigen, and finally the formation of long-lived plasma cells and memory B cells. Moreover, it has been shown that the CD40 pathway is important for the survival of many cell types including germinal center B cells, dendritic cells, and endothelial cells under normal and inflammatory conditions. Deregulation of CD40 signaling has been observed in various autoimmune diseases. Together, this breadth of functions underlines the importance of the CD40 receptor for the generation of an acquired immune response.

CD40 was initially characterized on B cells and is also expressed on dendritic cells, monocytes, platelets, and macrophages as well as on non-hematopoietic cells such as myofibroblasts, fibroblasts, epithelial, and endothelial cells. The ligand of CD40, known as CD154 or CD40L, is expressed primarily by activated T cells, as well as activated B cells and platelets, and under inflammatory conditions it is also induced in monocytic cells, natural killer cells, mast cells, and basophils.

Because CD40 can activate both the innate and adaptive immune system, it has been recognized as a suitable target for tumor immunotherapy. Several reports have confirmed that CD40 stimulation can enhance anti-tumor immune responses by means of dendritic cell maturation. Activation of dendritic cells with agonists of CD40 results in their increased survival, secretion of IL-1, IL-6, IL-8, IL-12, TNF-α, and macrophage inflammatory protein-1α. Additionally, CD40 activation induces the upregulation of costimulatory molecules such as MHC class II, LFA-3, CD80, and CD86 and promotes antigen presentation, priming and cross-priming of T helper cells (Th) and cytotoxic T lymphocytes (CTL), respectively. Agonistic antibodies against CD40 have proved efficacious in preclinical murine tumor models. However, although their use in the clinic has shown some anti-tumor efficacy, clinical development of agonistic anti-CD40 antibodies has likely been hampered by dose-limiting toxicities and resulting low efficacies.

Thus, there remains a need for new CD40-specific binding proteins, and for therapeutic and diagnostic approaches for the treatment and characterization of diseases, including cancer, benefitting from CD40-specific binding and activation. In particular, there is a need for new generation agonists that can effectively engage CD40 while avoiding undesired side effects.

SUMMARY OF THE INVENTION

Based on the disclosure provided herein, those skilled in the art will recognize, or be able to ascertain using no more than routine experimentation, many equivalents to the specific embodiments of the disclosure described herein. Such equivalents are intended to be encompassed by the following embodiments (E).

E1. A recombinant protein comprising a first ankyrin repeat domain that specifically binds fibroblast activation protein (FAP) and a second ankyrin repeat domain that specifically binds CD40.

E2. The recombinant protein of E1, further comprising a third ankyrin repeat domain that specifically binds CD40.

E3. The recombinant protein of E2, wherein said ankyrin repeat domains are arranged, from the N-terminus to C-terminus, according to the following formula: (FAP-binding domain)—(CD40 binding domain)—(CD40 binding domain).

E4 The recombinant protein of any one of E1-E3, further comprising a half-life extending moiety.

E5. The recombinant protein of E4, wherein said half-life extending moiety comprises a fourth ankyrin repeat domain that specifically binds serum albumin.

E6. The recombinant protein of E5, wherein said ankyrin repeat domains are arranged, from the N-terminus to C-terminus, according to the following formula: (serum albumin binding domain)—(FAP-binding domain)—(CD40 binding domain)—(CD40 binding domain).

E7. The recombinant protein of any one of E1-E6, further comprising a linker between any of said FAP-binding domain, said CD40 binding domain(s), and said half-life extending moiety.

E8. The recombinant protein of any one of E1-E7, comprising the following formula, from the N-terminus to C-terminus: (FAP-binding domain)—(linker)—(CD40 binding domain)—(linker)—(CD40 binding domain).

E9. The recombinant protein of any one of E1-E8, comprising the following formula, from the N-terminus to C-terminus: (serum albumin binding domain)—(linker)—(FAP-binding domain)—(linker)—(CD40 binding domain)—(linker)—(CD40 binding domain).

E10. The recombinant protein of E4, wherein said half-life extending moiety comprises an immunoglobulin heavy chain constant domain.

E11. The recombinant protein of E10, wherein said immunoglobulin domain is an Fc domain of an IgA1, IgA2, IgD, IgE, IgM, IgG1, IgG2, IgG3, or IgG4 immunoglobulin.

E12. The recombinant protein of E11, wherein said Fc domain is the Fc domain of human IgG1 immunoglobulin.

E13. The recombinant protein of E12, wherein said Fc domain is modified to reduce the effector function.

E14. The recombinant protein of any one of E1-E13, wherein said FAP is human FAP.

E15. The recombinant protein of any one of E1-E14, wherein said CD40 is human CD40.

E16. The recombinant protein of any one of E5-E19, wherein said serum albumin is human serum albumin (HSA).

E17. The recombinant protein of any one of E10-E13, wherein said immunoglobulin heavy chain constant domain is a human immunoglobulin heavy chain constant domain.

E18. The recombinant protein of any one of E1-E17, wherein binding of said recombinant protein to FAP does not reduce the protease activity of FAP by more than 25%, more than 20%, more than 15%, more than 10%, or more than 5%.

E19. The recombinant protein of any one of E1-E18, wherein said FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 2, and wherein optionally A at the second last position of SEQ ID NO: 2 is substituted with L and/or A at the last position of SEQ ID NO: 2 is substituted with N.

E20. The recombinant protein of E19, wherein said FAP-binding domain comprises the amino acid sequence of SEQ ID NO: 2.

E21. The recombinant protein of any one of E1-E18, wherein said FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 8, and wherein optionally A at the second last position of SEQ ID NO: 2 is substituted with L and/or A at the last position of SEQ ID NO: 8 is substituted with N.

E22. The recombinant protein of E21, wherein said FAP-binding domain comprises the amino acid sequence of SEQ ID NO: 8.

E23. The recombinant protein of any one of E1-E18, wherein said FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 9 and 28-38.

E24. The recombinant protein of E23, wherein said FAP-binding domain comprises the amino acid sequence of any one of SEQ ID NOs: 9 and 28-38.

E25. The recombinant protein of E23, wherein said FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 9, 28-31 and 38, and wherein optionally A at the second last position is substituted with L and/or A at the last position is substituted with N.

E26. The recombinant protein of E25, wherein said FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 28, and wherein optionally A at the second last position is substituted with L and/or A at the last position is substituted with N.

E27. The recombinant protein of E23, wherein said FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 32-37, and wherein optionally L at the second last position is substituted with A and/or N at the last position is substituted with A.

E28. The recombinant protein of E27, wherein said FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 34, and wherein optionally L at the second last position is substituted with A and/or N at the last position is substituted with A.

E29. The recombinant protein of any one of E1-E28, wherein said FAP-binding domain (i) comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, 01100% identical to any one of SEQ ID NOs: 2, 8, 9 and 28-37, and (ii) further comprises at its N-terminus, a G, an S, or a GS.

E30. The recombinant protein of any one of E1-E29, wherein said FAP-binding domain comprises an amino acid sequence that is at least 90% identical to any one of SEQ ID NOs: 2, 8, 9 and 28-37, and further comprises at its N-terminus, a G, an S, or a GS.

E31. The recombinant protein of any one of E1-E30, wherein said CD40-binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 3, and wherein optionally A at the second last position of SEQ ID NO: 3 is substituted with L and/or A at the last position of SEQ ID NO: 3 is substituted with N.

E32. The recombinant protein of any one of E1-E31, wherein said CD40 binding domain or each of said CD40 binding domains comprises the amino acid sequence of SEQ ID NO: 3.

E33. The recombinant protein of any one of E1-E30, wherein said CD40-binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 10 and 43-50.

E34. The recombinant protein of any one of E1-E30 and E33, wherein said CD40-binding domain or each of said CD40 binding domains comprises the amino acid sequence of any one of SEQ ID NOs: 10 and 43-50.

E35. The recombinant protein of any one of E1-E30 and E33, wherein said CD40 binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 10, 43, 44, and 48-50, and wherein optionally A at the second last position is substituted with L and/or A at the last position is substituted with N.

E36. The recombinant protein of E35, wherein said CD40 binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 43, and wherein optionally A at the second last position is substituted with L and/or A at the last position is substituted with N.

E37. The recombinant protein of any one of E1-E30 and E33, wherein said CD40 binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 45-47, and wherein optionally L at the second last position is substituted with A and/or N at the last position is substituted with A.

E38. The recombinant protein of E37, wherein said CD40 binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 47, and wherein optionally L at the second last position is substituted with A and/or N at the last position is substituted with A.

E39. The recombinant protein of any one E1-E38, wherein said CD40 binding domain or each of said CD40 binding domains independently (i) comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 3, 10 and 43-49, and (ii) further comprises at its N-terminus, a G, an S, or a GS.

E40. The recombinant protein of any one E1-E39, wherein said CD40 binding domain or each of said CD40 binding domains independently comprises an amino acid sequence that is at least 90% identical to any one of SEQ ID NOs: 3, 10 and 43-49, and further comprises at its N-terminus, a G, an S, or a GS E41. The recombinant protein of any one of E1-E40, wherein said CD40 binding domain or each of said CD40 binding domains independently comprises Q at position 8, L at position 15, R at position 143, and/or Q at position 147, wherein the position numbers correspond to the positions in SEQ ID NO: 3.

E42. The recombinant protein of any one of E1-E41, wherein said CD40 binding domain or each of said CD40 binding domains independently comprises Q at position 8, L at position 15, R at position 143, and Q at position 147, wherein the position numbers correspond to the positions in SEQ ID NO: 3.

E43. The recombinant protein of any one of E1-E42, wherein:

(a) said FAP binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 2, 8, 9 and 28-37; wherein its N-terminus optionally further comprises a G, an S, or a GS; and wherein the second last position can be L or A, and the last position can be N or A; and (b) said CD40 binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 3, 10 and 43-49; wherein its N-terminus optionally further comprises a G, an S, or a GS; and wherein the second last position can be L or A, and the last position can be N or A.

E44. The recombinant protein of E43, wherein:

(a) said FAP binding domain comprises an amino acid sequence that is at least 90% identical to any one of SEQ ID NOs: 2, 8, 9 and 28-37; wherein its N-terminus optionally further comprises a G, an S, or a GS; and wherein the second last position can be L or A, and the last position can be N or A; and (b) said CD40 binding domain or each of said CD40 binding domains independently comprises an amino acid sequence that is at least 90% identical to any one of SEQ ID NOs: 3, 10 and 43-49; wherein its N-terminus optionally further comprises a G, an S, or a GS; and wherein the second last position can be L or A, and the last position can be N or A.

E45. The recombinant protein of E43, wherein:

(a) said FAP binding domain comprises an amino acid sequence that is at least 95% identical to any one of SEQ ID NOs: 2, 8, 9 and 28-37; wherein its N-terminus optionally further comprises a G, an S, or a GS; and wherein the second last position can be L or A, and the last position can be N or A; and (b) said CD40 binding domain or each of said CD40 binding domains independently comprises an amino acid sequence that is at least 95% identical to any one of SEQ ID NOs: 3, 10 and 43-49; wherein its N-terminus optionally further comprises a G, an S, or a GS; and wherein the second last position can be L or A, and the last position can be N or A.

E46. The recombinant protein of E43, wherein:
(a) said FAP binding domain comprises the amino acid sequence of any one of SEQ ID NOs: 2, 8, 9 and 28-37; wherein its N-terminus optionally further comprises a G, an S, or a GS; and wherein the second last position can be L or A, and the last position can be N or A; and
(b) said CD40 binding domain or each of said CD40 binding domains independently comprises the amino acid sequence of any one of SEQ ID NOs: 3, 10 and 43-49; wherein its N-terminus optionally further comprises a G, an S, or a GS; and wherein the second last position can be L or A, and the last position can be N or A.

E47. The recombinant protein of any one of E5-E9, E14-E16, and E18-E46, wherein said serum albumin binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 1, and wherein optionally A at the second last position is substituted with L and/or A at the last position is substituted with N.

E48. The recombinant protein of any one of E5-E9, E14-E16, and E18-E47, wherein said serum albumin binding domain comprises the amino acid sequence of SEQ ID NO: 1.

E49. The recombinant protein of any one of E5-E9, E14-E16, and E18-E46, wherein said serum albumin binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96% at least 97%, at least 98%, at least 99%, or 100% identical to any one of SEQ ID NOs: 39-42, and wherein optionally A at the second last position of any one of SEQ ID NOs: 39-40 and 42 is substituted with L and/or A at the last position of any one of SEQ ID NOs: 39-40 and 42 is substituted with N, and wherein optionally L at the second last position of SEQ ID NO: 41 is substituted with A and/or N at the last position of SEQ ID NO: 41 is substituted with A.

E50. The recombinant protein of any one of E5-E9, E14-E16, E18-E45, and E49, wherein said serum albumin binding domain comprises the amino acid sequence of any one of SEQ ID NOs: 39-42.

E51. The recombinant protein of any one of E5-E9, E14-E16, and E18-E50, wherein said serum albumin binding domain (i) comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 1 and 39-41, or (ii) comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 42 and further comprises at its N-terminus, a G, an S, or a GS.

E52. The recombinant protein of any one of E5-E9, E14-E16, and E18-E51, wherein said serum albumin binding domain comprises (i) an amino acid sequence that is at least 90% identical to any one of SEQ ID NOs: 1 and 39-41, or (ii) comprises an amino acid sequence that is at least 90% identical to SEQ ID NO: 42 and further comprises at its N-terminus, a G, an S, or a GS.

E53. The recombinant protein of any one of E5-E9, E14-E16, and E18-E52, wherein said serum albumin binding domain comprises (i) the amino acid sequence of any one of SEQ ID NOs: 1 and 39-41, or (ii) comprises the amino acid sequence of SEQ ID NO: 42 and further comprises at its N-terminus, a G, an S, or a GS.

E54. The recombinant protein of any one of E8-E53, wherein said linker comprises the amino acid sequence of SEQ ID NO: 4.

E55. The recombinant protein of any one of E1-E54, wherein said protein comprises exactly four ankyrin repeat domains.

E56. A recombinant protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 5 or SEQ ID NO: 6 or SEQ ID NO: 7, wherein said protein specifically binds FAP and CD40.

E57. The recombinant protein of E56 wherein said protein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 5.

E58. The recombinant protein of any one of E56-E57, wherein said protein comprises an amino acid sequence that is at least 90% identical to SEQ ID NO: 5.

E59. The recombinant protein of any one of E56-E58, wherein said protein comprises the amino acid sequence of SEQ ID NO: 5.

E60. The recombinant protein of E56, wherein said protein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 6.

E61. The recombinant protein of E56 or E60, wherein said protein comprises an amino acid sequence that is at least 90% identical to SEQ ID NO: 6.

E62. The recombinant protein of any one of E56 and E60-E61, wherein said protein comprises the amino acid sequence of SEQ ID NO: 6.

E63. The recombinant protein of any one of E56-E62, wherein said FAP is human FAP.

E64. The recombinant protein of any one of E56-E63, wherein said CD40 is human CD40.

E65. The recombinant protein of any one of E1-E64, wherein said FAP-binding domain binds human FAP with a KD value of or below: 100 nM, 90 nM, 80 nM, 75 nM, 70 nM, 60 nM, 50 nM, 40 nM, 30 nM, 20 nM, 10 nM, 5 nM, 2 nM, 1 nM, 900 pM, 800 pM, 700 pM, 600 pM, 500 pM, 400 pM, 300 pM, 250 pM, 200 pM, 150 pM, 140 pM, 130 pM, or 120 pM.

E66. The recombinant protein of any one of E1-E65, wherein said FAP-binding domain binds human FAP with a KD value of or below 100 nM.

E67. The recombinant protein of any one of E1-E66, wherein said FAP-binding domain binds human FAP with a KD value of or below 1 nM.

E68. The recombinant protein of any one of E1-E67, wherein said FAP-binding domain binds human FAP with a KD value of or below 120 pM.

E69. The recombinant protein of any one of E1-E68, wherein said CD40-binding domain or each of said CD40-binding domains independently binds human CD40 with a KD value of or below: 100 nM, 90 nM, 80 nM, or 75 nM.

E70. The recombinant protein of any one of E1-E69, wherein said CD40-binding domain or each of said CD40-binding domains independently binds human CD40 with a KD value of or below 100 nM.

E71. The recombinant protein of any one of E1-E70, wherein said CD40-binding domain or each of said CD40-binding domains independently binds human CD40 with a KD value of or below 75 nM.

E72. The recombinant protein of any one of E1-E71, wherein said serum albumin binding domain binds human serum albumin with a KD value of or below: 100 nM, 90 nM, 80 nM, 75 nM, 70 nM, 60 nM, 50 nM, 40 nM, or 35 nM.

E73. The recombinant protein of any one of E1-E72, wherein said serum albumin binding domain binds human serum albumin with a KD value of or below 100 nM.

E74. The recombinant protein of any one of E1-E73, wherein said serum albumin binding domain binds human serum albumin with a KD value of or below 50 nM.

E75. The recombinant protein of any one of E1-E74, wherein said serum albumin binding domain binds human serum albumin with a KD value of or below 35 nM.

E76. The recombinant protein of any one of E1-E75, wherein said recombinant protein binds human FAP with a KD value of or below: 100 nM, 90 nM, 80 nM, 75 nM, 70 nM, 60 nM, 50 nM, 40 nM, 30 nM, 20 nM, 10 nM, 5 nM, 2 nM, 1 nM, 900 pM, 800 pM, 700 pM, 600 pM, 500 pM, 400 pM, or 300 pM.

E77. The recombinant protein of any one of E1-E76, wherein said recombinant protein binds human FAP with a KD value of or below 100 nM.

E78. The recombinant protein of any one of E1-E77, wherein said recombinant protein binds human FAP with a KD value of or below 1 nM.

E79. The recombinant protein of any one of E1-E78, wherein said recombinant protein binds human FAP with a KD value of or below 500 pM.

E80. The recombinant protein of any one of E1-E79, wherein said recombinant protein binds human FAP with a KD value of or below 300 pM.

E81. The recombinant protein of any one of E1-E80, wherein said recombinant protein binds human CD40 with a KD value of or below: 100 nM, 90 nM, 80 nM, 75 nM, 70 nM, 60 nM, 50 nM, 40 nM, 30 nM, 20 nM, 10 nM, 5 nM, 2 nM, 1 nM, 900 pM, 800 pM, 700 pM, 600 pM, 500 pM, 400 pM, 300 pM, 250 pM, 200 pM, 150 pM, 140 pM, 130 pM, 120 pM, 115 pM, 110 pM, 105 pM or 100 pM.

E82. The recombinant protein of any one of E1-E81, wherein said recombinant protein binds human CD40 with a KD value of or below 100 nM.

E83. The recombinant protein of any one of E1-E82, wherein said recombinant protein binds human CD40 with a KD value of or below 1 nM.

E84. The recombinant protein of any one of E1-E83, wherein said recombinant protein binds human CD40 with a KD value of or below 500 pM.

E85. The recombinant protein of any one of E1-E84, wherein said recombinant protein binds human CD40 with a KD value of or below 100 pM.

E86. The recombinant protein of any one of E1-E85, wherein said recombinant protein binds human serum albumin with a KD value of or below: 100 nM, 90 nM, 80 nM, 75 nM, 70 nM, 60 nM, or 50 nM.

E87. The recombinant protein of any one of E1-E86, wherein said recombinant protein binds human serum albumin with a KD value of or below 100 nM.

E88. The recombinant protein of any one of E1-E87, wherein said recombinant protein binds human serum albumin with a KD value of or below 75 nM.

E89. The recombinant protein of any one of E1-E88, wherein said recombinant protein binds human serum albumin with a KD value of or below 50 nM.

E90. The recombinant protein of any one of E65-E89, wherein said KD is measured in PBS by surface plasmon resonance (SPR).

E91. The recombinant protein of E90, wherein said KD is measured using a Biacore T200 instrument.

E92. The recombinant protein of any one of E65-E89, wherein said KD is measured by bio-layer interferometry (BLI).

E93. The recombinant protein of E92, wherein said KD is measured using a ForteBio Octet instrument.

E94. The recombinant protein of any one of E1-E93, wherein said recombinant protein has a half maximal effective concentration ($EC_{50}$) of no more than about 100 nM, no more than about 75 nM, no more than about 65 nM, no more than about 55 nM, no more than about 45 nM, no more than about 35 nM, no more than about 25 nM, no more than about 15 nM, no more than about 10 nM, no more than about 5 nM, no more than about 4 nM, no more than about 3 nM, no more than about 2 nM, no more than about 1 nM, nor more than about 0.1 nM, from about 0.01 nM to about 50 nM, from about 0.01 nM to about 25 nM, from about 0.01 nM to about 10 nM, from about 0.01 nM to about 5 nM, from about 0.01 nM to about 1 nM, from about 0.01 nM to about 0.1 nM, from about 0.01 nM to about 0.07 nM, from about 0.04 nM to about 50 nM, from about 0.04 nM to about 25 nM, from about 0.04 nM to about 10 nM, from about 0.04 nM to about 5 nM, from about 0.04 nM to about 1 nM, from about 0.04 nM to about 0.1 nM, from about 0.04 nM to about 0.07 nM, from about 0.1 nM to about 50 nM, from about 0.1 nM to about 25 nM, from about 0.1 nM to about 10 nM, from about 0.1 nM to about 5 nM, from about 0.1 nM to about 1 nM, from about 0.1 nM to about 0.9 nM, from about 0.1 nM to about 0.85 nM, from about 0.18 nM to about 0.85 nM as assessed by an in vitro B cell activation assay.

E95. The recombinant protein of any one of E1-E94, wherein said recombinant protein has an EC50 of no more than about 10 nM, as assessed by an in vitro B cell activation assay.

E96. The recombinant protein of any one of E1-E95, wherein said recombinant protein has an EC50 of no more than about 1 nM, as assessed by an in vitro B cell activation assay.

E97. The recombinant protein of any one of E1-E96, wherein said recombinant protein has an EC50 of from about 0.1 nM to about 1 nM, or from about 0.18 nM to about 0.85 nM, as assessed by an in vitro B cell activation assay.

E98. The recombinant protein of any one of E1-E97, wherein said recombinant protein has an EC50 of from about 0.01 nM to about 0.1 nM, or from about 0.04 nM to about 0.07 nM, as assessed by an in vitro B cell activation assay.

E99. The recombinant protein of any one of E94-E98, wherein said B cells activation assay is a human B cell activation assay.

E100. The recombinant protein of any one of E94-E99, wherein said EC50 is measured using GraphPad Prism (version 8.1.2).

E101. A recombinant protein comprising:
a first ankyrin repeat domain that specifically binds serum albumin, a second ankyrin repeat domain that specifically binds fibroblast activation protein (FAP), a third ankyrin repeat domain that specifically binds CD40, and a fourth ankyrin repeat domain that specifically binds CD40, wherein said ankyrin repeat domains are arranged, from the N-terminus to the C-terminus, according to the following formula: (serum albumin binding domain)—(FAP-binding domain)—(CD40 binding domain)—(CD40 binding domain).

E102. The recombinant protein of E101, wherein said FAP binding domain comprises an amino acid sequence that is at least 90% identical to SEQ ID NO: 2, and binds human FAP with a Ko value of or below 100 nM, of or below 1 nM, or of or below 120 pM.

E103. The recombinant protein of E101 or E102, wherein said FAP binding domain comprises the amino acid sequence of SEQ ID NO: 2 or of SEQ ID NO: 8.

E104. The recombinant protein of any one of E101-E103, wherein each of said CD40 binding domains independently comprises an amino acid sequence that is at least 90% identical to SEQ ID NO: 3, and binds human CD40 with a $K_D$ value of or below 100 nM, or of or below 75 nM.

E105. The recombinant protein of any one of E101-E104, wherein each of said CD40 binding domains independently comprises Q at position 8, L at position 15, R at position 143, and/or Q at position 147, wherein the position numbers correspond to the positions in SEQ ID NO: 3, or wherein each of said CD40 binding domains independently comprises Q at position 8, L at position 15, R at position 143, and Q at position 147, wherein the position numbers correspond to the positions in SEQ ID NO: 3.

E106. The recombinant protein of any one of E101-E105, wherein each of said CD40 binding domains comprises the amino acid sequence of SEQ ID NO: 3.

E107. The recombinant protein of any one of E101-E106, wherein said serum albumin binding domain comprises an amino acid sequence that is at least 90% identical to SEQ ID NO: 1, and binds human serum albumin with a $K_D$ value of or below 100 nM, of or below 50 nM, or of or below 35 nM.

E108. The recombinant protein of any one of E101-E107, wherein the serum albumin domain comprises the amino acid sequence of SEQ ID NO: 1.

E109. The recombinant protein of any one of E101-E108, comprising the following formula, from the N-terminus to C-terminus: (serum albumin binding domain)—(linker)—(FAP-binding domain)-(linker)—(CD40 binding domain)—(linker)—(CD40 binding domain), wherein the linker comprises the amino acid sequence of SEQ ID NO: 4.

E110. The recombinant protein of any one of E101-E110, wherein said protein comprises exactly four ankyrin repeat domains.

E111. A recombinant protein comprising the amino acid sequence of SEQ ID NO: 5 or of SEQ ID NO: 6.

E112. A recombinant protein comprising the amino acid sequence of SEQ ID NO: 5.

E113. A recombinant protein comprising the amino acid sequence of SEQ ID NO: 6.

E114. A recombinant protein comprising an amino acid sequence that is at least 90% identical to SEQ ID NO: 5, and binds human FAP, human CD40, and human serum albumin with a $K_D$ value of or below 100 nM.

E115. The recombinant protein of any one of E5-E114, wherein said protein is capable of binding to CD40, FAP, and serum albumin simultaneously.

E116. The recombinant protein of any one of E1-E115, wherein said protein has a half maximal effective concentration (EC50) from about 0.1 nM to about 5 nM, as assessed by an in vitro human B cell activation assay.

E117. The recombinant protein of any one of E1-E116, wherein binding of said protein to FAP does not inhibit the prolyl endopeptidase activity of FAP by more than 25%.

E117a. The recombinant protein of any one of E1-E117, wherein said recombinant protein specifically binds to the N-terminal cysteine-rich domain 1 (CRD1) (amino acids 23-59 of SEQ ID NO: 51) of the CD40 receptor.

E118. A nucleic acid encoding the recombinant protein of any one of E1-E117 or an ankyrin repeat domain as defined in any one of E1-E117.

E119. The nucleic acid of E118, comprising the nucleotide sequence of SEQ ID NO: 58.

E120. A recombinant protein comprising an amino acid sequence encoded by the nucleotide sequence of SEQ ID NO: 58.

E121. A recombinant protein comprising an amino acid sequence encoded by a nucleotide sequence that is at least 85%, 90%, 95%, or 99% identical to the sequence of SEQ ID NO: 58.

E122. A recombinant protein comprising an amino acid sequence encoded by a nucleotide sequence capable of hybridizing under highly stringent conditions to the nucleotide sequence of SEQ ID NO: 58.

E123. A vector comprising the nucleic acid of E118 or E119.

E124. A host cell comprising the nucleic acid of E118 or E119.

E125. A host cell comprising the vector of E123.

E126. The host cell of E124 or E125, wherein said host cell is a bacterial cell.

E127. The host cell of any one of E124-E126, wherein said host cell is E. coli.

E128. The host cell of E124 or E125, wherein said host cell is a eukaryotic cell.

E129. A method of producing the recombinant protein of any one of E1-E117 and E120-E122, comprising culturing the host cell of any one of E124-E128 under conditions wherein said recombinant protein is expressed.

E130. The method of E129, further comprising isolating said recombinant protein.

E131. A pharmaceutical composition comprising the recombinant protein of any one of E1-E117 and E120-E122 or the nucleic acid of E118 or E119, and optionally a pharmaceutically acceptable carrier or excipient.

E132. A method of localized activation of CD40 in CD40-expressing cells in a mammal, including a human, the method comprising the step of administering to said mammal the recombinant protein of any one of E1-E117 and E120-E122, the nucleic acid of E118 or E119, or the pharmaceutical composition of E131.

E133. The method of E132, wherein said CD40-expressing cells are located in a tumor, such as a solid tumor.

E134. The method of E133, wherein said tumor comprises cells that express FAP.

E135. A method of treating a medical condition, comprising administering to a subject in need thereof a therapeutically effective amount of the recombinant protein of any one of E1-E117 and E120-E122, the nucleic acid of E118 or E119, or the pharmaceutical composition of E131.

E136. The method of E134, wherein said subject is a human.

E137. The method of E134 or E135, wherein said medical condition is a cancer.

E138. The method of E136, wherein said cancer is a solid tumor.

E139. The method of E136 or E137, wherein said cancer comprises cells that express FAP.

E140. The method of any one of E137-E139, wherein said cancer is brain cancer, bladder cancer, breast cancer, clear cell kidney cancer, cervical cancer, colon cancer, rectal cancer, endometrial cancer, gastric cancer, head and neck cancer, head/neck squamous cell carcinoma, lip cancer, oral cancer, liver cancer, cervix cancer, lung squamous cell carcinoma, melanoma, mesothelioma, non-small-cell lung cancer (NSCLC), non-melanoma skin cancer, ovarian cancer, pancreatic cancer, prostate cancer, renal cell carcinoma, urothelial carcinoma, sarcoma, small-cell lung cancer (SCLC), Squamous Cell Carcinoma of the Head and Neck (SCCHN), triple negative breast cancer, or thyroid cancer.

E141. The method of any one of E137-E140, wherein said cancer is adrenocortical tumor, alveolar soft part sarcoma, carcinoma, chondrosarcoma, colorectal carcinoma, desmoid tumors, desmoplastic small round cell tumor, endocrine tumors, endodermal sinus tumor, epithelioid hemangioendothelioma, Ewing sarcoma, germ cell tumor, hepatoblastoma, hepatocellular carcinoma, melanoma, nephroma, neuroblastoma, non-rhabdomyosarcoma soft tissue sarcoma (NRSTS), osteosarcoma, paraspinal sarcoma, renal cell carcinoma, retinoblastoma, rhabdomyosarcoma, synovial sarcoma, or Wilms tumor.

E142. The method of E137, wherein the cancer is acute lymphoblastic leukemia (ALL), acute myeloid leukemia (AML), chronic lymphocytic leukemia (CLL), or chronic myeloid leukemia (CML).

E143. The method of E137, wherein the cancer is diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), or small lymphocytic lymphoma (SLL).

E144. The method of any one of E132-E143, wherein said recombinant protein, nucleic acid or pharmaceutical composition is administered intravenously.

E145. The method of any one of E132-E144, wherein said recombinant protein, nucleic acid or pharmaceutical composition is administered subcutaneously.

E146. The method of any one of E132-E145, wherein said recombinant protein, nucleic acid or pharmaceutical composition is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, or once every four months.

E147. The recombinant protein of any one of E1-E117 and E120-E122, the nucleic acid of E118 or E119, or the pharmaceutical composition of E131 for use as a medicament.

E148. The recombinant protein of any one of E1-E117 and E120-E122, or the nucleic acid of E118 or E119, or the pharmaceutical composition of E131 for use in the treatment of a medical condition in a subject.

E149. The recombinant protein for use of E148, wherein said medical condition is cancer.

E150. Use of the recombinant protein of any one of E1-E117 and E120-E122, the nucleic acid of E118 or E119, or the pharmaceutical composition of E131 in the manufacture of a medicament for treating cancer in a subject.

E151. Use of the recombinant protein of any one of E1-E117 and E120-E122, the nucleic acid of E118 or E119, or the pharmaceutical composition of E131 for treating a medical condition in a subject.

E152. The use of E151, wherein said medical condition is cancer.

E153. A kit comprising a container, a composition within the container comprising the recombinant protein of any one of E1-E117 and E120-E122, or the nucleic acid of E118 or E119, or the pharmaceutical composition of E131, and a package insert containing instructions for administering a therapeutically effective amount of the recombinant protein, the nucleic acid or the pharmaceutical composition for treatment of a patient in need thereof.

E154. A method of inducing an anti-tumor immunological memory in a mammal, including a human, the method comprising the step of administering to said mammal the recombinant protein of any one of E1-E117 and E120-E122, the nucleic acid of E118 or E119, or the pharmaceutical composition of E131.

E155. The method of E154, wherein the immunological memory is not limited to FAP-related antigens.

E156. The recombinant protein of any one of E1-E117 and E120-E122, wherein said recombinant protein is capable of preferentially localizing and/or accumulating in a tumor in a mammal, including a human.

E157. The recombinant protein of E156, wherein said tumor comprises cells that express FAP.

E158. The recombinant protein of any one of E1-E117, E120-E122 and E156-E157, wherein said recombinant protein is capable of inducing an anti-tumor immunological memory in a mammal, including a human.

E159. The recombinant protein of E158, wherein said immunological memory is not limited to FAP-related antigens.

The use of section headings herein is merely for the convenience of reading, and not intended to be limiting per se. The entire document is intended to be viewed as a unified disclosure, and it should be understood that all combinations of features described herein are contemplated.

BRIEF DESCRIPTION OF THE FIGURES

FIG. 12A: early time point termination: mice were sacrificed 4 days after the first treatment and tumors were analyzed by FACS analysis (studies PD1033 and PD1038); FIG. 12B: Late time point termination: mice were euthanized 10-11 days after the first treatment, tumor size was measured over time for anti-tumor efficacy assessment and at the day of termination, tumors were investigated by FACS analysis (studies PD1032 and PD1035). Mice were treated i.p. with AS598, AS608 or anti-CD40 antibody at the indicated time points.

FIG. 16A: A representative SPECT/CT image of a MC38-FAP tumor-bearing mouse 96 hours after having been injected with indium-111-labelled Protein #7. Maximum intensity projections (MIP) generated using a normalized intensity setting are shown. Labelled Protein #7 localized and accumulated preferentially in the tumor. FIG. 16B: Detection of Protein #7 (upper image) or a control DARPin® protein (lower image) by immunohistochemistry (IHC) in MC38-FAP tumors 24 hours post-injection. Size bars are shown in the right bottom corners of the images. FIG. 16C: Time course of tissue distribution of indium-111-labeled DARPin® molecules. Tissue distribution of control DARPin® molecule (solid bars) and Protein #7 (striped bars) was analyzed in tumor (left graph) and muscle (right graph) at the indicated time points. Data are given in percentage of the injected dose of DARPin® molecule per gram of tissue (% ID/g) and expressed as mean±SD. N=4 mice per time point.

FIG. 17A: Schematic representation of the experimental design of an anti-tumor efficacy study in vivo. FIG. 17B Mean tumor growth volume during the anti-tumor efficacy study. Mice were treated and tumor volume measured as described in FIG. 17A and in Example 9. Mean tumor volume per treatment group (±SEM, n=10) is shown for vehicle (triangle symbols), AS598 (round symbols) and anti-CD40 antibody (square symbols). The arrow indicates the start of the treatment.

FIG. 19A: The experiment shown in FIG. 18A was followed for a longer time period, with the mean tumor growth curves shown for MC38-FAP tumor bearing mice treated with vehicle (open triangles pointing up), AS598 (open circles), and AS608 (negative control) (open triangles pointing down). Short arrows represent the treatment time-points. At about 120 days, tumor-free mice previously treated with AS598 were re-challenged with MC38-WT (solid triangles pointing down) or MC38-FAP (solid triangles pointing up) tumor cells and monitored up to day 200. Mean tumor growth curves are shown of 8 mice per group.

FIG. 19B: Naïve control mice were challenged with MC38-WT (triangles pointing down) or MC38-FAP (triangles pointing up) tumor cells at about 120 days. Mean tumor growth curves are shown of 5 mice per group.

FIG. 20A: Mice bearing MC38-FAP tumor were treated once with vehicle (n=10) (triangles pointing up), AS608 (negative control) (n=5) (triangles pointing down), AS598 (Protein #7) (n=10) (circles) or anti-mCD40 antibody (n=10) (squares) and after 24 hours serum cytokines were measured. Samples were collected from two independent experiments and analyzed together. FIG. 20B: Mice bearing MC38-FAP tumor were treated once with vehicle (triangles pointing up), AS608 (negative control) (triangles pointing down), AS598 (Protein #7) (circles) or anti-mCD40 antibody (squares) (5 mice per group) and after 24 hours serum aspartate aminotransferase (AST) and alanine aminotransferase (ALT) were measured. Samples were collected from two independent experiments and analyzed together. FIG. 20C: Mice bearing MC38-FAP tumor were treated once with vehicle, AS608 (negative control) (not shown), AS598 (Protein #7) or anti-mCD40 antibody (n=5-10) and after 24 hours livers were harvested an analyzed for tissue damage by immunohistochemistry (INC). Representative pictures of the different treatments are shown. NEC, necrosis; ICI, immune cell infiltration. Size bars are indicated in the right bottom corners of the pictures.

DETAILED DESCRIPTION OF THE INVENTION

1. Overview

Figure 1:
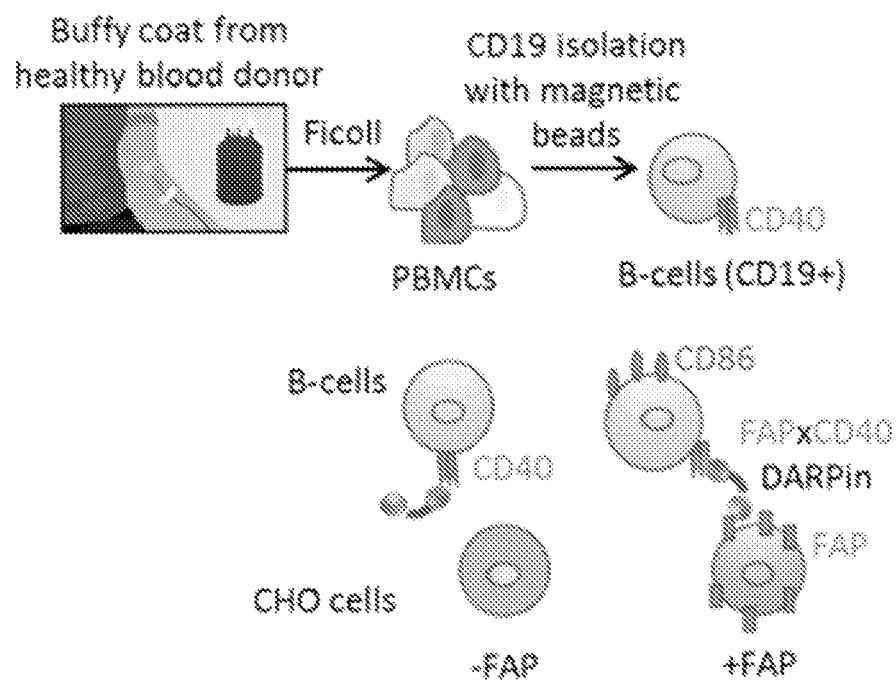
FIG. 1: A cartoon depicting the in vitro B cell activation assay. The assay was performed using purified primary human B cells and FAP expressing (+FAP) or non-FAP expressing (−FAP) CHO cells.

Disclosed herein are recombinant proteins comprising designed ankyrin repeat domains with binding specificity for FAP and CD40. Also disclosed are nucleic acids encoding the binding proteins, pharmaceutical compositions comprising the binding proteins or nucleic acids, and methods of using the binding proteins, nucleic acids, or pharmaceutical compositions. In one aspect, the materials and methods of the disclosure take advantage of FAP's expression in tumor-associated stroma, allowing, e.g., specific targeting of CD40-expressing cells in the tumor and selective activation of CD40 in those CD40-expressing cells.

CD40 agonist antibodies have demonstrated efficacy in preclinical murine tumor models, and their use in the clinic has also shown some anti-tumor efficacy. However, clinical development of agonistic anti-CD40 antibodies has likely been hampered by dose-limiting toxicities and resulting low efficacies.

The multispecific recombinant proteins described herein promote cancer target-mediated and tumor-localized clustering and activation of CD40, thereby addressing challenges associated with previous therapeutic approaches. In natural settings, clustering of CD40 is achieved by binding to trimeric CD40 ligand (CD40L, CD154), which is expressed as a membrane molecule on the surface of certain cells, e.g. activated CD4+ T cells. CD40 clustering in the cell membrane of a cell targeted, e.g., by CD40L is a prerequisite for activation of its signaling pathway. The multispecific recombinant proteins of the disclosure disclosed herein take advantage of this clustering effect; and the activation of CD40 is linked to the expression of the tumor antigen FAP.

Fibroblast-activation protein a (FAP, also known as Seprase) is a type II membrane-bound glycoprotein abundantly expressed in the stroma of many solid tumors by cancer-associated fibroblasts. FAP is expressed selectively in reactive stromal fibroblasts of more than 90% of epithelial malignancies (primary and metastatic), including lung, colorectal, bladder, ovarian and breast carcinomas, and in malignant mesenchymal cells of bone and soft tissue sarcomas, while it is generally absent from normal adult tissues (Brennen et al., Mol Cancer Ther. 11: 257-266 (2012); Garin-Chesa et al., Proc Natl Acad Sci USA 87, 7235-7239 (1990); Rettig et al., Cancer Res. 53:3327-3335 (1993); Rettig et al., Proc Natl Acad Sci USA 85, 3110-3 114 (1988)). FAP is also expressed on certain malignant tumor cells.

Although not wishing to be bound by a particular theory, in the absence of the tumor antigen FAP (normal, non-malignant, non-cancer associated cells), minimal clustering of CD40 will occur, and immune activation will be limited. In contrast, in cancer-associated fibroblasts, FAP is highly expressed, and therefore, through FAP-binding, the multi-specific proteins of the disclosure promote CD40 clustering and activation in CD40 expressing immune cells, such as, e.g., B cells and antigen presenting cells. The advantages of this strategy are twofold: systemic toxicities should be limited because activation will be largely confined to tissue expressing FAP, and tumor-mediated CD40 clustering should drive potent agonism.

2. Definitions

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The terms "comprising," "having," "including," and "containing" are to be construed as open-ended terms unless otherwise noted. If aspects of the disclosure are described as "comprising" a feature, embodiments also are contemplated "consisting of" or "consisting essentially of" the feature. The use of any and all examples, or exemplary language (e.g., "such as") provided herein, is intended merely to better illustrate the disclosure and does not pose a limitation on the scope of the disclosure unless otherwise claimed. No language in the specification should be construed as indicating any non-claimed element as essential to the practice of the disclosure. Other than in the operating examples, or where otherwise indicated, all numbers expressing quantities of ingredients or reaction conditions used herein should be understood as modified in all instances by the term "about" as that term would be interpreted by the person skilled in the relevant art.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

The term "polypeptide" relates to a molecule consisting of one or more chains of multiple, i.e. two or more, amino acids linked via peptide bonds. In some embodiments, a polypeptide consists of more than eight amino acids linked via peptide bonds. The term "polypeptide" also includes multiple chains of amino acids, linked together by S—S bridges of cysteines. Polypeptides are well-known to the person skilled in the art.

The term "protein" refers to a molecule comprising a polypeptide, wherein at least part of the polypeptide has, or is able to acquire, a defined three-dimensional arrangement by forming secondary, tertiary, and/or quaternary structures within a single polypeptide chain and/or between multiple polypeptide chains. If a protein comprises two or more polypeptide chains, the individual polypeptide chains may be linked non-covalently or covalently, e.g. by a disulfide bond between two polypeptide chains. A part of a protein, which individually has, or is able to acquire, a defined three-dimensional arrangement by forming secondary and/or tertiary structures, is termed "protein domain". Such protein domains are well known to the practitioner skilled in the art.

Patent application WO2002/020565 and Forrer et al., 2003 (Forrer, P., Stumpp, M. T., Binz, H. K., Plückthun, A., 2003. FEBS Letters 539, 2-6), contain a general description of repeat protein, repeat domain and repeat module features, techniques and applications.

The term "repeat domain" refers to a protein domain comprising two or more consecutive repeat modules as structural units, wherein said repeat modules have structural and sequence homology. In some embodiments, a repeat domain also comprises an N-terminal and/or a C-terminal capping module. For clarity, a capping module can be a repeat module. Such repeat domains, repeat modules, and capping modules, sequence motives, as well as structural homology and sequence homology are well known to the practitioner in the art from examples of ankyrin repeat domains (Binz et al., J. Mol. Biol. 332, 489-503, 2003; Binz et al., 2004, loc. cit.; WO2002/020565; WO2012/069655), leucine-rich repeat domains (WO2002/020565), tetratricopeptide repeat domains (Main, E. R., Xiong, Y., Cocco, M. J., D'Andrea, L., Regan, L., Structure 11(5), 497-508, 2003), and armadillo repeat domains (WO2009/040338). It is further well known to the practitioner in the art, that such repeat domains are different from proteins comprising repeated amino acid sequences, where every repeated amino acid sequence is able to form an individual domain (for example FN3 domains of Fibronectin).

The term "ankyrin repeat domain" refers to a repeat domain comprising two or more consecutive ankyrin repeat modules as structural units, wherein said ankyrin repeat modules have structural and sequence homology.

The term "repeat modules" refers to the repeated amino acid sequence and structural units of the designed repeat domains, which are originally derived from the repeat units of naturally occurring repeat proteins. Each repeat module comprised in a repeat domain is derived from one or more repeat units of a family or subfamily of naturally occurring repeat proteins, such as the family of ankyrin repeat proteins. Accordingly, the term "ankyrin repeat module" refers to a repeat module, which is originally derived from the repeat units of naturally occurring ankyrin repeat proteins. Ankyrin repeat proteins are well known to the person skilled in the art. See, for example, International Patent Publication Nos. WO 2002/020565, WO 2010/060748, WO 2011/135067, WO 2012/069654, WO 2012/069655, WO 2014/001442, WO 2014/191574, WO 2014/083208, WO 2016/156596, and WO 2018/054971.

Ankyrin repeat domains may be modularly assembled into larger ankyrin repeat proteins according to the present disclosure, optionally with half-life extension domains, using standard recombinant DNA technologies (see, e.g., Forrer, P., et al., FEBS letters 539, 2-6, 2003, WO2012/069655, WO 2002/020565).

The term "designed" as used in designed repeat protein, designed repeat domain, designed ankyrin repeat domain, and the like refers to the property that such repeat proteins and repeat domains, respectively, are man-made and do not occur in nature.

The term "recombinant" as used in recombinant protein, recombinant binding protein, recombinant polypeptide, and the like, means that said protein or polypeptide is produced by the use of recombinant DNA technologies well known to the practitioner skilled in the art. For example, a recombinant DNA molecule (e.g. produced by gene synthesis) encoding a polypeptide can be cloned into a bacterial expression plasmid (e.g. pQE30, QlAgen), yeast expression plasmid, mammalian expression plasmid, or plant expression plasmid, or a DNA enabling in vitro expression. If, for example, such a recombinant bacterial expression plasmid is inserted into appropriate bacteria (e.g. *Escherichia coli*), these bacteria can produce the polypeptide(s) encoded by this recombinant DNA. The correspondingly produced polypeptide or protein is called a recombinant polypeptide or recombinant protein.

In the context of the present disclosure, the term "binding protein" refers to a protein comprising a binding domain. A binding protein may also comprise two, three, four, five or more binding domains. In some embodiments, said binding protein is a recombinant binding protein.

The term "binding domain" means a protein domain exhibiting binding specificity for a target. In some embodiments, said binding domain is a recombinant binding domain.

The term "target" refers to an individual molecule such as a nucleic acid molecule, a peptide, polypeptide or protein, a carbohydrate, or any other naturally occurring molecule, including any part of such individual molecule, or to complexes of two or more of such molecules, or to a whole cell or a tissue sample, or to any non-natural compound. In some embodiments, a target is a naturally occurring or non-natural polypeptide or protein, or a polypeptide or protein containing chemical modifications, for example, naturally occurring or non-natural phosphorylation, acetylation, or methylation. For example, the target of each of the designed ankyrin repeat domains consisting of SEQ ID NOs: 39 to 42, is serum albumin.

The term "has binding specificity for a target", "specifically binding to a target", "binding to a target with high specificity", "specific for a target" or "target specificity" and the like means that a binding protein or binding domain reacts or associates more frequently, more rapidly, with greater duration and/or with greater affinity with a particular target (e.g., cell or substance) than it does with alternative targets (e.g., cells or substances). For example, a binding domain that specifically binds FAP may be defined as a binding domain that binds in PBS to FAP with a lower dissociation constant (i.e. it binds with higher affinity) than it binds to an unrelated protein such as the *E. coli* maltose binding protein (MBP). In some embodiments, the dissociation constant ("$K_D$") in PBS for the target is at least $10^2$; at least $10^3$; at least $10^4$; or at least $10^5$ times lower than the corresponding dissociation constant for MBP. Methods to determine dissociation constants of protein-protein interactions, such as surface plasmon resonance (SPR) based technologies (e.g. SPR equilibrium analysis) or isothermal titration calorimetry (ITC) are well known to the person skilled in the art. The measured $K_D$ values of a particular protein-protein interaction can vary if measured under different conditions (e.g., salt concentration, pH). Thus, measurements of $K_D$ values may be made with standardized solutions of protein and a standardized buffer, such as PBS. It is also understood by reading this definition that, for example, an ankyrin repeat domain which specifically binds to a first target may or may not specifically or preferentially bind to a second target. As such, "specific binding" does not necessarily require (although it can include) exclusive binding. In general, under designated assay conditions, an ankyrin repeat domain binds preferentially to a particular target molecule and does not bind in a significant amount to other components present in a test sample.

A variety of assay formats may be used to select or characterize an ankyrin repeat domain that specifically binds a molecule of interest. For example, solid-phase ELISA immunoassay, immunoprecipitation, BIAcore™ (GE Healthcare, Piscataway, NJ), fluorescence-activated cell sorting (FACS), Octet™ (ForteBio, Inc., Menlo Park, CA) and Western blot analysis are among many assays that may be used to identify an ankyrin repeat domain that specifically reacts with a target. Typically, a specific or selective reaction will be at least twice background signal or noise and more typically more than 10 times background. Even more specifically, an ankyrin repeat domain is said to "specifically bind" a target when the equilibrium dissociation constant ($K_D$) value is <1 pM, such as <100 nM, <10 nM, <100 pM, <10 pM, or <1 pM.

The $K_D$ value is often referred to as binding affinity. Binding affinity measures the strength of the sum total of non-covalent interactions between contact residues of one binding partner (e.g., FAP or CD40 binding domains disclosed herein) and contact residues of its binding partner (e.g., FAP or CD40). Unless indicated otherwise, as used herein, binding affinity refers to binding affinity that reflects a 1:1 interaction between members of a binding pair or binding partners. In case of a binding protein comprising two binding domains for one binding partner, binding affinity may refer to binding affinity that reflects a 1:2 interaction between the binding protein and the binding partner.

A variety of methods of measuring binding affinity are known in the art, any of which can be used for purposes of the present disclosure. For example, as exemplified herein, the binding affinity can be expressed as $K_D$ value, which refers to the dissociation rate of a particular ankyrin repeat domain and its binding target. $K_D$ is the ratio of the rate of dissociation, also called the "off-rate ($K_{off}$)", to the association rate, or "on-rate ($K_{on}$)". Thus, $K_D$ equals $K_{off}/K_{on}$ and is expressed as a molar concentration (M), and the smaller the $K_D$, the stronger the affinity of binding.

$K_D$ values can be determined using any suitable method. One disclosed method for measuring $K_D$ is surface plasmon resonance (SPR) (see, e.g., Nguyen et al. Sensors (Basel). 2015 May 5; 15(5):10481-510). $K_D$ value may be measured by SPR using a biosensor system such as a BIACORE® system. BIAcore kinetic analysis comprises analyzing the binding and dissociation of an antigen from chips with immobilized molecules (e.g., molecules comprising epitope binding domains), on their surface. Another method for determining the $K_D$ of a protein is by using Bio-Layer Interferometry (see, e.g., Shah et al. J Vis Exp. 2014; (84): 51383). $K_D$ value may be measured using OCTET@ technology (Octet QKe system, ForteBio). Alternatively or in addition, a KinExA® (Kinetic Exclusion Assay) assay, available from Sapidyne Instruments (Boise, Id.) can also be used. Any method suitable for assessing the binding affinity between two binding partners is encompassed herein. In some embodiments, $K_D$ values are determined in PBS by SPR, e.g. as described in Example 2.

The term "polypeptide tag" refers to an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His (e.g. the His-tag consisting of SEQ ID NO: 57), myc, FLAG, or Strep-tags or moieties such as enzymes (for example enzymes like alkaline phosphatase), which allow the detection of said polypeptide/protein, or moieties which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-polypeptide moiety such as polyethylene glycol, or two polypeptide tags. Such additional domains, tags, non-polypeptide moieties and linkers are known to the person skilled in the relevant art. Examples of such polypeptide linkers are the linkers consisting of SEQ ID NOs: 4 and 56.

The terms "nucleic acid" or "nucleic acid molecule" refer to a polynucleotide molecule, which may be a ribonucleic acid (RNA) or deoxyribonucleic acid (DNA) molecule, either single stranded or double stranded, and includes modified and artificial forms of DNA or RNA. A nucleic acid molecule may either be present in isolated form, or be comprised in recombinant nucleic acid molecules or vectors.

In the context of the disclosure, the terms "medical condition", "disease" and "disorder" are used interchangeably and include but are not limited to autoimmune disorders, inflammatory disorders, retinopathies (particularly proliferative retinopathies), neurodegenerative disorders, infectious diseases, metabolic diseases, and neoplastic diseases. A "medical condition" may be one that is characterized by inappropriate cell proliferation. A medical condition may be a hyperproliferative condition. A medical condition may be a neoplastic disease. The term "neoplastic disease", as used herein, refers to an abnormal state or condition of cells or tissue characterized by rapidly proliferating cell growth or neoplasm. A medical condition may be a malignant neoplastic disease. A medical condition may be a cancer. The terms "cancer" and "cancerous" are used herein to refer to or describe the physiological condition in mammals that is typically characterized by unregulated cell growth. Cancer encompasses solid tumors and liquid tumors, as well as primary tumors and metastases. A "tumor" comprises one or more cancerous cells. Solid tumors typically also comprise tumor stroma. Examples of cancer include, but are not limited to, primary and metastatic carcinoma, lymphoma, blastoma, sarcoma, myeloma, melanoma and leukemia, and any other epithelial and blood cell malignancies. More particular examples of such cancers include brain cancer, bladder cancer, breast cancer, ovarian cancer, kidney cancer, colorectal cancer, gastric cancer, head and neck cancer, lung cancer, pancreatic cancer, prostate cancer, malignant melanoma, osteosarcoma, soft tissue sarcoma, carcinoma, squameous cell carcinoma, clear cell kidney cancer, head/neck squamous cell carcinoma, lung adenocarcinoma, lung squamous cell carcinoma, non-small-cell lung cancer (NSCLC), renal cell carcinoma, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), Squamous Cell Carcinoma of the Head and Neck (SCCHN), chronic myelogenous leukemia (CML), small lymphocytic lymphoma (SLL), malignant mesothelioma, liposarcoma, neuroblastoma, or synovial sarcoma.

The term "treat," as well as words related thereto, does not necessarily imply 100% or complete cure. Rather, there are varying degrees of treatment of which one of ordinary skill in the art recognizes as having a potential benefit or therapeutic effect. In this respect, the methods of treating cancer of the present disclosure can provide any amount or any level of treatment. Furthermore, the treatment provided by the method of the present disclosure can include treatment of (i.e., relief from) one or more conditions or symptoms. Also, the treatment provided by the methods of the present disclosure can encompass slowing the progression of the cancer. For example, the methods can treat cancer by virtue of enhancing the T cell activity or an immune response against the cancer, reducing tumor or cancer growth or appearance of new lesions, reducing metastasis of tumor cells, increasing cell death of tumor or cancer cells, inhibition of tumor or cancer cell survival, and the like. In some aspects, the methods treat by way of delaying the onset or recurrence of the cancer by 1 day, 2 days, 4 days, 6 days, 8 days, 10 days, 15 days, 30 days, two months, 4 months, 6 months, 1 year, 2 years, 4 years, or more. In some aspects, the methods treat by way increasing the survival of the subject. The term "treatment" also includes prophylactic treatment.

Therapeutic responses in any given disease or condition can be determined by standardized response criteria specific to that disease or condition. Tumor response can be assessed using screening techniques such as magnetic resonance imaging (MRI) scan, x-radiographic imaging, computed tomographic (CT) scan, positron emission tomography (PET) scan, bone scan, ultrasound, tumor biopsy sampling, counting of tumor cells in circulation, and/or measurement of tumor antigen (e.g., prostate specific antigen (PSA) and/or alphafeltoprotein (AFP)). In addition to these therapeutic responses, the subject undergoing therapy may experience the beneficial effect of an improvement in the symptoms associated with the disease.

The term "treatment" or "treating" refers to both therapeutic treatment and prophylactic or preventative measures. Those in need of treatment include those who have already the disorder as well as those in which the disorder is to be prevented.

The term "therapeutically effective amount" refers to the amount sufficient to induce a desired biological, pharmacological, or therapeutic outcome in a subject. A therapeutically effective amount in the context of the disclosure means a sufficient amount of the binding protein to treat or prevent a disease or disorder at a reasonable benefit/risk ratio applicable to any medical treatment.

The term "mammal" for purposes of treatment refers to any animal classified as a mammal, including human, domestic and farm animals, nonhuman primates, and zoo, sports, or pet animals, such as dogs, horses, cats, cows, etc.

The term "incubation" refers to incubation at pH 7.4. In one embodiment, said incubation at pH 7.4 refers to an incubation in PBS.

The term "PBS" means a phosphate buffered water solution containing 137 mM NaCl, 10 mM phosphate and 2.7 mM KCl and having a pH of 7.4.

The term improved pharmacokinetic properties refers to an increased area under the curve, a reduced clearance, or an increased terminal half-life. These parameters of pharmacokinetic properties and ways to determine them are well known in the art (see, e.g., Mahmood, I., Methods to determine pharmacokinetic profiles of therapeutic proteins, Drug Discov Today: Technol (2009), doi:10.1016/j.ddtec.2008.12.001).

In the context of the present disclosure, the term "any amino acids" preferably means any of the 20 most often naturally occurring amino acids, namely alanine (ala; A), arginine (arg; R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, VV), tyrosine (tyr, Y), valine (val, V).

3. Multispecific Molecules that Target FAP and CD40

Disclosed herein are multispecific molecules that target FAP and CD40. The molecules are useful for, e.g., treating cancer. In some embodiments of the present disclosure, the herein provided multispecific molecules that target FAP and CD40 are designed repeat proteins, such as designed ankyrin repeat proteins.

3.1. Ankyrin Repeat Domains and Ankyrin Repeat Proteins

Designed ankyrin repeat proteins are a class of binding molecules which have the potential to overcome limitations of monoclonal antibodies, hence allowing novel therapeutic approaches. Such ankyrin repeat proteins may comprise a single designed ankyrin repeat domain, or may comprise a combination of two, three, four, five or more designed ankyrin repeat domains with the same or different target specificities (Stumpp et al., Drug Discov. Today 13, 695-701, 2008; U.S. Pat. No. 9,458,211). Ankyrin repeat proteins comprising only a single designed ankyrin repeat domain are small proteins (14 kDa) which can be selected to bind a given target protein with high affinity and specificity. These characteristics, and the possibility of combining two, three, four, five or more designed ankyrin repeat domains in one protein, make designed ankyrin repeat proteins ideal agonistic, antagonistic and/or inhibitory drug candidates. Furthermore, such ankyrin repeat proteins can be engineered to carry various effector functions, e.g. cytotoxic agents or half-life extending agents, enabling completely new drug formats. Taken together, designed ankyrin repeat proteins are an example of the next generation of protein therapeutics with the potential to surpass existing antibody drugs.

The designed ankyrin repeat domains described herein generally comprise one or more designed repeat modules, such as ankyrin repeat modules, as structural units (thereafter also referred to as structural repeats or repeat units), wherein said repeat modules, such as said ankyrin repeat modules, have structural and sequence homology. An ankyrin repeat module generally comprises two anti-parallel α-helices followed by a beta-bulge and beta-hairpin containing loop connecting it to the next repeat, each of which has about 28-33 residues.

Recombinant proteins, or designed binding domains thereof, comprising designed ankyrin repeat modules are also referred herein as DARPin® proteins. See Stumpp et al., Curr Opin Drug Discov Devel. 10(2): 153-9 (2007); and Binz et al., Nature Biotech. 22(5): 575-582 (2004). DARPin® proteins can be considered as antibody mimetics with high specificity and high binding affinity to a target protein. In general, a DARPin® protein comprises at least one ankyrin repeat module, for example, at least 2, 3, or more ankyrin repeat modules. DARPin® is a trademark owned by Molecular Partners AG, Switzerland.

The ankyrin repeat domains described herein generally comprise a core scaffold that provides structure, and target binding residues that bind to a target. The structural core includes conserved amino acid residues, and the target binding surface includes amino acid residues that differ depending on the target. For example, an ankyrin repeat module can comprise the following sequence: xDxxGxTPLHLAxxxGxxxlVxVLLxxGADVNA (SEQ ID NO: 23), wherein "x" denotes any amino acid. In some embodiments, "x" is not cysteine, glycine, or proline. As other examples, an ankyrin repeat module can comprise the amino acid sequence of any of SEQ ID NOs: 24 to 27.

Designed repeat protein libraries, including designed ankyrin repeat protein libraries (WO2002/020565; Binz et al., Nat. Biotechnol. 22, 575-582, 2004; Stumpp et al., Drug Discov. Today 13, 695-701, 2008), can be used for the selection/screening of target-specific designed repeat domains that bind to their target with high affinity. Such target-specific designed repeat domains in turn can be used as valuable components of recombinant binding proteins for the treatment of diseases. Methods of making such libraries are known to the person skilled in the art (WO2002/020565).

Multiple ankyrin repeat domains can be linked (either through a covalent bond or non-covalent association) to form bispecific or multi-specific molecules. Such multispecific molecules are disclosed herein, including molecules in which one FAP-binding domain and two CD40-binding domains are linked. Such molecules may also include a half-life extending moiety at the N-terminus.

3.2. N-Terminal and C-Terminal Capping Modules

In some embodiments, the repeat domains, such as ankyrin repeat domains, of the recombinant protein disclosed herein comprise a N-terminal and/or a C-terminal capping module (thereafter also referred to as capping repeats or capping units). Capping modules are located at the N- and/or C-terminal end of an ankyrin repeat domain, typically forming tight tertiary interactions (i.e. tertiary structure interactions) with the ankyrin repeat module(s) in between, thereby providing a cap that shields the hydrophobic core of the ankyrin repeat domain at the side from exposure to the solvent.

The N- and/or C-terminal capping modules may be derived from, a capping unit or other structural unit found in a naturally occurring repeat protein adjacent to a repeat unit. Examples of capping sequences are described in International Patent Publication Nos. WO 2002/020565 and WO 2012/069655, in U.S. Patent Publication No. US20130296221, and by Interlandi et al., J Mol Biol. 2008 Jan. 18; 375(3):837-54. Examples of N-terminal capping modules (i.e. N-terminal capping repeats) are SEQ ID NOs: 11-16 and examples of C-terminal capping modules (i.e. C-terminal capping repeats) are SEQ ID NOs: 18-21.

In an embodiment, the N-terminal capping module comprises the amino acid sequence DLGKKLLEAARAGQDDEVRILLAAGADVNA (SEQ ID NO: 14) or DLGKKLLEAARAGQDDEVRELLKAGADVNA (SEQ ID NO: 15), wherein up to 9, up to 8, up to 7, up to 6, up to 5, up to 4, up to 3, up to 2 or up to 1 amino acids of SEQ ID NO: 14 or SEQ ID NO: 15 are optionally exchanged by any amino acids; and wherein SEQ ID NO: 14 or SEQ ID NO: 15 may optionally further comprise a "G," an "5," or a "GS" sequence at its N-terminus. In an embodiment, the C-terminal capping module comprises the amino acid sequence QDIFGKTPADIAADAGHEDIAEVLQKAA (SEQ ID NO: 19) or QDKSGKTPADLAADAGHEDIAEVLQKAA (SEQ ID NO: 20), wherein up to 9, up to 8, up to 7, up to 6, up to 5, up to 4, up to 3, up to 2 or up to 1 amino acids of SEQ ID NO: 19 or SEQ ID NO: 20 are optionally exchanged by any amino acids.

In some embodiments, certain amino acid residues in the N-terminal capping module and/or the C-terminal capping module of the designed ankyrin repeat domain herein provided are altered, resulting in improved pharmacokinetic properties, including a prolonged terminal half-life, of the designed ankyrin repeat domain and of the recombinant binding proteins comprising the designed ankyrin repeat domain. The altered amino acid residues are mostly surface-exposed residues. In some embodiments, the altered amino acids residues are the amino acid residues at positions 8 and 15 of an N-terminal capping module, wherein the position numbers correspond to the positions in SEQ ID NO: 11, and the amino acid residues at positions 14 and 18 of a C-terminal capping module, wherein the position numbers correspond to the positions in SEQ ID NO: 18.

In at least one embodiment, the designed ankyrin repeat domains provided herein comprise an N-terminal capping module having an amino acid sequence wherein the amino acid at position 8 is Q and/or the amino acid at position 15 is L. Examples of such N-terminal capping modules are SEQ ID NOs: 11, 12 and 13. In one embodiment, said designed ankyrin repeat domains comprise an N-terminal capping module having an amino acid sequence wherein the amino acid at position 4 is S, the amino acid at position 8 is Q, the amino acid at position 15 is L, the amino acid at position 17 is T, the amino acid at position 20 is T, and/or the amino acid at position 23 is Q. An example of such a N-terminal capping module is SEQ ID NO: 16. In at least one embodiment, said N-terminal capping module comprises an amino acid sequence of 30 amino acids. In at least one embodiment, said N-terminal capping module consists of an amino acid sequence of 30 amino acids. In at least one embodiment, said position numbers of positions of the N-terminal capping module are determined by alignment to SEQ ID NO: 11 using the position numbers of SEQ ID NO: 11. In at least one embodiment, said alignment comprises no amino acid gaps. Sequence alignment generation is a procedure well known in the art. Any of said N-terminal capping modules may optionally further comprise a "G," an "5," or a "GS" sequence at its N-terminus.

For example, an N-terminal capping module with altered amino acid residues can comprise the following sequence: DLGxxLLQAAxxGQLDxVRxLxxxGADVNA (SEQ ID NO: 17), wherein "x" denotes any amino acid.

In an embodiment, the N-terminal capping sequence comprises DLGKKLLQAARAGQLDEVRELLKAGADVNA (SEQ ID NO: 11), DLGKKLLQAARAGQLDEVRILLKAGADVNA (SEQ ID NO: 12) or DLGKKLLQAARAGQLDEVRILLAAGADVNA (SEQ ID NO: 13), wherein up to 9, up to 8, up to 7, up to 6, up to 5, up to 4, up to 3, up to 2 or up to 1 amino acids of SEQ ID NO: 11, SEQ ID NO: 12, or SEQ ID NO: 13 in positions other than positions 8 and 15 are optionally exchanged by any amino acids; and wherein SEQ ID NO: 11, SEQ ID NO: 12, or SEQ ID NO: 13 may optionally further comprise a "G," an "5," or a "GS" sequence at its N-terminus. Thus, in one embodiment, the designed repeat domain, such as ankyrin repeat domain, of the disclosure comprises an N-terminal capping module having the amino acid sequence DLGKKLLQAARAGQLDEVRELLKAGADVNA (SEQ ID NO: 11), wherein up to 9, up to 8, up to 7, up to 6, up to 5, up to 4, up to 3, up to 2 or up to 1 amino acids of SEQ ID NO: 11 in positions other than positions 8 and 15 are optionally exchanged by any amino acids; and wherein SEQ ID NO: 11 may optionally further comprise a "G," an "5," or a "GS" sequence at its N-terminus.

In another embodiment, the N-terminal capping sequence comprises DLGSKLLQAARAGQLDTVRTLLQAGADVNA (SEQ ID NO: 16), wherein up to 9, up to 8, up to 7, up to 6, up to 5, up to 4, up to 3, up to 2 or up to 1 amino acids of SEQ ID NO: 16 in positions other than positions 4, 8, 15, 17, 20 and 23 are optionally exchanged by any amino acids; and wherein SEQ ID NO: 16 may optionally further comprise a "G," an "5," or a "GS" sequence at its N-terminus.

In at least one embodiment, the designed repeat domains, such as ankyrin repeat domains, provided herein comprise a C-terminal capping module having an amino acid sequence wherein the amino acid at position 14 is R and/or the amino acid at position 18 is Q. Examples of such C-terminal capping modules are SEQ ID NOs: 18 and 19. In one embodiment, said designed ankyrin repeat domain comprises a C-terminal capping module having an amino acid sequence wherein the amino acid at position 3 is T, the amino acid at position 4 is Q, the amino acid at position 6 is T, the amino acid at position 14 is R, the amino acid at position 18 is Q, the amino acid at position 19 is Q, the amino acid at position 22 is S, and/or the amino acid at position 26 is Q. An example of such a C-terminal capping module is SEQ ID NO: 21. In at least one embodiment, said C-terminal capping module comprises an amino acid sequence of 28 amino acids. In at least one embodiment, said C-terminal capping module consists of an amino acid sequence of 28 amino acids. In at least one embodiment, said position numbers of positions of the C-terminal capping module are determined by alignment to SEQ ID NO: 18 using the position numbers of SEQ ID NO: 18. In at least one embodiment, said alignment comprises no amino acid gaps.

For example, a C-terminal capping module with altered amino acid residues can comprise the following sequence: xDxxGxTPADxAARxGHQxIAxVLQxAA (SEQ ID NO: 22), wherein "x" denotes any amino acid.

In an embodiment, the C-terminal capping sequence comprises QDKSGKTPADLAARAGHQDIAEVLQKAA (SEQ ID NO: 18), wherein up to 9, up to 8, up to 7, up to 6, up to 5, up to 4, up to 3, up to 2 or up to 1 amino acids of SEQ ID NO: 18 in positions other than positions 14 and 18 are optionally exchanged by any amino acids.

In another embodiment, the C-terminal capping sequence comprises QDTQGTTPADLAARAGHQQIASVLQQAA (SEQ ID NO: 21), wherein up to 9, up to 8, up to 7, up to 6, up to 5, up to 4, up to 3, up to 2 or up to 1 amino acids of SEQ ID NO: 21 in positions other than positions 3, 4, 6, 14, 18, 19, 22 and 26 are optionally exchanged by any amino acids.

3.3. FAP-Binding Domain

One attractive stromal cell target is the fibroblast activation protein (FAP), a transmembrane serine protease highly expressed in the cancer-associated stromal cells of virtually all epithelial cancers. FAP is also expressed during embryonic development, in tissues of healing wounds, and in chronic inflammatory and fibrotic conditions such as liver cirrhosis and idiopathic pulmonary fibrosis. However, FAP has not been detected by immunohistochemistry in benign tumors or in most normal quiescent adult stromal cells.

The recombinant protein described herein comprises an ankyrin repeat domain that specifically binds FAP, also referred herein as "FAP binding domain".

In some embodiments, the FAP binding domain described herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 2. In at least one embodiment, the FAP binding domain described herein comprises an amino acid sequence that is at least 90% identical to SEQ ID NO: 2. In at least one embodiment, the FAP binding domain described herein comprises the amino acid sequence of SEQ ID NO: 2. In some embodiments, the FAP binding domain described herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 8. In at least one embodiment, the FAP binding domain described herein comprises an amino acid sequence that is at least 90% identical to SEQ ID NO: 8. In at least one embodiment, the FAP binding domain described herein comprises the amino acid sequence of SEQ ID NO: 8. In some embodiments, the FAP binding domain described herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 9. In at least one embodiment, the FAP binding domain described herein comprises an amino acid sequence that is at least 90% identical to SEQ ID NO: 9. In another embodiment, the FAP binding domain described herein comprises the amino acid sequence of SEQ ID NO: 9. In some embodiments, the FAP binding domain described herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 28-38. In at least one embodiment, the FAP binding domain described herein comprises an amino acid sequence that is at least 90% identical to any one of SEQ ID NOs: 28-38. In another embodiment, the FAP binding domain described herein comprises the amino acid sequence of any one of SEQ ID NOs: 28-38.

In some embodiments, no more than 10, no more than 9, no more than 8, no more than 7, no more than 6, no more than 5, no more than 4, no more than 3, no more than 2, or no more than 1 substitution is made relative to the sequence of SEQ ID NO: 2. In some embodiments, no more than 5 substitutions are made relative to the sequence of SEQ ID NO: 2. In some embodiments, no more than 4 substitutions are made relative to the sequence of SEQ ID NO: 2. In some embodiments, no more than 3 substitutions are made relative to the sequence of SEQ ID NO: 2. In some embodiments, no more than 2 substitutions are made relative to the sequence of SEQ ID NO: 2. In some embodiments, no more than 1 substitution is made relative to the sequence of SEQ ID NO: 2. In some embodiments, the substitution(s) do not change the $K_D$ value by more than 1000-fold, more than 100-fold, or more than 10-fold, compared to the $K_D$ value of the protein comprising the sequence of SEQ ID NO: 2. In some embodiments, no more than 10, no more than 9, no more than 8, no more than 7, no more than 6, no more than 5, no more than 4, no more than 3, no more than 2, or no more than 1 substitution is made relative to the sequence of SEQ ID NO: 8. In some embodiments, no more than 5 substitutions are made relative to the sequence of SEQ ID NO: 8. In some embodiments, no more than 4 substitutions are made relative to the sequence of SEQ ID NO: 8. In some embodiments, no more than 3 substitutions are made relative to the sequence of SEQ ID NO: 8. In some embodiments, no more than 2 substitutions are made relative to the sequence of SEQ ID NO: 8. In some embodiments, no more than 1 substitution is made relative to the sequence of SEQ ID NO: 8. In some embodiments, the substitution(s) do not change the $K_D$ value by more than 1000-fold, more than 100-fold, or more than 10-fold, compared to the $K_D$ value of the protein comprising the sequence of SEQ ID NO: 8. In some embodiments, the substitution is a conservative substitution according to Table 1. In some embodiments, the substitution is made outside the structural core residues of the ankyrin repeat domain, e.g. in the beta loops that connect the alpha-helices. In some embodiments, the substitution is made within the structural core residues of the ankyrin repeat domain. For example, the ankyrin domain may comprise the consensus sequence: xDxxGxTPLHLAxxxGxxxIVxVLLxxGADVNA (SEQ ID NO: 23), wherein "x" denotes any amino acid; or xDxxGxTPLHLAxxxGHLEIVEVLLKzGADVNA (SEQ ID NO: 24), wherein "x" denotes any amino acid, and "z" is selected from the group consisting of asparagine, histidine, or tyrosine. In one embodiment, the substitution is made to residues designated as "x". In another embodiment, the substitution is made outside the residues designated as "x". In at least one embodiment, "x" is not cysteine, glycine, or proline.

In addition, the second last position can be "A" (see, e.g., SEQ ID NOs: 2, 8, 9, 28-31 and 38) or "L" (see, e.g., SEQ ID NOs: 32-37), and/or the last position can be "A" (see, e.g., SEQ ID NOs: 2, 8, 9, 28-31 and 38) or "N" (see, e.g., SEQ ID NOs: 32-37). Accordingly, in some embodiments, the FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 2, 8, 9, 28-31 and 38, and wherein optionally A at the second last position is substituted with L and/or A at the last position is substituted with N. In at least one embodiment, the FAP-binding domain comprises an amino acid sequence that is at least 90% identical to any one of SEQ ID NOs: 2, 8, 9, 28-31 and 38, and wherein optionally A at the second last position is substituted with L and/or A at the last position is substituted with N. In some embodiments, the FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 2, and wherein optionally A at the second last position is substituted with L and/or A at the last position is substituted with N. In at least one embodiment, the FAP-binding domain comprises an amino acid sequence that is at least 90% identical to SEQ ID NO: 2, and wherein optionally A at the second last position is substituted with L and/or A at the last position is substituted with N. In at least one embodiment, the FAP binding domain described herein comprises the amino acid sequence of SEQ ID NO: 2, and wherein optionally A at the second last position is substituted with L and/or A at the last position is substituted with N. In some embodiments, the FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 9, 28-31 and 38, and wherein optionally A at the second last position is substituted with L and/or A at the last position is substituted with N. In at least one embodiment, the FAP-binding domain comprises an amino acid sequence that is at least 90% identical to any one of SEQ ID NOs: 9, 28-31 and 38, and wherein optionally A at the second last position is substituted with L and/or A at the last position is substituted with N. In another embodiment, the FAP-binding domain comprises the amino acid sequence of any one of SEQ ID NOs: 9, 28-31 and 38, and wherein optionally A at the second last position is substituted with L and/or A at the last position is substituted with N. In some embodiments, the FAP-binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 32-37, and wherein optionally L at the second last position is substituted with A and/or N at the last position is substituted with A. In at least one embodiment, the FAP-binding domain comprises an amino acid sequence that is at least 90% identical to any one of SEQ ID NOs: 32-37, and wherein optionally L at the second last position is substituted with A and/or N at the last position is substituted with A. In another embodiment, the FAP-binding domain comprises the amino acid sequence of any one of SEQ ID NOs: 32-37, and wherein optionally L at the second last position is substituted with A and/or N at the last position is substituted with A. The sequences may optionally comprise at its N-terminus, a G, an S, or a GS (see below).

In addition, the FAP-binding domain may optionally further comprise a "G," an "S," or a "GS" sequence at its N-terminus (see, e.g., SEQ ID NO: 38 as compared with SEQ ID NO: 2). Accordingly, in some embodiments, the FAP-binding domain provided herein (i) comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 2, 8, 9, and 28-37, and (ii) further comprises at its N-terminus, a G, an S, or a GS. In at least one embodiment, the FAP-binding domain comprises an amino acid sequence that is at least 90% identical to any one of SEQ ID NOs: 2, 8, 9, and 28-37, and further comprises at its N-terminus, a G, an S, or a GS. In at least one embodiment, the FAP-binding domain comprises an amino acid sequence that is at least 95% identical to any one of SEQ ID NOs: 2, 8, 9, and 28-37, and further comprises at its N-terminus, a G, an S, or a GS. In at least one embodiment, the FAP-binding domain comprises the amino acid sequence of any one of SEQ ID NOs: 2, 8, 9, and 28-37, and further comprises at its N-terminus, a G, an S, or a GS. Also accordingly, in some embodiments, the FAP-binding domain provided herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 38, wherein G at position 1 and/or S at position 2 of SEQ ID NO: 38 are optionally missing.

Accordingly, in at least one embodiment, the FAP binding domain described herein comprises the amino acid sequence of SEQ ID NO: 2, wherein its N-terminus optionally further comprises a G, an S, or a GS, and wherein optionally A at the second last position is substituted with L and/or A at the last position is substituted with N.

In some embodiments, the affinity between the FAP binding domain or the recombinant protein comprising the FAP binding domain and its target (i.e., FAP) is described in terms of $K_D$. In at least one embodiment, the $K_D$ is about $10^{-1}$ M or less, about $10^{-2}$ M or less, about $10^{-3}$ M or less, about $10^{-4}$ M or less, about $10^{-5}$ M or less, about $10^{-6}$ M or less, about $10^{-7}$ M or less, about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less, from about $10^{-5}$ M to about $10^{-15}$ M, from about $10^{-6}$ M to about $10^{-15}$ M, from about $10^{-7}$ M to about $10^{-15}$ M, from about $10^{-8}$ M to about $10^{-15}$ M, from about $10^{-9}$ M to about $10^{-15}$ M, from about $10^{-10}$ M to about $10^{-15}$ M, from about $10^{-5}$ M to about $10^{-14}$ M, from about $10^{-6}$ M to about $10^{-14}$ M, from about $10^{-7}$ M to about $10^{-14}$ M, from about $10^{-8}$ M to about $10^{-14}$ M, from about $10^{-9}$ M to about $10^{-14}$ M, from about $10^{-10}$ M to about $10^{-14}$ M, from about $10^{-5}$ M to about $10^{-13}$ M, from about $10^{-6}$ M to about $10^{-13}$ M, from about $10^{-7}$ M to about $10^{-13}$ M, from about $10^{-8}$ M to about $10^{-13}$ M, from about $10^{-9}$ M to about $10^{-13}$ M, or from about $10^{-10}$ M to about $10^{-13}$ M.

In at least one embodiment, the FAP binding domain binds FAP with an $K_D$ value of, or below: about 100 nM, about 90 nM, about 80 nM, about 75 nM, about 60 nM, about 50 nM, about 40 nM, about 30 nM, about 20 nM, about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM. In at least one embodiment, the FAP binding domain binds FAP with a KD value of or below: 100 nM, 90 nM, 80 nM, 75 nM, 70 nM, 60 nM, 50 nM, 40 nM, 30 nM, 20 nM, 10 nM, 5 nM, 2 nM, 1 nM, 900 pM, 800 pM, 700 pM, 600 pM, 500 pM, 400 pM, 300 pM, 250 pM, 200 pM, 150 pM, 140 pM, 130 pM, or 120 pM. In at least one embodiment, the FAP binding domain binds FAP with a $K_D$ value of or below about 100 nM. In another embodiment, the FAP binding domain binds FAP with a $K_D$ value of or below about 10 nM. In another embodiment, the FAP binding domain binds FAP with a $K_D$ value of or below about 1 nM. In at least one embodiment, the FAP binding domain binds FAP with a $K_D$ value of or below about 120 pM. In at least one embodiment, the FAP binding domain has the amino acid sequence of SEQ ID NO: 2.

In some embodiments, the recombinant protein comprising the FAP binding domain binds FAP with an $K_D$ value of, or below: about 100 nM, about 90 nM, about 80 nM, about 75 nM, about 60 nM, about 50 nM, about 40 nM, about 30 nM, about 20 nM, about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM. In some embodiments, the recombinant protein comprising the FAP binding domain binds FAP with a KD value of or below: 100 nM, 90 nM, 80 nM, 75 nM, 70 nM, 60 nM, 50 nM, 40 nM, 30 nM, 20 nM, 10 nM, 5 nM, 2 nM, 1 nM, 900 pM, 800 pM, 700 pM, 600 pM, 500 pM, 400 pM, or 300 pM. In at least one embodiment, the recombinant protein binds FAP with a $K_D$ value of or below about 100 nM. In another embodiment, the FAP binding domain binds FAP with a $K_D$ value of or below about 10 nM. In another embodiment, the recombinant protein binds FAP with a $K_D$ value of or below about 1 nM. In another embodiment, the recombinant protein binds FAP with a $K_D$ value of or below about 500 pM. In at least one embodiment, the recombinant protein binds FAP with a $K_D$ value of or below about 300 pM. In at least one embodiment, the recombinant protein has the amino acid sequence of SEQ ID NO: 5.

In some embodiments, the FAP is human FAP (SEQ ID NO: 52).

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

3.4. CD40 Binding Domains

The recombinant proteins disclosed herein also take advantage of the immune cell co-stimulatory activities induced by CD40.

The recombinant protein described herein comprises an ankyrin repeat domain that specifically binds CD40, also referred herein as "CD40 binding domain". Like CD40 agonist antibodies, the CD40 binding domain activates the CD40/CD40L signaling pathway. The recombinant protein described herein may also comprise more than one CD40 binding domain, for example, two or three or more CD40 binding domains. Thus, the recombinant protein described herein may comprise a first and a second CD40 binding domain, or a first, a second and a third CD40 binding domain. The embodiments provided below describe such a first CD40 binding domain, second CD40 binding domain, and/or third CD40 binding domain. In at least one embodiment, the recombinant protein described herein comprises two CD40 binding domain, i.e. a first CD40 binding domain and a second CD40 binding domain.

In some embodiments, the CD40 binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 3. In at least one embodiment, the CD40 binding domain or each of said CD40 binding domains independently comprises an amino acid sequence that is at least 90% identical to SEQ ID NO: 3. In at least one embodiment, the CD40 binding domain or each of said CD40 binding domains comprises the amino acid sequence of SEQ ID NO: 3. In some embodiments, the CD40 binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 10. In at least one embodiment, the CD40 binding domain or each of said CD40 binding domains independently comprises an amino acid sequence that is at least 90% identical to SEQ ID NO: 10. In another embodiment, the CD40 binding domain or each of said CD40 binding domains comprises the amino acid sequence of SEQ ID NO: 10. In some embodiments, the CD40 binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 43-50. In at least one embodiment, the CD40 binding domain or each of said CD40 binding domains independently comprises an amino acid sequence that is at least 90% identical to any one of SEQ ID NOs: 43-50. In another embodiment, the CD40 binding domain or each of said CD40 binding domains independently comprises the amino acid sequence of any one of SEQ ID NOs: 43-50.

In some embodiments, no more than 10, no more than 9, no more than 8, no more than 7, no more than 6, no more than 5, no more than 4, no more than 3, no more than 2, or no more than 1 substitution is made relative to the sequence of SEQ ID NO: 3. In some embodiments, no more than 5 substitutions are made relative to the sequence of SEQ ID NO: 3. In some embodiments, no more than 4 substitutions are made relative to the sequence of SEQ ID NO: 3. In some embodiments, no more than 3 substitutions are made relative to the sequence of SEQ ID NO: 3. In some embodiments, no more than 2 substitutions are made relative to the sequence of SEQ ID NO: 3. In some embodiments, no more than 1 substitution is made relative to the sequence of SEQ ID NO: 3. In some embodiments, the substitution(s) do not change the $K_D$ value by more than 1000-fold, more than 100-fold, or more than 10-fold, compared to the $K_D$ value of the protein comprising the sequence of SEQ ID NO: 3. In some embodiments, the substitution is a conservative substitution according to Table 1. In some embodiments, the substitution is made outside the structural core residues of the ankyrin repeat domain, e.g. in the beta loops that connect the alpha-helices. In some embodiments, the substitution is made within the structural core residues of the ankyrin repeat domain. For example, the ankyrin domain or each the ankyrin binding domains may comprise the consensus sequence: xDxxGxTPLHLAxxxGxxxIVxVLLxxGADVNA (SEQ ID NO: 23), wherein "x" denotes any amino acid; or xDxxGxTPLHLAxxxGHLEIVEVLLKzGADVNA (SEQ ID NO: 24), wherein "x" denotes any amino acid, and "z" is selected from the group consisting of asparagine, histidine, or tyrosine. In one embodiment, the substitution is made to residues designated as "x". In another embodiment, the substitution is made outside the residues designated as "x". In at least one embodiment, "x" is not cysteine, glycine, or proline.

In addition, the second last position can be "A" (see, e.g., SEQ ID NOs: 3, 10, 43, 44, and 48-50) or "L" (see, e.g., SEQ ID NOs: 45-47), and/or the last position can be "A" (see, e.g., SEQ ID NOs: SEQ ID NOs: 3, 10, 43, 44, and 48-50) or "N" (see, e.g., SEQ ID NOs: 45-47). Accordingly, in some embodiments, the CD40-binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 3, 10, 43, 44, and 48-50, and wherein optionally A at the second last position is substituted with L and/or A at the last position is substituted with N. In at least one embodiment, the CD40-binding domain or each of said CD40 binding domains independently comprises an amino acid sequence that is at least 90% identical to any one of SEQ ID NOs: 3, 10, 43, 44, and 48-50, and wherein optionally A at the second last position is substituted with L and/or A at the last position is substituted with N. In some embodiments, the CD40-binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 3, and wherein optionally A at the second last position is substituted with L and/or A at the last position is substituted with N. In at least one embodiment, the CD40-binding domain or each of said CD40 binding domains independently comprises an amino acid sequence that is at least 90% identical to SEQ ID NO: 3, and wherein optionally A at the second last position is substituted with L and/or A at the last position is substituted with N. In at least one embodiment, the CD40 binding domain or each of said CD40 binding domains described herein comprises the amino acid sequence of SEQ ID NO: 3, and wherein optionally A at the second last position is substituted with L and/or A at the last position is substituted with N. In some embodiments, the CD40-binding domain or each of said CD40 binding domains independently comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 10, 43, 44, and 48-50, and wherein optionally A at the second last position is substituted with L and/or A at the last position is substituted with N. In at least one embodiment, the CD40-binding domain or each of said CD40 binding domains independently comprises an amino acid sequence that is at least 90% identical to any one of SEQ ID NOs: 10, 43, 44, and 48-50, and wherein optionally A at the second last position is substituted with L and/or A at the last position is substituted with N. In another embodiment, the CD40-binding domain or each of said CD40 binding domains independently comprises the amino acid sequence of any one of SEQ ID NOs: 10, 43, 44, and 48-50, and wherein optionally A at the second last position is substituted with L and/or A at the last position is substituted with N. The sequences may optionally comprise at its N-terminus, a G, an S, or a GS (see below).

In addition, the CD40-binding domain or each of said CD40 binding domains may optionally further comprise a "G," an "S," or a "GS" sequence at its N-terminus (see, e.g., SEQ ID NO: 50 as compared with SEQ ID NO: 3). Accordingly, in some embodiments, the CD40-binding domain or each of said CD40 binding domains independently provided herein (i) comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 3, 10, and 43-49, and (ii) further comprises at its N-terminus, a G, an S, or a GS. In at least one embodiment, the CD40-binding domain or each of said CD40 binding domains independently comprises an amino acid sequence that is at least 90% identical to any one of SEQ ID NOs: 3, 10, and 43-49, and further comprises at its N-terminus, a G, an S, or a GS. In at least one embodiment, the CD40-binding domain or each of said CD40 binding domains independently comprises an amino acid sequence that is at least 95% identical to any one of SEQ ID NOs: 3, 10, and 43-49, and further comprises at its N-terminus, a G, an S, or a GS. In at least one embodiment, the CD40-binding domain or each of said CD40 binding domains independently comprises the amino acid sequence of any one of SEQ ID NOs: 3, 10, and 43-49, and further comprises at its N-terminus, a G, an S, or a GS. Also accordingly, in some embodiments, the CD40-binding domain or each of said CD40 binding domains provided herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 50, wherein G at position 1 and/or S at position 2 of SEQ ID NO: 50 are optionally missing.

Accordingly, in at least one embodiment, the CD40 binding domain or each of said CD40 binding domains described herein comprises the amino acid sequence of SEQ ID NO: 3, wherein its N-terminus optionally further comprises a G, an S, or a GS, and wherein optionally A at the second last position is substituted with L and/or A at the last position is substituted with N.

In some embodiments, any of one of the CD40 binding domain described herein comprises Q at position 8, L at position 15, Rat position 143, and/or Q at position 147, wherein the position numbers correspond to the positions in SEQ ID NO: 3. Accordingly, in some embodiments, the CD40 binding domain or each of said CD40 binding domains described herein comprises (1) Q at position 8 and (2) R at position 143 and/or Q at position 147, wherein the position numbers correspond to the positions in SEQ ID NO: 3. In some embodiments, the CD40 binding domain or each of said CD40 binding domains described herein comprises (1) L at position 15 and (2) R at position 143 and/or Q at position 147, wherein the position numbers correspond to the positions in SEQ ID NO: 3. In some embodiments, the CD40 binding domain or each of said CD40 binding domains described herein comprises (1) Q at position 8 and L at position 15 and (2) R at position 143 and/or Q at position 147, wherein the position numbers correspond to the positions in SEQ ID NO: 3. Also accordingly, in some embodiments, the CD40 binding domain or each of said CD40 binding domains described herein comprises (1) Q at position 8 and/or L at position 15 and (2) R at position 143, wherein the position numbers correspond to the positions in SEQ ID NO: 3. In some embodiments, the CD40 binding domain or each of said CD40 binding domains described herein comprises (1) Q at position 8 and/or L at position 15 and (2) Q at position 147, wherein the position numbers correspond to the positions in SEQ ID NO: 3. In some embodiments, the CD40 binding domain or each of said CD40 binding domains described herein comprises (1) Q at position 8 and/or L at position 15 and (2) R at position 143 and Q at position 147, wherein the position numbers correspond to the positions in SEQ ID NO: 3. In some embodiments, the CD40 binding domain or each of said CD40 binding domains described herein comprises Q at position 8, L at position 15, R at position 143, and Q at position 147, wherein the position numbers correspond to the positions in SEQ ID NO: 3.

Furthermore, in some embodiments, the CD40 binding domain or each of said CD40 binding domains described herein comprises Q at position 8, L at position 15, R at position 143, and Q at position 147, wherein the position numbers correspond to the positions in SEQ ID NO: 3, resulting in improved pharmacokinetic properties of said CD40 binding domain compared to a CD40 binding domain with an identical amino acid sequence except for the amino acids at positions 8, 15, 143 and 147, which are different than Q, L, R and Q, respectively, wherein the position numbers correspond to the positions in SEQ ID NO: 3.

In some embodiments, the affinity between the CD40 binding domain or each of said CD40 binding domains, or the recombinant protein comprising the CD40 binding domain(s), and its target (i.e., CD40) is described in terms of $K_D$. In some embodiments, the $K_D$ is about $10^{-1}$ M or less, about $10^{-2}$ M or less, about $10^{-3}$ M or less, about $10^{-4}$ M or less, about $10^{-5}$ M or less, about $10^{-6}$ M or less, about $10^{-7}$ M or less, about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less, from about $10^{-5}$ M to about $10^{-15}$ M, from about $10^{-6}$ M to about $10^{-15}$ M, from about $10^{-7}$ M to about $10^{-15}$ M, from about $10^{-8}$ M to about $10^{-15}$ M, from about $10^{-9}$ M to about $10^{-15}$ M, from about $10^{-10}$ M to about $10^{-15}$ M, from about $10^{-5}$ M to about $10^{-14}$ M, from about $10^{-6}$ M to about $10^{-14}$ M, from about $10^{-7}$ M to about $10^{-14}$ M, from about $10^{-8}$ M to about $10^{-14}$ M, from about $10^{-9}$ M to about $10^{-14}$ M, from about $10^{-10}$ M to about $10^{-14}$ M, from about $10^{-5}$ M to about $10^{-13}$ M, from about $10^{-6}$ M to about $10^{-13}$ M, from about $10^{-7}$ M to about $10^{-13}$ M, from about $10^{-8}$ M to about $10^{-13}$ M, from about $10^{-9}$ M to about $10^{-13}$ M, or from about $10^{-10}$ M to about $10^{-13}$ M.

In some embodiments, the CD40 binding domain or each of said CD40 binding domain independently binds CD40 with an $K_D$ value of, or below: about 100 nM, about 90 nM, about 80 nM, about 75 nM, about 60 nM, about 50 nM, about 40 nM, about 30 nM, about 20 nM, about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM. In some embodiments, the CD40 binding domain or each of said CD40 binding domains independently bind CD40 with a KD value of or below: 100 nM, 90 nM, 80 nM, or 75 nM. In at least one embodiment, the CD40 binding domain or each of said CD40 binding domain independently binds CD40 with a $K_D$ value of or below about 100 nM. In at least one embodiment, the CD40 binding domain or each of said CD40 binding domain independently binds CD40 with a $K_D$ value of or below about 75 nM. In at least one embodiment, the CD40 binding domain or each of said CD40 binding domain has the amino acid sequence of SEQ ID NO: 3.

In some embodiments, the recombinant protein comprising two CD40 binding domains binds CD40 with an $K_D$ value of, or below: about 100 nM, about 90 nM, about 80 nM, about 75 nM, about 60 nM, about 50 nM, about 40 nM, about 30 nM, about 20 nM, about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM. In some embodiments, the recombinant protein comprising two CD40 binding domains binds CD40 with a KD value of or below: 100 nM, 90 nM, 80 nM, 75 nM, 70 nM, 60 nM, 50 nM, 40 nM, 30 nM, 20 nM, 10 nM, 5 nM, 2 nM, 1 nM, 900 pM, 800 pM, 700 pM, 600 pM, 500 pM, 400 pM, 300 pM, 250 pM, 200 pM, 150 pM, 140 pM, 130 pM, 120 pM, 115 pM, 110 pM, 105 pM or 100 pM. In at least one embodiment, the recombinant protein binds CD40 with a $K_D$ value of or below about 100 nM. In another embodiment, the recombinant protein binds CD40 with a $K_D$ value of or below about 1 nM. In another embodiment, the recombinant protein binds CD40 with a $K_D$ value of or below about 500 pM. In at least one embodiment, the recombinant protein binds CD40 with a $K_D$ value of or below about 100 pM. In at least one embodiment, the recombinant protein has the amino acid sequence of SEQ ID NO: 5.

Figure 4:
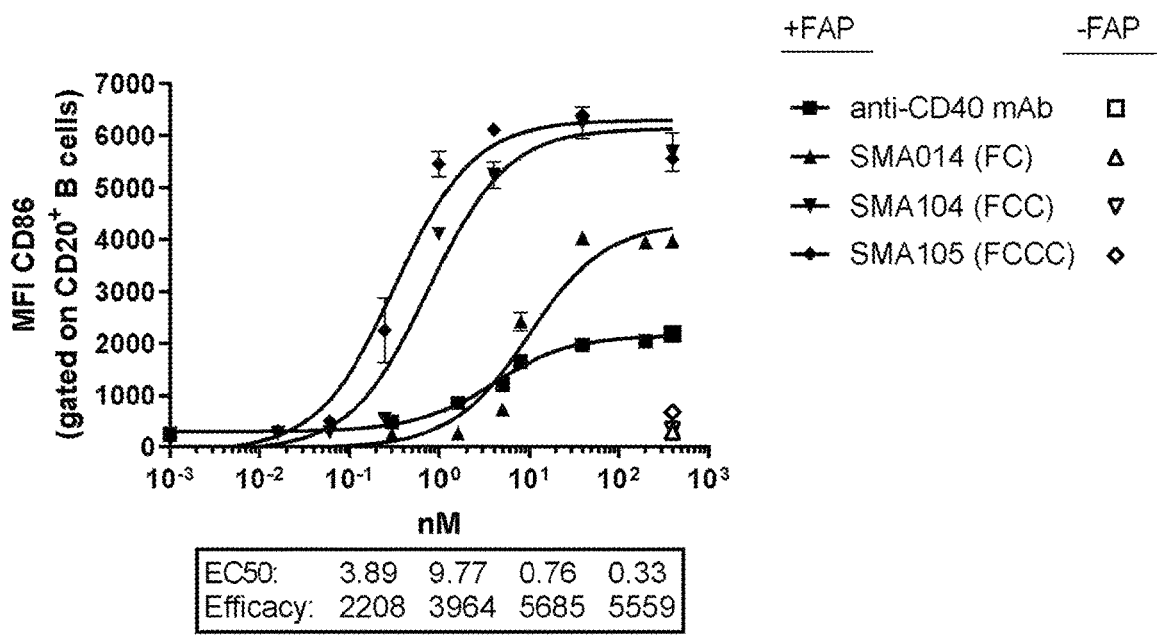
FIG. 4: CD40 bivalency strongly increases potency and efficacy of a bispecific FAPxCD40 ankyrin repeat binding protein. Human B cells were cultured in presence of FAP expressing CHO cells and treated with increasing concentrations of SMA014 (triangle pointing up), SMA104 (triangle pointing down), SMA105 (diamond) and agonist anti-CD40 mAb (square). As control, B cells were co-cultured in presence of FAP-negative CHO cells and treated only with the highest concentration of the respective constructs, depicted as empty symbols. Activation of human B cells was assessed in terms of upregulation of CD86 (measured as mean fluorescence intensity (MFI) and percentage of cells (%)) in absence of HSA. Each value depicts the average of duplicated measurements. The shown data are representative of two independent experiments. Error bars show±SEM. EC50 and efficacy values (in nM) for all constructs in presence of FAP-expressing CHO cells are shown in the depicted tables in the graphs.
Figure 4:
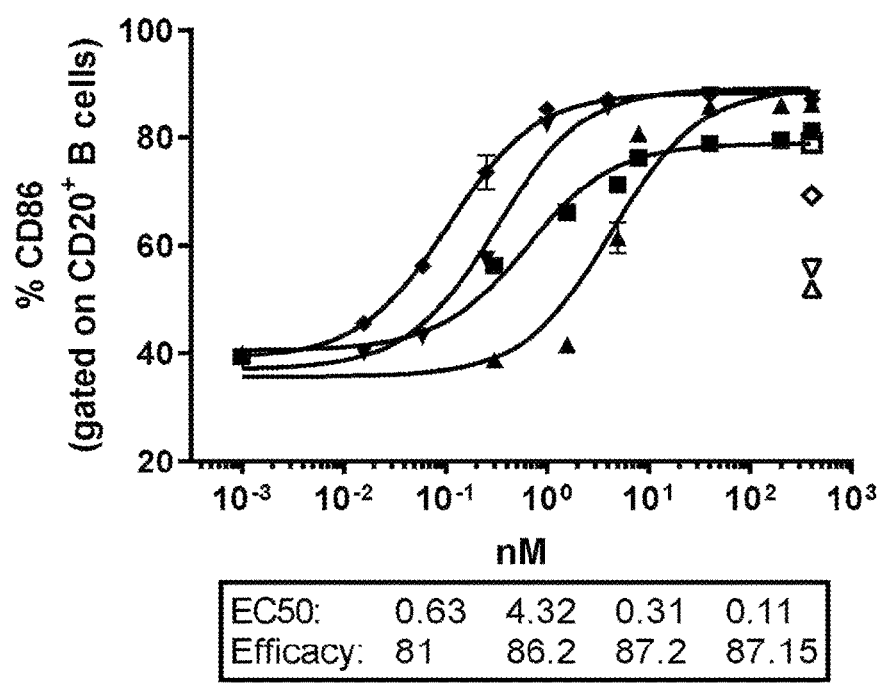

In some embodiments, two or more CD40 binding domains are preferred, to further promote CD40 clustering and immune cell co-stimulation. It has been reported that CD40 ligand binds to CD40 on immune cells as a trimer. However, trimerization alone is not sufficient to activate the CD40 signaling pathway. Higher order of clustering of CD40 is required for its activation. As described herein, through FAP-binding, the multispecific molecule already promotes CD40 clustering in the tumor environment. To further promote CD40 clustering, two or more CD40 binding domains can be used, to create a "cross-linking" effect on the cell surface. For example, as shown in FIG. 4, monovalent CD40 binder (FC) was sufficient to activate the CD40 pathway. Higher potency can be achieved by using two CD40 binding domains (FCC), or three CD40 binding domains (FCCC). FIG. 4 also shows that two CD40 binding domains are sufficient to activate the CD40 pathway with high potency, and it is not necessary to have three CD40 binding domains for efficient CD40 clustering.

In some embodiments, the CD40 is human CD40 (SEQ ID NO: 51).

3.5. Half-Life Extending Moieties

The "half-life extending moiety" extends the serum half-life in vivo of the recombinant proteins described herein, compared to the same protein without the half-life extending moiety. Examples of half-life extending moieties include, but are not limited to, polyhistidine, Glu-Glu, glutathione S transferase (GST), thioredoxin, protein A, protein G, an immunoglobulin domain, maltose binding protein (MBP), human serum albumin (HSA) binding domain, or polyethylene glycol (PEG).

In some embodiments, the recombinant multispecific protein described herein comprises an ankyrin repeat domain that specifically binds serum albumin, also referred herein as "serum albumin binding domain". The recombinant protein described herein may also comprise more than one serum albumin binding domain, for example, two or three or more serum albumin binding domains. Thus, the recombinant protein described herein may comprise a first and a second serum albumin binding domain, or a first, a second and a third serum albumin binding domain. The embodiments provided below describe such a first serum albumin binding domain, second serum albumin binding domain, and/or third serum albumin binding domain. In at least one embodiment, the recombinant protein described herein comprises only one serum albumin binding domain.

In some embodiments, the serum albumin binding domain described herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 1. In at least one embodiment, the serum albumin binding domain described herein comprises an amino acid sequence that is at least 90% identical to SEQ ID NO: 1. In at least one embodiment, the serum albumin binding domain described herein comprises the amino acid sequence of SEQ ID NO: 1. In some embodiments, the serum albumin binding domain described herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 39-42. In at least one embodiment, the serum albumin binding domain described herein comprises an amino acid sequence that is at least 90% identical to any one of SEQ ID NOs: 39-42. In another embodiment, the serum albumin binding domain described herein comprises the amino acid sequence of any one of SEQ ID NOs: 39-42.

In some embodiments, no more than 10, no more than 9, no more than 8, no more than 7, no more than 6, no more than 5, no more than 4, no more than 3, no more than 2, or no more than 1 substitution is made relative to the sequence of SEQ ID NO: 1. In some embodiments, no more than 5 substitutions are made relative to the sequence of SEQ ID NO: 1. In some embodiments, no more than 4 substitutions are made relative to the sequence of SEQ ID NO: 1. In some embodiments, no more than 3 substitutions are made relative to the sequence of SEQ ID NO: 1. In some embodiments, no more than 2 substitutions are made relative to the sequence of SEQ ID NO: 1. In some embodiments, no more than 1 substitution is made relative to the sequence of SEQ ID NO: 1. In some embodiments, the substitution(s) do not change the $K_D$ value by more than 1000-fold, more than 100-fold, or more than 10-fold, compared to the $K_D$ value of the protein comprising the sequence of SEQ ID NO: 1. In some embodiments, the substitution is a conservative substitution according to Table 1. In some embodiments, the substitution is made outside the structural core residues of the ankyrin repeat domain, e.g. in the beta loops that connect the alpha-helices. In some embodiments, the substitution is made within the structural core residues of the ankyrin repeat domain. For example, the ankyrin domain may comprise the consensus sequence: xDxxGxTPLHLAxxxGxxxlVxVLLxxGADVNA (SEQ ID NO: 23), wherein "x" denotes any amino acid; or xDxxGxTPLHLAxxxGHLEIVEVLLKzGADVNA (SEQ ID NO: 24), wherein "x" denotes any amino acid, and "z" is selected from the group consisting of asparagine, histidine, or tyrosine. In one embodiment, the substitution is made to residues designated as "x". In another embodiment, the substitution is made outside the residues designated as "x". In at least one embodiment, "x" is not cysteine, glycine, or proline.

In addition, the second last position can be "A" (see, e.g., SEQ ID NOs: 1, 39, 40 and 42) or "L" (see, e.g., SEQ ID NO: 41), and/or the last position can be "A" (see, e.g., SEQ ID NOs: 1, 39, 40 and 42) or "N" (see, e.g., SEQ ID NO: 1). Accordingly, in some embodiments, the serum albumin binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, 01100% identical to any one of SEQ ID NOs: 1, 39, 40 and 42, and wherein optionally A at the second last position is substituted with L and/or A at the last position is substituted with N. In at least one embodiment, the serum albumin binding domain comprises an amino acid sequence that is at least 90% identical to any one of SEQ ID NOs: 1, 39, 40 and 42, and wherein optionally A at the second last position is substituted with L and/or A at the last position is substituted with N. In some embodiments, the serum albumin binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 1, and wherein optionally A at the second last position is substituted with L and/or A at the last position is substituted with N. In at least one embodiment, the serum albumin binding domain comprises an amino acid sequence that is at least 90% identical to SEQ ID NO: 1, and wherein optionally A at the second last position is substituted with L and/or A at the last position is substituted with N. In at least one embodiment, the serum albumin binding domain described herein comprises the amino acid sequence of SEQ ID NO: 1, and wherein optionally A at the second last position is substituted with L and/or A at the last position is substituted with N. In some embodiments, the serum albumin binding domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 39, 40 and 42, and wherein optionally A at the second last position is substituted with L and/or A at the last position is substituted with N. In at least one embodiment, the serum albumin binding domain comprises an amino acid sequence that is at least 90% identical to any one of SEQ ID NOs: 39, 40 and 42, and wherein optionally A at the second last position is substituted with L and/or A at the last position is substituted with N. In another embodiment, the serum albumin binding domain comprises the amino acid sequence of any one of SEQ ID NOs: 39, 40 and 42, and wherein optionally A at the second last position is substituted with L and/or A at the last position is substituted with N. The sequences may optionally comprise at its N-terminus, a G, an S, or a GS (see below).

In addition, the serum albumin binding domain may optionally further comprise a "G," an "S," or a "GS" sequence at its N-terminus (see, e.g., SEQ ID NO: 1 as compared with SEQ ID NO: 42). Accordingly, in some embodiments, the serum albumin binding domain provided herein (i) comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 42, and (ii) further comprises at its N-terminus, a G, an S, or a GS. In at least one embodiment, the serum albumin binding domain comprises an amino acid sequence that is at least 90% identical to SEQ ID NO: 42, and further comprises at its N-terminus, a G, an S, or a GS. In at least one embodiment, the serum albumin binding domain comprises an amino acid sequence that is at least 95% identical to SEQ ID NO: 42, and further comprises at its N-terminus, a G, an S, or a GS. In at least one embodiment, the serum albumin binding domain comprises the amino acid sequence of SEQ ID NO: 42, and further comprises at its N-terminus, a G, an S, or a GS. Also accordingly, in some embodiments, the serum albumin binding domain provided herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 1, and 39-41, wherein G at position 1 and/or S at position 2 of any one of SEQ ID NOs: 1, and 39-41 are optionally missing. In at least one embodiment, the serum albumin binding domain comprises an amino acid sequence that is at least 90% identical to any one of SEQ ID NOs: 1, and 39-41, wherein G at position 1 and/or S at position 2 of any one of SEQ ID NOs: 1, and 39-41 are optionally missing.

Accordingly, in at least one embodiment, the serum albumin binding domain described herein comprises the amino acid sequence of SEQ ID NO: 1, wherein G at position 1 and/or S at position 2 are optionally missing, and wherein optionally A at the second last position is substituted with L and/or A at the last position is substituted with N.

In some embodiments, the affinity between the serum albumin binding domain or the recombinant protein comprising the serum albumin binding domain and its target (i.e., serum albumin) is described in terms of $K_D$. In at least one embodiments, the $K_D$ is about $10^1$ M or less, about $10^{-2}$ M or less, about $10^{-3}$ M or less, about $10^{-4}$ M or less, about $10^{-5}$ M or less, about $10^{-8}$ M or less, about $10^{-7}$ M or less, about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less, from about $10^{-5}$ M to about $10^{-15}$ M, from about $10^{-8}$ M to about $10^{-15}$ M, from about $10^{-7}$ M to about $10^{-15}$ M, from about $10^{-8}$ M to about $10^{-15}$ M, from about $10^{-9}$ M to about $10^{-15}$ M, from about $10^{-10}$ M to about $10^{-15}$ M, from about $10^{-5}$ M to about $10^{-7}$ M, from about $10^{-8}$ M to about $10^{-14}$ M, from about $10^{-7}$ M to about $10^{-14}$ M, from about $10^{-8}$ M to about $10^{-14}$ M, from about $10^{-9}$ M to about $10^{-14}$ M, from about $10^{-10}$ M to about $10^{-14}$ M, from about $10^{-5}$ M to about $10^{-13}$ M, from about $10^{-8}$ M to about $10^{-13}$ M, from about $10^{-7}$ M to about $10^{-13}$ M, from about $10^{-8}$ M to about $10^{-13}$ M, from about $10^{-9}$ M to about $10^{-13}$ M, or from about $10^{-10}$ M to about $10^{-13}$ M.

In some embodiments, the serum albumin binding domain binds serum albumin with an $K_D$ value of, or below: about 100 nM, about 90 nM, about 80 nM, about 75 nM, about 60 nM, about 50 nM, about 40 nM, about 30 nM, about 20 nM, about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM. In some embodiments, the serum albumin binding domain binds serum albumin with a KD value of or below: 100 nM, 90 nM, 80 nM, 75 nM, 70 nM, 60 nM, 50 nM, 40 nM, or 35 nM. In at least one embodiment, the serum albumin binding domain binds serum albumin with a $K_D$ value of or below about 100 nM. In another embodiment, the serum albumin binding domain binds serum with a $K_D$ value of or below about 50 nM. In at least one embodiment, the serum albumin binding domain binds serum albumin with a $K_D$ value of or below about 35 pM. In at least one embodiment, the serum albumin binding domain has the amino acid sequence of SEQ ID NO: 1.

In some embodiments, the recombinant protein comprising the serum albumin domain binds serum albumin with an $K_D$ value of, or below: about 100 nM, about 90 nM, about 80 nM, about 75 nM, about 60 nM, about 50 nM, about 40 nM, about 30 nM, about 20 nM, about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM. In some embodiments, the recombinant protein comprising the serum albumin domain binds serum albumin with a KD value of or below: 100 nM, 90 nM, 80 nM, 75 nM, 70 nM, 60 nM, or 50 nM. In at least one embodiment, the recombinant protein binds serum albumin with a $K_D$ value of or below about 100 nM. In another embodiment, the recombinant protein binds serum albumin with a $K_D$ value of or below about 75 nM. In at least one embodiment, the recombinant protein binds serum albumin with a $K_D$ value of or below about 50 nM. In at least one embodiment, the recombinant protein has the amino acid sequence of SEQ ID NO: 5.

In some embodiments, the serum albumin is human serum albumin (SEQ ID NO: 53).

In some embodiments, the half-life extending moiety comprises an immunoglobulin domain. In some embodiments, the immunoglobulin domain comprises an Fc domain. In some embodiments, the Fc domain is derived from any one of the known heavy chain isotypes: IgG (γ), IgM (μ), IgD (δ), IgE (ε), or IgA (α). In some embodiments, the Fc domain is derived from any one of the known heavy chain isotypes or subtypes: IgG$_1$ (γ1), IgG$_2$ (γ2), IgG$_3$ (γ3), IgG$_4$ (γ4), IgA$_1$ (α1), IgA$_2$ (α2). In some embodiments, the Fc domain is the Fc domain of human IgG$_1$.

In some embodiments, the Fc domain comprises an uninterrupted native sequence (i.e., wild type sequence) of an Fc domain. In some embodiments, the immunoglobulin Fc domain comprises a variant Fc domain resulting in altered biological activity. For example, at least one point mutation or deletion may be introduced into the Fc domain so as to reduce or eliminate the effector activity (e.g., International Patent Publication No. WO 2005/063815), and/or to increase the homogeneity during the production of the recombinant protein. In some embodiments, the Fc domain is the Fc domain of human IgG$_1$ and comprises one or more of the following effector-null substitutions: L234A, L235A, and G237A (Eu numbering). In some embodiments, the Fc domain does not comprise the lysine located at the C-terminal position of human IgG1 (i.e., K447 by Eu numbering). The absence of the lysine may increase homogeneity during the production of the recombinant protein. In some embodiments, the Fc domain comprises the lysine located at the C-terminal position (K447, Eu numbering).

3.6. Linkers

The recombinant proteins described herein may comprise a linker. A "linker" is a molecule or group of molecules that binds two separate entities (e.g., FAP-binding domain and CD40 binding domain) to one another and can provide spacing and flexibility between the two entities such that they are able to achieve a conformation in which they, e.g., specifically bind their respective targets (e.g., FAP and CD40). Protein linkers are particularly preferred, and they may be expressed as a component of the recombinant protein using standard recombinant DNA techniques well-known in the art.

The ankyrin repeat domains can be linked either covalently, for example, by a disulfide bond, a polypeptide bond or a crosslinking agent; or non-covalently, to produce a heterodimeric protein. The recombinant protein can comprise a linker between any of the binding domains, including FAP, and CD40 binding domainss, and between any binding domain and the optional half-life extending moiety (which itself also can be a binding domain).

In some embodiments, the linker is a peptidyl linker. In some embodiments, the peptidyl linker comprises about 1 to 30 amino acid residues. Exemplary linkers includes, e.g., a glycine rich peptide; a peptide comprising glycine and serine; a peptide having a sequence [Gly-Gly-Ser]$_n$, wherein n is 1, 2, 3, 4, 5, or 6; or a peptide having a sequence [Gly-Gly-Gly-Gly-Ser]$_n$ (SEQ ID NO: 56), wherein n is 1, 2, 3, 4, 5, or 6. A glycine rich peptide linker comprises a peptide linker, wherein at least 25% of the residues are glycine. Glycine rich peptide linkers are well known in the art (e.g., Chichili et al. Protein Sci. 2013 February; 22(2): 153-167).

In some embodiments, the peptidyl linker is a proline-threonine rich peptide linker. In at least one embodiment, the linker is the proline-threonine rich peptide linker of SEQ ID NO: 4.

In some embodiments, the linker comprises the amino acid sequence of SEQ ID NO: 4.

3.7. FAP/CD40 Dual Targeting Bispecific or Multispecific Molecules

The multispecific molecules of the disclosure comprise any kind of combinations of the binding domains and optionally linkers described herein. That is, any one of the domains and linkers described in sections 3.3 to 3.6 above can be combined in the multispecific molecules of the disclosure. Furthermore, the binding domains of the multispecific molecules of the disclosure may comprise any of the N-terminal capping modules and/or C-terminal capping modules described in section 3.2 above.

In some embodiments, the recombinant protein of the disclosure comprises, from the N-terminus to the C-terminus: (i)) a first ankyrin repeat domain that specifically binds serum albumin, (ii) a second ankyrin repeat domain that specifically binds FAP, (iii) a third ankyrin repeat domain that specifically binds CD40, and (iv) a fourth ankyrin repeat domain that specifically binds CD40. Said first ankyrin repeat domain may be any one of the serum albumin binding domains as described in section 3.5 above, said second ankyrin repeat domain may be any one of the FAP binding domains as described in section 3.3 above, and said third and fourth ankyrin repeats domains may be any one of the CD40 binding domains as described in section 3.4 above. The third and fourth ankyrin repeat domains may have identical sequences, or may have different sequences.

In some embodiments, the multispecific recombinant protein of the disclosure comprises, from the N-terminus to the C-terminus: (serum albumin binding domain)—(linker)—(FAP binding domain)—(linker)—(CD40 binding domain)—(linker)—(CD40 binding domain). In some embodiments, the linker comprises the amino sequence of SEQ ID NO: 4.

In some embodiments, the recombinant protein of the disclosure comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 5. In at least one embodiment, the recombinant protein of the disclosure comprises an amino acid sequence that is at least 90% identical to SEQ ID NO: 5. In at least one embodiment, the recombinant protein of the disclosure comprises the amino acid sequence of SEQ ID NO: 5.

In some embodiments, no more than 10, no more than 9, no more than 8, no more than 7, no more than 6, no more than 5, no more than 4, no more than 3, no more than 2, or no more than 1 substitution is made relative to any one of the four binding domains of SEQ ID NO: 5. In some embodiments, no more than 10 substitutions are made relative any one of the four binding domains of SEQ ID NO: 5. In some embodiments, no more than 5 substitutions are made relative to any one of the four binding domains of SEQ ID NO: 5. In some embodiments, no more than 4 substitutions are made relative to any one of the four binding domains of SEQ ID NO: 5. In some embodiments, no more than 3 substitutions are made relative any one of the four binding domains of SEQ ID NO: 5. In some embodiments, no more than 2 substitutions are made relative to any one of the four binding domains of SEQ ID NO: 5. In some embodiments, no more than 1 substitution is made relative to any one of the four binding domains of SEQ ID NO: 5. In some embodiments, the substitution(s) do not change the $K_D$ value for FAP-binding or CD40 binding or serum albumin-binding by more than 1000-fold, more than 100-fold, or more than 10-fold, compared to the $K_D$ value of the protein comprising the sequence of SEQ ID NO: 5. In some embodiments, the substitution is a conservative substitution according to Table 1.

In some embodiments, the recombinant protein of the disclosure comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 6.

In some embodiments, the multispecific recombinant protein of the disclosure binds human CD40 in PBS with a dissociation constant ($K_D$) below $10^{-8}$M, below $10^{-9}$M, below $5 \times 10^{-10}$M, below $3 \times 10^{-10}$M, or below $2 \times 10^{-10}$M. In at least one embodiment, the recombinant protein of the disclosure binds human CD40 in PBS with a dissociation constant ($K_D$) below $10^{-9}$M.

In some embodiments, the multispecific recombinant protein of the disclosure binds human FAP in PBS with a dissociation constant ($K_D$) below $10^{-8}$M, below $10^{-9}$M, below $5 \times 10^{-10}$M, or below $3 \times 10^{-10}$M. In at least one embodiment, the recombinant protein of the disclosure binds human FAP in PBS with a dissociation constant ($K_D$) below $10^{-9}$M.

In some embodiments, the multispecific recombinant protein of the disclosure binds human serum albumin in PBS with a dissociation constant ($K_D$) below $10^{-7}$M, below $7 \times 10^{-8}$M, or below $5 \times 10^{-8}$M. In at least one embodiment, the recombinant protein of the disclosure binds human serum albumin in PBS with a dissociation constant ($K_D$) below $10^{-7}$M.

In some embodiments, the multispecific recombinant protein of the disclosure binds human CD40 in PBS with a dissociation constant ($K_D$) below $10^{-8}$M, below $10^{-9}$M, below $5 \times 10^{-10}$M, below $3 \times 10^{10}$M, or below $2 \times 10^{-10}$M, and/or the recombinant protein binds human FAP in PBS with a dissociation constant ($K_D$) below $10^{-8}$M, below $10^{-9}$M, below $5 \times 10^{-10}$M, or below $3 \times 10^{-10}$M. In at least one embodiment, the recombinant protein of the disclosure binds human CD40 in PBS with a dissociation constant ($K_D$) below $10^{-9}$M and the recombinant protein binds human FAP in PBS with a dissociation constant ($K_D$) below $10^{-9}$M.

In some embodiments, the recombinant protein of the disclosure binds human CD40 in PBS with a dissociation constant ($K_D$) below $10^{-8}$M, below $10^{-9}$M, below $5 \times 10^{-10}$M, below $3 \times 10^{-10}$M, or below $2 \times 10^{-10}$M, and/or the recombinant protein binds human FAP in PBS with a dissociation constant ($K_D$) below $10^{-8}$M, below $10^{-9}$M, below $5 \times 10^{-10}$M, or below $3 \times 10^{-10}$M, and/or the recombinant protein binds human serum albumin in PBS with a dissociation constant ($K_D$) below $10^{-7}$M, below $7 \times 10^{-8}$M, or below $5 \times 10^{-8}$M. In at least one embodiment, the recombinant protein of the disclosure binds human CD40 in PBS with a dissociation constant ($K_D$) below $10^{-9}$M and the recombinant protein binds human FAP in PBS with a dissociation constant ($K_D$) below $10^{-9}$M. In at least one embodiment, the recombinant protein of the disclosure binds human CD40 in PBS with a dissociation constant ($K_D$) below $10^{-9}$M and the recombinant protein binds human FAP in PBS with a dissociation constant ($K_D$) below $10^{-9}$M and the recombinant protein binds human serum albumin in PBS with a dissociation constant ($K_D$) below $10^{-7}$M.

In some embodiments, the recombinant binding protein of the disclosure is capable of binding FAP, CD40 and serum albumin simultaneously. In some embodiments, said simultaneous binding is measured by surface plasmon resonance (SPR), further as described in Example 3.

In some embodiments, the multispecific recombinant protein of the disclosure induces activation of B cells upon binding to FAP and CD40. In some embodiments, the B cells are human B cells. In some embodiments, the biological activity of the multispecific recombinant protein is assessed by an in vitro B cell activation assay that measures the expression of co-stimulatory molecules, such as CD86 and CD69. It has been reported that increased expression of these co-stimulatory molecules (CD86 and CD69) in B cells is indicative of CD40 activation.

In some embodiments, the multispecific recombinant protein of the disclosure activates human CD40 in CD40-expressing B cells in the presence of FAP-expressing CHO cells with an EC50 value of about $10^{-8}$M or less, or about $10^{-9}$M or less.

In some embodiments, the multispecific recombinant protein has a half maximal effective concentration ($EC_{50}$) of no more than about 100 nM, no more than about 75 nM, no more than about 65 nM, no more than about 55 nM, no more than about 45 nM, no more than about 35 nM, no more than about 25 nM, no more than about 15 nM, no more than about 10 nM, no more than about 5 nM, no more than about 4 nM, no more than about 3 nM, no more than about 2 nM, no more than about 1 nM, nor more than about 0.1 nM, from about 0.01 nM to about 50 nM, from about 0.01 nM to about 25 nM, from about 0.01 nM to about 10 nM, from about 0.01 nM to about 5 nM, from about 0.01 nM to about 1 nM, from about 0.01 nM to about 0.1 nM, from about 0.01 nM to about 0.07 nM, from about 0.04 nM to about 50 nM, from about 0.04 nM to about 25 nM, from about 0.04 nM to about 10 nM, from about 0.04 nM to about 5 nM, from about 0.04 nM to about 1 nM, from about 0.04 nM to about 0.1 nM, from about 0.04 nM to about 0.07 nM, from about 0.1 nM to about 50 nM, from about 0.1 nM to about 25 nM, from about 0.1 nM to about 10 nM, from about 0.1 nM to about 5 nM, from about 0.1 nM to about 1 nM, from about 0.1 nM to about 0.9 nM, from about 0.1 nM to about 0.85 nM, from about 0.18 nM to about 0.85 nM, as assessed by an in vitro B cell activation assay.

In at least one embodiment, the multispecific recombinant protein has an EC50 of no more than about 10 nM, as assessed by an in vitro B cell activation assay. In another embodiment, the multispecific recombinant protein has an EC50 of no more than about 1 nM, as assessed by an in vitro B cell activation assay. In another embodiment, the multispecific recombinant protein has an EC50 of from about 0.01 nM to about 10 nM. In at least one embodiment, the multispecific recombinant protein has an EC50 of from about 0.1 nM to about 1.0 nM or from about 0.18 nM to about 0.85 nM, as assessed by an in vitro B cell activation assay. In another embodiment, the multispecific recombinant protein has an EC50 of from about 0.01 nM to about 0.1 nM, or from about 0.04 nM to about 0.07 nM, as assessed by an in vitro B cell activation assay.

In some embodiments, the B cell activation assay is a human B cell activation assay. In at least one embodiment, $EC_{50}$ is measured using GraphPad Prism (version 8.1.2), according to the manufacturer's instructions. In at least one embodiment, $EC_{50}$ value is determined by fitting the data with the four-parameter logistical fit model using Graphpad Prism software. In at least one embodiment, $EC_{50}$ value is determined using the method described in the Examples.

In some embodiments, the multispecific recombinant protein has a terminal half-life in a mouse model of at least 10 hours, at least 20 hours, at least 30 hours, at least 40 hours, or about 44 hours. In some embodiments, the multispecific recombinant protein has a terminal half-life in a cynomolgus monkey model of at least 1 day, at least 2 days, at least 3 days, at least 4 days, or about 2.8 days, or about 4.5 days.

In some embodiments, the multispecific recombinant protein of the disclosure is capable of inhibiting tumor growth in a FAP-expressing MC38 colon carcinoma mouse model. In one embodiment, the recombinant protein of the disclosure is capable of inhibiting tumor growth in a FAP-expressing MC38 colon carcinoma mouse model with treatment conditions as described in Example 6.

In some embodiments, the multispecific recombinant protein does not inhibit FAP protease activity. In some embodiments, in the presence of the multispecific recombinant protein, FAP protease activity is reduced by no more than 25%, by no more than 20%, by no more than 15%, by no more than 10%, no more than 9%, no more than 8%, no more than 7%, no more than 6%, no more than 5%, no more than 4%, no more than 3%, or no more than 2%, as compared to a control (the control can be the FAP protease activity in the absence of the multispecific recombinant protein). In at least one embodiment, the FAP activity is measured using the method as exemplified in Example 7.

In some embodiments, the multispecific recombinant protein of the disclosure comprises two CD40 binding domains, wherein one of said CD40 binding domains or each of said CD40 binding domains independently comprises Q at position 8, L at position 15, R at position 143, and/or Q at position 147, wherein the position numbers correspond to the positions in SEQ ID NO: 3. In at least one embodiment, the multispecific recombinant protein of the disclosure comprises two CD40 binding domains, wherein each of said two CD40 binding domains comprises Q at position 8, L at position 15, R at position 143, and Q at position 147, wherein the position numbers correspond to the positions in SEQ ID NO: 3.

In one embodiment, the multispecific recombinant protein of the disclosure comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 5 and further has any one or any combination of the following properties: (i) the recombinant protein binds human CD40 in PBS with a dissociation constant ($K_D$) below $10^{-8}$M, below $10^{-9}$M, below $5\times10^{-10}$M, below $3\times10^{-10}$M, or below $2\times10^{-10}$M; (ii) the recombinant protein binds human FAP in PBS with a dissociation constant ($K_D$) below $10^{-8}$M, below $10^{-9}$M, below $5\times10^{-10}$M, or below $3\times10^{-10}$M; (iii) the recombinant protein binds human serum albumin in PBS with a dissociation constant ($K_D$) below $10^{-7}$M, below $7\times10^{-8}$M, or below $5\times10^{-8}$M; (iv) the recombinant protein activates human CD40 in CD40-expressing B cells in the presence of FAP-expressing CHO cells with an EC50 value of about $10^{-8}$M or less, or about $10^{-9}$M or less; (v) the recombinant binding protein is capable of binding FAP, CD40 and serum albumin simultaneously; (vi) the recombinant protein does not inhibit FAP protease activity, or the reduction in FAP protease activity in the presence of the recombinant protein is no more than 25%, no more than 20%, no more than 15%, or no more than 10%; (vii) the recombinant protein has a terminal half-life in a mouse model of at least 10 hours, at least 20 hours, at least 30 hours, at least 40 hours, or about 44 hours; (viii) the recombinant protein has a terminal half-life in a cynomolgus monkey model of at least 1 day, at least 2 days, at least 3 days, at least 4 days, or about 2.8 days, or about 4.5 days; (ix) the recombinant protein is capable of inhibiting tumor growth in a FAP-expressing MC38 colon carcinoma mouse model; and (x) one of the two CD40 binding domains or each of said two CD40 binding domains independently comprises Q at position 8, L at position 15, R at position 143, and/or Q at position 147, wherein the position numbers correspond to the positions in SEQ ID NO: 3, or each of said two CD40 binding domains comprises Q at position 8, L at position 15, R at position 143, and Q at position 147, wherein the position numbers correspond to the positions in SEQ ID NO: 3.

In some embodiments, the multispecific recombinant protein of the disclosure comprises an amino acid sequence that is at least 90% identical to SEQ ID NO: 5, wherein said recombinant protein binds human CD40 in PBS with a dissociation constant ($K_D$) below $10^{-9}$M, and/or binds human FAP in PBS with a dissociation constant ($K_D$) below $10^{-9}$M.

In some embodiments, the multispecific recombinant protein of the disclosure comprises an amino acid sequence that is at least 90% identical to SEQ ID NO: 5, wherein said recombinant protein binds human CD40 in PBS with a dissociation constant ($K_D$) below $10^{-9}$M, binds human FAP in PBS with a dissociation constant ($K_D$) below $10^{-9}$M, and binds human serum albumin in PBS with a dissociation constant ($K_D$) below $10^{-7}$M.

In some embodiments, the multispecific recombinant protein of the disclosure comprises an amino acid sequence that is at least 90% identical to SEQ ID NO: 5 and activates human CD40 in CD40-expressing B cells in the presence of FAP-expressing CHO cells with an EC50 value of about $10^{-8}$M or less, or about $10^{-9}$M or less.

In some embodiments, the multispecific recombinant protein of the disclosure comprises an amino acid sequence that is at least 90% identical to SEQ ID NO: 5 and is capable of binding simultaneously to human CD40, human FAP and human serum albumin. In some embodiments, the simultaneous binding is measured by surface plasmon resonance (SPR), as described in Example 3.

In some embodiments, the multispecific recombinant protein of the disclosure comprises an amino acid sequence that is at least 90% identical to SEQ ID NO: 5, wherein said recombinant protein does not inhibit FAP protease activity, or the reduction in FAP protease activity in the presence of the recombinant protein is no more than 25%, no more than 20%, no more than 15%, or no more than 10%.

In some embodiments, the multispecific recombinant protein of the disclosure comprises an amino acid sequence that is at least 90% identical to SEQ ID NO: 5 and has a terminal half-life in a mouse model of at least 10 hours, at least 20 hours, at least 30 hours, at least 40 hours, or about 44 hours.

In some embodiments, the multispecific recombinant protein of the disclosure comprises an amino acid sequence that is at least 90% identical to SEQ ID NO: 5 and has a terminal half-life in a cynomolgus monkey model of at least 1 day, at least 2 days, at least 3 days, at least 4 days, or about 2.8 days, or about 4.5 days.

In some embodiments, the multispecific recombinant protein of the disclosure comprises an amino acid sequence that is at least 90% identical to SEQ ID NO: 5, wherein said recombinant protein is capable of inhibiting tumor growth in a FAP-expressing MC38 colon carcinoma mouse model. In some embodiments, the tumor inhibition is measured as described in Example 6.

In some embodiments, the multispecific recombinant protein of the disclosure comprises an amino acid sequence that is at least 90% identical to SEQ ID NO: 5, wherein one of the two CD40 binding domains or each of said two CD40 binding domains independently comprises Q at position 8, L at position 15, R at position 143, and/or Q at position 147, wherein the position numbers correspond to the positions in SEQ ID NO: 3. In some embodiments, the multispecific recombinant protein of the disclosure comprises an amino acid sequence that is at least 90% identical to SEQ ID NO: 5, wherein each of said two CD40 binding domains comprises Q at position 8, L at position 15, R at position 143, and Q at position 147, wherein the position numbers correspond to the positions in SEQ ID NO: 3.

In at least one embodiment, the recombinant protein of the disclosure comprises an amino acid sequence that is at least 90% identical to SEQ ID NO: 5, wherein said recombinant protein binds human FAP, human CD40, and human serum albumin with a $K_D$ value of or below 100 nM, and wherein said recombinant protein has a terminal half-life in a cynomolgus monkey model of at least 1 day, at least 2 days, at least 3 days, at least 4 days, or about 2.8 days, or about 4.5 days.

In at least one embodiment, the recombinant protein of the disclosure comprises an amino acid sequence that is at least 90% identical to SEQ ID NO: 5, wherein said recombinant protein binds human FAP, human CD40, and human serum albumin with a $K_D$ value of or below 100 nM, and wherein in the presence of said recombinant protein, FAP protease activity is reduced by no more than 25%, no more than 20%, no more than 15%, no more than 10%, no more than 9%, no more than 8%, no more than 7%, no more than 6%, no more than 5%, no more than 4%, no more than 3%, or no more than 2%, as compared to a control. In some embodiments, the control is the FAP protease activity in the absence of said recombinant protein. In some embodiments, the FAP protease activity is measured as described in Example 7.

In one embodiment, the recombinant protein of the disclosure comprises an amino acid sequence that is at least 90% identical to SEQ ID NO: 5, wherein said recombinant protein binds human FAP, human CD40, and human serum albumin with a $K_D$ value of or below 100 nM, and wherein said recombinant protein has a terminal half-life in a cynomolgus monkey model of at least 1 day, at least 2 days, at least 3 days, at least 4 days, or about 2.8 days, or about 4.5 days, and wherein in the presence of said recombinant protein, FAP protease activity is reduced by no more than 25%, no more than 20%, no more than 15%, no more than 10%, no more than 9%, no more than 8%, no more than 7%, no more than 6%, no more than 5%, no more than 4%, no more than 3%, or no more than 2%, as compared to a control. In some embodiments, the control is the FAP protease activity in the absence of said recombinant protein. In some embodiments, the FAP protease activity is measured as described in Example 7.

In some embodiments, the multispecific recombinant protein of the disclosure comprises an amino acid sequence that is at least 90% identical to SEQ ID NO: 5; wherein said protein binds human CD40 in PBS with a dissociation constant ($K_D$) below $10^{-9}$M; wherein said protein binds human FAP in PBS with a dissociation constant ($K_D$) below $10^{-9}$M; wherein said protein activates human CD40 in CD40-expressing B cells in the presence of FAP-expressing CHO cells with an EC50 value of about $10^{-8}$M or less; wherein said protein is capable of binding FAP and CD40 simultaneously; wherein said protein does not inhibit FAP protease activity, or the reduction in FAP protease activity in the presence of the recombinant protein is no more than 25%; wherein said protein has a terminal half-life in a mouse model of at least 10 hours.

In some embodiments, the recombinant protein described here comprises a first ankyrin repeat domain that specifically binds serum albumin, a second ankyrin repeat domain that specifically binds fibroblast activation protein (FAP), a third ankyrin repeat domain that specifically binds CD40, and a fourth ankyrin repeat domain that specifically binds CD40, wherein said ankyrin repeat domains are arranged, from the N-terminus to C-terminus, according to the following formula: (serum albumin binding domain)—(linker)—(FAP-binding domain)—(linker)—(CD40 binding domain)—(linker)—(CD40 binding domain), and wherein said recombinant protein specifically binds human FAP in PBS with a dissociation constant ($K_D$) below $10^{-9}$M, and wherein said recombinant protein specifically binds human CD40 in PBS with a dissociation constant ($K_D$) below $10^{-9}$M, and wherein said recombinant protein specifically binds human serum albumin in PBS with a dissociation constant ($K_D$) below $10^{-7}$M, and wherein said FAP binding domain is any one of the FAP binding domains described in section 3.3, and wherein each of said two CD40 binding domains are independently any one of the CD40 binding domains described in section 3.4, and wherein said serum albumin binding domain is any one of the serum albumin binding domains described in section 3.5, and wherein the linker is any one of the linkers described in section 3.6. In some embodiments, said multispecific recombinant protein is capable of simultaneously binding to human CD40, human FAP and human serum albumin. In some embodiments, the simultaneous binding is measured by surface plasmon resonance (SPR). In some embodiments, the simultaneous binding is measured as described in Example 3. In some embodiments, the recombinant protein activates human CD40 in CD40-expressing B cells in the presence of FAP-expressing CHO cells with an EC50 value of about $10^{-8}$M or less. In some embodiments, said multispecific recombinant protein does not inhibit FAP protease activity, or the reduction in FAP protease activity in the presence of the recombinant protein is no more than 25%. In some embodiments, said multispecific recombinant protein has a terminal half-life in a mouse model of at least 20 hours. In some embodiments, said multispecific recombinant protein said protein has a terminal half-life in a cynomolgus monkey model of at least 3 days. In some embodiments, said multispecific recombinant protein is capable of inhibiting tumor growth in a FAP-expressing MC38 colon carcinoma mouse model. In some embodiments, the tumor growth inhibition is measured as described in Example 6. In some embodiments, one of said two CD40 binding domains or each of said two CD40 binding domains of said multispecific recombinant protein independently comprises Q at position 8, L at position 15, R at position 143, and/or Q at position 147, wherein the position numbers correspond to the positions in SEQ ID NO: 3. In some embodiments, each of said two CD40 binding domains of said multispecific recombinant protein comprises Q at position 8, L at position 15, R at position 143, and Q at position 147, wherein the position numbers correspond to the positions in SEQ ID NO: 3. In some embodiments, said multispecific recombinant protein comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 5. In some embodiments, said multispecific recombinant protein comprises an amino acid sequence that is at least 90% identical to SEQ ID NO: 5. In some embodiments, said multispecific recombinant protein comprises a polypeptide, wherein said polypeptide has an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 5. In some embodiments, said multispecific recombinant protein comprises a polypeptide, wherein said polypeptide has an amino acid sequence that is at least 90% identical to SEQ ID NO: 5.

3.8. Nucleic Acids and Methods of Producing Multispecific Proteins

The disclosure also provides polynucleotides encoding the recombinant proteins described herein. The disclosure also provides a method of producing any of the polynucleotides described herein. The disclosure also provides recombinant proteins obtained by said method. Polynucleotides can be generated and expressed by procedures known in the art.

In one aspect, the disclosure provides polynucleotides or compositions comprising polynucleotides encoding a recombinant multispecific protein, wherein sad protein comprises a first ankyrin repeat domain that specifically binds fibroblast activation protein (FAP), and a second ankyrin repeat domain that specifically binds CD40, and optionally, a half-life extending moiety.

In one aspect, the disclosure provides polynucleotides or compositions comprising polynucleotides comprising a nucleic acid sequence encoding a recombinant protein comprising SEQ ID NO: 1, 2, 3, and/or 4. In one aspect, the disclosure provides polynucleotides or compositions comprising polynucleotides comprising a nucleic acid sequence encoding a recombinant protein comprising SEQ ID NO: 5 or 6. In one embodiment, the disclosure provides a nucleic acid comprising the nucleic acid sequence of SEQ ID NO: 58.

In another aspect, the disclosure provides polynucleotides and variants thereof encoding a recombinant protein, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any nucleic acid disclosed herein, such as a nucleic acid comprising the nucleic acid sequence of SEQ ID NO: 58.

In another aspect, the disclosure provides polynucleotides and variants thereof encoding a recombinant protein, wherein such variant polynucleotides are capable of hybridizing under highly stringent conditions to the sequence of SEQ ID NO: 58. "Highly stringent conditions" includes those that: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 pg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

Polynucleotides complementary to any such sequences are also encompassed by the present disclosure. Polynucleotides may be single-stranded (coding or antisense) or double-stranded, and may be DNA (recombinant, cDNA or synthetic) or RNA molecules. RNA molecules include hnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

It will be appreciated by those of ordinary skill in the art that, as a result of the degeneracy of the genetic code, there are many nucleotide sequences that encode a recombinant protein (or its individual domains) comprising an amino acid sequence as described herein. Some of these polynucleotides bear minimal homology to the nucleotide sequence of any native gene. Polynucleotides that vary due to differences in codon usage are specifically contemplated by the present disclosure.

The present disclosure also includes codon-optimized polynucleotides wherein the nucleic acid sequence has been optimized to maximize expression in a particular cell. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the original sequence with codons that are more frequently or most frequently used in the genes of that host cell while maintaining the original amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, and these tables can be adapted in a number of ways (e.g., Nakamura, Y., et al. "Codon usage tabulated from the international DNA sequence databases: status for the year 2000" Nucl. Acids Res. 28:292 (2000)). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a recombinant protein correspond to the most frequently used codon for a particular amino acid.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Exemplary host cells include an *E. coli* cell, a yeast cell, an insect cell, a simian COS cell, a Chinese hamster ovary (CHO) cell, or a myeloma cell. Preferred host cells include an *E. coli* cell, a CHO cell, a Human embryonic kidney (HEK) 293 cell, or a Sp2.0 cell, among many cells well-known in the art.

4. Methods of Treatment

The recombinant proteins described herein can be used to, e.g., treat a subject that has a medical condition such as, e.g., cancer.

The disclosure provides a method of treating a medical condition, comprising administering to a subject in need thereof a therapeutically effective amount of a recombinant protein, a nucleic acid or a pharmaceutical composition described herein. In some embodiments, the subject is a human. In some embodiments, the medical condition is cancer. In some embodiments, the cancer is a solid tumor. In some embodiments, the cancer cell expresses FAP. In some embodiments, tumor stromal cells express FAP.

In some embodiments, the cancer is brain cancer, bladder cancer, breast cancer, clear cell kidney cancer, cervical cancer, colon and rectal cancer, endometrial cancer, gastric cancer, head and neck cancer, head/neck squamous cell carcinoma, lip cancer, oral cancer, liver cancer, cervix cancer, lung squamous cell carcinoma, melanoma, mesothelioma, non-small-cell lung cancer (NSCLC), non-melanoma skin cancer, ovarian cancer, pancreatic cancer, prostate cancer, renal cell carcinoma, urothelial carcinoma, sarcoma, small-cell lung cancer (SCLC), Squamous Cell Carcinoma of the Head and Neck (SCCHN), triple negative breast cancer, or thyroid cancer.

In some embodiments, the cancer is cancer is adrenocortical tumor, alveolar soft part sarcoma, carcinoma, chondrosarcoma, colorectal carcinoma, desmoid tumors, desmoplastic small round cell tumor, endocrine tumors, endodermal sinus tumor, epithelioid hemangioendothelioma, Ewing sarcoma, germ cell tumor, hepatoblastoma, hepatocellular carcinoma, melanoma, nephroma, neuroblastoma, non-rhabdomyosarcoma soft tissue sarcoma (NRSTS), osteosarcoma, paraspinal sarcoma, renal cell carcinoma, retinoblastoma, rhabdomyosarcoma, synovial sarcoma, or Wilms tumor.

In some embodiments, the cancer is acute lymphoblastic leukemia (ALL), acute myeloid leukemia (AML), chronic lymphocytic leukemia (CLL), or chronic myeloid leukemia (CML).

In some embodiments, the cancer is diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), or small lymphocytic lymphoma (SLL).

Indeed, cancers that can be treated include, but are not limited to, alveolar rhabdomyosarcoma, bone cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, esophageal cancer, gastrointestinal carcinoid tumor, hypopharynx cancer, larynx cancer, nasopharynx cancer, peritoneum, omentum, and mesentery cancer, pharynx cancer, small intestine cancer, soft tissue cancer, stomach cancer, testicular cancer, ureter cancer, and urinary bladder cancer.

In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, and bronchioloalveolar carcinoma.

In some embodiments, the cancer is non-small cell lung cancer (NSCLC), head and neck cancer, renal cancer, triple negative breast cancer, or gastric cancer. In some embodiments, the cancer is non-small cell lung cancer (NSCLC), small cell lung cancer (SCLC), head and neck cancer, renal cancer, breast cancer, melanoma, ovarian cancer, liver cancer, pancreatic cancer, colon cancer, prostate cancer, gastric cancer, lymphoma or leukemia. In some embodiments, the cancer is brain cancer.

The recombinant proteins described herein may be used prior to or following surgery to remove a tumor and may be used prior to, during or after radiation therapy. The recombinant protein may be used to treat a tumor that is large enough to be found by palpation or by imaging techniques well known in the art, such as MRI, ultrasound, or CAT scan. In some embodiments, the recombinant protein is used to treat an advanced stage tumor having dimensions of at least about 200 mm$^3$, 300 mm$^3$, 400 mm$^3$, 500 mm$^3$, 750 mm$^3$, or up to 1000 mm$^3$.

5. Pharmaceutical Compositions and Administration

In another aspect, the disclosure also provides pharmaceutical compositions comprising the recombinant multispecific proteins described herein.

The pharmaceutical compositions may comprise a pharmaceutically acceptable carrier, diluent, or excipient. Standard pharmaceutical carriers include a phosphate buffered saline solution, water, emulsions such as an oil/water or water/oil emulsion, and various types of wetting agents.

The pharmaceutical compositions can comprise any pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the *Handbook of Pharmaceutical Excipients*, Third Edition, A. H. Kibbe (Pharmaceutical Press, London, U K, 2000). *Remington's Pharmaceutical Sciences*, Sixteenth Edition, E. W. Martin (Mack Publishing Co., Easton, Pa., 1980).

The pharmaceutical compositions can be formulated to achieve a physiologically compatible pH. In some embodiments, the pH of the pharmaceutical composition can be, for example, between about 4 or about 5 and about 8.0, or between about 4.5 and about 7.5, or between about 5.0 and about 7.5. In some embodiments, the pH of the pharmaceutical composition is between 5.5 and 7.5.

The recombinant multispecific proteins described herein can be administered to the subject via any suitable route of administration, such as parenteral, nasal, oral, pulmonary, topical, vaginal, or rectal administration. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. For additional details, see *Pharmaceutics and Pharmacy Practice*, J. B. Lippincott Company, Philadelphia, PA, Banker and Chalmers, eds., pages 238-250 (1982), and *ASHP Handbook on Injectable Drugs*, Toissel, 4th ed., pages 622-630 (1986)).

The dose of the active agent of the present disclosure administered over the course of a therapeutic regimen should be sufficient to treat cancer in a clinically-acceptable time frame (e.g., 1 to 4 weeks or longer (such as 5 to 20 or more weeks)) from the time of administration. In some embodiments, the time period could be even longer. The dose will be determined by the efficacy of the particular active agent and the condition of the animal (e.g., human), as well as, at times, the body weight of the animal (e.g., human) to be treated. The extent to which cancer is treated upon administration of a certain dose can be represented by, for example, the cytotoxicity of the active agent or the extent of tumor regression achieved with the active agent. Methods of measuring cytotoxicity of the recombinant multispecific proteins and methods of assaying tumor regression are known in the art. By way of example and not intending to limit the present disclosure, the dose of the active agent of the present disclosure can be about 0.0001 to about 1 g/kg body weight of the subject being treated/day, from about 0.0001 to about 0.001 g/kg body weight/day, or about 0.01 mg to about 1 g/kg body weight/day. Dosage units may be also expressed in rag/m², which refer to the quantity in milligrams per square meter of body surface area.

The recombinant multispecific proteins described herein may be used in combination with another therapeutic agent, such as another anti-cancer agent. Each therapeutic agent may be administered simultaneously (e.g., in the same medicament or at the same time), concurrently (i.e., in separate medicaments administered one right after the other in any order) or sequentially in any order. Sequential administration may be useful when the therapeutic agents in the combination therapy are in different dosage forms (e.g., one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

EXAMPLES

Example 1—Design of Multispecific Binding Proteins

Multispecific binding proteins in various formats were generated and their FAP-specificity, efficacy and potency of CD40 activation were determined. These multispecific proteins all comprised a FAP-specific binding domain and a CD40-specific binding domain. The impact of (i) adding human serum albumin (HSA)-binding domain(s), (ii) increasing valency by adding further CD40-binding domain (s), and (iii) changing the order of the binding domains within the protein were evaluated.

To compare the different formats, an in vitro assay was set up measuring the upregulation of the co-stimulatory receptor, CD86, expressed on human B cells upon CD40 triggering. This cellular assay used primary human B cells in the presence or absence of FAP-expressing cells. The upregulation of CD86 co-stimulatory molecule was evaluated as a marker of B cell activation. An anti-CD40 monoclonal antibody, whose mechanism of action is independent on FAP-mediated cross-linking, was used as reference material.

Multispecific proteins of different formats. Starting with a parental molecule (SEQ ID NO: 59; SMA014) comprising one FAP-specific binding domain and one CD40-specific binding domain, several multispecific protein formats were generated, as summarized in Table 2.

TABLE 2

Multispecific proteins in various domain formats

| SEQ ID NO/Construct Name | Format |
| --- | --- |
| SEQ ID NO: 59/SMA014 | FC |
| SEQ ID NO: 60/SMA087 | HFC |
| SEQ ID NO: 61/SMA095 | HFCH |
| SEQ ID NO: 62/SMA104 | FCC |
| SEQ ID NO: 63/SMA091 | HFCC |
| SEQ ID NO: 64/SMA099 | HFCCH |
| SEQ ID NO: 65/AS579 | HHFCC |
| SEQ ID NO: 66/SMA105 | FCCC |

"C", "F", and "H" in Table 2 indicate ankyrin repeat domains specifically binding CD40, FAP and HSA, respectively. The order of the different domains as indicated in Table 2 reflects the actual sequence of the domains from N-terminus to C-terminus in the molecular structure of the proteins. All the proteins additionally had a His-tag (SEQ ID NO: 57) at the N-terminus for ease of purification.

Materials and Methods

As a reference, a CD40 monoclonal antibody was used. Binding of this CD40 mAb (an IgG2 mAb) to CD40 leads to the activation of antigen presenting cells independently of FAP. The anti-CD40 mAb corresponds to sequence 21.4.1 of U.S. Pat. No. 7,338,660 B2.

CHO cells were cultured at 37° C., 5% $CO_2$ in DMEM media containing 10% FBS and splitted every 2-3 days using accutase to detach cells.

The FAP-expressing CHO cell line is a stably transfected clonal cell line expressing human FAP on the cell surface. A plasmid containing a GFP-fusion of the ORF of human FAP was obtained from OriGene Technologies (#RG204692). The cDNA coding for human FAP (without GFP) was sub-cloned using standard molecular biology techniques. This plasmid was then transfected into CHO cells to produce stable transfectants overexpressing human FAP using Lipofectamine. Selection pressure was applied using different concentrations of Geneticin G-418 (Promega, V8091). Expression of FAP was analyzed by flow cytometry using an anti-FAP antibody corresponding to ESC11 (WO2011/040972). The population of FAP-CHO transfectants from condition 1.9 mg/mL G-418 (FAP-CHO-1.9) showed a lower expression level of FAP and those from condition 1.7 mg/mL (FAP-CHO-1.7) showed a higher expression level of FAP. The data in this Example were generated using FAP-CHO-1.7.

In vitro B cell activation assay. The design of the in vitro B cell activation assay is schematically shown in FIG. 1. Buffy coats were obtained from the Zurich blood donation center and diluted with PBS. Peripheral blood mononuclear cells (PBMCs) were then isolated by density centrifugation using Leucosep tubes. After several washing steps, human CD19+ B cells were enriched from PBMCs using a positive selection (human CD19 MicroBeads Kit) according to the manufacturers recommendations. CD19+ B cells at $1 \times 10^5$/well and FAP-expressing CHO cells or CHO wildtype (WT-CHO) cells at $5 \times 10^4$ cells/well were seeded together in RPMI 1640 media+10% FBS with or without 600 pM HSA into 96-well plates together with dose titrations (400, 200, 40, 8, 5, 1.6, 0.3, 0 nM) of the indicated molecules. Cultures were incubated for 24 hours at 37° C., 5% $CO_2$ and the upregulation of CD86 and CD69 on CD20+ B cells was assessed by flow cytometry using AttuneNxT.

Figure 2:
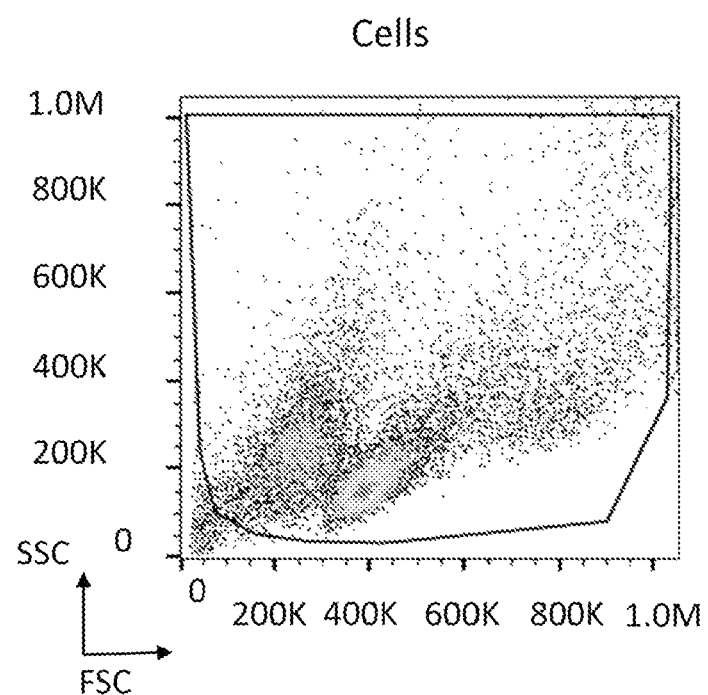
FIG. 2: Overview of the gating strategy used to determine MFI and percentage of cells positive for CD86. The following settings were used: FSC: 200; SSC: 400; Acquisition: 200 ul 1min, 100.000 events. Abbreviations: FMO=Fluorescence minus one, SSC=Side scatter, FSC=Forward scatter, FSC—A=Forward scatter area, FSC—H=Forward scatter height.
Figure 2:
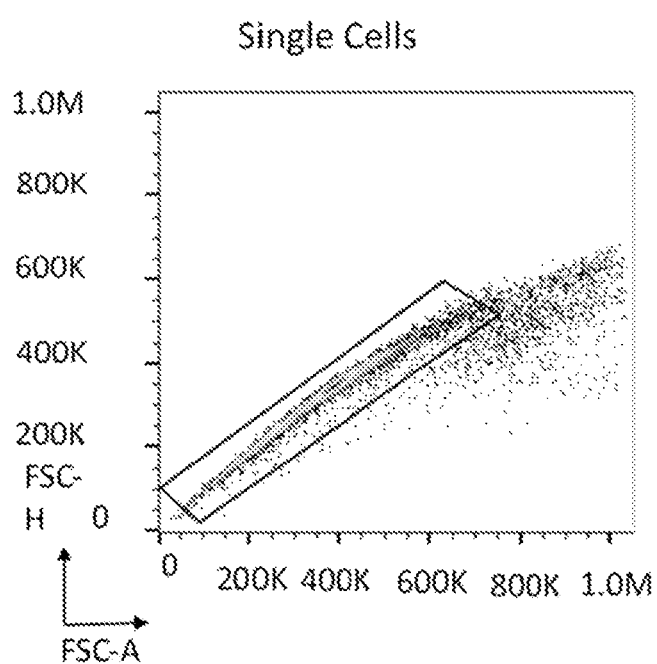
Figure 2:
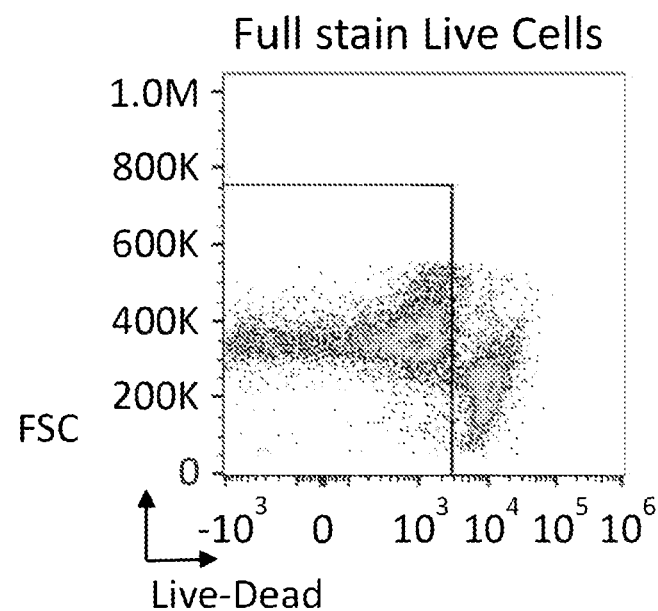
Figure 2:
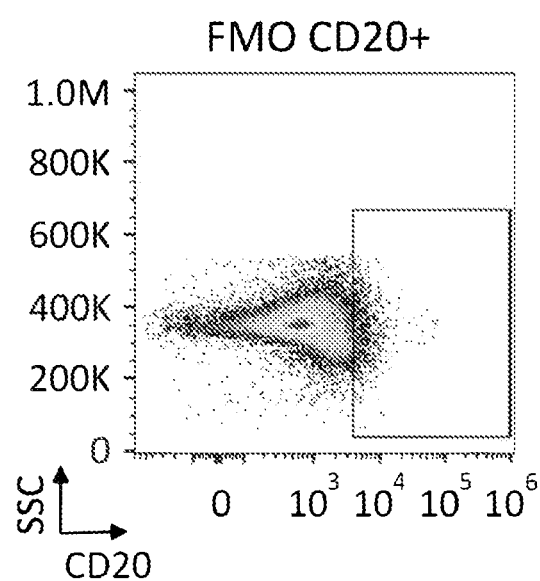
Figure 2:
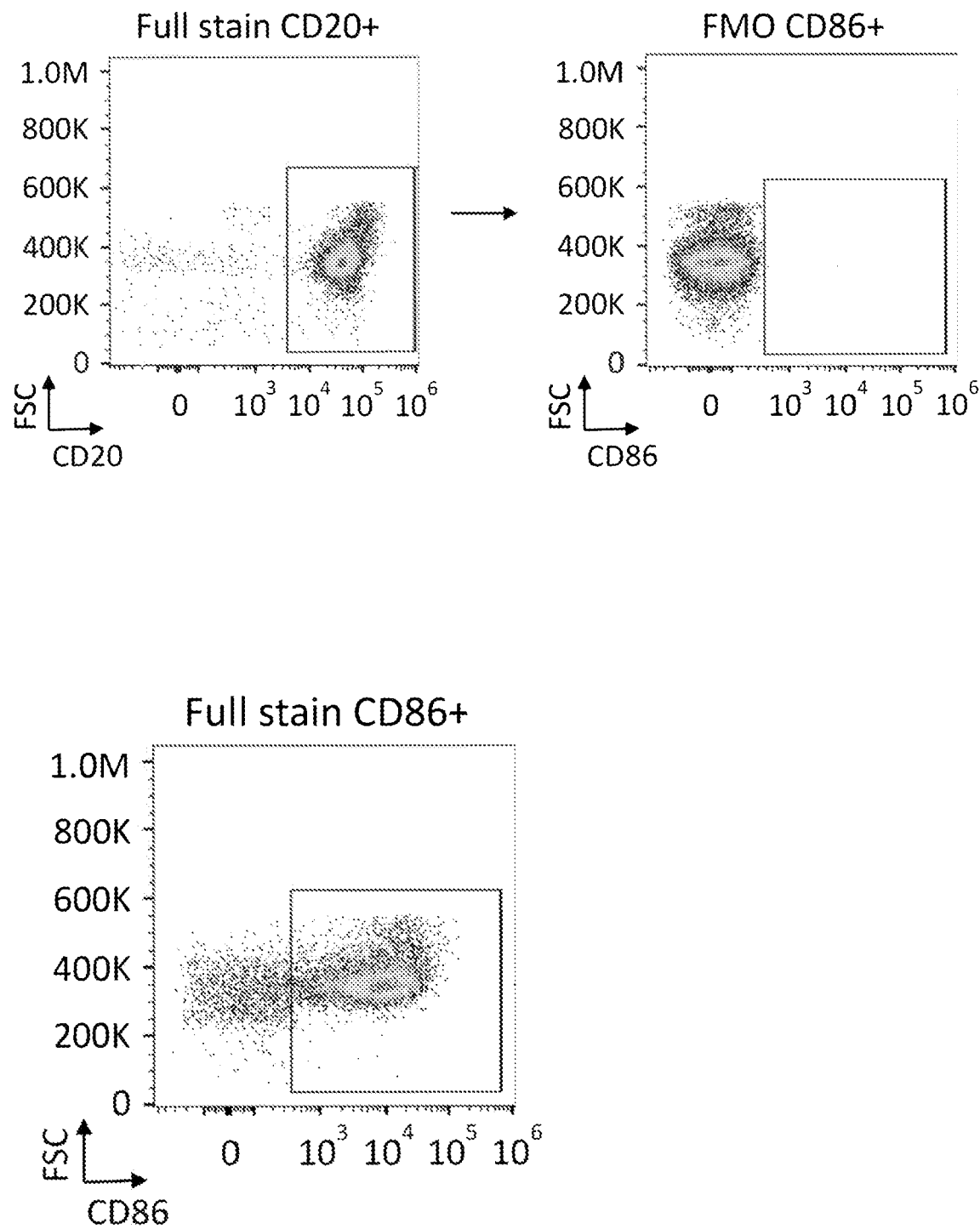
Figure 3A:
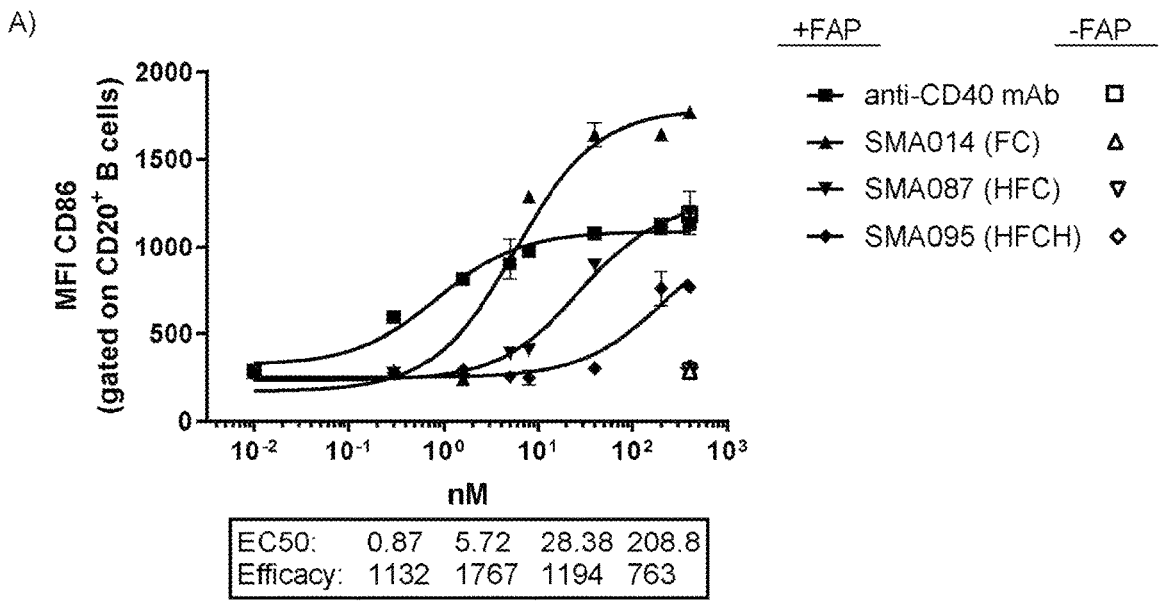
FIGS. 3A and 3B: HSA-binding domain(s) impair potency and efficacy of a bispecific FAPxCD40 ankyrin repeat binding protein. Human B cells were co-cultured in presence of FAP-expressing CHO cells (full symbols) and treated with increasing concentrations of SMA014 (triangle pointing up), SMA087 (triangle pointing down), SMA095 (diamond) and agonist anti-CD40 mAb (square). As control, B cells were co-cultured in presence of FAP-negative CHO cells and treated only with the highest concentration of the respective constructs, depicted as empty symbols. Activation of human B cells was assessed in terms of upregulation of CD86 (measured as mean fluorescence intensity (MFI) and percentage of cells (%)) in absence A) and in presence B) of 600 pM HSA. Each value depicts the average of duplicated measurements. The shown data are representative of two independent experiments. Error bars show±SEM. EC50 and efficacy values (in nM) for all constructs in presence of FAP-expressing CHO cells are shown in the depicted tables in the graphs.
Figure 3A:
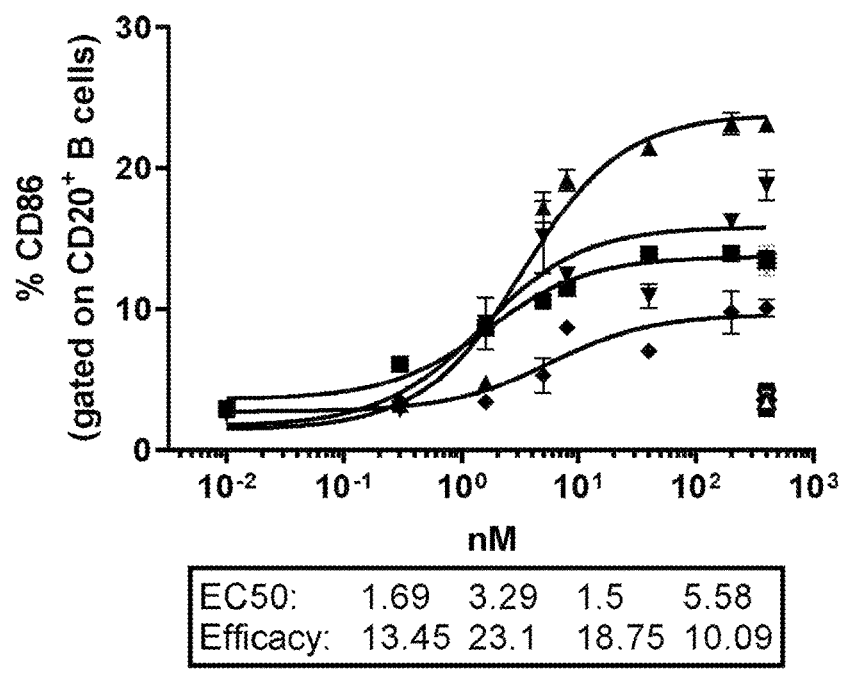
Figure 3B:
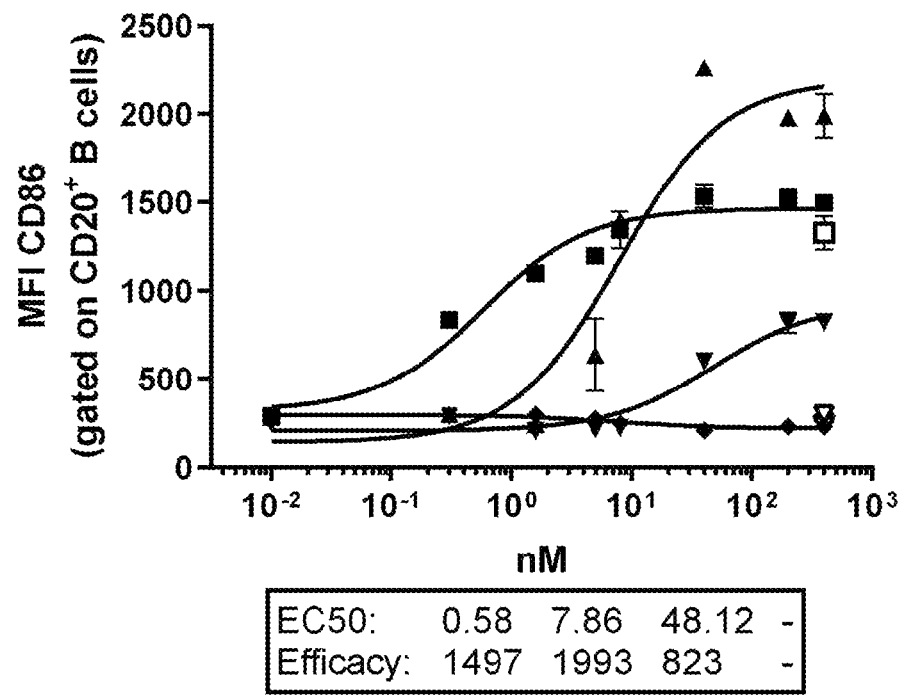
Figure 3B:
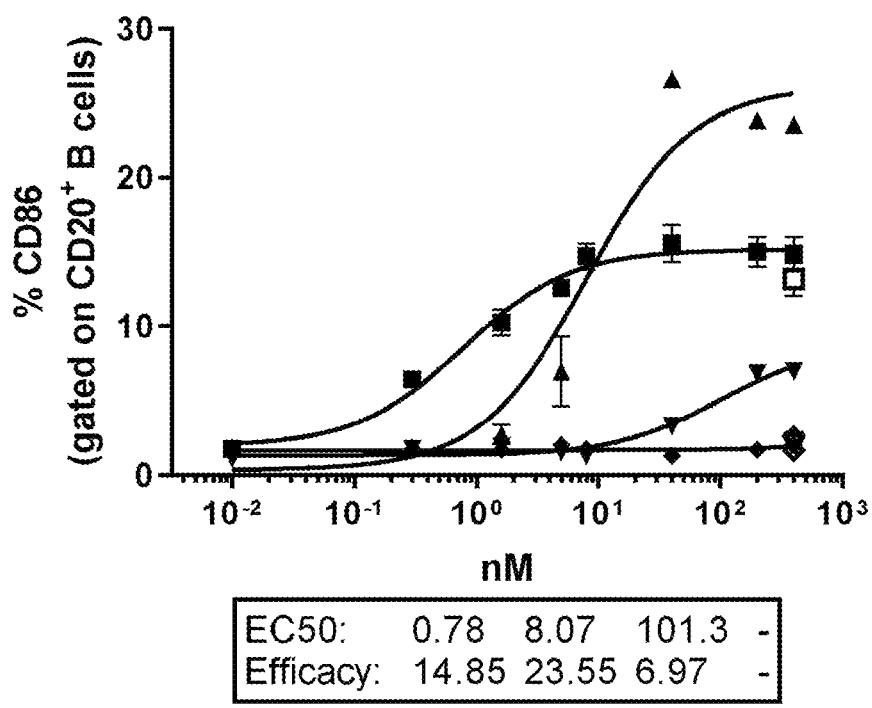

FACS staining, flow cytometer settings and antibody dilutions. Cells were first washed with 150 µl PBS and then incubated for 20 minutes at room temperature (RD with 100 µl of BD human Fc-Block diluted (1:100) in PBS. After Fc-blocking incubation, the cells were incubated with 100 µl of directly labelled antibodies diluted (see Table 3 below for the dilution factors) in FACS buffer and incubated for another 20 minutes at 4° C. in the dark. Cells were washed with PBS, resuspended in 100 µl Live/Dead staining diluted (1:1000) in PBS and incubated for 20 minutes at 4° C. in the dark. One hundred µl of FACS buffer containing FBS reaction was added to stop the Live/Dead staining reaction. Cells were washed again with PBS and fixed using BD Cell Fix solution diluted (1:10) in water according to the manufacturers recommendations. Dilutions of antibodies and FACS settings are summarized in Table 3 below. Compensation of the FACS machine was done with compensation beads according to the manufacturers recommendations (ThermoFisher; AbC™ Total Antibody Compensation Bead Kit). Raw_fcs files were analyzed using FlowJo software (version 10.0.3). Cells were gated on live cells using Live-Dead discriminating dye followed by gating on CD20 positive cells as shown in FIG. 2 for CD86. The MFI and percentage of positive cells for CD86 were exported and plotted using GraphPad prism software, version 8.1.2.

TABLE 3

| FSC: 200 SSC: 400 Acquisition: 200ul/min, 100.000 events | | | | | |
|---|---|---|---|---|---|
| Target | Fluorochrome | Dilution | Dilution media | Channel | Voltages |
| CD20 | APC-Cy7 | 1:100 | FACS buffer | BL2 | 400 |
| CD86 | PE | 1:200 | FACS buffer | YL1 | 380 |
| CD69 | APC | 1:200 | FACS buffer | RL-1 | 400 |
| Live/Dead | Aqua | 1:1000 | PBS | VL2 | 400 |

EC50 Determinations. EC50 values were determined using GraphPad Prism version 7.02 by converting the x values (concentrations) in a log mode and fitting in a non-linear mode log (agonist) vs. response with a variable slope (three parameter) equation for determination of EC50 values.

Efficacy Determination. Efficacy values were determined using GraphPad Prism version 7.02 by calculating the average of duplicates for the MFI values at the highest concentration (400 nM).

Results

HSA binding domain(s) impair potency and efficacy of a bispecific FAPxCD40 ankyrin repeat binding protein (F-C format). A bispecific FAPxCD40 DARPin® molecule in the F-C format, SMA014, was cloned in different formats adding one (H—F—C, SMA087) or two (H—F—C—H, SMA095) HSA-binding ankyrin repeat domains and tested in the in vitro B cell activation assay. As shown in FIG. 3, the HSA binding domain(s) impaired both the potency and the efficacy of the original bispecific binding protein in the F-C format and the level of impairment correlated with the number of HSA binding domains added to the binding protein. Importantly, the inhibition was more pronounced in presence of 600 pM of albumin mimicking the physiological concentration of albumin in the human serum. It is plausible to hypothesize that the complex HSA binder/albumin could be a steric impairment for the binding, and consequently the activity, of the CD40 and/or FAP domain(s). As expected, the DARPin® proteins and the anti-CD40 mAb upregulated CD86 in a dose dependent manner and the DARPin® proteins were active only in presence of FAP-expressing CHO cells (FIG. 3). In absence and presence of HSA, HSA binding domains did not influence the FAP specific mode of action. As expected, the agonistic anti-CD40 mAb induced activation of human B-cells independently of FAP expression, activating B-cells in the presence of either FAP-CHO or WT-CHO cells. EC50 (potency) and maximum MFI (efficacy) mean values of two independent experiments are summarized in Table 4 and Table 5 for FAP-CHO and in Table 6 for WT-CHO, respectively.

In summary, the addition of half-life extending HSA-binding domain(s) impaired the functionality of the bispecific FAPxCD40 binding protein (F-C format), the inhibition increased with the number of added HSA binding domains, and the inhibition was more pronounced in presence of physiological concentration of albumin.

Figure 5A:
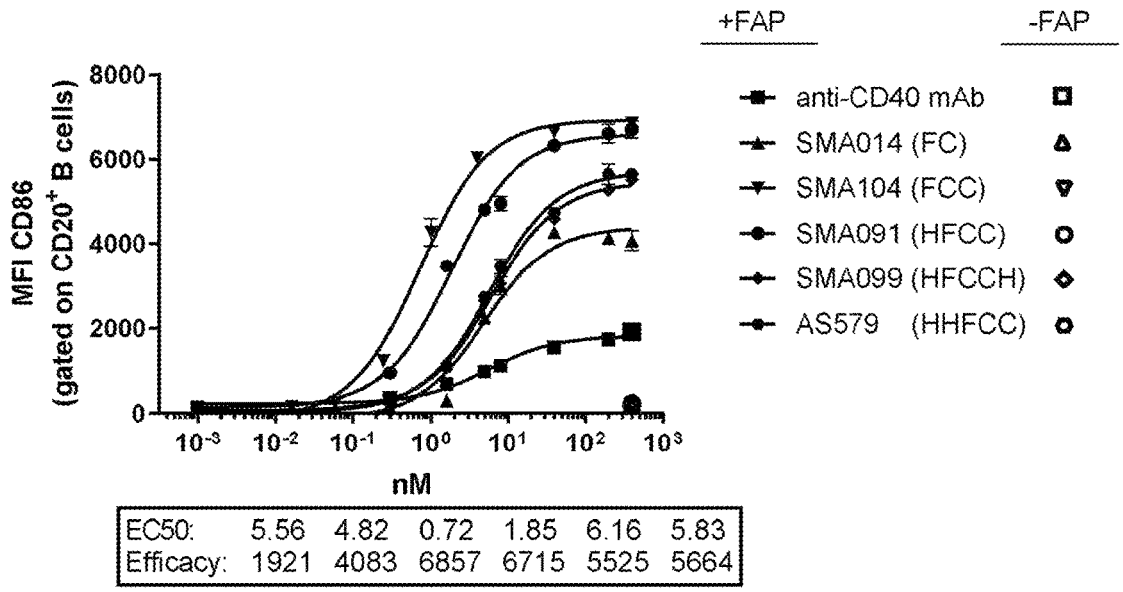
FIG. 5: CD40 bivalency rescues the inhibitory effect induced by a HSA binding domain. Human B cells were cultured in presence of FAP expressing CHO cells and treated with increasing concentrations of SMA014 (triangle pointing up), SMA104 (triangle pointing down), SMA091 (circle), SMA099 (diamond), AS579 (hexagon) and agonist anti-CD40 mAb (square). As control, B cells were co-cultured in presence of FAP-negative CHO cells and treated only with the highest concentration of the respective constructs, depicted as empty symbol. Activation of human B cells was assessed in terms of upregulation of CD86 (measured as mean fluorescence intensity (MFI) and percentage of cells (%)) in absence A) and in presence B) of HSA. Each value depicts the average of duplicated measurements. The shown data are representative of two independent experiments. Error bars show±SEM. EC50 and efficacy values (in nM) for all constructs in presence of FAP expressing CHO cells are shown in the depicted tables in the graphs.
Figure 5A:
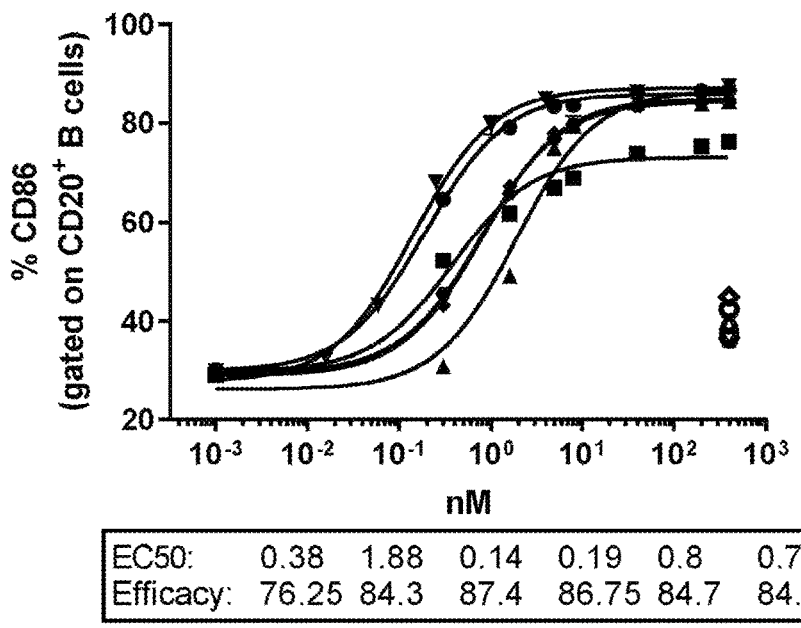
Figure 5B:
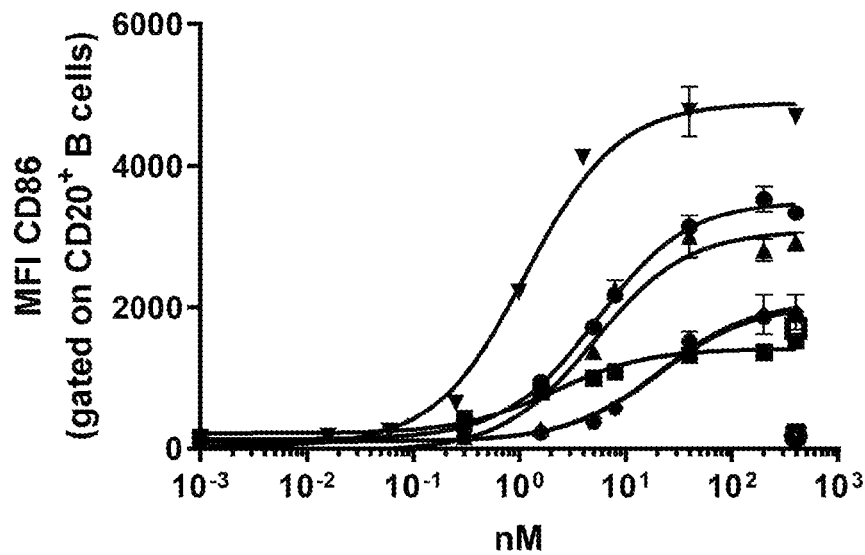
Figure 5B:
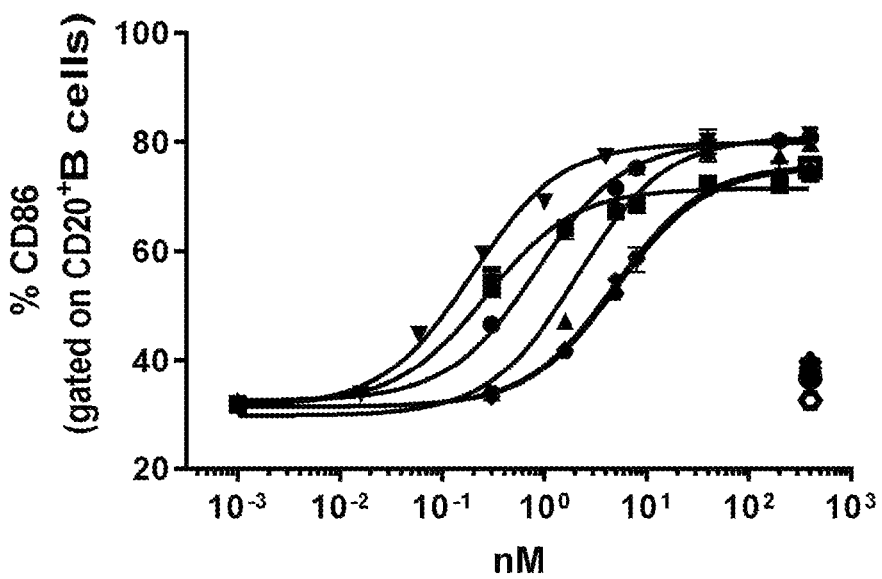

Bivalency for CD40 increases potency and efficacy and rescues the inhibitory effect induced by HSA-binding domain. Applicant then investigated how CD40 valency affects the performance of the bispecific FAPxCD40 DARPin® molecule. The bispecific FAPxCD40 DARPin® molecule in the F-C format, SMA014, was cloned in different formats adding one (F—C—C, SMA104) or two (F—C—C—C, SMA105) CD40-binding DARPin domains, and tested in the in vitro B-cell activation assay. As shown in FIG. 4, the bivalent and trivalent formats induced a stronger upregulation of CD86, indicating that valency contributes favorably to the performance of the molecule. Specifically, CD40 bivalency (SMA104) strongly increased potency (20×) and efficacy (2×) of the molecule in presence of FAP expressing CHO cells. CD40 trivalency (SMA105) only caused slightly increased potency of the molecule compared to CD40 bivalency, but did not further impact the efficacy. In absence of FAP, the bivalent CD40 format (SMA104) did not induce upregulation of CD86 on human B cells, while the trivalent CD40 format (SMA105) showed slight activation also in absence of FAP at the highest concentration, suggesting a possible FAP-independent activation induced by the trivalent CD40 binder. In view of these results, the bivalent CD40 format was selected for further characterization. In particular, Applicant tested if the CD40 bivalency could rescue the inhibitory effect of the HSA binding domain. To address this question, the bivalent CD40 construct SMA104 was cloned with additional HSA binding domain(s) in different positions (clones SMA091, SMA099 and AS579; see Table 2 above for information on their domain formats). All the tested formats showed improved potency and efficacy compared to SMA014 (FIG. 5A). Importantly, in a more physiological condition in presence of HSA, activity of all formats with HSA binding domain was reduced, but SMA091 still showed improved activity compared to SMA014 (FIG. 5B). None of the ankyrin repeat binding proteins enhanced expression of CD86 on the B cells in absence of FAP even at highest concentration (FIGS. 5A and B). As expected, the agonistic anti-CD40 mAb induced activation of human B-cells independently on FAP expression, activating B-cells either with FAP-CHO or WT-CHO. EC50 (potency) and maximum MFI (efficacy) mean values of two independent experiments are summarized in Table 4 and Table 5 for FAP-CHO and in Table 6 for VVT-CHO, respectively.

TABLE 4

| | EC50 [nM] | | | |
|---|---|---|---|---|
| | MFI CD86 | | % CD86 | |
| Protein | w/o HSA | w HSA | w/o HSA | w HSA |
| SMA014 | 8.46 | 7.7 | 4.21 | 6.15 |
| SMA087 | 28.92 | 52.01 | 11.44 | 72.34 |
| SMA095 | 287.55 | — | 89.84 | — |
| CD40 mAb | 1.13 | 0.51 | 1.9 | 0.88 |
| SMA091 | 3.93 | 8.05 | 0.76 | 2.98 |
| SMA099 | 18.23 | 19.41 | 4.68 | 7.5 |
| SMA104 | 0.74 | | 0.23 | |
| SMA105 | 0.33 | | 0.11 | |
| AS579 | 10.01 | 23.1 | 2.27 | 10.25 |
| CD40 mAb | 4.73 | 2.05 | 0.51 | 0.3 |

TABLE 5

| | Efficacy [MFI at highest dose] | | | |
|---|---|---|---|---|
| | MFI CD86 | | % CD86 | |
| Protein | w/o HSA | w HSA | w/o HSA | w HSA |
| SMA014 | 2436.25 | 2189.75 | 48.4 | 47 |
| SMA087 | 1643.25 | 799.25 | 43.4 | 27.01 |
| SMA095 | 773 | 232.25 | 28.7 | — |
| CD40 mAb | 1339.5 | 1528.5 | 38.6 | 45.05 |
| SMA091 | 6230.25 | 2983.25 | 78.15 | 75.63 |
| SMA099 | 4954 | 1718.75 | 84.4 | 71.68 |
| SMA104 | 6270.75 | | 86.8 | |
| SMA105 | 5558.5 | | 87.15 | |
| AS579 | 4864.5 | 1781.75 | 82.98 | 71.9 |
| CD40 mAb | 2064.25 | 1867.25 | 78.63 | 76.63 |

TABLE 6

| | Efficacy [MFI at highest dose] | | | |
|---|---|---|---|---|
| | MFI CD86 | | % CD86 | |
| Protein | w/o HSA | w HSA | w/o HSA | w HSA |
| SMA014 | 293.75 | 310 | 13.15 | 13.29 |
| SMA087 | 291 | 299 | 12.53 | 13.73 |
| SMA095 | 299 | 306.5 | 12.48 | 13.68 |
| CD40 mAb | 1389.5 | 1473 | 38.83 | 40.05 |
| SMA091 | 289.5 | 295.5 | 47.78 | 43.13 |
| SMA099 | 289.25 | 273.75 | 47.38 | 42.53 |
| SMA104 | 251.75 | | 46.05 | |
| SMA105 | 672.5 | | 69.25 | |
| AS579 | 252.5 | 242.5 | 42.05 | 40.13 |
| CD40 mAb | 2053.75 | 1902 | 79 | 77.83 |

Conclusions: The bispecific FAPxCD40 ankyrin repeat protein in the F-C format showed good biological activity in functional cell assays and good physical properties. However, this binding protein may require a half-life extension domain to allow its clinical development. Thus, different formats were analyzed to determine if and how the number and location of half-life extension HSA-binding domains impacts the activity of the molecule. It was observed that a half-life extension domain had a detrimental effect on the activity of the molecule and that this effect increased with the number of half-extension domains and the presence of HSA. Furthermore, it was then surprisingly found that CD40 bivalency (by having two CD40 binding domains) strongly increased the potency (20×) and the efficacy (2×) of the binding protein and maintained a stringent FAP-specific mechanism of action, but that CD40 trivalency (by having three CD40 binding domains) increased only slightly the potency compared to CD40 bivalency and did not show any further impact on the efficacy. In addition, the trivalent CD40 binding protein showed slight activation also in absence of FAP at the highest concentration, suggesting a partial loss of FAP-specific mode of action. CD40 bivalency was further found to be able to rescue the inhibitory effect of one half-life extension domain, by increasing the potency and the efficacy of the binding protein. Specifically, at physiological concentration of HSA, the binding protein in the H—F—C—C format retained an activity and FAP-specificity comparable to the binding protein in the F-C format. In conclusion, by adding a second CD40 binding domain we could prevent the detrimental effect of a HSA binding half-life extension domain and generate a molecule with similar functional properties to the parental binding protein in the F-C format but equipped with the half-life extension domain that will facilitate its clinical development. For all these reasons, H—F—C—C domain format was chosen for further investigations. This format is used in the binding proteins of the disclosure comprising the amino acid sequence of SEQ ID NO: 5 (DARPin® Protein #5 or just "Protein #5"), SEQ ID NO: 6 (DARPin® Protein #6 or just "Protein #6") or SEQ ID NO: 7 (DARPin® Protein #7 or just "Protein #7") described in the following Examples.

Example 2—Biophysical Properties, Binding Affinities, and Binding Specificities of a Multi-Specific Binding Protein This Example describes experiments which were conducted to determine (1) biophysical properties, such as aggregate formation, and (2) binding affinity to the various target proteins (i.e. FAP, CD40 and serum albumin) and species cross-reactivity, of a multi-specific binding protein of the disclosure.

Aggregate Formation

Figure 6:
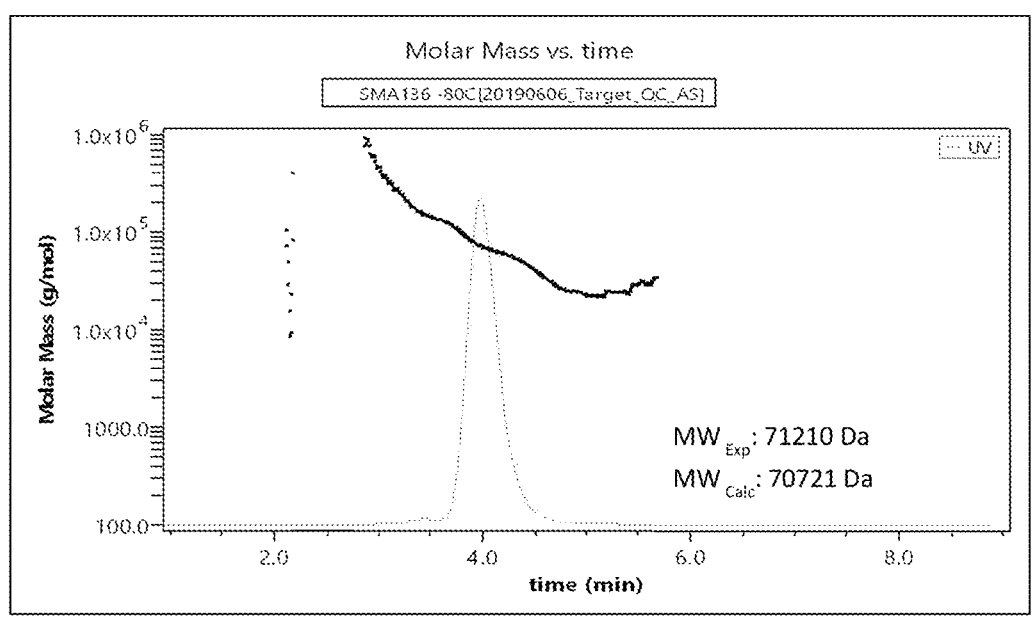
FIG. 6: Analysis of Protein #5 (also called SMA136) by size exclusion chromatography (SEC) and multiangle light scattering (MALS). The graph shows the SEC profile as molar mass over time. The determined molecular weight of Protein #5 is indicated.

Protein #5 (also sometimes called SMA136 herein) was analyzed by size exclusion chromatography (SEC) and multiangle light scattering (MALS). FIG. 6 shows the results of this analysis. This SEC profile demonstrates that Protein #5 is monomeric and monodisperse in solution and does not form aggregates.

Binding Affinity to Target Proteins

Figure 7:
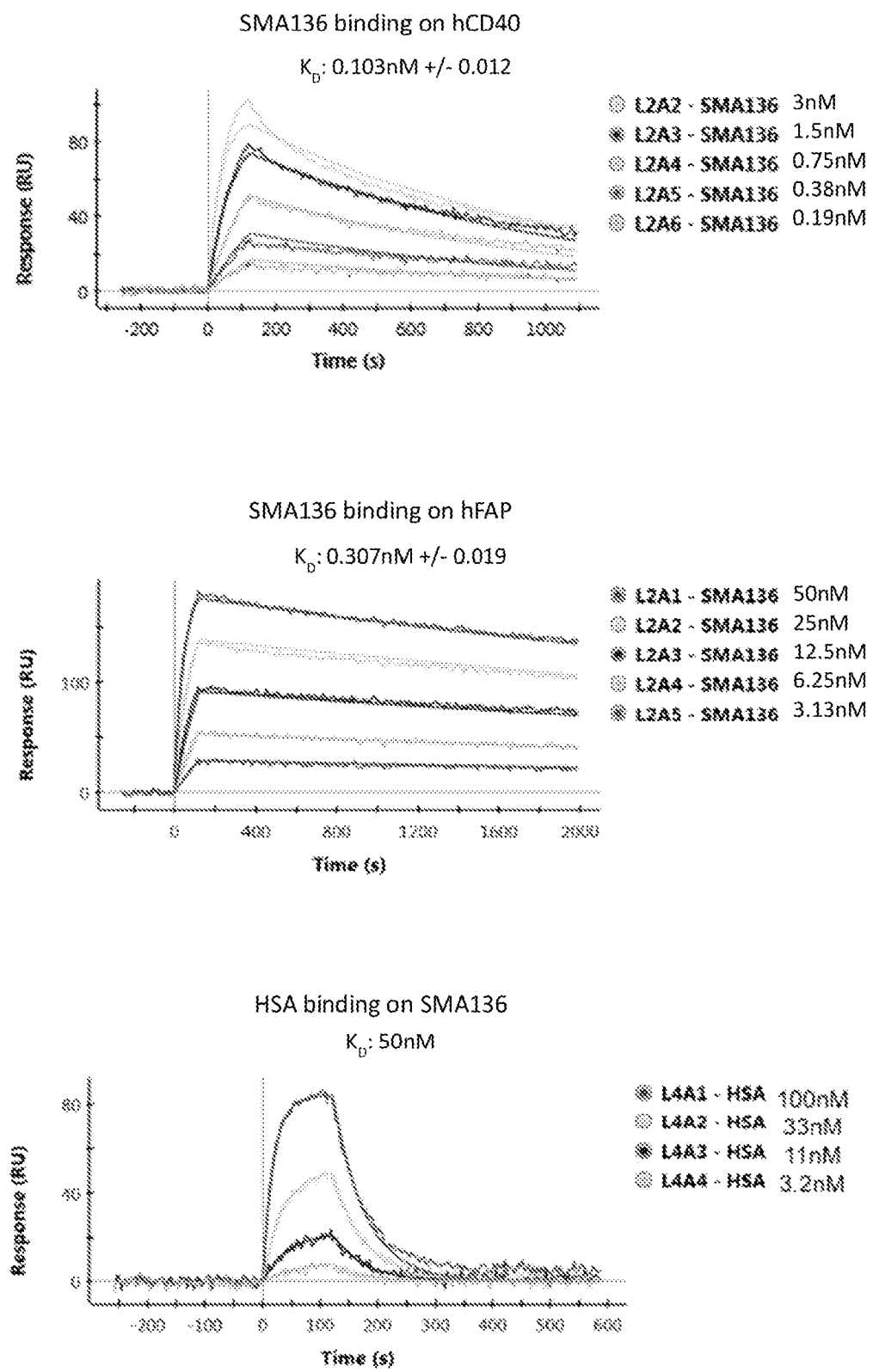
FIG. 7: Surface plasmon resonance (SPR) traces showing binding of Protein #5 (also called SMA136) to human CD40 (A), human FAP (B) and human serum albumin (C). The determined $K_D$ values are indicated.

Summary. The binding of DARPin® Protein #5 ("Protein #5") to CD40, FAP and serum albumin from human, cynomolgus monkey and mouse was analyzed by surface plasmon resonance (SPR). The results showed that Protein #5 binds specifically to (i) CD40 of human and cynomolgus origin, (ii) serum albumin of human, mouse and cynomolgus origin, and (iii) FAP of human and cynomolgus origin. No specific binding was detected to mouse CD40 and mouse FAP. Kinetic parameters of Protein #5 are summarized in Table 7. SPR traces of binding of Protein #5 to human CD40, human FAP and human serum albumin are shown in FIG. 7.

TABLE 7

Kinetic parameters of Protein #5 binding to CD40, serum albumin and FAP of different species (human, mouse or cynomolgus).

| Protein Name | $K_{on}$ [$M^{-1}s^{-1}$] | $K_{off}$ [$s^{-1}$] | $K_d$ [nM] | STDEV $K_d$ [nM] | Rmax [RU] | Chi$^2$/Rmax† [%] |
|---|---|---|---|---|---|---|
| Bio-hCD40* | 1.01E+07 | 1.03E−03 | 0.103 | 0.012 | 95 | 7.5 |
| Bio-cCD40* | 8.25E+06 | 8.24E−04 | 0.101 | 0.011 | 116 | 9.6 |
| Bio-mCD40* | | | No specific binding detected | | | |
| HSA | 3.58E+05 | 1.79E−02 | 50 | n.d. | 126 | 2.3 |
| CSA | 5.32E+05 | 2.17E−01 | 409 | n.d. | 134 | 7.6 |
| MSA | 3.15E+05 ! | 1.26E−02 ! | 40 ! | n.d. | 86 | 13.1† |
| hFAP** | 4.09E+05 | 1.26E−04 | 0.307 | 0.019 | 154 | 5 |
| cFAP | 4.32E+05 | 1.46E−04 | 0.339 | n.d. | 110 | 4 |
| mFAP* | | | No specific binding detected | | | |

*The values represent the average of a duplicate measurement
**The values represent the average of a triplicate measurement
† Chi$^2$/Rmax >10% defined as inaccurate fit
! $K_D$ of MSA binding on Protein #5 is overestimated due to the strong nonspecific binding of MSA on the chip n.d.: Standard deviation not determined as no replicates were performed Materials and Methods.

All SPR measurements were performed using a ProteOn XPR36 instrument (BioRad) and a running buffer of PBS pH 7.4 containing 0.005% Tween 20® (PBST). The 1:1 Langmuir model was used for the fitting of SPR traces.

ProteOn setup for Protein #5 binding to CD40 of different species. CD40 proteins (Acro Biosystem) of different species (human, cynomolgus, mouse) were biotinylated with standard methods known in the art, resulting in bio-hCD40, bio-cCD40 and bio-mCD40 proteins. The bio-hCD40, bio-cCD40 and bio-mCD40 proteins were immobilized on an NLC chip (BioRad) to a level of respectively 300 RU, 250 RU and 300 RU. The interaction of Protein #5 with CD40 was measured by injecting Protein #5 in a serial dilution of 3, 1.5, 0.75, 0.38 and 0.19 nM with an association of 120 s and dissociation of 900 s using a constant flow of 100 µl/min. The measurement was repeated two or three times and the targets were regenerated between the individual measurements using 10 mM glycine pH 2 for 18 s at a flow of 100 µl/min. The signals were double referenced against the running buffer (PBST) treated control lanes.

ProteOn setup for Protein #5 binding to serum albumin of different species. First, human FAP (hFAP) was coated on a GLC chip (BioRad) to a level of 700 RU before 50 nM Protein #5 was immobilized as analyte for 120 s (dissociation of 0 s) at constant flow of 100 µl/min to a level of 120 RU. The binding of the serum albumin to Protein #5 was measured by injecting human serum albumin (HSA), cynomolgus serum albumin (CSA) and mouse serum albumin (MSA) in a serial dilution of 100, 33, 11 and 3.7 nM with an association of 120 s and a dissociation of 600 s at a constant flow of 100 µl/min. HSA, CSA and MSA binding was measured serially and the hFAP/Protein #5 complex was regenerated each time with 10 mM glycine pH2 for 18 s at a flow of 100 µl/min. Thus, Protein #5 had to be re-immobilized on hFAP after each regeneration step. The signals were double referenced against the control lanes ((a) PBST running buffer; (b) coated with a non-relevant target to which Protein #5 does not bind). The kinetic was calculated on the first 300 s of dissociation.

ProteOn setup for Protein #5 binding to FAP of different species. hFAP, cynomolgus FAP (cFAP) and mouse FAP (mFAP) were immobilized on a GLC chip (BioRad) in 10 mM Na Acetate buffer pH5.3 to a level of 1200 RU, 800 RU and 2000 RU, respectively. The interaction of FAP and Protein #5 was measured by applying Protein #5 in a serial dilution of 50, 25, 12, 6.5 and 3.13 nM with an association of 120 s and dissociation of 1800 s using a constant flow of 100 µl/min. The targets were regenerated using 10 mM glycine pH 2 and 124 mM $H_3PO_4$. The signals were double referenced against the PBST treated control lanes.

Results and Conclusions

Surface plasmon resonance measurements showed that Protein #5 binds tightly to human and cynomolgus CD40 with essentially identical binding affinities ($K_D$) of 103±12 pM and 101±11 pM, respectively. Protein #5 is not cross-reactive to mouse CD40, potentially due to low sequence identity of the extracellular domain of only 57.5%. Protein #5 showed binding to human serum albumin with a binding affinity ($K_D$) of 50 nM. Furthermore, Protein #5 showed binding to human and cynomolgus FAP with similar binding affinities ($K_D$) of 0.307 nM and 0.339 nM, respectively, while no cross-reactivity could be detected for mouse FAP.

Example 3—Simultaneous Binding of Protein #5 to CD40, FAP and Serum Albumin Analyzed by Surface Plasmon Resonance The following experiment describes a surface plasmon resonance experiment that was performed to analyze the simultaneous binding of a multi-specific protein comprising SEQ ID NO:5 to human CD40, human FAP and human serum albumin, respectively.

Materials and Methods. SPR measurements were performed using a ProteOn XPR36 instrument (BioRad). The running buffer was PBS pH 7.4 containing 0.005% Tween 20® (PBST). Biotinylated human CD40 (bio-hCD40-Fc) was immobilized on a NeutrAvidin coated NLC sensor chip to a level of 550 RUs. In a first analyst step (analyte 1) 25 nM of Protein #5 was immobilized on bio-hCD40 with an association of 120 s and dissociation of 0 s. This first step was directly followed by a second analyte step (analyte 2) during which either PBST, 25 nM Protein #5 or 50 nM hFAP were injected with an association of 120 s and dissociation of 0 s. In a third step (analyte 3), either PBST, 50 nM hFAP or 50 nM HSA were applied with an association of 120 s and dissociation of 600 s (injection scheme: see Table 8). The entire experiment was performed at a constant flow of 100 µl/min. The setup allowed binding of hFAP and HSA only if Protein #5 (analyte 1) was already bound to CD40 (immobilized on the chip). The signals were double referenced to the PBST treated control lane of L6 and A6.

TABLE 8

Injection scheme of the SPR measurement

| Analysis | Symbol | Immobilization | Analyte 1 | Analyte 2 | Analyte 3 |
|---|---|---|---|---|---|
| A1 | diamond | Bio-hCD40-Fc | Protein #5 | hFAP | HSA |
| A2 | triangle | Bio-hCD40-Fc | Protein #5 | hFAP | HSA |
| A3 | cross X | Bio-hCD40-Fc | Protein #5 | Protein #5 | PBST |
| A4 | circle | Bio-hCD40-Fc | Protein #5 | hFAP | hFAP |
| A6 | not depicted (used for referencing) | Bio-hCD40-Fc | PBST | PBST | PBST |

Figure 8:
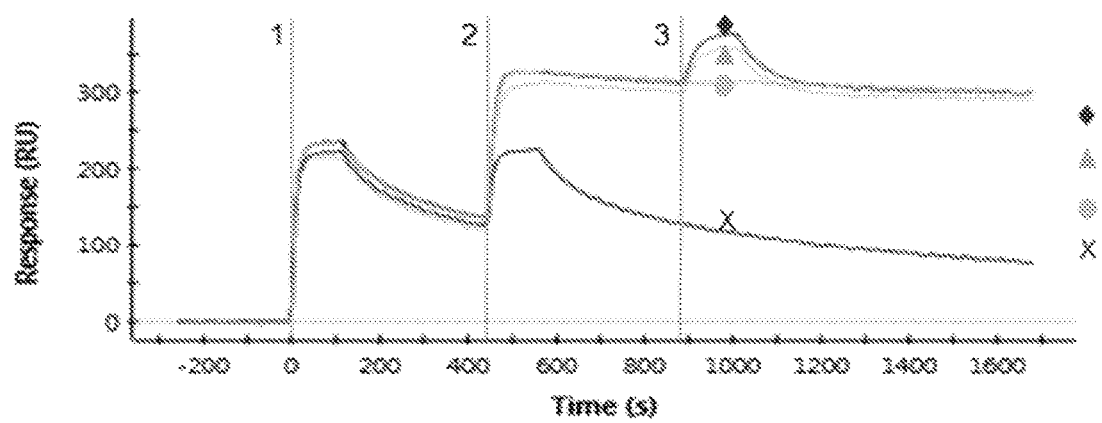
FIG. 8: Surface plasmon resonance (SPR) trace showing simultaneous binding of Protein #5 to hCD40, hFAP and HSA. The vertical lines (1, 2 and 3) indicate the three injections: (1) Binding of Protein #5 to immobilized bio-hCD40; (2) Binding of hFAP (diamond ♦, triangle ▲, and circle ● symbols) or Protein #5 (control; cross×symbol) to the bio-hCD40/Protein #5 complex; (3) Binding of HSA (diamond ♦, triangle ▲ symbols) or hFAP (control; circle ● symbol) to the bio-hCD40/Protein #5/hFAP complex, followed by a 600 s dissociation phase. The injection scheme is depicted in Table 8 using the same symbols. The simultaneous binding of hCD40/Protein #5/hFAP/HSA is measured in duplicate on two different lanes (diamond and triangle symbols).

Results. SPR traces of simultaneous binding of Protein #5 to hCD40, hFAP and HSA are depicted in FIG. 8. Briefly, 550 RUs of biotinylated human CD40 were immobilized on a neutravidin chip. In a first association step, Protein #5 was bound to saturation to hCD40, reaching a total signal of 200 RUs as depicted in FIG. 8, injection 1. In a second association step (FIG. 8, injection 2), hFAP was bound to the complex Protein #5/CD40, resulting in an increase of 200 RUs. It has to be noted that Protein #5 already started to dissociate from hCD40 during the interval of time between injection 1 and injection 2 (loss of 75 RUs). A third association step (FIG. 8, injection 3) resulted in the binding of human serum albumin to the complex hCD40/Protein #5/hFAP (increase of 80 RUs), indicating that simultaneous binding of Protein #5 to all three targets occurred.

In conclusion, the results of the surface plasmon resonance study show that Protein #5 is capable of binding to CD40, FAP and serum albumin simultaneously.

Example 4—Activation of Human B Cells Via CD40

The aim of the study was to assess the biological activity and the FAP-specific mechanism of action of multispecific binding proteins, Protein #5, comprising SEQ ID NO: 5, and Protein #6, comprising SEQ ID NO: 6. Protein #5 and Protein #6 were tested in a cell assay using primary human B cells in presence or absence of FAP-expressing cells. The upregulation of costimulatory molecules, in particular CD86 and CD69, was evaluated as markers of B cell activation mediated by CD40 signaling. An anti-CD40 monoclonal antibody, which has a mechanism of action that is independent on FAP-mediated cross-linking, was used as reference material. Potency, efficacy and FAP-specificity of Protein #5 or Protein #6, in comparison to the reference material, were evaluated.

The in vitro data obtained in the human B cell activation assay showed that Protein #5 and Protein #6 can activate B cells via CD40 activation, as reflected by the upregulation of CD86 and CD69, and that Protein #5 and Protein #6 can activate B cells only in the presence of FAP-positive cells, but not in the presence of FAP-negative cells, confirming a mechanism of action that is strictly dependent on FAP-mediated cross-linking.

Materials and Methods

The in vitro B cell activation assay, FACS staining, flow cytometer settings and antibody dilutions, EC50 determinations and efficacy determinations were performed essentially as described in Example 1.

The anti-CD40 antibody used as a reference as well as the FAP expressing and FAP non-expressing CHO cells were as described in Example 1.

Results

Figure 9:
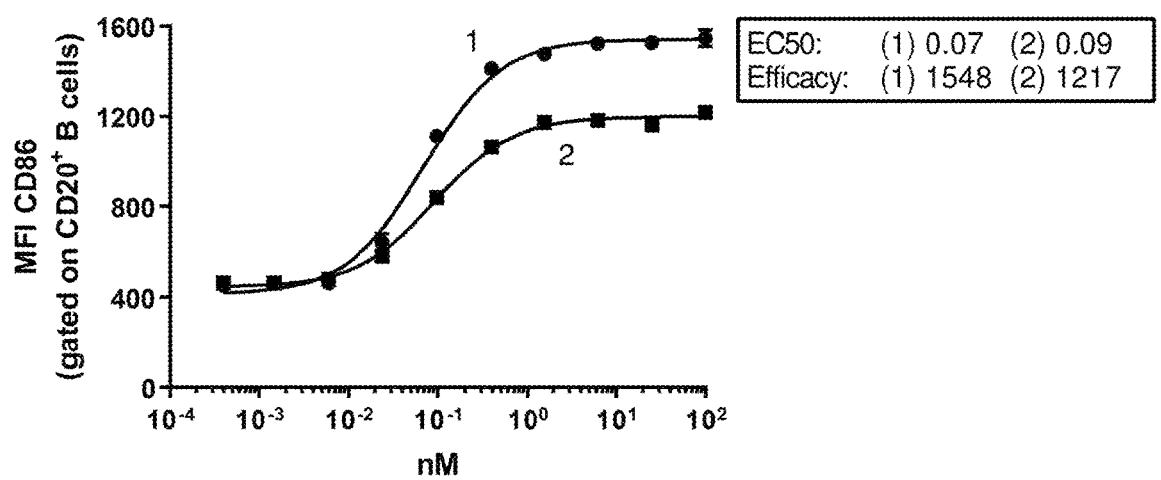
FIG. 9: Protein #5 activates human B cells via CD40 in vitro. Human B cells were cultured in presence of FAP expressing CHO cells and treated with increasing concentrations of Protein #5 (circle symbols) and anti-CD40 mAb (square symbols). Activation of human B cells was assessed in terms of upregulation of CD86 and CD69 (measured as mean fluorescence intensity (MFI) and percentage of cells (%)). Each value depicts the average of duplicated measurements. The shown data are representative of thirteen independent experiments. Error bars show±SEM. The depicted tables show EC50 and efficacy values for Protein #5 (left column) and anti-CD40 mAb (right column).
Figure 9:
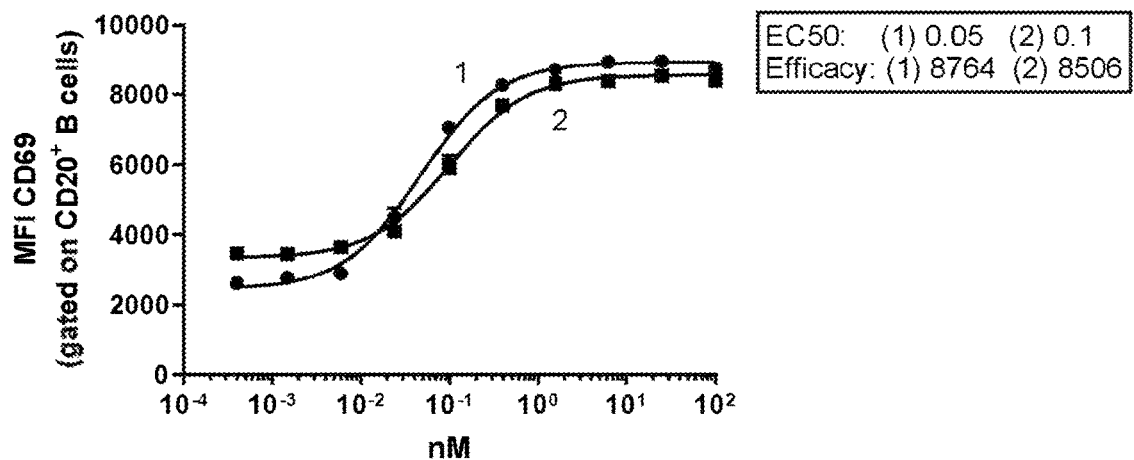
Figure 9:
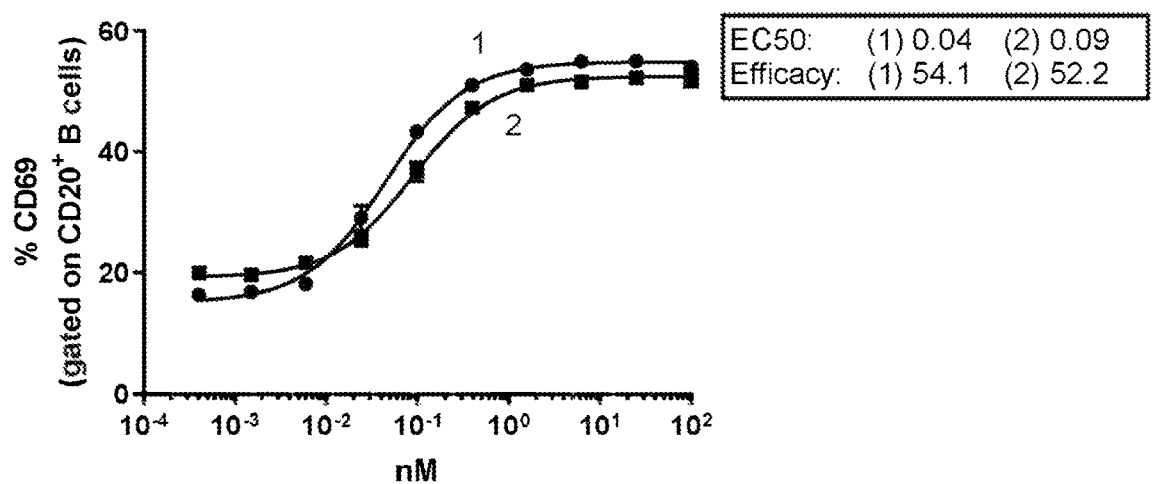
Figure 9:
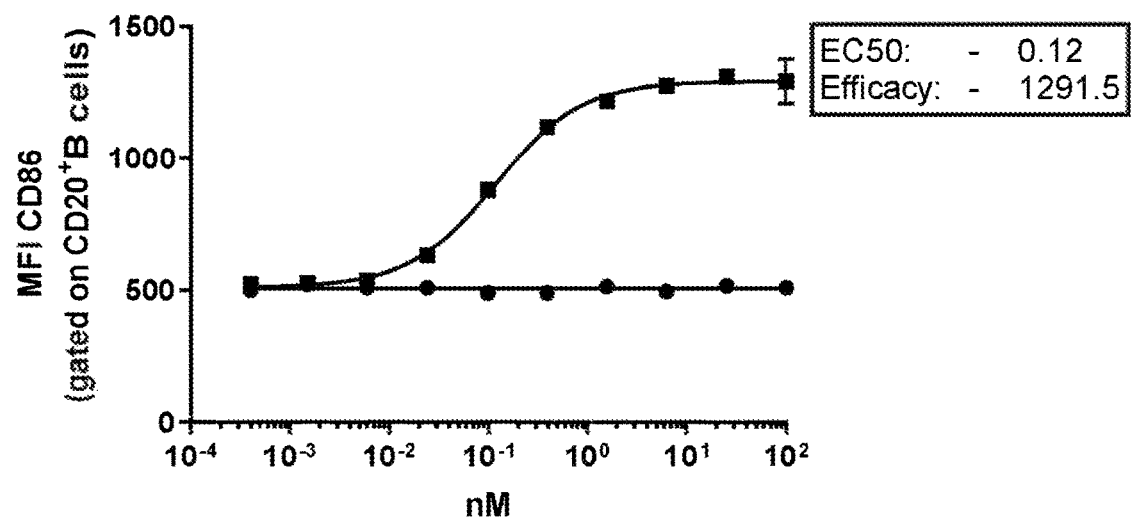
Figure 10:
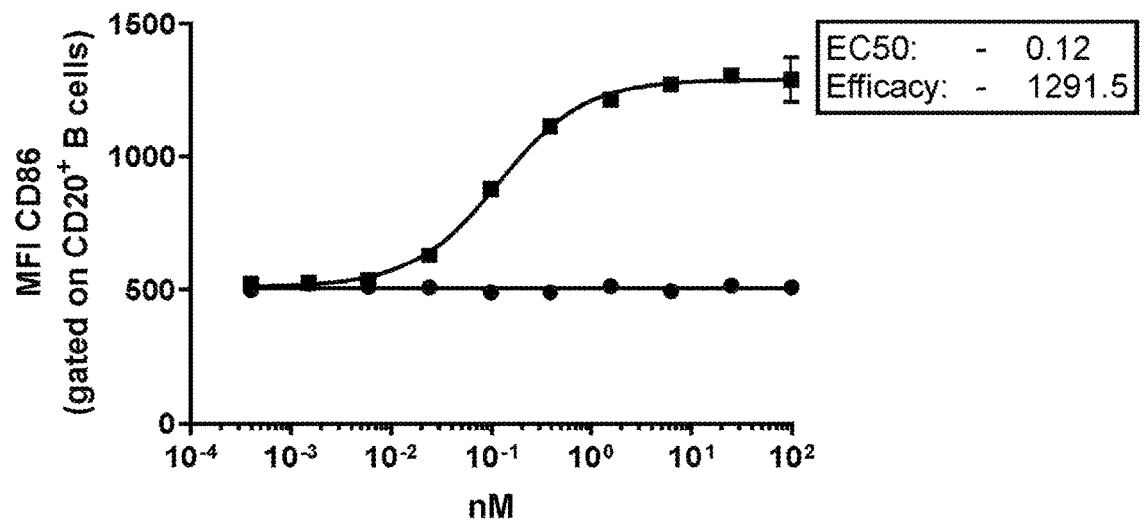
FIG. 10: Activation of human B cells by Protein #5 in vitro is FAP-dependent. The data show that Protein #5 does not induce upregulation of CD86 and CD69 in human B cells in the absence of FAP expressing CHO cells in vitro. The experiment and data plotting were performed as described in FIG. 9, i.e. with Protein #5 (circle symbols) and anti-CD40 mAb (square symbols), but in presence of FAP-negative CHO cells. The shown data are representative of thirteen independent experiments. Error bars show±SEM. The depicted tables show EC50 and efficacy values for anti-CD40 mAb only.
Figure 10:
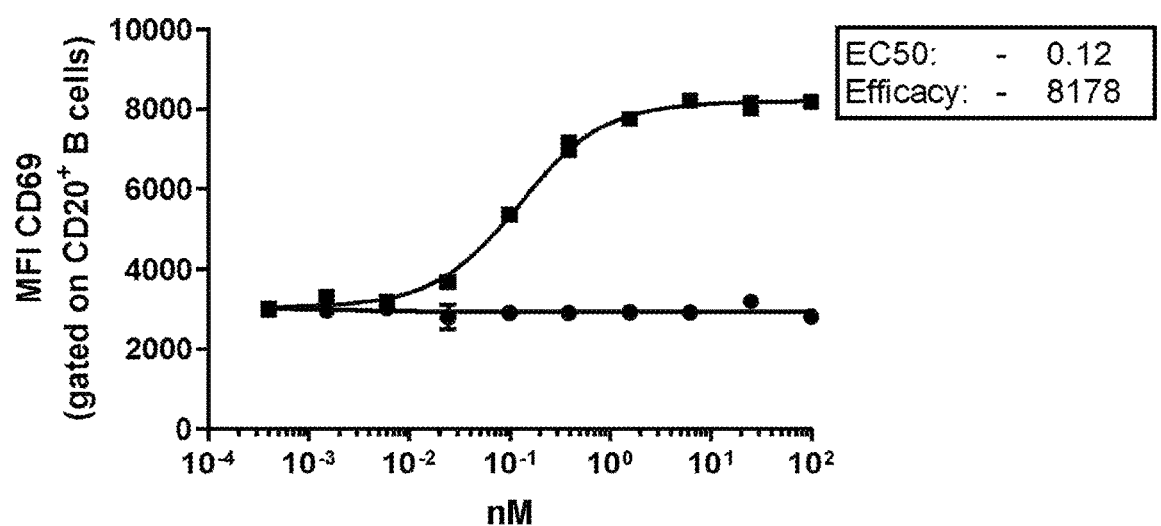
Figure 10:
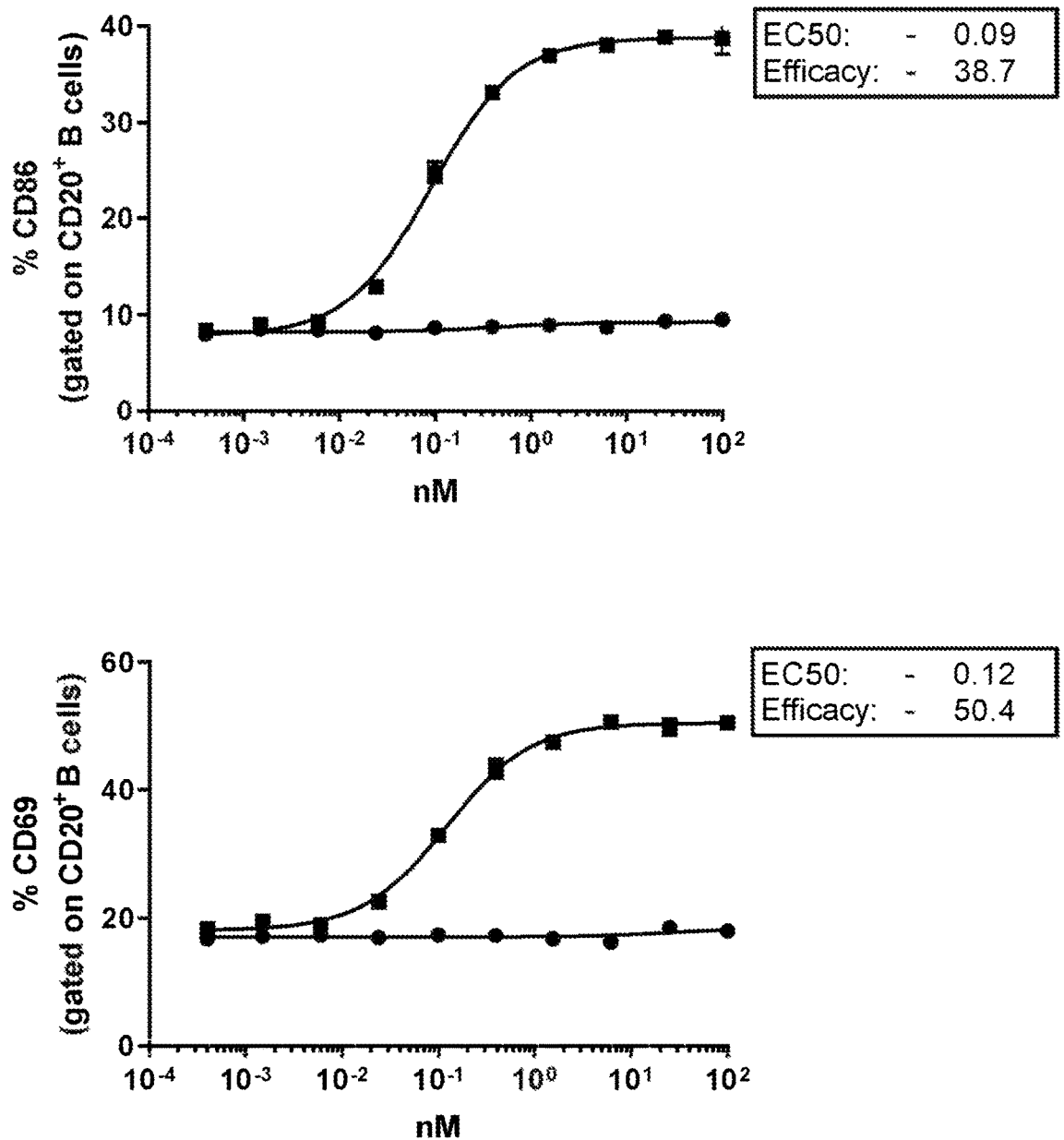

Protein #5 and Protein #6 induce upregulation of co-stimulatory molecules in human B cells with a FAP-dependent mechanism of action. Protein #5 and Protein #6 were assessed for their ability to activate human B cells via CD40 in the presence of FAP-expressing CHO cells. Protein #5 induced upregulation of co-stimulatory molecules CD86 and CD69 in human B cells co-cultured with FAP-expressing CHO cells with an EC50 of 0.04-0.07 nM (FIG. 9). Conversely, Protein #5 did not activate human B cells in presence of non-FAP expressing CHO cells, wild type (WT)-CHO cells (FIG. 10). As expected, the agonistic anti-CD40 mAb induced activation of human B cells independently on FAP expression, activating B cells either with FAP-CHO or WT-CHO. Similar results as for Protein #5 were obtained for Protein #6.

Conclusions

Protein #5 and Protein #6 induced upregulation of two different co-stimulatory molecules, CD86 and CD69, in primary human B cells only in the presence of FAP-positive CHO cells, but not in the presence of FAP-negative CHO cells, confirming a mechanism of action that is strictly dependent on FAP-mediated cross-linking. Protein #5, in presence of FAP, showed similar potency and efficacy as the comparator anti-CD40 monoclonal antibody. Protein #5 induced the upregulation of co-stimulatory molecules in a dose-dependent manner with an EC50 of 0.04-0.07 nM, in the presence of FAP expressing CHO cells. Similar results were obtained for Protein #6.

Example 5—Activation of Human Dendritic Cells Via CD40

Figure 11:
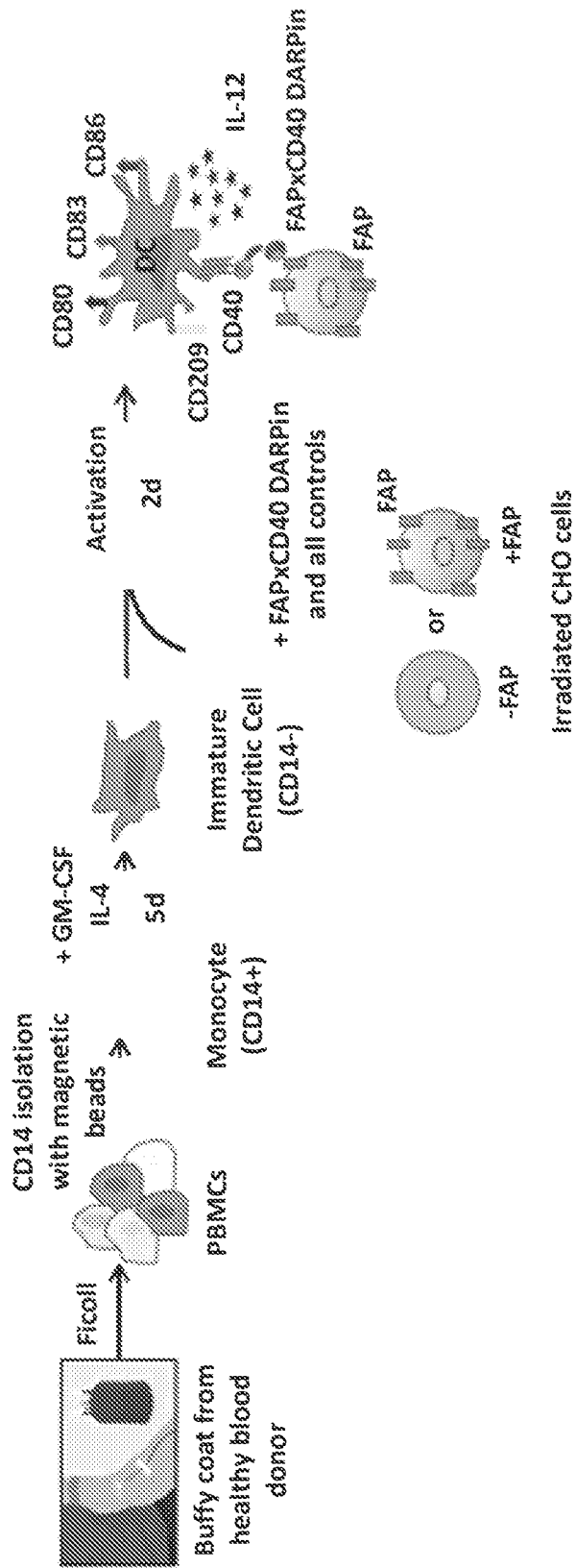
FIG. 11: Schematic representation of a human monocyte-derived dendritic cell (MDDC) activation assay using in vitro differentiated MDDC and irradiated FAP expressing (+FAP) or non-FAP expressing (−FAP) CHO cells.
Figure 12A:
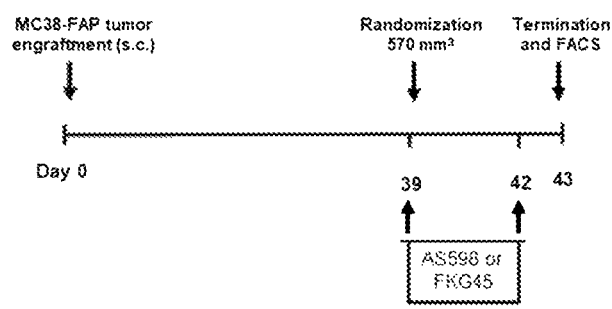
FIGS. 12A and 12B: Schematic representation of the experimental design of anti-tumor efficacy studies in vivo. Mice were inoculated subcutaneously with MC38-FAP colon carcinoma cells on day 0. Mice were randomized into treatment groups based on tumor size and on the days as indicated in FIGS. 12A and 12B for the respective studies. Four different experiments with different schedules were performed.
Figure 12A:
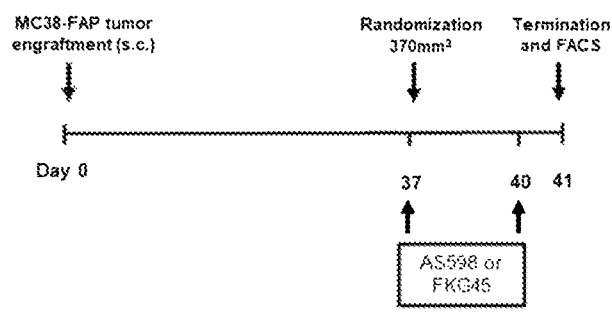
Figure 12B:
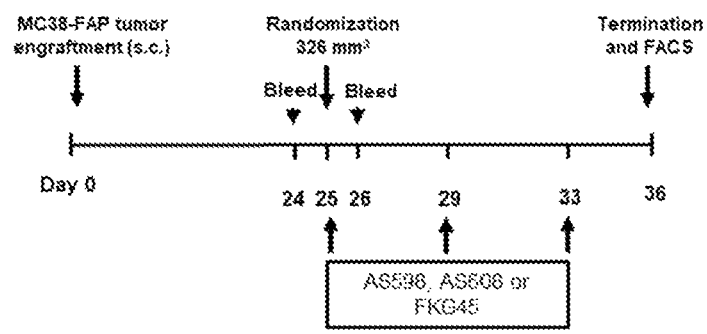
Figure 12B:
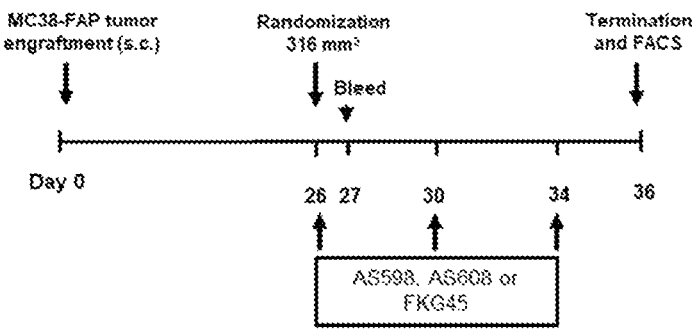

A conceptually similar study as the one described for B cells in Example 4 was performed with human monocyte-derived dendritic cell (MDDC) (see schematic representation in FIG. 11).

The aim of the study was to assess the biological activity and the FAP-specific mechanism of action of multispecific binding proteins, Protein #5, comprising SEQ ID NO: 5, and Protein #6, comprising SEQ ID NO: 6, on MDDC. Protein #5 and Protein #6 were tested in a cell assay using human MDDC in presence or absence of FAP-expressing cells. The upregulation of costimulatory molecules, in particular CD86, CD83 and CD80, and the secretion of IL-12 were evaluated as markers of MDDC activation mediated by CD40 signaling. An anti-CD40 monoclonal antibody, which has a mechanism of action that is independent on FAP-mediated cross-linking, was used as reference material. Potency, efficacy and FAP-specificity of Protein #5 or Protein #6, in comparison to the reference material, were evaluated.

The in vitro data obtained in the human MDDC activation assay showed that Protein #5 and Protein #6 can activate MDDC via CD40 activation, as reflected by the upregulation of the costimulatory molecules and the secretion of IL-12, and that Protein #5 and Protein #6 can activate MDDC only in the presence of FAP-positive cells, but not in the presence of FAP-negative cells, confirming a mechanism of action that is strictly dependent on FAP-mediated cross-linking. Protein #5 was able to induce the upregulation of co-stimulatory molecules and the secretion of IL-12 in a dose-dependent manner with an EC50 of 0.03-7.67 nM and 0.83-7.63 nM, respectively, in the presence of FAP expressing CHO cells, but not in the presence of FAP negative CHO cells. Similar results were obtained with Protein #6.

In conclusion, this study showed that Protein #5 and Protein #6 are able to activate human MDDC via CD40 in vitro, in a FAP-dependent manner.

Example 6—Protein #7 Demonstrated Anti-Tumor Activity In Vivo

The following Example evaluated the dose-dependent in vivo efficacy of repeated doses of the multi-specific binding protein, DARPin® Protein #7, in a murine MC38 colon carcinoma model. Protein #7 is a mouse surrogate for Protein #5 or Protein #6 comprising a FAP binding domain that binds mouse FAP and CD40 binding domains that bind mouse CD40. The MC38 carcinoma model has previously been shown to be susceptible to CD40 agonist treatment. Since syngeneic mouse tumors such as MC38 have generally been found to express very low levels of stromal FAP compared to the human tumor stroma, the MC38 cell line was transfected to express FAP, thereby mimicking better the FAP expression observed in human tumors.

In the described studies PD1032, PD1033, PD1035 and PD1038, Protein #7 (with a N-terminal His-tag (SEQ ID NO: 57); also called AS598) was tested at dose of 2.5 mg/kg, and in studies PD1032 and PD1033 it was also tested at dose of 12.5 mg/kg. The commercially available anti-CD40 antibody (FGK45; BioXell), which binds mouse CD40, was used as a positive control. A non-FAP binding variant of Protein #7 (called AS608; SEQ ID NO: 67 with a N-terminal His-tag (SEQ ID NO: 57)), in which the FAP binding domain was replaced by a non-binding ankyrin repeat domain, was used as a negative control molecule to demonstrate dependence of the pharmacological activity of Protein #7 on binding to mFAP.

The multi-specific binding proteins of the disclosure, such as, e.g., Protein #7, are intended to activate CD40 locally in the tumor tissue in order to reduce systemic toxicity. Therefore, to assess the safety profile of Protein #7, in comparison to anti-mCD40 antibody, which is known to induce liver toxicity, several parameters of systemic toxicity, including weight loss, serum cytokine and transaminase elevation and liver tissue damage, were determined in addition to tumor growth and inhibition.

Materials and Methods

Tumor experiment: The tumor experiments were performed as shown schematically in FIG. 12. Syngeneic mice (C57BL/6JRj) were inoculated subcutaneously into the right flank region with MC38-mFAP polyclonal tumor cells (day 0). Mice were randomized into treatment groups and treated the same day (PD1032 at day 25, PD1033 at day 39, PD1035 at day 26, PD1038 at day 37). The test articles (AS598, AS608, FGK45) were then administered to the tumor-bearing mice according to the predetermined regimen as shown in Table 9 (see also FIG. 12). Tumor growth was monitored every 3 to 4 days by caliper measurement until day 36, 43, 36 and 40 after inoculation, respectively. On day 36 (PD1032 and PD1035) of the experiment, mice were sacrificed, tumors removed, and immune-phenotyping was performed by flow cytometry. On day 43 (PD1033) and on day 40 (PD1038) of the experiment, mice were sacrificed, tumors removed, and immune-phenotyping was performed by flow cytometry.

PD1032 and PD1035 were two independent main studies of anti-tumor efficacy, while PD1033 and PD1038 were two adjacent studies for tumor environment analysis by FACS. In the main studies, AS598 was administered at doses of 2.5 mg/kg (studies PD1032, PD1035) and 12.5 mg/kg (study PD1032) three times every four days. The non-FAP targeted control AS608 was administered at 2.5 mg/kg three times every four days (study PD1035). In the early termination studies for FACS analysis, AS598 was administered at doses of 2.5 mg/kg (studies PD1033, PD1038) and 12.5 mg/kg (study PD1033) two times with three days in between. The non-FAP targeted control AS608 was similarly administered at dose 2.5 mg/kg two times with three days in between (study PD1038). The anti-CD40 antibody FGK45 was used as positive control in all studies and administered at 5 mg/kg (equal molar dose to AS598 at 2.5 mg/kg) at the same schedule as the DARPin® proteins.

TABLE 9

Study design-experimental groups

| Group | N | Inoculum (s.c.) | Treatment | Dose (mg/kg) | Dosing Route | Treatment Schedule | Termination/FACS |
|---|---|---|---|---|---|---|---|
| PD1032 and PD1035: | | | | | | | |
| 1 | 10 | MC38_mFAP_polyclonal 9×10⁶ cells | Vehicle | | i.p. | D0-4-8 | Spleen and Tumor |
| 2 | 10 | | AS598 | 2.5 mg/kg | i.p. | D0-4-8 | Spleen and Tumor |
| 3 | 10 | | AS598 (PD1032) or AS608 (PD1035) | 2.5 mg/kg (AS608) or 12.5 mg/kg (AS598) | i.p. | D0-4-8 | Spleen and Tumor |
| 4 | 10 | | FGK45 (anti-CD40) | 5 mg/kg | i.p. | D0-4-8 | Spleen and Tumor |

TABLE 9-continued

Study design-experimental groups

| Group | N | Inoculum (s.c.) | Treatment | Dose (mg/kg) | Dosing Route | Treatment Schedule | Termination/ FACS |
|---|---|---|---|---|---|---|---|
| PD1033 and PD1038: | | | | | | | |
| 1 | 5/6 | MC38_mFAP_polyclonal 9×10⁶ cells | Vehicle | | i.p. | D0-3 | Spleen and Tumor |
| 2 | 5/6 | | AS598 | 2.5 mg/kg | i.p. | D0-3 | Spleen and Tumor |
| 3 | 5/6 | | AS598 (PD1033) or AS608 (PD1038) | 2.5 mg/kg (AS608) or 12.5 mg/kg (AS598) | i.p. | D0-3 | Spleen and Tumor |
| 4 | 5/6 | | FGK45 (anti-CD40) | 5 mg/kg | i.p. | D0-3 | Spleen and Tumor |

Note:
N: animal number; Number of mice/group in PD10033 was different from PD1038 (N/N)

Tumor inoculation: Under standard isoflurane anesthesia, 90 (PD1032+PD1033) or 105 (PD1035+PD1038) female C57BL6 mice were inoculated subcutaneously into the right hind flank/back region with MC38-mFAP polyclonal tumor cells (9×10⁶) in 0.2 mL of PBS for tumor development.

Tumor measurement: Tumor measurement was performed twice a week from day 15 (PD1032 and PD1033) or day 14 (PD1035 and PD1038) post tumor inoculation. The length and the width of the tumor was measured with calipers. The tumor volume was calculated with the formula: $(length \times (width)^2 \times \pi)/6$.

Randomization: Group randomization based on tumor volume was performed on day 25, 39, 26 and 37 post tumor inoculation. From the original 90 (PD1032 and PD1033) mice engrafted with tumor, 40 were randomized respectively into 4 sub-groups of 10 animals 25 days after tumor inoculation (PD1032). The 50 mice left were randomized respectively into 4 sub-groups of 5 animals 39 days after tumor inoculation (PD1033). From the original 105 (PD1035 and PD1038) mice engrafted with tumor, 40 were randomized respectively into 4 sub-groups of 10 animals 26 days after tumor inoculation (PD1035). The 65 mice left were randomized respectively into 4 sub-groups of 6 animals 37 days after tumor inoculation (PD1038).

Observations and Data Collection: After group randomization, the animals were checked twice weekly, during which body weight and tumor measurements were performed. The animals were also checked for any effects of tumor growth and treatments on normal behavior such as mobility, visual estimation of food and water consumption, body weight gain/loss, eye/hair matting and any other abnormal effect. Death and observed clinical signs were recorded on the basis of the numbers of animals within each subset.

Sampling: Tumors were removed, weighed and used for FACS and remaining material fixed in Formalin. Spleens were removed and one half used for FACS and the other half fixed in Formalin. Livers were removed and fixed in Formalin. Blood samples were taken at day 24, 26 and 36 for PD1032, day 43 for PD1033, day 27 and 36 for PD1035 and day 41 for PD1038 in Multivette 600Z Gel (Sarstedt #15.1674) and centrifuged at 15,000 rpm for 5 minutes. The serum was harvested and stored at minus 80° C. for possible later analysis.

Statistical analysis: Statistical analysis was performed with the Prism 8.2.0 software (GraphPad Software). All statistic with multiple comparisons were performed by using Kruskal-Wallis non-parametric test followed by Dunn's multiple comparisons test for all groups compared to vehicle. For comparison between two groups for difference, non-parametric Mann-Whitney 2-tail analysis was performed.

Liver enzymes. In murine models as well as in clinical trials in humans, agonistic antibodies against CD40 have been demonstrated to increase significantly, but transiently, liver enzymes such as aspartate aminotransferase (AST) and alanine aminotransferase (ALT). In humans, AST is found in a variety of tissues, including the liver, brain, pancreas, heart, kidneys, lungs, and skeletal muscles. If any of these tissues are damaged, AST will be released into the bloodstream. While increased AST levels are indicative of a tissue injury, it is not specific to the liver per se. By contrast, ALT is found primarily in the liver. Any elevation of the ALT is a direct indication of a liver injury.

Therefore, the levels of AST and ALT were determined in these experiments as a measure of liver toxicity. Measurements were performed at 24-hour time-points after treatment. The 24-hour time point after treatment was the most appropriate based on the literature and in-house time-titration experiments. ALT and AST analyses were performed using the kits MAK052 and MAK055 (Sigma-Aldrich), respectively, according to the manufacturer's guidelines.

Cytokine levels. Blood from MC38-FAP colon carcinoma tumor bearing mice treated according to FIG. 12 was taken 24 hours after the first injection (main studies=PD1032 and PD1035), 24 hours after the second injection (adjacent studies=PD1033 and PD1038) and at study end (main studies=PD1032 and PD1035). 11 different cytokines (TNF-alpha, IL-6, IFN-gamma, IL12p70, MCP-1, MIP-1 alpha, MIP-1 beta, IP-10, IL-10, IL-2 and IL-1 beta) were analyzed using Luminex assays (R&D Systems) according to manufacturer's recommendations.

Immunohistochemistry (IHC) analysis of liver tissue. Livers were harvested 24 h after the first injection, washed in PBS, immediately fixed in formalin and embedded in paraffin blocks. Hematoxylin/Eosin staining was performed on sections of the paraffined-embedded livers and analyzed by a pathologist in blinded manner.

Results

Figure 13A:
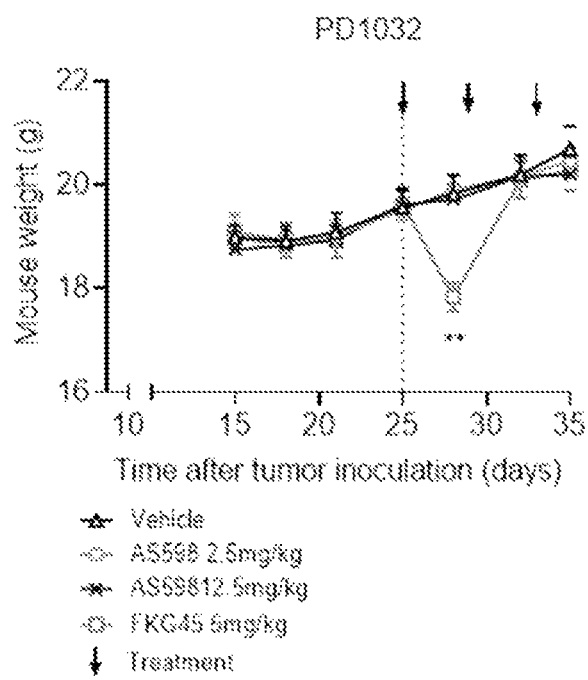
FIGS. 13A and 13B: Mouse body weight during the anti-tumor efficacy studies. Mice were treated as described in FIG. 12. Mean body weights per treatment group (±SEM, n=10) are shown for study PD1032 (FIG. 13A) and study PD1035 (FIG. 13B). Dotted lines indicate the time point of randomization and start of the treatment. The statistical analysis was done using Kruskal-Wallis with multiple comparison to vehicle. Results were considered significant when *p<0.05, p<0.01*p<0.001.
Figure 13B:
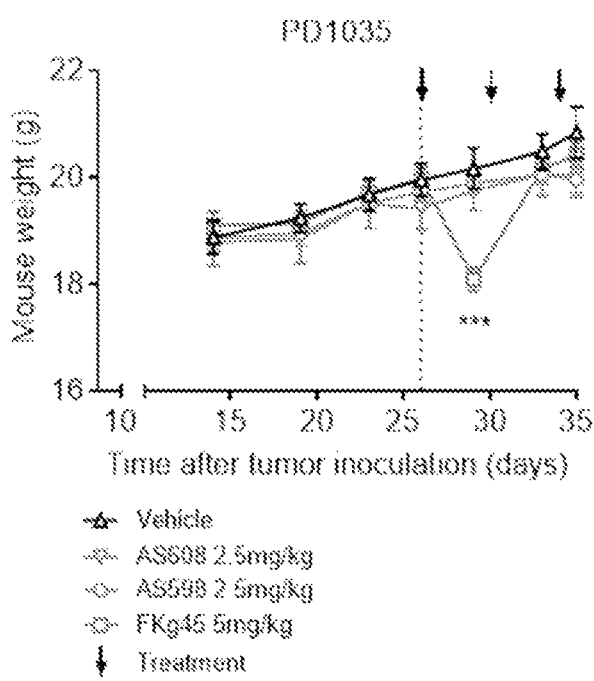

Overall health and weight. During the study duration, no signs of negative health effects or weight decrease of the mice were observed with AS598 treatment (FIGS. 13A and B). In contrast, and consistent with previous reports, FGK45 treatment resulted in significant, but transient, weight loss after the first injection (FIGS. 13A and B).

Tumor growth. Tumor growth was measured every 3-4 days over the duration of the study. The treatment in studies PD1032 and PD1035 was started at days 25 and 26, respectively, when the mean tumor volume exceeded 300 mm³. The mean tumor growth curves of different treatment groups in both studies are shown in FIGS. 14A and B.

Figure 14A:
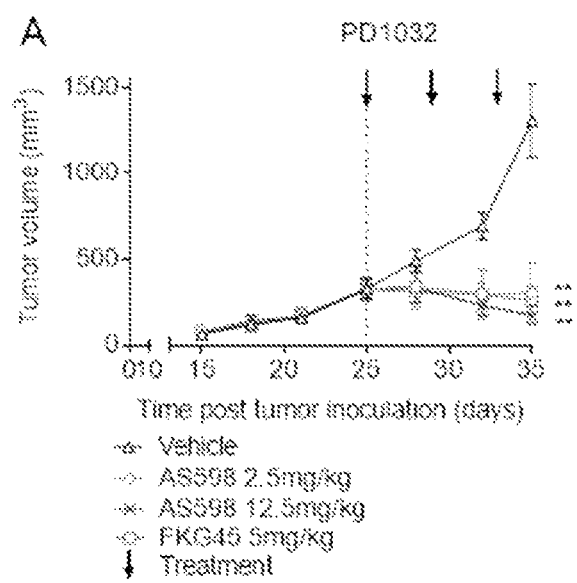
FIGS. 14A and 14B: Mean tumor growth volume during the anti-tumor efficacy studies. Mice were treated as described in FIG. 12 and the tumor volume was measured every 3-4 days. Mean tumor volume per treatment group (±SEM, n=10) is shown for study PD1032 (FIG. 14A) and for study PD1035 (FIG. 14B). The dotted lines indicate the time point of randomization and start of the treatment. The arrows indicate the time points of treatment. The statistical analysis was done using Kruskall-Wallis with multiple comparison to vehicle, or to the negative control AS608 (in parentheses) at termination. Results were considered significant when p<0.01 *p<0.001 ****p<0.0001.

AS598 demonstrated statistically significant anti-tumor efficacy compared to vehicle group at both doses tested (FIGS. 14A and B). The anti-tumor efficacy was similar to the one observed with the positive control anti-CD40 antibody FGK45. The non-FAP-binding control AS608 used in study PD1035 did not have any anti-tumor efficacy, demonstrating that the anti-tumor efficacy observed in this tumor model was FAP-dependent.

In addition to tumor volume measurements, the tumors were dissected from the mice at the end of the study and the tumor weight was determined. The results and conclusions from the tumor weight measurements were consistent with those from the tumor volume measurements (data not shown).

Furthermore, results obtained in the studies PD1033 and PD1038 were consistent with those obtained in the studies PD1032 and PD1035 (data not shown).

Figure 20A:
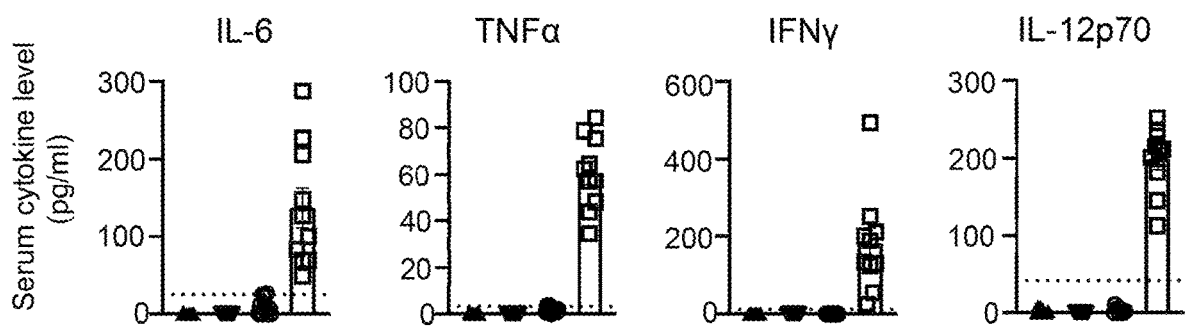
FIGS. 20A, 20B, and 20C: Toxicity assessments.

Blood cytokine levels. FGK45 significantly increased blood levels of eight of the measured cytokines, namely of TNF-alpha, IL-6, IFN-gamma, IL12p70, MCP-1, MIP-1 alpha, MIP-1 beta, and IP-10 (FIG. 20A and data not shown). In contrast, AS598 (2.5 mg/kg or 12.5 mg/kg), AS608 or vehicle did not increase blood levels of any of the measured cytokines (FIG. 20A and data not shown).

Figure 20B:
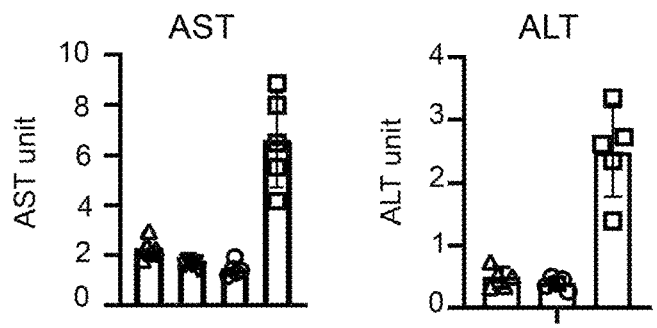

Liver enzymes and injury. As expected, FGK45 induced a significant increase of the ALT levels, which was detected 24 hours after the first injection but not after subsequent injections (FIG. 20B). This was in accordance with the literature and with previous studies in-house. In contrast to FGK45, AS598 did not induce any increases of ALT levels (FIG. 20B). In addition to ALT, also AST was increased 24 hours after the first injection in the FGK45 treatment group, but not in the AS598 or control treated animals (FIG. 20B).

Figure 20C:
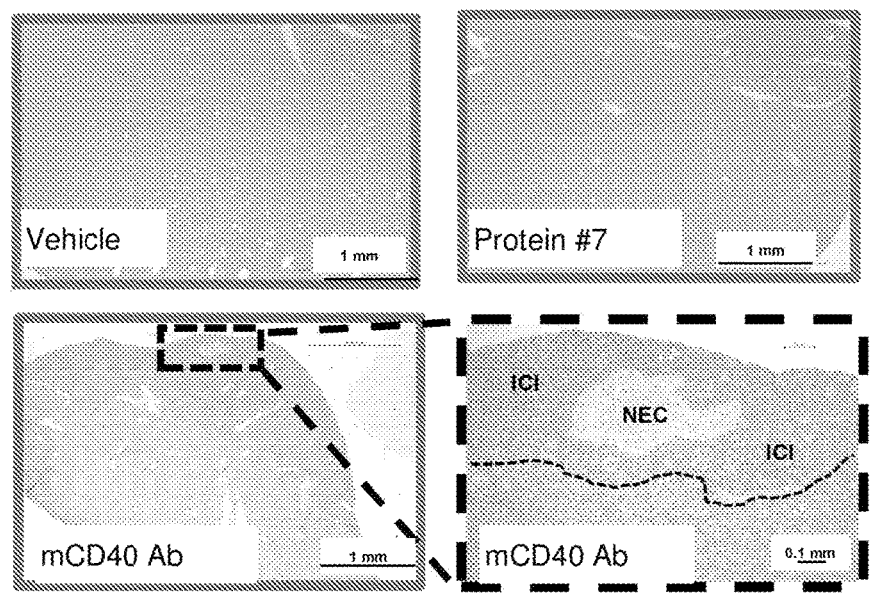

IHC of liver tissue. Histological analysis revealed a diffused tissue damage characterized by vascular-centered multifocal inflammation with aggregates of mononuclear leukocytes, thrombosis and necrosis when mice were treated with anti-mCD40 antibody (FIG. 20C). In contrast, IHC analysis of livers from mice treated with Protein #7 did not show evidence of hepatocellular toxicity, having a similar histological profile to the one observed in vehicle-treated livers (FIG. 20C).

Taken together, in contrast to anti-mCD40 antibody, Protein #7 did not show signs of systemic toxicity in terms of weight loss, elevation of proinflammatory cytokines (e.g. IL-6, TNFα, IFNγ and IL-12p70), increased levels of transaminases (AST and ALT) or liver tissue damage.

Conclusions

A surrogate mouse-specific binding protein, Protein #7, with binding specificity for mouse FAP and mouse CD40 in addition to serum albumin, was generated. Protein #7 tested in murine cell-based in vitro assays showed comparable results as Protein #5 and Protein #6 in human cell-based in vitro assays (see, e.g., Example 4), displaying a strict FAP-dependent activation of CD40 (data not shown). As shown in this Example, Protein #7 (with a N-terminal His-tag; AS598) was also active in vivo and inhibited substantially the progression of FAP-positive tumors. Moreover, in contrast to an anti-mouse CD40 antibody (FGK45), the antitumor activity of Protein #7 was neither associated with elevated blood cytokine levels nor with the tested indicators of hepatotoxicity. Elevated blood cytokine levels and hepatotoxicity manifest as dose limiting toxicities of some of the clinical CD40 activating antibodies. The presented data support a mode of action, both in vitro and in vivo, that is dependent on FAP-mediated crosslinking of CD40 receptor, resulting in a tumor-localized CD40 activation without peripheral or off-tumor organ toxicity.

In conclusion, a tumor-targeted, CD40 agonistic, multi-specific DARPin® protein has been generated, which is able to activate the CD40 receptor locally in FAP-positive tumors and to cause substantial antitumor activity in the absence of systemic toxicity.

Example 7: Protease Activity of FAP in the Presence or Absence of Multi-Specific Binding Proteins This example describes a FAP activity assay that was performed in the presence or absence of various multi-specific binding proteins of the disclosure to determine whether the intrinsic FAP enzymatic activity is inhibited upon binding of the multispecific recombinant proteins.

FAP is a type II single transmembrane serine protease whose expression is highly upregulated on sites of tissue remodeling like tumors (e.g. expressed at the surface of stromal fibroblasts in >90% of epithelial cancers), wound healing, embryonic tissue and sites of inflammations (e.g. atherosclerosis/arthritis), while FAP expression is difficult to detect in non-diseased adult organs. This atypical serine protease has both dipeptidyl peptidase (exopeptidase) and endopeptidase activities, cleaving substrates at a post-proline bond. Structurally, FAP consists of a short cytoplasmic N-terminal sequence (4 aa), a single transmembrane helix (21 aa) and an extracellular domain (735 aa) which forms an eight bladed β-propeller and a α/β-hydrolase domain. FAP is active as a homodimer. The catalytic triad, essential for FAP protease activity, is composed of residues Ser624, Asp702 and His734. The active site is accessible either through the central hole of the beta-propeller or through a cavity at the interface of the beta-propeller and the hydrolase domain.

The protease activity of FAP produces cleavage of a variety of substrates, including neuropeptide Y, type I collagen and a2-antiplasmin but also the substrate Z-GLY-PRO-AMC, which can be cleaved by both the exopeptidase or endopeptidase activity into a product that can be measured with a fluorescence reader.

Molecules tested in the FAP activity assay are summarized in Table 10.

TABLE 10

Recombinant proteins used in the assay

| Molecule No | Name | Format and Description |
|---|---|---|
| 1 | Multi-specific binding protein (SEQ ID NO: 5) | HFCC |
| 2 | Multi-specific binding protein (SEQ ID NO: 7 with N-terminal His-tag) | HF*C*C* |
| 3 | FAP-binding domain only (SEQ ID NO: 2 with N-terminal His-tag) | F |

TABLE 10-continued

Recombinant proteins used in the assay

| Molecule No | Name | Format and Description |
|---|---|---|
| 4 | FAP-binding domain only (SEQ ID NO: 9 with N-terminal His-tag) | F* |
| 5 | Alternative FAP-binding domain (SEQ ID NO: 59 with N-terminal His-tag); This FAP-binding domain served as an assay control | Con |

H Albumin binding domain
F FAP-binding domain comprised in SEQ ID NO: 5
F* FAP-binding domain comprised in SEQ ID NO: 7
C CD40 binding domain comprised in SEQ ID NO: 5
C* CD40-binding domain comprised in SEQ ID NO: 7
Con A FAP-binding domain which partially inhibited FAP activity and served as assay control FAP Activity Assay. The human FAP (hFAP) target was diluted to 0.67 nM in the assay buffer (50 mM Tris, 1 M NaCl, 1 mg/ml BSA, pH 7.5) and 45 µl per well was added to a 96 well plate (leading to a final hFAP concentration of 0.3 nM in the activity assay). Molecules 1-5, as shown in Table 10, were applied at a 500-fold molar excess by adding 5 µl of 3 pM molecule to the target sample (final concentration 150 nM). Finally, 50 µl of 100 pM Z-GLY-PRO-AMC substrate (final concentration 50 pM) was added to obtain a total volume of 100 µl in each well. Molecule No. 5 was used as control to show partial inhibition of the FAP activity.

Prior to measurement, the plate was centrifuged for 2 min at 4000 rpm to remove any assay interfering bubbles. The fluorescence was measured every 5 min over a period of 95 min at 380 nm excitation and 460 nm emission using a fluorescence reader with a manual gain set at 105%. Quadruplet measurements were performed and illustrated as mean and standard deviation.

Results. In a first step, dose response curves were measured using FAP concentrations from 0.01 nM up to 1.2 nM at fixed substrate concentration of 50 pM. A linear time-dependent signal increase was observed at an rhFAP target concentration of 0.3 nM over a time period of 95 min (measured every 5 minutes with an $R^2$ of 0.999). To determine the effect of protein binding on the enzymatic activity of FAP, the assay was conducted under FAP saturating conditions by adding the FAP-binding-molecules (e.g. Molecule No. 1 (SEQ ID NO: 5)) in a 500-fold molar (150 nM) excess over FAP (0.3 nM). This concentration of Molecule No. 1 (SEQ ID NO: 5) was 500-fold above the binding affinity of Molecule No. 1 (SEQ ID NO: 5) against human FAP (Kd=0.3 nM).

Figure 15:
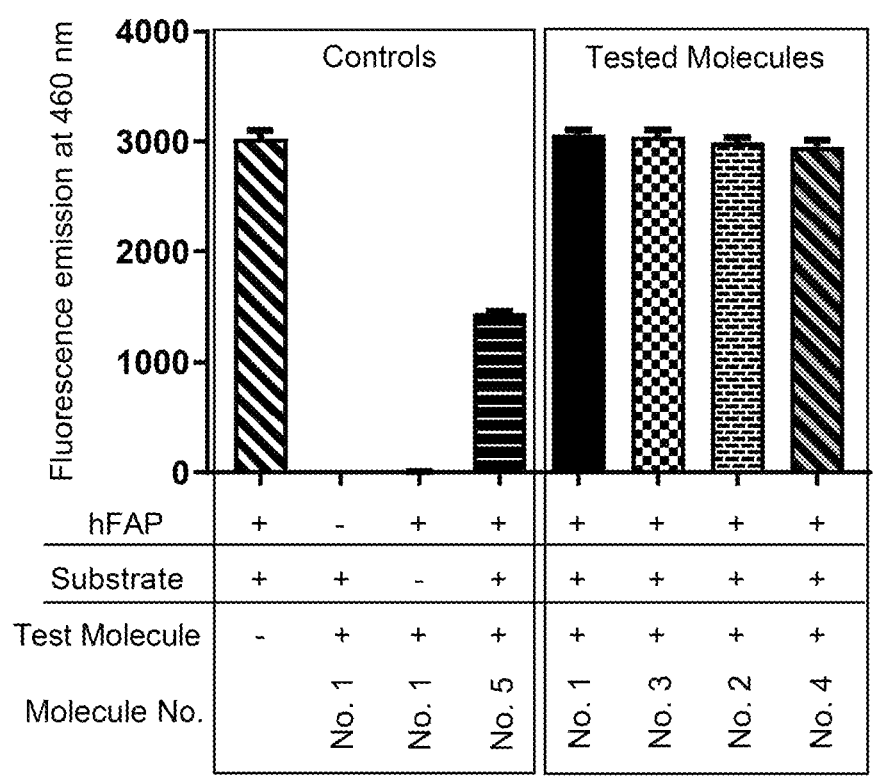
FIG. 15: Average FAP activity in presence of various FAP-specific recombinant binding proteins. Conversion of substrate Z-GLY-PRO-AMC into a fluorescence product by recombinant human FAP was measured in the presence or absence of various recombinant proteins. FAP activity after incubation for 95 minutes is shown. In comparison to the FAP activity in the absence of a test molecule (first control: hFAP and substrate), all tested recombinant proteins containing a FAP-binding domain (Molecules 1-4) showed no inhibitory effect on the FAP enzymatic activity. Partial inhibition of FAP activity was observed for Molecule No. 5 (used as an assay control). Average FAP activity and standard deviation are shown from quadruplet measurements.

As summarized in FIG. 15, Molecules Nos. 1-4 did not inhibit the intrinsic dipeptidyl FAP enzymatic activity. Partial FAP activity inhibition was observed by an alternative FAP-binding molecule (Molecule No. 5), which was used as an assay control.

Conclusion. Binding of multi-specific binding proteins of the disclosure, such as Molecule No. 1 (HFCC) or Molecule No. 2 (HF*C*C*), or of their FAP-binding domains (F or F*), to FAP did not affect the protease activity of FAP, as measured by its ability to cleave the fluorogenic substrate Z-GLY-PRO-AMC.

Example 8: Preferential Localization and Accumulation of a Multi-Specific Binding Protein in Tumor Tissue This Example describes experiments that were performed to investigate if multi-specific binding proteins of the disclosure can preferentially localize and accumulate in tumor tissue, presumably via binding to FAP expressed in the tumor tissue. For this purpose, the syngeneic MC38-FAP mouse model described in Example 6 was used as a suitable experimental system. Protein #7, also described in Example 6, was used as a representative multi-specific binding protein of the disclosure.

Three different methodologies were used to investigate localization and accumulation of Protein #7 in the tumor tissue, namely SPECT/CT imaging, immunohistochemistry (IHC), and in vivo tissue distribution analysis.

Materials and Methods

Tumor inoculation and treatments: As previously described, mice were subcutaneously inoculated into the right shoulder flank with 9×10$^6$ of MC38-FAP mouse colon carcinoma cells. When tumors reached the size of 500 mm$^3$, mice were injected with approximately 150 KBq of radio-conjugated molecules (Protein #7 or a control DARPin® protein, which has a corresponding four ankyrin repeat domain structure and binds to HSA, but does not bind to FAP or CD40) into the tail vein corresponding to 2.5 mg/kg=50 pg/mouse.

Indium-111 labeling: To label the DARPin® molecules with indium-111, maleimide-DTPA (Chematech, Cat Number: C107), a bifunctional chelator with a specific reactivity toward sulfhydryl (SH) groups, was used to conjugate the radio label to the free SH-group of a cysteine added at the C-terminal end of DARPin® molecules. Molecules were stirred in metal-free PBS (pH 7.4, PSI grade) and 0.05 mM EDTA for 1 hour at room temperature (RT). A 10-fold molar excess of maleimide-DTPA in DMSO (Sigma-Aldrich) over the amount of protein was added and incubated for 1 hour at RT. The reaction solution was transferred into ultrafiltration tubes (Amicon Amicon Ultra 15, 10 kDa MW cut-off) and 4 mL of metal-free PBS was added. Tubes were centrifuged for 6 min at 4000×g at RT. After the spinning, flow-through was discarded, another 4 mL of metal-free PBS was added and the tubes were centrifuged again as described above. Filter supernatant was transferred to a low protein binding Eppendorf reaction tube and concentration was determined. Site-specific conjugation was determined using electron-spray ionization time of flight mass spectrometry (ESI-TOF-MS). The final conjugated products were stored at 4°.

Figure 16A:
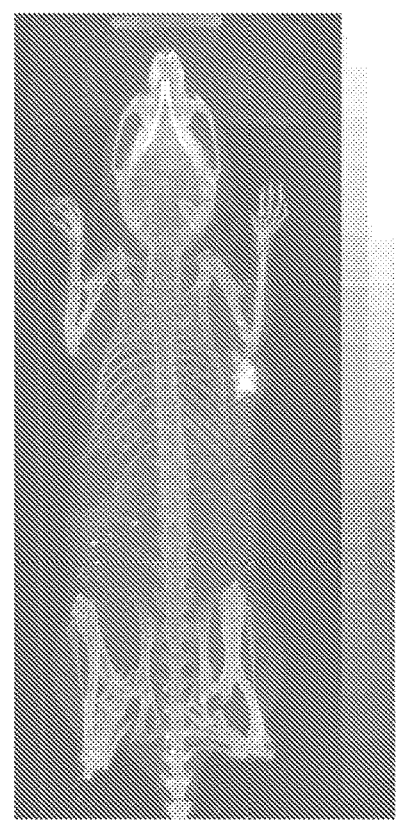
FIGS. 16A, 16B, and 16C.

SPECT/CT imaging study: Single Photon emission computed tomography (SPECT)/X-Ray computed tomography (CT) images were performed with the NanoSPECT/CTPlus camera (version 1.2, Bioscan). Acquisitions of SPECT and CT were performed with the software Nucline (version 1.02). The CT was reconstructed with the software Nucline, whereas for the SPECT the software HISPECT was used (version 1.4.3049, Scivis GmbH). Fusions of SPECT and CT-data were analyzed with the VivoQuant™ post-processing software (Version 3.5, Invicro, USA). Whole-body activity was measured in a gamma counter tube prior to imaging acquisition. SPECT/CT in vivo images were taken from anesthetized mice (by inhalation of a 2% isofluorane/oxygen mixture) at time points 4, 24, 48, 72, 96 hours post injection of 111 In-DARPin® molecules. The image taken 96 hours post-injection is shown in FIG. 16A. Every SPECT projection took 20 sec to 60 sec per frame, resulting in scan time of 15 min to 45 min per image. CT scans were performed with a tube voltage of 55 kVp and a tube current of 145 pA and an exposure time of 1000 msec per projection.

IHC study: Formalin-fixed paraffin embedded (FFPE)-tumor tissue slides were initially deparaffined by 3 cycles of 8 minutes at 70° C. followed by a cycle of 95° C. for 48 minutes at pH 7.4 (EDTA based solution, CC1 condition on Ventana auto-stainer) for antigen retrieval step. Slides were then incubated for 2 hours at 37° C. with rabbit anti-DARPin® antibody conjugate (produced in house, working concentration: 2.0 pg/mL). The anti-DARPin® antibody complex was detected by the HRP system using the Omni Rabbit HRP auto dispenser (Roche Diagnostics) for 20 minutes at 37° C. Finally, the slides were stained with hematoxylin, dehydrated in a gradient of ethanol (70%>90%>100%&100%, 1 minute each step), washed in xylene for 2 minutes and coverslips were applied to the slides with cytoseal mounting medium. The slides were scanned with Vectra Polaris and assessed qualitatively for the DARPin® protein accumulation.

In vivo tissue distribution study: MC38-FAP tumor bearing mice were treated as described above (Tumor inoculation and treatments), and euthanized 4, 24, 48, 72, or 96 hours post-injection. Organs of interest were dissected, weighed and the radioactivity was determined as counts per minute (CPM) with a γ-counter (Packard Cobra II Gamma D5010). CPM values per analyzed organ were then converted to pg DARPin® protein per organ (µg DARPin® protein/organ) using the total amount of DARPin® protein per mouse as reference value. µg DARPin® protein/organ was converted to µg DARPin® protein per gram tissue (µg DARPin® protein/g tissue) and plotted in the graphs as percentage of the injected dose per gram of tissue (% ID/g) and expressed as mean±SD, using 4 mice per time point.

Results

The SPECT/CT imaging experiment revealed a preferential localization and accumulation of the multi-specific binding protein of the disclosure, Protein #7, in tumor tissue (FIG. 16A). Some off-tumor uptake was observed mainly in the spleen, probably because of the on-target distribution induced by the CD40-specific domains of Protein #7.

Figure 16B:
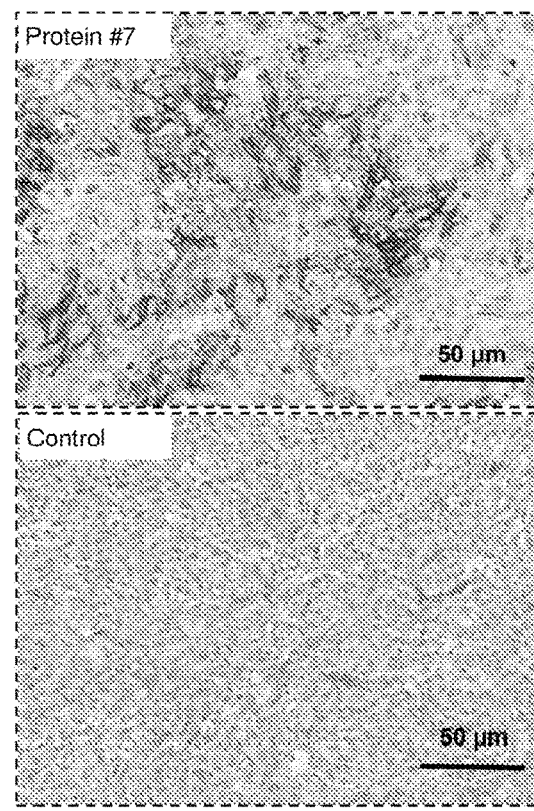

MC38-FAP tumor-bearing mice were sacrificed and tumors analyzed for the presence of DARPin® molecules by IHC. IHC analysis showed a strong presence of the multi-specific binding protein of the disclosure, Protein #7, in the tumor tissue (FIG. 16B, upper panel). In contrast, the negative control DARPin® molecule, which binds HSA but not FAP or CD40, was not detected at significant levels in the tumor tissue (FIG. 16B, lower panel). These data confirmed that tumor localization and accumulation of Protein #7 were mediated by the FAP- and/or CD40-specific binding domains. Any minor signal observed in tumors treated with the negative control was likely caused by the presence of albumin in the tumor microenvironment and binding of the negative control DARPin® molecule to it or was simply due to tissue permeability leading to molecule diffusion.

Figure 16C:
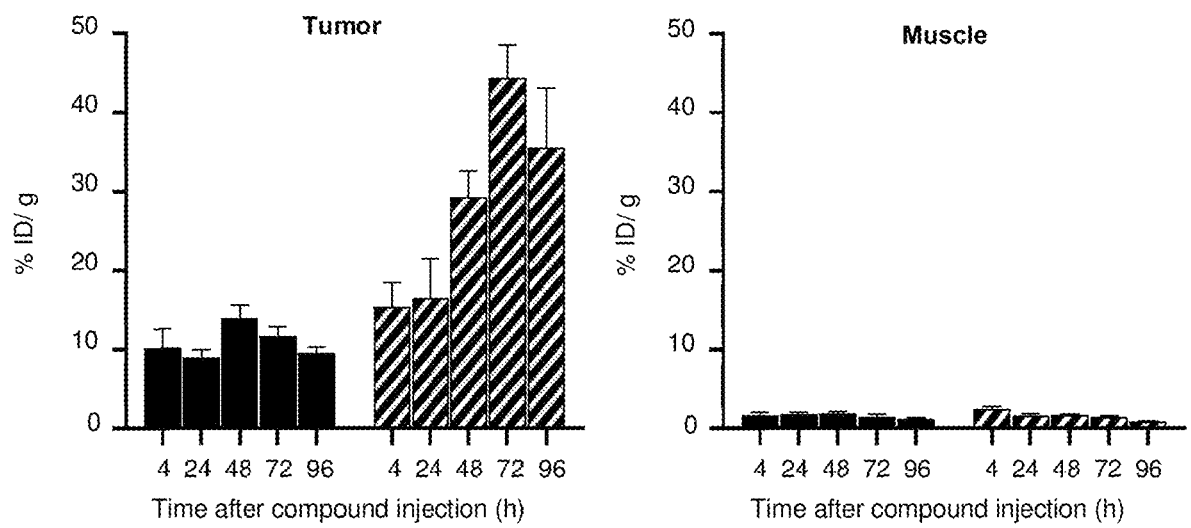

The in vivo tissue distribution study, in which radiolabeled Protein #7 or control DARPin® protein was injected in MC38-FAP tumor-bearing mice, showed an accumulation of the multi-specific binding protein of the disclosure, Protein #7, specifically in tumor tissue (FIG. 16C, left panel), but not in other organs, such as, e.g., muscle (FIG. 16C, right panel), bone marrow, liver and kidney (data not shown). Consistent with the SPECT/CT study, some off-tumor accumulation was only observed in the spleen, most likely because of the expression of CD40 in this lymphoid organ (data not shown). Importantly, the radiolabeled negative control DARPin® protein, which binds HSA but neither FAP nor CD40, did not accumulate in tumor or any other tissue. This confirmed that the tumor localization and accumulation of Protein #7 occurred via a mechanism mediated by FAP- and/or CD40-specific binding.

Conclusions

The data presented in this Example provide experimental evidence that a multi-specific binding protein of the disclosure can preferentially localize and accumulate in tumor tissue in a FAP- and/or CD40-dependent manner. These results are consistent with findings that a FAP-specific ankyrin repeat domain can effectively mediate tumor localization and accumulation of a multi-specific binding protein via binding to tumor-expressed FAP.

Example 9: Tumor Inhibition by a Multi-Specific Binding Protein of the Disclosure is Dependent on FAP Expression in the Tumor Example 6 showed that Protein #7 (with a N-terminal His-tag; AS598) was active in vivo and inhibited substantially the progression of FAP-positive tumors. In this Example, a syngeneic mouse model with a low FAP expression was used to provide further evidence of the FAP-dependent mechanism of action of Protein #7. Specifically, the non-transfected MC38-WT cell line, which generates tumors with very low expression levels of FAP in vivo, was used for performing the efficacy study.

Materials and Methods

Figure 17A:
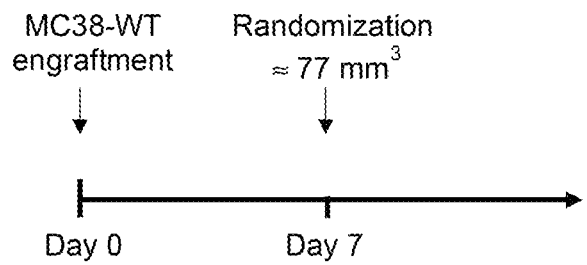
FIGS. 17A and 17B.

Tumor experiment: The tumor experiment was performed as shown schematically in FIG. 17A. Female syngeneic mice (C57BL/6J) were inoculated subcutaneously into the flank region with MC38-WT colon carcinoma tumor cells (day 0). Mice were randomized into treatment groups based on the tumor size of approximately 77 mm$^3$ on the day 7. The test articles (Protein #7 (with a N-terminal His-tag; AS598) and anti-CD40 antibody) were administered to the tumor-bearing mice intraperitoneally (i.p.) according to the predetermined regimen as shown in Table 11. The test articles were administered every 4 days and at equimolar concentrations to each other. Tumor growth was monitored every 3 to 4 days by caliper measurement until the individual mice were terminated due to the ethical tumor volume limit.

TABLE 11

Study design-experimental groups

| Group | N | Inoculum (s.c.) | Treatment | Dose (mg/kg) | Dosing Route | Treatment Schedule |
|---|---|---|---|---|---|---|
| 1 | 10 | MC38-WT | Vehicle | | i.p. | DRO-4-8-12-16 |
| 2 | 10 | | AS598 | 2.5 mg/kg | i.p. | DRO-4-8-12-16 |
| 3 | 10 | | anti-CD40 Ab | 5 mg/kg | i.p. | DRO-4-8 |

N: animal number

Tumor inoculation: Under standard isoflurane anesthesia, mice were inoculated subcutaneously into the flank with 1×10$^6$ MC38-WT tumor cells in 0.1 mL of PBS.

Tumor measurement: Tumor measurement was performed twice a week post-tumor inoculation. The length and the width of the tumor was measured with calipers. The tumor volume was calculated with the formula: V=(L×W×W)/2

Randomization: Randomization was performed based on "Matched distribution" randomization method (StudyDirector™ software) on day 7.

Observations and Data Collection: After tumor cell inoculation, the animals were checked daily for morbidity and mortality. At the time of routine monitoring, the animals were checked for any effects of tumor growth and treatments on behavior such as mobility, food and water consumption, body weight gain/loss and any other abnormalities. Mortality and observed clinical signs were recorded for individual animals.

Statistical analysis. The statistical analysis was done using Kruskal-Wallis non-parametric test followed by Dunn's multiple comparisons test for all groups compared to vehicle. Results were considered significant when $*p<0.05$ $p<0.01 *p<0.001$.

Results and Conclusions

Figure 17B:
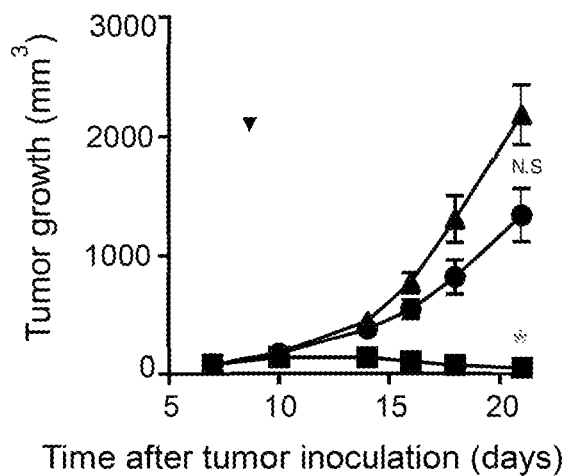

As shown in FIG. 17B, Protein #7 did not show any statistically significant anti-tumor efficacy compared to vehicle in this $FAP^{LOW}$ tumor model, thus providing further evidence of the FAP-dependent mechanism of action of Protein #7. Differently, the anti-CD40 antibody, whose in vivo activity is not related to the presence of FAP in the tumor microenvironment, inhibited tumor progression as expected, thus confirming the susceptibility of the MC38-WT tumor cell line to CD40 agonist.

Example 10: Long-Term Anti-Tumor Effects of a Multi-Specific Binding Protein

This Example describes a study in which MC38-FAP tumor bearing mice were treated and then followed for a longer time period in order to further investigate the full therapeutic potential of a multi-specific binding protein of the disclosure.

Materials and Methods

Figure 14B:
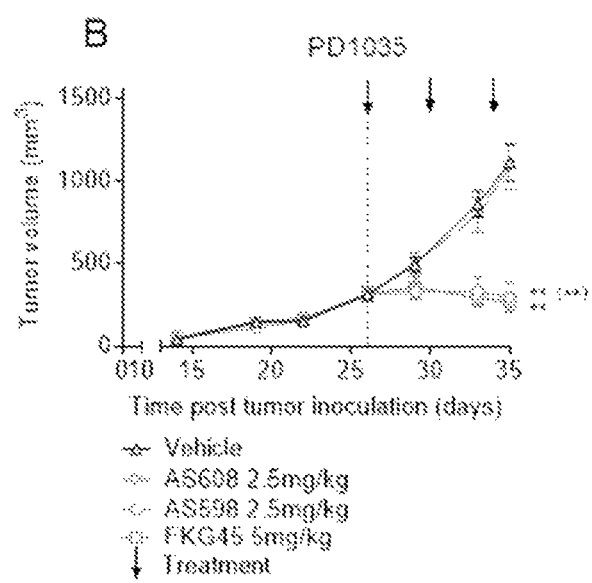

Tumor experiment: The tumor experiment was essentially performed as previously described in Example 6 for Study PD1035 and FIG. 14B, but in this case the mice were monitored over time and sacrificed only when either they showed signs of distress, as defined in the government-approved animal protocol, or when tumors exceeded the endpoint defined by a predetermined tumor size of 2000 $mm^3$. The test articles (Protein #7 (with a N-terminal His-tag; AS598) and a non-FAP binding variant of Protein #7 (AS608; SEQ ID NO: 67 with a N-terminal His-tag (SEQ ID NO: 57)) as a negative control molecule) were administered to the tumor-bearing mice according to the predetermined regimen as shown in Table 12. Tumor growth was monitored every 3 to 4 days by caliper measurement until the individual mice were terminated due to the ethical tumor volume limit.

TABLE 12

Study design-experimental groups

| Group | N | Inoculum (s.c.) | Treatment | Dose (mg/kg) | Dosing Route | Treatment Schedule |
|---|---|---|---|---|---|---|
| 1 | 8 | MC38-FAP | Vehicle | | i.p. | DRO-4-8 |
| 2 | 5 | | AS608 | 5 mg/kg | i.p. | DRO-4-8 |
| 3 | 8 | | AS598 | 5 mg/kg | i.p. | DRO-4-8 |

N: animal number

Tumor inoculation and randomization: Under standard isoflurane anesthesia, mice were inoculated subcutaneously into the flank with $9\times10^6$ MC38-FAP tumor cells in 0.2 mL of PBS. When tumors reached the average size of approximately 300 $mm^3$, mice were randomized as previously described.

Tumor measurement: Tumor measurement was performed twice a week post tumor inoculation. The length and the width of the tumor was measured with calipers. The tumor volume was calculated with the formula: $V=(L\times W\times W\times \pi)/6$ Observations and Data Collection: At the time of routine monitoring, the animals were checked for any effects of tumor growth and treatments on behavior such as mobility, food and water consumption, body weight gain/loss and any other abnormalities. Mortality and observed clinical signs were recorded for individual animals.

Results and Conclusions

Figure 18A:
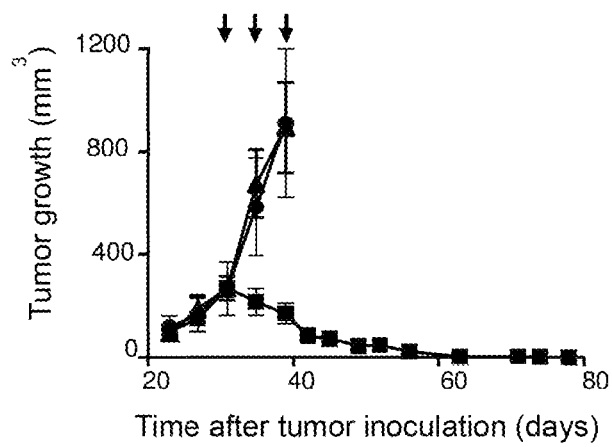
FIGS. 18A and 18B: Long-term effects in anti-tumor efficacy studies. Mice bearing MC38-FAP tumor were treated with vehicle (triangle symbols), AS598 (square symbols), and AS608 (negative control) (round symbols) as described in Example 10 and the tumor volume was measured every 3-4 days. The mean tumor volume per treatment group (±SEM) is shown in (FIG. 18A) and Kaplan-Meier survival curves are shown in (FIG. 18B). Arrows represent the treatment time-points.
Figure 18B:
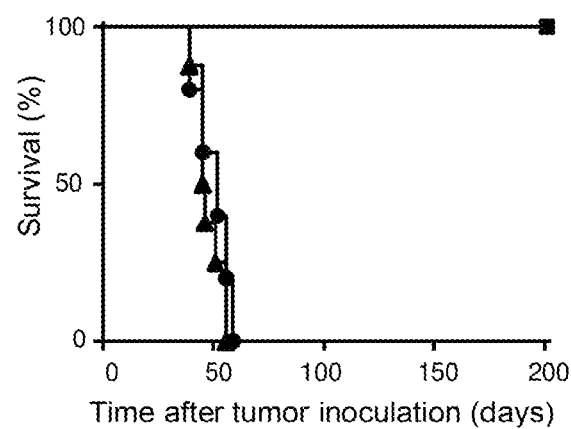

The results provide evidence that Protein #7 was able to inhibit and reject MC38-FAP tumors and to confer long-term protection against tumor relapse. MC38-FAP tumors were no longer detectable approximately 20 days after the last treatment with Protein #7 (FIG. 18A). Furthermore, the mice treated with Protein #7 survived for at least 200 days post-inoculation (i.e. the entire measurement period), demonstrating that the anti-tumor effect of Protein #7 was durable and long-term (FIG. 18B). In contrast, MC38-FAP tumors treated with the negative control, which binds CD40 target, but not FAP target, progressed similarly to the vehicle group (FIG. 18A) and the mice died or had to be sacrificed at a similar rate as in the vehicle group (FIG. 18B). These data confirmed the FAP-dependency of the anti-tumor mechanism of action of Protein #7 in vivo. All together, these data provided evidence that a multi-specific binding protein of the disclosure can elicit strong and durable anti-tumor activity in a FAP-dependent manner in the MC38-FAP tumor mouse model.

Example 11: Induction of Protective Anti-Tumor Immunological Memory by a Multi-Specific Binding Protein Mice bearing well-established MC38-FAP tumors were able to reject tumors to undetectable size after treatment with Protein #7, as shown in FIG. 18. The same tumor free mice were re-challenged with MC38-FAP tumor cells in order to study possible anti-tumor immunological memory induced by Protein #7.

Materials and Methods

Tumor experiment: The tumor experiment and treatments were performed essentially as previously described in Example 6 for Study PD1035 and FIG. 14B and in Example 10 for FIG. 18B, and mice treated with Protein #7 were monitored for about 120 days before being re-challenged with MC38-WT or MC38-FAP tumor cells (1 or $9\times10^6$ cell/mouse, respectively, in 0.2 mL of PBS). In parallel, naïve mice were challenged with exactly the same tumor cells. Tumor growth was monitored every 3 to 4 days by caliper measurement until the individual mice were terminated due to the ethical tumor volume limit.

Results and Conclusions

Figure 19A:
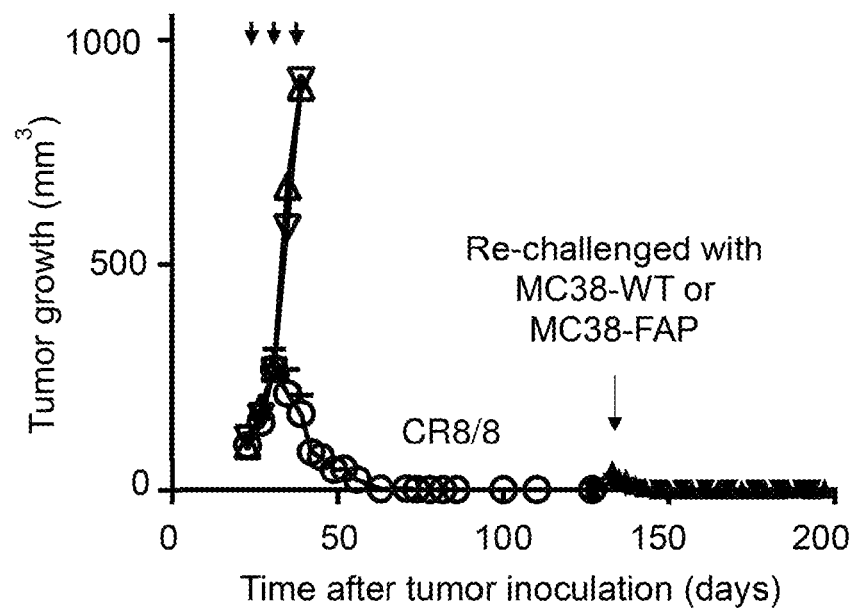
FIGS. 19A and 19B: Induction of anti-tumor immunological memory.
Figure 19B:
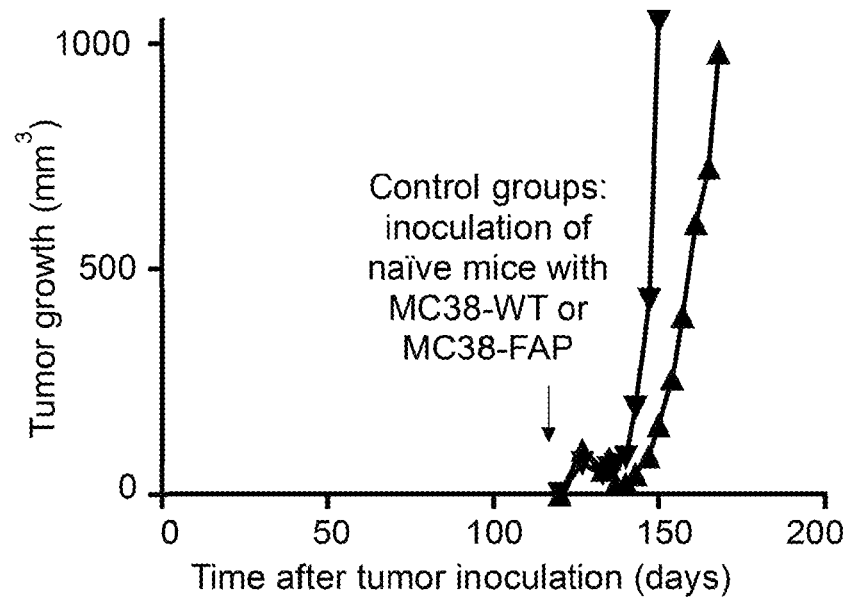

After an initial and weak tumor growth, all mice previously treated with Protein #7 rejected completely the re-challenged MC38-FAP tumors (FIG. 19A), suggesting the presence of an immunological anti-tumor memory response. Interestingly, the same phenomenon was observed in mice re-challenged with MC38-WT tumor cells (FIG. 19A), suggesting that Protein #7 contributed to the establishment of an immunological memory, which was not limited to the FAP-related antigens, but was more broadly directed to tumor antigens. Furthermore, the naïve control groups, inoculated either with MC38-WT or MC38-FAP tumor cells, showed clearly the tumorigenic capacity of the used tumor cells (FIG. 19B), thus confirming that the absence of tumor growth in the re-challenged mice shown in FIG. 19A was due to an immune-mediated anti-tumor response. In conclusion, experimental evidence was obtained suggesting that a multi-specific binding protein of the disclosure has the capacity to induce protective anti-tumor immunological memory and furthermore that this immunological memory is not limited to the FAP-related antigens in the MC38-FAP tumor model.

Example 12: X-Ray Structure Analysis of a Complex of Human Tumor Necrosis Factor Receptor Superfamily Member 5 (hCD40) Bound by a CD40-Specific Binding Protein The aim of this study was to generate and analyze complexes of recombinant hCD40 bound by a CD40-specific binding protein of the disclosure using X-ray crystallography. The CD40-specific binding protein used for this structural analysis was the DARPin® protein with the amino acid sequence of SEQ ID NO: 3.

Materials and Methods

Protein production. hCD40 was expressed in Hi5 cells in the presence of tunicamycin to block glycosylation. Protein from culture supernatant was purified via HIS-Trap, THB-digest, negative HIS-Trap and SEC. Purified hCD40 was mixed in a 1:1.2 ratio with CD40-specific DARPin® protein (SEQ ID NO: 3). Excess of DARPin® protein was removed from the hCD40: DARPin® protein complex via SEC in 10 mM HEPES/NaOH pH 7, 150 mM NaCl. Sample was concentrated to 36.7 mg/ml. This procedure yielded homogenous protein with a purity greater than 95% as judged from Coomassie stained SDS-PAGE.

Crystallization. The purified protein was used in crystallisation trials employing both, a standard screen with approximately 1200 different conditions, as well as crystallisation conditions identified using literature data. Conditions initially obtained were optimised using standard strategies, systemically varying parameters critically influencing crystallisation, such as temperature, protein concentration, drop ratio, and others. These conditions were also refined by systematically varying pH or precipitant concentrations.

Final crystallisation condition:
30% w/v PEG 4K
0.24 M LiSO4
0.1 M Tris pH=8.50
0.35 M NaBr Data collection and processing. Crystals were flash-frozen and measured at a temperature of 100 K. The X-ray diffraction data were collected from complex crystals of hCD40 bound to the ligand DARPin® protein (SEQ ID NO: 3) at the SWISS LIGHT SOURCE (SLS, Villigen, Switzerland) using cryogenic conditions. The crystals belong to space group C 2. Data were processed using the programmes autoPROC, XDS and autoPROC, AIMLESS. The data collection and processing statistics for the DARPin® protein are listed in Table 13 below.

TABLE 13

| Ligand | DARPin hC23 |
|---|---|
| X-ray source | PXII/X10SA (SLS[1]) |
| Wavelength [Å] | 0.9998 |
| Detector | EIGER |
| Temperature [K] | 100 |
| Space Group | C 2 |
| Cell: a; b; c; [Å] | 193.67; 59.56; 81.84 |
| α; β; γ; [°] | 90.0; 107.0; 90.0 |
| Resolution [Å] | 2.29 (2.33-2.29) |
| Unique reflections | 39800 (1932) |
| Multiplicity | 4.3 (4.4) |
| Completeness [%] | 97.8 (97.3) |
| $R_{pim}$ [%] | 4.3 (61.8) |
| $R_{sym}$ [%] | 7.8 (114.9) |
| $R_{meas}$ [%] | 8.9 (130.9) |
| CC1/2 [%] | 99.70 (43.00) |
| Mean(I)/sd | 101.1 (1.3) |

[1]SWISS LIGHT SOURCE (SLS, Villigen, Switzerland)
[2]values in parenthesis refer to the highest resolution bin.

$$^3 R_{sym} = \frac{\sum_h \sum_i^{n_h} |\hat{I}_h - I_{h,i}|}{\sum_h \sum_i^{n_h} I_{h,i}} \text{ with } \hat{I}_h = \frac{1}{n_h}\Sigma_i^{n_h} I_{h,i}$$

where $I_{h,i}$ is the intensity value of the ith measurement of h $$^4 R_{meas} = \frac{\sum_h \sqrt{\frac{n_h}{n_h - 1}\sum_i^{n_h} |\hat{I}_h - I_{h,i}|}}{\sum_h \sum_i^{n_h} I_{h,i}} \text{ with } \hat{I}_h = \frac{1}{n_h}\Sigma_i^{n_h} I_{h,i}$$

where $I_{h,i}$ is the intensity value of the ith measurement of h
[5]calculated from independent reflections $$^6\text{Precision-indicating } R_{pim} = \frac{\sum_h \sqrt{1/(N-1)} \, |I_{hl} - <I_h>|}{\sum_h <I_h>}$$

Structure modelling and refinement. The phase information necessary to determine and analyse the structure was obtained by molecular replacement. A previously solved structure of hCD40 was used as a search model. Subsequent model building and refinement was performed according to standard protocols with COOT and the software package CCP4, respectively. For calculation of the free R-factor, a measure to cross-validate the correctness of the final model, about 4.9% of measured reflections were excluded from the refinement procedure (see Table 14 below). TLS refinement (using REFMAC5, CCp4) was carried out, which resulted in lower R-factors and higher quality of the electron density map. Automatically generated local NCS restraints were applied (keyword "ncsr local" of newer REFMAC5 versions). The ligand parameterisation and generation of the corresponding library files were carried out with GRADE (Global Phasing Limited). The water model was built with the "Find waters"-algorithm of COOT by putting water molecules in peaks of the $F_o$-$F_c$ map contoured at 3.0 with REFMAC5 and checking all waters with validation tool of COOT. The criteria for the list of suspicious waters were: B-factor greater 80 Å[2], 2$F_o$-$F_c$ map less than 1.2 σ, distance to closest contact less than 2.3 Å, or more than 3.5 Å. The suspicious water molecules and those in the ligand binding site (distance to ligand less than 10 Å) were checked manually. The Ramachandran Plot of the final model shows 92.2% of all residues in the most favoured region, 7.8% in the additionally allowed region, and 0.0% in the generously allowed region. No residues are found in the disallowed region (Table 14). Statistics of the final structure and the refinement process are listed in Table 14 below.

TABLE 14[1]

| Ligand | DARPin hC23 |
|---|---|
| Resolution [Å] | 92.61-2.29 |
| Number of reflections | 37835/1962 |
| $R_{cryst}$ [%] | 21.9 |
| $R_{free}$ [%][2] | 25.1 |
| Total number of atoms: | |
| Protein | 4894 |
| Water | 208 |
| Sodium | 2 |
| Deviation from ideal geometry: [3] | |
| Bond lengths [Å] | 0.014 |
| Bond angles [°] | 1.59 |
| Bonded B's [Å][4] | 2.9 |
| Ramachandran plot: [5] | |
| Most favoured regions [%] | 92.2 |
| Additional allowed regions [%] | 7.8 |
| Generously allowed regions [%] | 0.0 |
| Disallowed regions [%] | 0.0 |

Figure 21A:
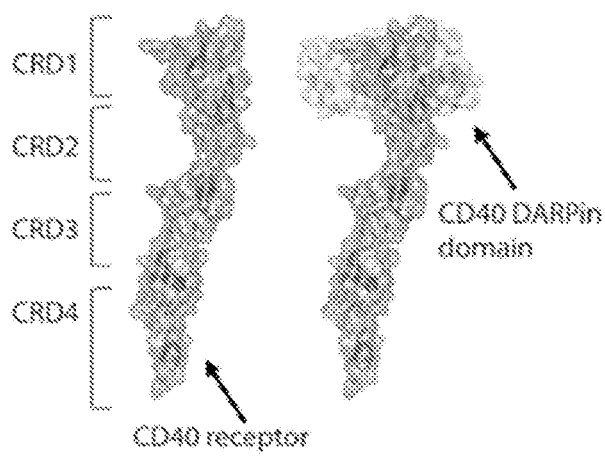
FIGS. 21A and 21B: Structure determination by X-ray crystallography of human tumor necrosis factor receptor superfamily member 5 (hCD40) in complex with a DARPin® protein with the amino acid sequence of SEQ ID NO: 3.
Figure 21B:
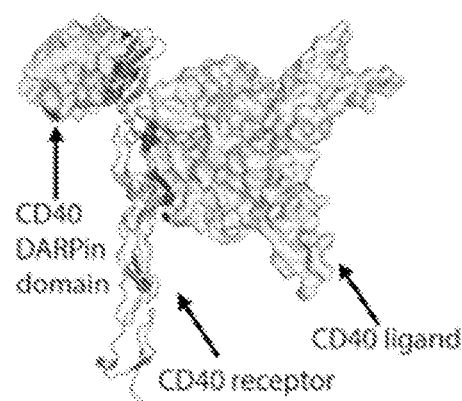

[1]Values as defined in REFMACS, without sigma cut-off
[2]Test-set contains 4.9% of measured reflections
[3] Root mean square deviations from geometric target values
[4] Calculated with MOLEMAN
[5] Calculated with PROCHECK Results The structure was solved and refined to a final resolution of 2.29 Å. The structure analyses using X-ray crystallography revealed that the DARPin® protein (SEQ ID NO: 3) bound to cysteine-rich domain (CRD) 1 (amino acids 23-59) of the CD40 receptor (SEQ ID NO: 51) and that it bound to the CD40 receptor at one side opposite to the binding site of the CD40 ligand (CD40L), indicating the absence of direct binding site competition between the DARPin protein and the CD40L (FIGS. 21A and 21B). The CRD1 domain of the CD40 receptor is located distant from the cell membrane.

It has been reported that potent CD40 agonist antibodies bind membrane distal epitopes of the CD40 receptor (Yu et al., Cancer Cell 33, 664-675 e664 (2018)). Similarly, the X-ray crystallography study described in this Example showed that the CD40-specific binding protein (SEQ ID NO: 3) interacts with the CRD1 of CD40 receptor, distant from the cell membrane. As it has already been suggested for CD40 agonist antibodies, a more cell membrane-distant epitope may lead to less steric hindrance, allowing better access to a CD40-specific binding protein comprising a localizer molecule (such as a recombinant protein comprising the amino acid sequence of SEQ ID NO: 5 or SEQ ID NO: 6) and a more efficient clustering, and consequently a more efficient activation, of the CD40 receptor. Moreover, the region of interaction between the CD40-specific binding protein (SEQ ID NO: 3) and CRD1 was shown to be opposite to the binding site of CD40L, suggesting the absence of direct binding competition between the binding protein of the disclosure and the CD40L. A compound that does not compete for CD40L may have an additive or synergistic effect with the ligand, resulting in a better activation of the receptor (see, e.g., Yu et al., loc. cit.; Challa et al., Allergy 54, 576-583 (1999); Pound et al., Int Immunol 11, 11-20 (1999)).

The specification is most thoroughly understood in light of the teachings of the references cited within the specification. The embodiments within the specification provide an illustration of embodiments of the disclosure and should not be construed to limit the scope of the disclosure. The skilled artisan readily recognizes that many other embodiments are encompassed by the disclosure. All publications, patents, and GenBank sequences cited in this disclosure are incorporated by reference in their entirety. To the extent the material incorporated by reference contradicts or is inconsistent with this specification, the specification will supersede any such material. The citation of any references herein is not an admission that such references are prior art to the present disclosure.

Those skilled in the art will recognize, or be able to ascertain using no more than routine experimentation, many equivalents to the specific embodiments of the disclosure described herein. Such equivalents are intended to be encompassed by the following embodiments.

The invention claimed is:

1. A recombinant protein comprising:
    a first ankyrin repeat domain that specifically binds serum albumin;
    a second ankyrin repeat domain that specifically binds fibroblast activation protein (FAP);
    a third ankyrin repeat domain that specifically binds CD40; and
    a fourth ankyrin repeat domain that specifically binds CD40;
    wherein said ankyrin repeat domains are arranged, from the N-terminus to the C-terminus, according to the following formula: (serum albumin binding domain)—(FAP-binding domain)—(CD40 binding domain)—(CD40 binding domain);
    wherein said serum albumin binding domain comprises an amino acid sequence that is at least 90% identical to SEQ ID NO: 1;
    wherein said FAP binding domain comprises an amino acid sequence that is at least 90% identical to SEQ ID NO: 2; and
    wherein each of said CD40 binding domains independently comprises an amino acid sequence that is at least 90% identical to SEQ ID NO: 3.

2. The recombinant protein of claim 1, wherein said FAP binding domain comprises the amino acid sequence of SEQ ID NO: 2 or of SEQ ID NO: 8.

3. The recombinant protein of claim 1, wherein each of said CD40 binding domains comprises the amino acid sequence of SEQ ID NO: 3.

4. The recombinant protein of claim 1, wherein said protein binds to the N-terminal cysteine-rich domain 1 (CRD1) (amino acids 23-59 of SEQ ID NO: 51) of CD40.

5. The recombinant protein of claim 1, wherein each of said CD40 binding domains independently comprises Q at position 8, L at position 15, R at position 143, and/or Q at position 147, wherein the position numbers correspond to the positions in SEQ ID NO: 3.

6. The recombinant protein of claim 1, wherein said serum albumin binding domain comprises the amino acid sequence of SEQ ID NO: 1.

7. The recombinant protein of claim 1, comprising the following formula, from the N-terminus to C-terminus: (serum albumin binding domain)—(linker)—(FAP-binding domain)—(linker)—(CD40 binding domain)—(linker)—(CD40 binding domain), wherein the linker comprises the amino acid sequence of SEQ ID NO: 4.

8. The recombinant protein of claim 1, wherein said FAP binding domain binds human FAP with a $K_D$ value of or below 100 nM, and/or wherein each of said CD40 binding domains binds human CD40 with a $K_D$ value of or below 100 nM, and/or wherein said serum albumin binding domain binds human serum albumin with a $K_D$ value of or below 100 nM.

9. The recombinant protein of claim 1, wherein said protein has a half maximal effective concentration ($EC_{50}$) of from about 0.01 nM to about 10 nM, as assessed by an in vitro human B cell activation assay.

10. A recombinant protein comprising an amino acid sequence that is at least 90% identical to SEQ ID NO: 5, wherein said recombinant protein binds human FAP, human CD40, and human serum albumin with a $K_D$ value of or below 100 nM.

11. The recombinant protein of claim 10, wherein said protein comprises an amino acid sequence that is at least 95% identical to SEQ ID NO: 5.

12. The recombinant protein of claim 10, wherein said protein comprises an amino acid sequence that is at least 98% identical to SEQ ID NO: 5.

13. The recombinant protein of claim 10, wherein said protein has a half maximal effective concentration ($EC_{50}$) of from about 0.01 nM to about 10 nM, as assessed by an in vitro human B cell activation assay.

14. The recombinant protein of claim 10, wherein binding of said protein to FAP does not inhibit the prolyl endopeptidase activity of FAP by more than 25%.

15. A recombinant protein comprising the amino acid sequence of SEQ ID NO: 5.

16. A pharmaceutical composition comprising the recombinant protein of claim 10, and optionally a pharmaceutically acceptable carrier or excipient.

17. A method of treating a medical condition, the method comprising the step of administering to a subject in need thereof a therapeutically effective amount of the recombinant protein of claim 10, wherein said medical condition is cancer, and wherein said cancer is a solid tumor.

18. The recombinant protein of claim 10, wherein said recombinant protein comprises the amino acid sequence of SEQ ID NO: 5 or SEQ ID NO: 6.

19. The method of claim 17, wherein said subject is a human.

* * * * *

SEQUENCE LISTING

```
<160> NUMBER OF SEQ ID NOS: 67

<210> SEQ ID NO 1
<211> LENGTH: 126
<212> TYPE: PRT
<213> ORGANISM: Artificial Sequence
<220> FEATURE:
<223> OTHER INFORMATION: N-terminal HSA binding domain

<400> SEQUENCE: 1

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60
```

Ala Lys Asp Phe Ala Gly Lys Thr Pro Leu His Leu Ala Ala Ala Asp
65                  70                  75                  80

Gly His Leu Glu Ile Val Glu Val Leu Lys Ala Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala
            115                 120                 125

<210> SEQ ID NO 2
<211> LENGTH: 157
<212> TYPE: PRT
<213> ORGANISM: Artificial Sequence
<220> FEATURE:
<223> OTHER INFORMATION: FAP binding domain

<400> SEQUENCE: 2

Asp Leu Gly Lys Lys Leu Leu Glu Ala Ala Arg Ala Gly Gln Asp Asp
1               5                   10                  15

Glu Val Arg Ile Leu Leu Ala Ala Gly Ala Asp Val Asn Ala Lys Asp
                20                  25                  30

Val Leu Gly Trp Thr Pro Leu His Leu Ala Ala Phe Glu Gly His Leu
            35                  40                  45

Glu Ile Val Glu Val Leu Leu Lys Ala Gly Ala Asp Val Asn Ala Lys
50                  55                  60

Asp Lys Lys Gly Trp Thr Pro Leu Gln Leu Ala Ala Arg Thr Gly His
65                  70                  75                  80

Leu Glu Ile Val Glu Val Leu Leu Lys Ala Gly Ala Asp Val Asn Ala
                85                  90                  95

Lys Asp His Ile Gly Ala Thr Pro Leu His Leu Ala Ala Trp Gln Gly
                100                 105                 110

His Pro Glu Ile Val Glu Val Leu Leu Lys Ala Gly Ala Asp Val Asn
            115                 120                 125

Ala Gln Asp Lys Ser Gly Lys Thr Pro Ala Asp Leu Ala Ala Asp Ala
        130                 135                 140

Gly His Glu Asp Ile Ala Glu Val Leu Gln Lys Ala Ala
145                 150                 155

<210> SEQ ID NO 3
<211> LENGTH: 157
<212> TYPE: PRT
<213> ORGANISM: Artificial Sequence
<220> FEATURE:
<223> OTHER INFORMATION: CD40 binding domain

<400> SEQUENCE: 3

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
                20                  25                  30

Thr Trp Gly Phe Thr Pro Leu His Ile Ala Ala Glu Ser Gly His Leu
            35                  40                  45

Glu Ile Val Glu Val Leu Leu Lys Ala Gly Ala Asp Val Asn Ala Lys
    50                  55                  60

Asp Val Gln Gly Arg Thr Pro Leu His Ile Ala Ala His Ser Gly His
65                  70                  75                  80

Leu Glu Ile Val Glu Val Leu Leu Lys Ala Gly Ala Asp Val Asn Ala
                85                  90                  95

```
Lys Asp Phe Arg Gly Trp Thr Pro Leu His Leu Ala Ala Trp Ser Gly
                100                 105                 110

His Leu Glu Ile Val Glu Ile Leu Leu Lys Ala Gly Ala Asp Val Asn
            115                 120                 125

Ala Gln Asp Lys Ser Gly Lys Thr Pro Ala Asp Leu Ala Ala Arg Ala
130                 135                 140

Gly His Gln Asp Ile Ala Glu Val Leu Gln Lys Ala Ala
145                 150                 155

<210> SEQ ID NO 4
<211> LENGTH: 24
<212> TYPE: PRT
<213> ORGANISM: Artificial Sequence
<220> FEATURE:
<223> OTHER INFORMATION: Linker

<400> SEQUENCE: 4

Gly Ser Pro Thr Pro Thr Pro Thr Thr Pro Thr Pro Thr Pro Thr Thr
1                   5                   10                  15

Pro Thr Pro Thr Pro Thr Gly Ser
                20

<210> SEQ ID NO 5
<211> LENGTH: 669
<212> TYPE: PRT
<213> ORGANISM: Artificial Sequence
<220> FEATURE:
<223> OTHER INFORMATION: Full sequence of FAP/CD40 bispecific

<400> SEQUENCE: 5

Gly Ser Asp Leu Gly Lys Lys Leu Leu Glu Ala Ala Arg Ala Gly Gln
1                   5                   10                  15

Asp Asp Glu Val Arg Glu Leu Leu Lys Ala Gly Ala Asp Val Asn Ala
                20                  25                  30

Lys Asp Tyr Phe Ser His Thr Pro Leu His Leu Ala Ala Arg Asn Gly
            35                  40                  45

His Leu Lys Ile Val Glu Val Leu Leu Lys Ala Gly Ala Asp Val Asn
        50                  55                  60

Ala Lys Asp Phe Ala Gly Lys Thr Pro Leu His Leu Ala Ala Ala Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala Gly Ser
            115                 120                 125

Pro Thr Pro Thr Pro Thr Thr Pro Thr Pro Thr Pro Thr Thr Pro Thr
130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Ile Leu Leu Ala Ala Gly Ala
                165                 170                 175

Asp Val Asn Ala Lys Asp Val Leu Gly Trp Thr Pro Leu His Leu Ala
            180                 185                 190

Ala Phe Glu Gly His Leu Glu Ile Val Glu Val Leu Leu Lys Ala Gly
        195                 200                 205

Ala Asp Val Asn Ala Lys Asp Lys Lys Gly Trp Thr Pro Leu Gln Leu
```

```
                 210                 215                 220
Ala Ala Arg Thr Gly His Leu Glu Ile Val Glu Val Leu Leu Lys Ala
225                 230                 235                 240

Gly Ala Asp Val Asn Ala Lys Asp His Ile Gly Ala Thr Pro Leu His
                245                 250                 255

Leu Ala Ala Trp Gln Gly His Pro Glu Ile Val Glu Val Leu Leu Lys
                260                 265                 270

Ala Gly Ala Asp Val Asn Ala Gln Asp Lys Ser Gly Lys Thr Pro Ala
            275                 280                 285

Asp Leu Ala Ala Asp Ala Gly His Glu Asp Ile Ala Glu Val Leu Gln
            290                 295                 300

Lys Ala Ala Gly Ser Pro Thr Pro Thr Pro Thr Thr Pro Thr Pro Thr
305                 310                 315                 320

Pro Thr Thr Pro Thr Pro Thr Pro Thr Gly Ser Asp Leu Gly Lys Lys
                325                 330                 335

Leu Leu Gln Ala Ala Arg Ala Gly Gln Leu Asp Glu Val Arg Glu Leu
                340                 345                 350

Leu Lys Ala Gly Ala Asp Val Asn Ala Lys Asp Thr Trp Gly Phe Thr
            355                 360                 365

Pro Leu His Ile Ala Ala Glu Ser Gly His Leu Glu Ile Val Glu Val
            370                 375                 380

Leu Leu Lys Ala Gly Ala Asp Val Asn Ala Lys Asp Val Gln Gly Arg
385                 390                 395                 400

Thr Pro Leu His Ile Ala Ala His Ser Gly His Leu Glu Ile Val Glu
                405                 410                 415

Val Leu Leu Lys Ala Gly Ala Asp Val Asn Ala Lys Asp Phe Arg Gly
                420                 425                 430

Trp Thr Pro Leu His Leu Ala Ala Trp Ser Gly His Leu Glu Ile Val
            435                 440                 445

Glu Ile Leu Leu Lys Ala Gly Ala Asp Val Asn Ala Gln Asp Lys Ser
            450                 455                 460

Gly Lys Thr Pro Ala Asp Leu Ala Ala Arg Ala Gly His Gln Asp Ile
465                 470                 475                 480

Ala Glu Val Leu Gln Lys Ala Ala Gly Ser Pro Thr Pro Thr Pro Thr
                485                 490                 495

Thr Pro Thr Pro Thr Pro Thr Pro Thr Pro Thr Pro Thr Pro Thr Gly Ser
            500                 505                 510

Asp Leu Gly Lys Lys Leu Leu Gln Ala Ala Arg Ala Gly Gln Leu Asp
            515                 520                 525

Glu Val Arg Glu Leu Leu Lys Ala Gly Ala Asp Val Asn Ala Lys Asp
530                 535                 540

Thr Trp Gly Phe Thr Pro Leu His Ile Ala Ala Glu Ser Gly His Leu
545                 550                 555                 560

Glu Ile Val Glu Val Leu Leu Lys Ala Gly Ala Asp Val Asn Ala Lys
                565                 570                 575

Asp Val Gln Gly Arg Thr Pro Leu His Ile Ala Ala His Ser Gly His
            580                 585                 590

Leu Glu Ile Val Glu Val Leu Leu Lys Ala Gly Ala Asp Val Asn Ala
            595                 600                 605

Lys Asp Phe Arg Gly Trp Thr Pro Leu His Leu Ala Ala Trp Ser Gly
            610                 615                 620

His Leu Glu Ile Val Glu Ile Leu Leu Lys Ala Gly Ala Asp Val Asn
625                 630                 635                 640
```

```
Ala Gln Asp Lys Ser Gly Lys Thr Pro Ala Asp Leu Ala Ala Arg Ala
                645                 650                 655

Gly His Gln Asp Ile Ala Glu Val Leu Gln Lys Ala Ala
            660                 665

<210> SEQ ID NO 6
<211> LENGTH: 669
<212> TYPE: PRT
<213> ORGANISM: Artificial Sequence
<220> FEATURE:
<223> OTHER INFORMATION: Full sequence of FAP/CD40 bispecific

<400> SEQUENCE: 6

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Ala Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Val Leu Gly Trp Thr Pro Leu His Leu Ala
            180                 185                 190

Ala Phe Glu Gly His Leu Glu Ile Val Glu Val Leu Leu Lys Ala Gly
        195                 200                 205

Ala Asp Val Asn Ala Lys Asp Lys Gly Trp Thr Pro Leu Gln Leu
210                 215                 220

Ala Ala Arg Thr Gly His Leu Glu Ile Val Glu Val Leu Leu Lys Ala
225                 230                 235                 240

Gly Ala Asp Val Asn Ala Lys Asp His Ile Gly Ala Thr Pro Leu His
                245                 250                 255

Leu Ala Ala Trp Gln Gly His Pro Glu Ile Val Glu Val Leu Leu Lys
            260                 265                 270

Ala Gly Ala Asp Val Asn Ala Gln Asp Lys Ser Gly Lys Thr Pro Ala
        275                 280                 285

Asp Leu Ala Ala Asp Ala Gly His Glu Asp Ile Ala Glu Val Leu Gln
    290                 295                 300

Lys Ala Ala Gly Ser Pro Thr Pro Thr Pro Thr Thr Pro Thr Pro Thr
305                 310                 315                 320

Pro Thr Thr Pro Thr Pro Thr Pro Thr Gly Ser Asp Leu Gly Lys Lys
                325                 330                 335
```

Leu Leu Gln Ala Ala Arg Ala Gly Gln Leu Asp Glu Val Arg Glu Leu
                340                 345                 350

Leu Lys Ala Gly Ala Asp Val Asn Ala Lys Asp Thr Trp Gly Phe Thr
            355                 360                 365

Pro Leu His Ile Ala Ala Glu Ser Gly His Leu Glu Ile Val Glu Val
370                 375                 380

Leu Leu Lys Ala Gly Ala Asp Val Asn Ala Lys Asp Val Gln Gly Arg
385                 390                 395                 400

Thr Pro Leu His Ile Ala Ala His Ser Gly His Leu Glu Ile Val Glu
                405                 410                 415

Val Leu Leu Lys Ala Gly Ala Asp Val Asn Ala Lys Asp Phe Arg Gly
            420                 425                 430

Trp Thr Pro Leu His Leu Ala Ala Trp Ser Gly His Leu Glu Ile Val
        435                 440                 445

Glu Ile Leu Leu Lys Ala Gly Ala Asp Val Asn Ala Gln Asp Lys Ser
    450                 455                 460

Gly Lys Thr Pro Ala Asp Leu Ala Ala Arg Ala Gly His Gln Asp Ile
465                 470                 475                 480

Ala Glu Val Leu Gln Lys Ala Ala Gly Ser Pro Thr Pro Thr Pro Thr
                485                 490                 495

Thr Pro Thr Pro Thr Pro Thr Thr Pro Thr Pro Thr Pro Thr Gly Ser
            500                 505                 510

Asp Leu Gly Lys Lys Leu Leu Gln Ala Ala Arg Ala Gly Gln Leu Asp
        515                 520                 525

Glu Val Arg Glu Leu Leu Lys Ala Gly Ala Asp Val Asn Ala Lys Asp
    530                 535                 540

Thr Trp Gly Phe Thr Pro Leu His Ile Ala Ala Glu Ser Gly His Leu
545                 550                 555                 560

Glu Ile Val Glu Val Leu Leu Lys Ala Gly Ala Asp Val Asn Ala Lys
                565                 570                 575

Asp Val Gln Gly Arg Thr Pro Leu His Ile Ala Ala His Ser Gly His
            580                 585                 590

Leu Glu Ile Val Glu Val Leu Leu Lys Ala Gly Ala Asp Val Asn Ala
        595                 600                 605

Lys Asp Phe Arg Gly Trp Thr Pro Leu His Leu Ala Ala Trp Ser Gly
    610                 615                 620

His Leu Glu Ile Val Glu Ile Leu Leu Lys Ala Gly Ala Asp Val Asn
625                 630                 635                 640

Ala Gln Asp Lys Ser Gly Lys Thr Pro Ala Asp Leu Ala Ala Arg Ala
                645                 650                 655

Gly His Gln Asp Ile Ala Glu Val Leu Gln Lys Ala Ala
            660                 665

<210> SEQ ID NO 7
<211> LENGTH: 636
<212> TYPE: PRT
<213> ORGANISM: Artificial Sequence
<220> FEATURE:
<223> OTHER INFORMATION: Full sequence of FAP/CD40 bispecific

<400> SEQUENCE: 7

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
 50                  55                  60

Ala Lys Asp Phe Ala Gly Lys Thr Pro Leu His Leu Ala Ala Ala Asp
 65                  70                  75                  80

Gly His Leu Glu Ile Val Glu Val Leu Leu Lys Ala Gly Ala Asp Val
                 85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
            115                 120                 125

Pro Thr Pro Thr Pro Thr Thr Pro Thr Pro Thr Pro Thr Thr Pro Thr
        130                 135                 140

Pro Thr Pro Thr Gly Ser Asp Leu Gly Glu Lys Leu Leu Val Ala Ala
145                 150                 155                 160

Leu Tyr Gly Gln Asp Glu Val Arg Glu Leu Leu Lys Ala Gly Ala
            165                 170                 175

Asp Val Asn Ala Lys Asp Gln Trp Gly Leu Thr Pro Leu His Lys Ala
        180                 185                 190

Ala Leu Gln Gly His Leu Glu Ile Val Glu Val Leu Leu Lys Ala Gly
            195                 200                 205

Ala Asp Val Asn Ala Lys Asp Glu Arg Gly His Thr Pro Leu His Trp
        210                 215                 220

Ala Ala Arg Phe Gly His Leu Glu Ile Val Glu Val Leu Leu Lys Ala
225                 230                 235                 240

Gly Ala Asp Val Asn Ala Gln Asp Gln Lys Gly Tyr Thr Pro Ala Asp
            245                 250                 255

Leu Ala Ala Leu Trp Gly His Glu Asp Ile Ala Glu Val Leu Gln Lys
        260                 265                 270

Ala Ala Gly Ser Pro Thr Pro Thr Pro Thr Thr Pro Thr Pro Thr Pro
            275                 280                 285

Thr Thr Pro Thr Pro Thr Pro Thr Gly Ser Asp Leu Gly Lys Lys Leu
        290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Thr Leu Gly Ser Thr Pro
            325                 330                 335

Leu His Leu Ala Ala Trp Glu Gly His Leu Glu Ile Val Glu Val Leu
        340                 345                 350

Leu Lys Ala Gly Ala Asp Val Asn Ala Lys Asp Ile Glu Gly Arg Thr
            355                 360                 365

Pro Leu His Leu Ala Ala Arg Val Gly His Leu Glu Ile Val Glu Val
        370                 375                 380

Leu Leu Lys Ala Gly Ala Asp Val Asn Ala Lys Asp Ala Tyr Gly Phe
385                 390                 395                 400

Thr Pro Leu His Leu Ala Ala Glu Ser Gly His Leu Glu Ile Val Glu
            405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

```
Glu Val Leu Gln Lys Ala Ala Gly Ser Pro Thr Pro Thr Thr
    450                 455                 460
Pro Thr Pro Thr Pro Thr Thr Pro Thr Pro Thr Pro Gly Ser Asp
465                 470                 475                 480
Leu Gly Lys Lys Leu Leu Gln Ala Ala Arg Ala Gly Gln Leu Asp Glu
                485                 490                 495
Val Arg Glu Leu Leu Lys Ala Gly Ala Asp Val Asn Ala Lys Asp Thr
            500                 505                 510
Leu Gly Ser Thr Pro Leu His Leu Ala Ala Trp Glu Gly His Leu Glu
            515                 520                 525
Ile Val Glu Val Leu Leu Lys Ala Gly Ala Asp Val Asn Ala Lys Asp
545                 550                 555                 560
Glu Ile Val Glu Val Leu Leu Lys Ala Gly Ala Asp Val Asn Ala Lys
                565                 570                 575
Asp Ala Tyr Gly Phe Thr Pro Leu His Leu Ala Ala Glu Ser Gly His
            580                 585                 590
Leu Glu Ile Val Glu Val Leu Leu Lys Ala Gly Ala Asp Val Asn Ala
            595                 600                 605
Gln Asp Lys Ser Gly Lys Thr Pro Ala Asp Leu Ala Ala Arg Ala Gly
610                 615                 620
His Gln Asp Ile Ala Glu Val Leu Gln Lys Ala Ala
625                 630                 635

<210> SEQ ID NO 8
<211> LENGTH: 157
<212> TYPE: PRT
<213> ORGANISM: Artificial Sequence
<220> FEATURE:
<223> OTHER INFORMATION: FAP binding domain

<400> SEQUENCE: 8

Asp Leu Gly Lys Lys Leu Leu Glu Ala Ala Arg Ala Gly Gln Asp Asp
1               5                   10                  15
Glu Val Arg Glu Leu Leu Lys Ala Gly Ala Asp Val Asn Ala Lys Asp
                20                  25                  30
Val Leu Gly Trp Thr Pro Leu His Leu Ala Ala Phe Glu Gly His Leu
            35                  40                  45
Glu Ile Val Glu Val Leu Leu Lys Ala Gly Ala Asp Val Asn Ala Lys
        50                  55                  60
Asp Lys Lys Gly Trp Thr Pro Leu Gln Leu Ala Ala Arg Thr Gly His
65                  70                  75                  80
Leu Glu Ile Val Glu Val Leu Leu Lys Ala Gly Ala Asp Val Asn Ala
                85                  90                  95
Lys Asp His Ile Gly Ala Thr Pro Leu His Leu Ala Ala Trp Gln Gly
            100                 105                 110
His Pro Glu Ile Val Glu Val Leu Leu Lys Ala Gly Ala Asp Val Asn
        115                 120                 125
Ala Gln Asp Lys Ser Gly Lys Thr Pro Ala Asp Leu Ala Ala Asp Ala
    130                 135                 140
Gly His Glu Asp Ile Ala Glu Val Leu Gln Lys Ala Ala
145                 150                 155

<210> SEQ ID NO 9
<211> LENGTH: 124
```

```
<212> TYPE: PRT
<213> ORGANISM: Artificial Sequence
<220> FEATURE:
<223> OTHER INFORMATION: FAP binding domain

<400> SEQUENCE: 9

Asp Leu Gly Glu Lys Leu Leu Val Ala Ala Leu Tyr Gly Gln Asp Asp
1               5                   10                  15

Glu Val Arg Glu Leu Leu Lys Ala Gly Ala Asp Val Asn Ala Lys Asp
            20                  25                  30

Gln Trp Gly Leu Thr Pro Leu His Lys Ala Ala Leu Gln Gly His Leu
        35                  40                  45

Glu Ile Val Glu Val Leu Leu Lys Ala Gly Ala Asp Val Asn Ala Lys
50                  55                  60

Asp Glu Arg Gly His Thr Pro Leu His Trp Ala Ala Arg Phe Gly His
65                  70                  75                  80

Leu Glu Ile Val Glu Val Leu Leu Lys Ala Gly Ala Asp Val Asn Ala
                85                  90                  95

Gln Asp Gln Lys Gly Tyr Thr Pro Ala Asp Leu Ala Ala Leu Trp Gly
            100                 105                 110

His Glu Asp Ile Ala Glu Val Leu Gln Lys Ala Ala
            115                 120

<210> SEQ ID NO 10
<211> LENGTH: 157
<212> TYPE: PRT
<213> ORGANISM: Artificial Sequence
<220> FEATURE:
<223> OTHER INFORMATION: CD40 binding domain

<400> SEQUENCE: 10

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30

Thr Leu Gly Ser Thr Pro Leu His Leu Ala Ala Trp Glu Gly His Leu
        35                  40                  45

Glu Ile Val Glu Val Leu Leu Lys Ala Gly Ala Asp Val Asn Ala Lys
50                  55                  60

Asp Ile Glu Gly Arg Thr Pro Leu His Leu Ala Ala Arg Val Gly His
65                  70                  75                  80

Leu Glu Ile Val Glu Val Leu Leu Lys Ala Gly Ala Asp Val Asn Ala
                85                  90                  95

Lys Asp Ala Tyr Gly Phe Thr Pro Leu His Leu Ala Ala Glu Ser Gly
            100                 105                 110

His Leu Glu Ile Val Glu Val Leu Leu Lys Ala Gly Ala Asp Val Asn
                115                 120                 125

Ala Gln Asp Lys Ser Gly Lys Thr Pro Ala Asp Leu Ala Ala Arg Ala
            130                 135                 140

Gly His Gln Asp Ile Ala Glu Val Leu Gln Lys Ala Ala
145                 150                 155

<210> SEQ ID NO 11
<211> LENGTH: 30
<212> TYPE: PRT
<213> ORGANISM: Artificial Sequence
<220> FEATURE:
<223> OTHER INFORMATION: N-terminal Capping sequence
```

```
<400> SEQUENCE: 11

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: N-terminal Capping sequence

<400> SEQUENCE: 12

Asp Leu Gly Lys Lys Leu Leu Gln Ala Ala Arg Ala Gly Gln Leu Asp
1               5                   10                  15

Glu Val Arg Ile Leu Leu Lys Ala Gly Ala Asp Val Asn Ala
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: N-terminal Capping sequence

<400> SEQUENCE: 13

Asp Leu Gly Lys Lys Leu Leu Gln Ala Ala Arg Ala Gly Gln Leu Asp
1               5                   10                  15

Glu Val Arg Ile Leu Leu Ala Ala Gly Ala Asp Val Asn Ala
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: N-terminal Capping sequence

<400> SEQUENCE: 14

Asp Leu Gly Lys Lys Leu Leu Glu Ala Ala Arg Ala Gly Gln Asp Asp
1               5                   10                  15

Glu Val Arg Ile Leu Leu Ala Ala Gly Ala Asp Val Asn Ala
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: N-terminal Capping sequence

<400> SEQUENCE: 15

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: N-terminal Capping sequence
```

```
<400> SEQUENCE: 16

Asp Leu Gly Ser Lys Leu Leu Gln Ala Ala Arg Ala Gly Gln Leu Asp
1               5                   10                  15

Thr Val Arg Thr Leu Leu Gln Ala Gly Ala Asp Val Asn Ala
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: N-terminal Capping sequence
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 5
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid

<400> SEQUENCE: 17

Asp Leu Gly Xaa Xaa Leu Leu Gln Ala Ala Xaa Xaa Gly Gln Leu Asp
1               5                   10                  15

Xaa Val Arg Xaa Leu Xaa Xaa Xaa Gly Ala Asp Val Asn Ala
            20                  25                  30

<210> SEQ ID NO 18
<211> LENGTH: 28
<212> TYPE: PRT
<213> ORGANISM: Artificial Sequence
<220> FEATURE:
<223> OTHER INFORMATION: C-terminal Capping sequence

<400> SEQUENCE: 18

Gln Asp Lys Ser Gly Lys Thr Pro Ala Asp Leu Ala Ala Arg Ala Gly
1               5                   10                  15

His Gln Asp Ile Ala Glu Val Leu Gln Lys Ala Ala
            20                  25

<210> SEQ ID NO 19
```

```
<211> LENGTH: 28
<212> TYPE: PRT
<213> ORGANISM: Artificial Sequence
<220> FEATURE:
<223> OTHER INFORMATION: C-terminal Capping sequence

<400> SEQUENCE: 19

Gln Asp Ile Phe Gly Lys Thr Pro Ala Asp Ile Ala Ala Asp Ala Gly
1               5                   10                  15

His Glu Asp Ile Ala Glu Val Leu Gln Lys Ala Ala
            20                  25

<210> SEQ ID NO 20
<211> LENGTH: 28
<212> TYPE: PRT
<213> ORGANISM: Artificial Sequence
<220> FEATURE:
<223> OTHER INFORMATION: C-terminal Capping sequence

<400> SEQUENCE: 20

Gln Asp Lys Ser Gly Lys Thr Pro Ala Asp Leu Ala Ala Asp Ala Gly
1               5                   10                  15

His Glu Asp Ile Ala Glu Val Leu Gln Lys Ala Ala
            20                  25

<210> SEQ ID NO 21
<211> LENGTH: 28
<212> TYPE: PRT
<213> ORGANISM: Artificial Sequence
<220> FEATURE:
<223> OTHER INFORMATION: C-terminal Capping sequence

<400> SEQUENCE: 21

Gln Asp Thr Gln Gly Thr Thr Pro Ala Asp Leu Ala Ala Arg Ala Gly
1               5                   10                  15

His Gln Gln Ile Ala Ser Val Leu Gln Gln Ala Ala
            20                  25

<210> SEQ ID NO 22
<211> LENGTH: 28
<212> TYPE: PRT
<213> ORGANISM: Artificial Sequence
<220> FEATURE:
<223> OTHER INFORMATION: C-terminal Capping sequence
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
```

```
<222> LOCATION: 19
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 26
<223> OTHER INFORMATION: Xaa can be any naturally occuring amino acid

<400> SEQUENCE: 22

Xaa Asp Xaa Xaa Gly Xaa Thr Pro Ala Asp Xaa Ala Ala Arg Xaa Gly
1               5                   10                  15

His Gln Xaa Ile Ala Xaa Val Leu Gln Xaa Ala Ala
            20                  25

<210> SEQ ID NO 23
<211> LENGTH: 33
<212> TYPE: PRT
<213> ORGANISM: Artificial Sequence
<220> FEATURE:
<223> OTHER INFORMATION: Ankyrin repeat module
<220> FEATURE:
<221> NAME/KEY: VARIANT
<222> LOCATION: 1
<223> OTHER INFORMATION: Xaa can be any naturally occuring amino acid,
      preferably not cysteine, glycine, or proline
<220> FEATURE:
<221> NAME/KEY: VARIANT
<222> LOCATION: 3
<223> OTHER INFORMATION: Xaa can be any naturally occuring amino acid,
      preferably not cysteine, glycine, or proline
<220> FEATURE:
<221> NAME/KEY: VARIANT
<222> LOCATION: 4
<223> OTHER INFORMATION: Xaa can be any naturally occuring amino acid,
      preferably not cysteine, glycine, or proline
<220> FEATURE:
<221> NAME/KEY: VARIANT
<222> LOCATION: 6
<223> OTHER INFORMATION: Xaa can be any naturally occuring amino acid,
      preferably not cysteine, glycine, or proline
<220> FEATURE:
<221> NAME/KEY: VARIANT
<222> LOCATION: 13
<223> OTHER INFORMATION: Xaa can be any naturally occuring amino acid,
      preferably not cysteine, glycine, or proline
<220> FEATURE:
<221> NAME/KEY: VARIANT
<222> LOCATION: 14
<223> OTHER INFORMATION: Xaa can be any naturally occuring amino acid,
      preferably not cysteine, glycine, or proline
<220> FEATURE:
<221> NAME/KEY: VARIANT
<222> LOCATION: 15
<223> OTHER INFORMATION: Xaa can be any naturally occuring amino acid,
      preferably not cysteine, glycine, or proline
<220> FEATURE:
<221> NAME/KEY: VARIANT
<222> LOCATION: 17
<223> OTHER INFORMATION: Xaa can be any naturally occuring amino acid,
      preferably not cysteine, glycine, or proline
<220> FEATURE:
<221> NAME/KEY: VARIANT
<222> LOCATION: 18
<223> OTHER INFORMATION: Xaa can be any naturally occuring amino acid,
      preferably not cysteine, glycine, or proline
<220> FEATURE:
<221> NAME/KEY: VARIANT
<222> LOCATION: 19
<223> OTHER INFORMATION: Xaa can be any naturally occuring amino acid,
      preferably not cysteine, glycine, or proline
<220> FEATURE:
<221> NAME/KEY: VARIANT
<222> LOCATION: 22
```

```
<223> OTHER INFORMATION: Xaa can be any naturally occuring amino acid,
      preferably not cysteine, glycine, or proline
<220> FEATURE:
<221> NAME/KEY: VARIANT
<222> LOCATION: 26
<223> OTHER INFORMATION: Xaa can be any naturally occuring amino acid,
      preferably not cysteine, glycine, or proline
<220> FEATURE:
<221> NAME/KEY: VARIANT
<222> LOCATION: 27
<223> OTHER INFORMATION: Xaa can be any naturally occuring amino acid,
      preferably not cysteine, glycine, or proline

<400> SEQUENCE: 23

Xaa Asp Xaa Xaa Gly Xaa Thr Pro Leu His Leu Ala Xaa Xaa Xaa Gly
1               5                   10                  15

Xaa Xaa Xaa Ile Val Xaa Val Leu Leu Xaa Xaa Gly Ala Asp Val Asn
            20                  25                  30

Ala

<210> SEQ ID NO 24
<211> LENGTH: 33
<212> TYPE: PRT
<213> ORGANISM: Artificial Sequence
<220> FEATURE:
<223> OTHER INFORMATION: Ankyrin repeat module
<220> FEATURE:
<221> NAME/KEY: VARIANT
<222> LOCATION: 1
<223> OTHER INFORMATION: Xaa can be any naturally occuring amino acid,
      preferably not cysteine, glycine, or proline
<220> FEATURE:
<221> NAME/KEY: VARIANT
<222> LOCATION: 3
<223> OTHER INFORMATION: Xaa can be any naturally occuring amino acid,
      preferably not cysteine, glycine, or proline
<220> FEATURE:
<221> NAME/KEY: VARIANT
<222> LOCATION: 4
<223> OTHER INFORMATION: Xaa can be any naturally occuring amino acid,
      preferably not cysteine, glycine, or proline
<220> FEATURE:
<221> NAME/KEY: VARIANT
<222> LOCATION: 6
<223> OTHER INFORMATION: Xaa can be any naturally occuring amino acid,
      preferably not cysteine, glycine, or proline
<220> FEATURE:
<221> NAME/KEY: VARIANT
<222> LOCATION: 13
<223> OTHER INFORMATION: Xaa can be any naturally occuring amino acid,
      preferably not cysteine, glycine, or proline
<220> FEATURE:
<221> NAME/KEY: VARIANT
<222> LOCATION: 14
<223> OTHER INFORMATION: Xaa can be any naturally occuring amino acid,
      preferably not cysteine, glycine, or proline
<220> FEATURE:
<221> NAME/KEY: VARIANT
<222> LOCATION: 15
<223> OTHER INFORMATION: Xaa can be any naturally occuring amino acid,
      preferably not cysteine, glycine, or proline
<220> FEATURE:
<221> NAME/KEY: VARIANT
<222> LOCATION: 27
<223> OTHER INFORMATION: Xaa is selected from the group consisting of
      asparagine, histidine, or tyrosine

<400> SEQUENCE: 24

Xaa Asp Xaa Xaa Gly Xaa Thr Pro Leu His Leu Ala Xaa Xaa Xaa Gly
1               5                   10                  15

His Leu Glu Ile Val Glu Val Leu Leu Lys Xaa Gly Ala Asp Val Asn
            20                  25                  30
```

Ala

```
<210> SEQ ID NO 25
<211> LENGTH: 33
<212> TYPE: PRT
<213> ORGANISM: Artificial Sequence
<220> FEATURE:
<223> OTHER INFORMATION: Ankyrin repeat module
<220> FEATURE:
<221> NAME/KEY: VARIANT
<222> LOCATION: 1
<223> OTHER INFORMATION: Xaa can be any naturally occuring amino acid,
      preferably not cysteine, glycine, or proline
<220> FEATURE:
<221> NAME/KEY: VARIANT
<222> LOCATION: 3
<223> OTHER INFORMATION: Xaa can be any naturally occuring amino acid,
      preferably not cysteine, glycine, or proline
<220> FEATURE:
<221> NAME/KEY: VARIANT
<222> LOCATION: 4
<223> OTHER INFORMATION: Xaa can be any naturally occuring amino acid,
      preferably not cysteine, glycine, or proline
<220> FEATURE:
<221> NAME/KEY: VARIANT
<222> LOCATION: 6
<223> OTHER INFORMATION: Xaa can be any naturally occuring amino acid,
      preferably not cysteine, glycine, or proline
<220> FEATURE:
<221> NAME/KEY: VARIANT
<222> LOCATION: 11
<223> OTHER INFORMATION: Xaa can be any naturally occuring amino acid,
      preferably not cysteine, glycine, or proline
<220> FEATURE:
<221> NAME/KEY: VARIANT
<222> LOCATION: 14
<223> OTHER INFORMATION: Xaa can be any naturally occuring amino acid,
      preferably not cysteine, glycine, or proline
<220> FEATURE:
<221> NAME/KEY: VARIANT
<222> LOCATION: 15
<223> OTHER INFORMATION: Xaa can be any naturally occuring amino acid,
      preferably not cysteine, glycine, or proline
<220> FEATURE:
<221> NAME/KEY: VARIANT
<222> LOCATION: 27
<223> OTHER INFORMATION: Xaa can be any naturally occuring amino acid,
      preferably not cysteine, glycine, or proline

<400> SEQUENCE: 25

Xaa Asp Xaa Xaa Gly Xaa Thr Pro Leu His Xaa Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 26
<211> LENGTH: 33
<212> TYPE: PRT
<213> ORGANISM: Artificial Sequence
<220> FEATURE:
<223> OTHER INFORMATION: Ankyrin repeat module
<220> FEATURE:
<221> NAME/KEY: VARIANT
<222> LOCATION: 3
<223> OTHER INFORMATION: Xaa can be any naturally occuring amino acid,
      preferably not cysteine, glycine, or proline
<220> FEATURE:
<221> NAME/KEY: VARIANT
<222> LOCATION: 4
<223> OTHER INFORMATION: Xaa can be any naturally occuring amino acid,
      preferably not cysteine, glycine, or proline
<220> FEATURE:
<221> NAME/KEY: VARIANT
```

```
<222> LOCATION: 6
<223> OTHER INFORMATION: Xaa can be any naturally occuring amino acid,
      preferably not cysteine, glycine, or proline
<220> FEATURE:
<221> NAME/KEY: VARIANT
<222> LOCATION: 14
<223> OTHER INFORMATION: Xaa can be any naturally occuring amino acid,
      preferably not cysteine, glycine, or proline
<220> FEATURE:
<221> NAME/KEY: VARIANT
<222> LOCATION: 15
<223> OTHER INFORMATION: Xaa can be any naturally occuring amino acid,
      preferably not cysteine, glycine, or proline

<400> SEQUENCE: 26

Lys Asp Xaa Xaa Gly Xaa Thr Pro Leu His Leu Ala Ala Xaa Xaa Gly
1               5                   10                  15

His Leu Glu Ile Val Glu Val Leu Leu Lys Ala Gly Ala Asp Val Asn
            20                  25                  30

Ala

<210> SEQ ID NO 27
<211> LENGTH: 33
<212> TYPE: PRT
<213> ORGANISM: Artificial Sequence
<220> FEATURE:
<223> OTHER INFORMATION: Ankyrin repeat module
<220> FEATURE:
<221> NAME/KEY: VARIANT
<222> LOCATION: 3
<223> OTHER INFORMATION: Xaa can be any naturally occuring amino acid,
      preferably not cysteine, glycine, or proline
<220> FEATURE:
<221> NAME/KEY: VARIANT
<222> LOCATION: 4
<223> OTHER INFORMATION: Xaa can be any naturally occuring amino acid,
      preferably not cysteine, glycine, or proline
<220> FEATURE:
<221> NAME/KEY: VARIANT
<222> LOCATION: 6
<223> OTHER INFORMATION: Xaa can be any naturally occuring amino acid,
      preferably not cysteine, glycine, or proline
<220> FEATURE:
<221> NAME/KEY: VARIANT
<222> LOCATION: 11
<223> OTHER INFORMATION: Xaa can be any naturally occuring amino acid,
      preferably not cysteine, glycine, or proline
<220> FEATURE:
<221> NAME/KEY: VARIANT
<222> LOCATION: 14
<223> OTHER INFORMATION: Xaa can be any naturally occuring amino acid,
      preferably not cysteine, glycine, or proline
<220> FEATURE:
<221> NAME/KEY: VARIANT
<222> LOCATION: 15
<223> OTHER INFORMATION: Xaa can be any naturally occuring amino acid,
      preferably not cysteine, glycine, or proline

<400> SEQUENCE: 27

Lys Asp Xaa Xaa Gly Xaa Thr Pro Leu His Xaa Ala Ala Xaa Xaa Gly
1               5                   10                  15

His Leu Glu Ile Val Glu Val Leu Leu Lys Ala Gly Ala Asp Val Asn
            20                  25                  30

Ala

<210> SEQ ID NO 28
<211> LENGTH: 157
<212> TYPE: PRT
<213> ORGANISM: Artificial Sequence
<220> FEATURE:
<223> OTHER INFORMATION: FAP binding domain
```

<400> SEQUENCE: 28

Asp Leu Gly Lys Lys Leu Leu Glu Ala Ala Arg Ala Gly Gln Asp Asp
1               5                   10                  15

Glu Val Arg Ile Leu Leu Lys Ala Gly Ala Asp Val Asn Ala Lys Asp
            20                  25                  30

Val Leu Gly Trp Thr Pro Leu His Leu Ala Ala Phe Glu Gly His Leu
        35                  40                  45

Glu Ile Val Glu Val Leu Leu Lys Ala Gly Ala Asp Val Asn Ala Lys
    50                  55                  60

Asp Lys Lys Gly Trp Thr Pro Leu Gln Leu Ala Ala Arg Thr Gly His
65                  70                  75                  80

Leu Glu Ile Val Glu Val Leu Leu Lys Ala Gly Ala Asp Val Asn Ala
                85                  90                  95

Lys Asp His Ile Gly Ala Thr Pro Leu His Leu Ala Ala Trp Gln Gly
                100                 105                 110

His Pro Glu Ile Val Glu Val Leu Leu Lys Ala Gly Ala Asp Val Asn
            115                 120                 125

Ala Gln Asp Lys Ser Gly Lys Thr Pro Ala Asp Leu Ala Ala Asp Ala
        130                 135                 140

Gly His Glu Asp Ile Ala Glu Val Leu Gln Lys Ala Ala
145                 150                 155

<210> SEQ ID NO 29
<211> LENGTH: 157
<212> TYPE: PRT
<213> ORGANISM: Artificial Sequence
<220> FEATURE:
<223> OTHER INFORMATION: FAP binding domain

<400> SEQUENCE: 29

Asp Leu Gly Lys Lys Leu Leu Glu Ala Ala Arg Ala Gly Gln Asp Asp
1               5                   10                  15

Glu Val Arg Ile Leu Leu Lys Ala Gly Ala Asp Val Asn Ala Lys Asp
            20                  25                  30

Val Leu Gly Trp Thr Pro Leu His Leu Ala Ala Phe Glu Gly His Leu
        35                  40                  45

Glu Ile Val Glu Val Leu Leu Lys Ala Gly Ala Asp Val Asn Ala Lys
    50                  55                  60

Asp Lys Lys Gly Trp Thr Pro Leu Gln Leu Ala Ala Arg Thr Gly His
65                  70                  75                  80

Leu Glu Ile Val Glu Val Leu Leu Lys Ala Gly Ala Asp Val Asn Ala
                85                  90                  95

Lys Asp His Ile Gly Ala Thr Pro Leu His Leu Ala Ala Trp Gln Gly
                100                 105                 110

His Pro Glu Ile Val Glu Val Leu Leu Lys Ala Gly Ala Asp Val Asn
            115                 120                 125

Ala Gln Asp Lys Ser Gly Lys Thr Pro Ala Asp Leu Ala Ala Asp Ala
        130                 135                 140

Gly His Glu Asp Ile Ala Glu Val Leu Gln Lys Ala Ala
145                 150                 155

<210> SEQ ID NO 30
<211> LENGTH: 157
<212> TYPE: PRT
<213> ORGANISM: Artificial Sequence
<220> FEATURE:

<223> OTHER INFORMATION: FAP binding domain

<400> SEQUENCE: 30

Asp Leu Gly Lys Lys Leu Leu Glu Ala Ala Arg Ala Gly Gln Asp Asp
1               5                   10                  15

Glu Val Arg Ile Leu Leu Lys Ala Gly Ala Asp Val Asn Ala Lys Asp
            20                  25                  30

Val Leu Gly Trp Thr Pro Leu His Leu Ala Ala Phe Glu Gly His Leu
        35                  40                  45

Glu Ile Val Glu Val Leu Leu Lys Ala Gly Ala Asp Val Asn Ala Lys
    50                  55                  60

Asp Lys Lys Gly Trp Thr Pro Leu Gln Leu Ala Arg Thr Gly His
65                  70                  75                  80

Leu Glu Ile Val Glu Val Leu Leu Lys Ala Gly Ala Asp Val Asn Ala
                85                  90                  95

Lys Asp His Ile Gly Ala Thr Pro Leu His Leu Ala Ala Trp Gln Gly
            100                 105                 110

His Leu Glu Ile Val Glu Val Leu Leu Lys Ala Gly Ala Asp Val Asn
        115                 120                 125

Ala Gln Asp Lys Ser Gly Lys Thr Pro Ala Asp Leu Ala Ala Asp Ala
    130                 135                 140

Gly His Glu Asp Ile Ala Glu Val Leu Gln Lys Ala Ala
145                 150                 155

<210> SEQ ID NO 31
<211> LENGTH: 157
<212> TYPE: PRT
<213> ORGANISM: Artificial Sequence
<220> FEATURE:
<223> OTHER INFORMATION: FAP binding domain

<400> SEQUENCE: 31

Asp Leu Gly Lys Lys Leu Leu Glu Ala Ala Arg Ala Gly Gln Asp Asp
1               5                   10                  15

Glu Val Arg Ile Leu Leu Ala Ala Gly Ala Asp Val Asn Ala Lys Asp
            20                  25                  30

Val Leu Gly Trp Thr Pro Leu His Leu Ala Ala Phe Glu Gly His Leu
        35                  40                  45

Glu Ile Val Glu Val Leu Leu Lys Ala Gly Ala Asp Val Asn Ala Lys
    50                  55                  60

Asp Lys Lys Gly Trp Thr Pro Leu Gln Leu Ala Arg Thr Gly His
65                  70                  75                  80

Leu Glu Ile Val Glu Val Leu Leu Lys Ala Gly Ala Asp Val Asn Ala
                85                  90                  95

Lys Asp His Ile Gly Ala Thr Pro Leu His Leu Ala Ala Trp Gln Gly
            100                 105                 110

His Leu Glu Ile Val Glu Val Leu Leu Lys Ala Gly Ala Asp Val Asn
        115                 120                 125

Ala Gln Asp Lys Ser Gly Lys Thr Pro Ala Asp Leu Ala Ala Asp Ala
    130                 135                 140

Gly His Glu Asp Ile Ala Glu Val Leu Gln Lys Ala Ala
145                 150                 155

<210> SEQ ID NO 32
<211> LENGTH: 157
<212> TYPE: PRT
<213> ORGANISM: Artificial Sequence
<220> FEATURE:
<223> OTHER INFORMATION: FAP binding domain

<400> SEQUENCE: 32

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Val Leu Gly Trp Thr Pro Leu His Leu Ala Ala Phe Glu Gly His Leu
        35                  40                  45

Glu Ile Val Glu Val Leu Leu Lys Ala Gly Ala Asp Val Asn Ala Lys
    50                  55                  60

Asp Lys Lys Gly Trp Thr Pro Leu Gln Leu Ala Ala Arg Thr Gly His
65                  70                  75                  80

Leu Glu Ile Val Glu Val Leu Leu Lys Ala Gly Ala Asp Val Asn Ala
                85                  90                  95

Lys Asp His Ile Gly Ala Thr Pro Leu His Leu Ala Ala Trp Gln Gly
            100                 105                 110

His Pro Glu Ile Val Glu Val Leu Leu Lys Ala Gly Ala Asp Val Asn
        115                 120                 125

Ala Gln Asp Lys Ser Gly Lys Thr Pro Ala Asp Leu Ala Ala Asp Ala
    130                 135                 140

Gly His Glu Asp Ile Ala Glu Val Leu Gln Lys Leu Asn
145                 150                 155

<210> SEQ ID NO 33
<211> LENGTH: 157
<212> TYPE: PRT
<213> ORGANISM: Artificial Sequence
<220> FEATURE:
<223> OTHER INFORMATION: FAP binding domain

<400> SEQUENCE: 33

Asp Leu Gly Lys Lys Leu Leu Glu Ala Ala Arg Ala Gly Gln Asp Asp
1               5                   10                  15

Glu Val Arg Ile Leu Leu Ala Ala Gly Ala Asp Val Asn Ala Lys Asp
            20                  25                  30

Val Leu Gly Trp Thr Pro Leu His Leu Ala Ala Phe Glu Gly His Leu
        35                  40                  45

Glu Ile Val Glu Val Leu Leu Lys Ala Gly Ala Asp Val Asn Ala Lys
    50                  55                  60

Asp Lys Lys Gly Trp Thr Pro Leu Gln Leu Ala Ala Arg Thr Gly His
65                  70                  75                  80

Leu Glu Ile Val Glu Val Leu Leu Lys Ala Gly Ala Asp Val Asn Ala
                85                  90                  95

Lys Asp His Ile Gly Ala Thr Pro Leu His Leu Ala Ala Trp Gln Gly
            100                 105                 110

His Pro Glu Ile Val Glu Val Leu Leu Lys Ala Gly Ala Asp Val Asn
        115                 120                 125

Ala Gln Asp Lys Ser Gly Lys Thr Pro Ala Asp Leu Ala Ala Asp Ala
    130                 135                 140

Gly His Glu Asp Ile Ala Glu Val Leu Gln Lys Leu Asn
145                 150                 155

<210> SEQ ID NO 34
<211> LENGTH: 157
<212> TYPE: PRT

```
<213> ORGANISM: Artificial Sequence
<220> FEATURE:
<223> OTHER INFORMATION: FAP binding domain

<400> SEQUENCE: 34

Asp Leu Gly Lys Lys Leu Leu Glu Ala Ala Arg Ala Gly Gln Asp Asp
1               5                   10                  15

Glu Val Arg Ile Leu Leu Lys Ala Gly Ala Asp Val Asn Ala Lys Asp
            20                  25                  30

Val Leu Gly Trp Thr Pro Leu His Leu Ala Ala Phe Glu Gly His Leu
        35                  40                  45

Glu Ile Val Glu Val Leu Leu Lys Ala Gly Ala Asp Val Asn Ala Lys
    50                  55                  60

Asp Lys Lys Gly Trp Thr Pro Leu Gln Leu Ala Ala Arg Thr Gly His
65                  70                  75                  80

Leu Glu Ile Val Glu Val Leu Leu Lys Ala Gly Ala Asp Val Asn Ala
                85                  90                  95

Lys Asp His Ile Gly Ala Thr Pro Leu His Leu Ala Ala Trp Gln Gly
                100                 105                 110

His Leu Glu Ile Val Glu Val Leu Leu Lys Ala Gly Ala Asp Val Asn
            115                 120                 125

Ala Gln Asp Lys Ser Gly Lys Thr Pro Ala Asp Leu Ala Ala Asp Ala
        130                 135                 140

Gly His Glu Asp Ile Ala Glu Val Leu Gln Lys Leu Asn
145                 150                 155

<210> SEQ ID NO 35
<211> LENGTH: 124
<212> TYPE: PRT
<213> ORGANISM: Artificial Sequence
<220> FEATURE:
<223> OTHER INFORMATION: FAP binding domain

<400> SEQUENCE: 35

Asp Leu Gly Glu Lys Leu Leu Val Ala Ala Leu Tyr Gly Gln Asp Asp
1               5                   10                  15

Glu Val Arg Ile Leu Leu Ala Ala Gly Ala Asp Val Asn Ala Lys Asp
            20                  25                  30

Gln Trp Gly Leu Thr Pro Leu His Lys Ala Ala Leu Gln Gly His Leu
        35                  40                  45

Glu Ile Val Glu Val Leu Leu Lys Ala Gly Ala Asp Val Asn Ala Lys
    50                  55                  60

Asp Glu Arg Gly His Thr Pro Leu His Trp Ala Ala Arg Phe Gly His
65                  70                  75                  80

Leu Glu Ile Val Glu Val Leu Leu Lys Ala Gly Ala Asp Val Asn Ala
                85                  90                  95

Gln Asp Gln Lys Gly Tyr Thr Pro Ala Asp Leu Ala Ala Leu Trp Gly
                100                 105                 110

His Glu Asp Ile Ala Glu Val Leu Gln Lys Leu Asn
            115                 120

<210> SEQ ID NO 36
<211> LENGTH: 157
<212> TYPE: PRT
<213> ORGANISM: Artificial Sequence
<220> FEATURE:
<223> OTHER INFORMATION: FAP binding domain

<400> SEQUENCE: 36
```

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Glu Val Gly Arg Thr Pro Leu His Leu Ala Ala Gln Ile Gly His Leu
            35                  40                  45

Glu Ile Val Glu Val Leu Leu Lys Ala Gly Ala Asp Val Asn Ala Lys
        50                  55                  60

Asn Arg Trp Gly Val Thr Pro Leu His Val Ala Ala Trp Val Gly His
65                  70                  75                  80

Leu Glu Ile Val Glu Val Leu Leu Lys Ala Gly Ala Asp Val Asn Ala
                85                  90                  95

Lys Asp Gln Gln Gly Ala Thr Pro Leu His Leu Ala Ala Ile Arg Gly
                100                 105                 110

His Leu Glu Ile Val Glu Val Leu Leu Lys Ala Gly Ala Asp Val Asn
            115                 120                 125

Ala Gln Asp Lys Ser Gly Lys Thr Pro Ala Asp Leu Ala Ala Asp Ala
        130                 135                 140

Gly His Glu Asp Ile Ala Glu Val Leu Gln Lys Leu Asn
145                 150                 155
```

<210> SEQ ID NO 37
<211> LENGTH: 157
<212> TYPE: PRT
<213> ORGANISM: Artificial Sequence
<220> FEATURE:
<223> OTHER INFORMATION: FAP binding domain
<400> SEQUENCE: 37

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Glu Trp Gly Lys Thr Pro Leu His Leu Ala Ala Ile Arg Gly His Leu
            35                  40                  45

Glu Ile Val Glu Val Leu Leu Lys Ala Gly Ala Asp Val Asn Ala Lys
        50                  55                  60

Asp Thr His Gly Ile Thr Pro Leu His Leu Ala Ala Phe Val Gly His
65                  70                  75                  80

Leu Glu Ile Val Glu Val Leu Leu Lys Ala Gly Ala Asp Val Asn Ala
                85                  90                  95

Lys Asp Tyr Leu Gly Arg Thr Pro Leu His Ile Ala Ala Lys Gly
                100                 105                 110

His Leu Glu Ile Val Glu Val Leu Leu Lys Ala Gly Ala Asp Val Asn
            115                 120                 125

Ala Gln Asp Lys Ser Gly Lys Thr Pro Ala Asp Leu Ala Ala Asp Ala
        130                 135                 140

Gly His Glu Asp Ile Val Glu Val Leu Gln Lys Leu Asn
145                 150                 155
```

<210> SEQ ID NO 38
<211> LENGTH: 159
<212> TYPE: PRT
<213> ORGANISM: Artificial Sequence
<220> FEATURE:
<223> OTHER INFORMATION: FAP binding domain

<400> SEQUENCE: 38

Gly Ser Asp Leu Gly Lys Lys Leu Leu Glu Ala Ala Arg Ala Gly Gln
1               5                   10                  15

Asp Asp Glu Val Arg Ile Leu Leu Ala Ala Gly Ala Asp Val Asn Ala
            20                  25                  30

Lys Asp Val Leu Gly Trp Thr Pro Leu His Leu Ala Ala Phe Glu Gly
        35                  40                  45

His Leu Glu Ile Val Glu Val Leu Leu Lys Ala Gly Ala Asp Val Asn
    50                  55                  60

Ala Lys Asp Lys Lys Gly Trp Thr Pro Leu Gln Leu Ala Ala Arg Thr
65                  70                  75                  80

Gly His Leu Glu Ile Val Glu Val Leu Leu Lys Ala Gly Ala Asp Val
                85                  90                  95

Asn Ala Lys Asp His Ile Gly Ala Thr Pro Leu His Leu Ala Ala Trp
            100                 105                 110

Gln Gly His Pro Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Asp Ala Gly His Glu Asp Ile Ala Glu Val Leu Gln Lys Ala Ala
145                 150                 155

<210> SEQ ID NO 39
<211> LENGTH: 126
<212> TYPE: PRT
<213> ORGANISM: Artificial Sequence
<220> FEATURE:
<223> OTHER INFORMATION: HSA binding domain

<400> SEQUENCE: 39

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala
        115                 120                 125

<210> SEQ ID NO 40
<211> LENGTH: 126
<212> TYPE: PRT
<213> ORGANISM: Artificial Sequence
<220> FEATURE:
<223> OTHER INFORMATION: HSA binding domain

<400> SEQUENCE: 40

Gly Ser Asp Leu Gly Lys Lys Leu Leu Glu Ala Ala Arg Ala Gly Gln
1               5                   10                  15

```
Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
         35                  40                  45

His Leu Lys Ile Val Glu Val Leu Leu Lys Ala Gly Ala Asp Val Asn
     50                  55                  60

Ala Lys Asp Phe Ala Gly Lys Thr Pro Leu His Leu Ala Ala Asp Ala
 65                  70                  75                  80

Gly His Leu Glu Ile Val Glu Val Leu Leu Lys Ala Gly Ala Asp Val
                 85                  90                  95

Asn Ala Gln Asp Ile Phe Gly Lys Thr Pro Ala Asp Ile Ala Ala Asp
             100                 105                 110

Ala Gly His Glu Asp Ile Ala Glu Val Leu Gln Lys Ala Ala
         115                 120                 125
```

<210> SEQ ID NO 41
<211> LENGTH: 126
<212> TYPE: PRT
<213> ORGANISM: Artificial Sequence
<220> FEATURE:
<223> OTHER INFORMATION: HSA binding domain

<400> SEQUENCE: 41

```
Gly Ser Asp Leu Gly Lys Lys Leu Leu Glu Ala Ala Arg Ala Gly Gln
 1               5                  10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
         35                  40                  45

His Leu Lys Ile Val Glu Val Leu Leu Lys Ala Gly Ala Asp Val Asn
     50                  55                  60

Ala Lys Asp Phe Ala Gly Lys Thr Pro Leu His Leu Ala Ala Ala Asp
 65                  70                  75                  80

Gly His Leu Glu Ile Val Glu Val Leu Leu Lys Ala Gly Ala Asp Val
                 85                  90                  95

Asn Ala Gln Asp Ile Phe Gly Lys Thr Pro Ala Asp Ile Ala Ala Asp
             100                 105                 110

Ala Gly His Glu Asp Ile Ala Glu Val Leu Gln Lys Leu Asn
         115                 120                 125
```

<210> SEQ ID NO 42
<211> LENGTH: 124
<212> TYPE: PRT
<213> ORGANISM: Artificial Sequence
<220> FEATURE:
<223> OTHER INFORMATION: HSA binding domain

<400> SEQUENCE: 42

```
Asp Leu Gly Lys Lys Leu Leu Glu Ala Ala Arg Ala Gly Gln Asp Asp
 1               5                  10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
         35                  40                  45

Lys Ile Val Glu Val Leu Leu Lys Ala Gly Ala Asp Val Asn Ala Lys
     50                  55                  60

Asp Phe Ala Gly Lys Thr Pro Leu His Leu Ala Ala Ala Asp Gly His
 65                  70                  75                  80
```

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala
        115                 120

<210> SEQ ID NO 43
<211> LENGTH: 157
<212> TYPE: PRT
<213> ORGANISM: Artificial Sequence
<220> FEATURE:
<223> OTHER INFORMATION: CD40 binding domain

<400> SEQUENCE: 43

Asp Leu Gly Lys Lys Leu Leu Gln Ala Ala Arg Ala Gly Gln Leu Asp
1               5                   10                  15

Glu Val Arg Ile Leu Leu Lys Ala Gly Ala Asp Val Asn Ala Lys Asp
            20                  25                  30

Thr Trp Gly Phe Thr Pro Leu His Ile Ala Ala Glu Ser Gly His Leu
        35                  40                  45

Glu Ile Val Glu Val Leu Leu Lys Ala Gly Ala Asp Val Asn Ala Lys
    50                  55                  60

Asp Val Gln Gly Arg Thr Pro Leu His Ile Ala Ala His Ser Gly His
65                  70                  75                  80

Leu Glu Ile Val Glu Val Leu Leu Lys Ala Gly Ala Asp Val Asn Ala
                85                  90                  95

Lys Asp Phe Arg Gly Trp Thr Pro Leu His Leu Ala Ala Trp Ser Gly
            100                 105                 110

His Leu Glu Ile Val Glu Ile Leu Leu Lys Ala Gly Ala Asp Val Asn
        115                 120                 125

Ala Gln Asp Lys Ser Gly Lys Thr Pro Ala Asp Leu Ala Ala Arg Ala
    130                 135                 140

Gly His Gln Asp Ile Ala Glu Val Leu Gln Lys Ala Ala
145                 150                 155

<210> SEQ ID NO 44
<211> LENGTH: 157
<212> TYPE: PRT
<213> ORGANISM: Artificial Sequence
<220> FEATURE:
<223> OTHER INFORMATION: CD40 binding domain

<400> SEQUENCE: 44

Asp Leu Gly Lys Lys Leu Leu Gln Ala Ala Arg Ala Gly Gln Leu Asp
1               5                   10                  15

Glu Val Arg Ile Leu Leu Ala Ala Gly Ala Asp Val Asn Ala Lys Asp
            20                  25                  30

Thr Trp Gly Phe Thr Pro Leu His Ile Ala Ala Glu Ser Gly His Leu
        35                  40                  45

Glu Ile Val Glu Val Leu Leu Lys Ala Gly Ala Asp Val Asn Ala Lys
    50                  55                  60

Asp Val Gln Gly Arg Thr Pro Leu His Ile Ala Ala His Ser Gly His
65                  70                  75                  80

Leu Glu Ile Val Glu Val Leu Leu Lys Ala Gly Ala Asp Val Asn Ala
                85                  90                  95

Lys Asp Phe Arg Gly Trp Thr Pro Leu His Leu Ala Ala Trp Ser Gly

His Leu Glu Ile Val Glu Ile Leu Leu Lys Ala Gly Ala Asp Val Asn
            115                 120                 125

Ala Gln Asp Lys Ser Gly Lys Thr Pro Ala Asp Leu Ala Ala Arg Ala
        130                 135                 140

Gly His Gln Asp Ile Ala Glu Val Leu Gln Lys Ala Ala
145                 150                 155

<210> SEQ ID NO 45
<211> LENGTH: 157
<212> TYPE: PRT
<213> ORGANISM: Artificial Sequence
<220> FEATURE:
<223> OTHER INFORMATION: CD40 binding domain

<400> SEQUENCE: 45

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30

Thr Trp Gly Phe Thr Pro Leu His Ile Ala Ala Glu Ser Gly His Leu
        35                  40                  45

Glu Ile Val Glu Val Leu Leu Lys Ala Gly Ala Asp Val Asn Ala Lys
    50                  55                  60

Asp Val Gln Gly Arg Thr Pro Leu His Ile Ala Ala His Ser Gly His
65                  70                  75                  80

Leu Glu Ile Val Glu Val Leu Leu Lys Ala Gly Ala Asp Val Asn Ala
                85                  90                  95

Lys Asp Phe Arg Gly Trp Thr Pro Leu His Leu Ala Ala Trp Ser Gly
            100                 105                 110

His Leu Glu Ile Val Glu Ile Leu Leu Lys Ala Gly Ala Asp Val Asn
        115                 120                 125

Ala Gln Asp Lys Ser Gly Lys Thr Pro Ala Asp Leu Ala Ala Arg Ala
    130                 135                 140

Gly His Gln Asp Ile Ala Glu Val Leu Gln Lys Leu Asn
145                 150                 155

<210> SEQ ID NO 46
<211> LENGTH: 157
<212> TYPE: PRT
<213> ORGANISM: Artificial Sequence
<220> FEATURE:
<223> OTHER INFORMATION: CD40 binding domain

<400> SEQUENCE: 46

Asp Leu Gly Lys Lys Leu Leu Gln Ala Ala Arg Ala Gly Gln Leu Asp
1               5                   10

```
Lys Asp Phe Arg Gly Trp Thr Pro Leu His Leu Ala Ala Trp Ser Gly
                100                 105                 110

His Leu Glu Ile Val Glu Ile Leu Leu Lys Ala Gly Ala Asp Val Asn
            115                 120                 125

Ala Gln Asp Lys Ser Gly Lys Thr Pro Ala Asp Leu Ala Ala Arg Ala
        130                 135                 140

Gly His Gln Asp Ile Ala Glu Val Leu Gln Lys Leu Asn
145                 150                 155

<210> SEQ ID NO 47
<211> LENGTH: 157
<212> TYPE: PRT
<213> ORGANISM: Artificial Sequence
<220> FEATURE:
<223> OTHER INFORMATION: CD40 binding domain

<400> SEQUENCE: 47

Asp Leu Gly Lys Lys Leu Leu Gln Ala Ala Arg Ala Gly Gln Leu Asp
1               5                   10                  15

Glu Val Arg Ile Leu Leu Ala Ala Gly Ala Asp Val Asn Ala Lys Asp
            20                  25                  30

Thr Trp Gly Phe Thr Pro Leu His Ile Ala Ala Glu Ser Gly His Leu
        35                  40                  45

Glu Ile Val Glu Val Leu Leu Lys Ala Gly Ala Asp Val Asn Ala Lys
    50                  55                  60

Asp Val Gln Gly Arg Thr Pro Leu His Ile Ala Ala His Ser Gly His
65                  70                  75                  80

Leu Glu Ile Val Glu Val Leu Leu Lys Ala Gly Ala Asp Val Asn Ala
                85                  90                  95

Lys Asp Phe Arg Gly Trp Thr Pro Leu His Leu Ala Ala Trp Ser Gly
                100                 105                 110

His Leu Glu Ile Val Glu Ile Leu Leu Lys Ala Gly Ala Asp Val Asn
            115                 120                 125

Ala Gln Asp Lys Ser Gly Lys Thr Pro Ala Asp Leu Ala Ala Arg Ala
        130                 135                 140

Gly His Gln Asp Ile Ala Glu Val Leu Gln Lys Leu Asn
145                 150                 155

<210> SEQ ID NO 48
<211> LENGTH: 157
<212> TYPE: PRT
<213> ORGANISM: Artificial Sequence
<220> FEATURE:
<223> OTHER INFORMATION: CD40 binding domain

<400> SEQUENCE: 48

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30

Glu Phe Gly Gln Thr Pro Leu His Ile Ala Ala Lys Ser Gly His Leu
        35                  40                  45

Glu Ile Val Glu Val Leu Leu Lys Ala Gly Ala Asp Val Asn Ala Lys
    50                  55                  60

Asp Val Tyr Gly Arg Thr Pro Leu His Leu Ala Ala Gln Tyr Gly His
65                  70                  75                  80

Leu Glu Ile Val Glu Val Leu Leu Lys Ala Gly Ala Asp Val Asn Ala
                85                  90                  95
```

```
Lys Asp Thr Gln Gly Val Thr Pro Leu His Val Ala Ala Phe Lys Gly
            100                 105                 110

His Leu Glu Ile Val Glu Val Leu Leu Lys Ala Gly Ala Asp Val Asn
            115                 120                 125

Ala Gln Asp Lys Ser Gly Lys Thr Pro Ala Asp Leu Ala Ala Arg Ala
        130                 135                 140

Gly His Gln Asp Ile Ala Glu Val Leu Gln Lys Ala Ala
145                 150                 155

<210> SEQ ID NO 49
<211> LENGTH: 157
<212> TYPE: PRT
<213> ORGANISM: Artificial Sequence
<220> FEATURE:
<223> OTHER INFORMATION: CD40 binding domain

<400> SEQUENCE: 49

Asp Leu Gly Lys Lys Leu Leu Trp Ala Ala Ala Gly Gln Leu Asp
1               5                   10                  15

Glu Val Arg Glu Leu Leu Lys Ala Gly Ala Asp Val Asn Ala Lys Asp
            20                  25                  30

His Val Gly Tyr Thr Pro Leu His Ile Ala Ala Leu Ala Gly His Leu
        35                  40                  45

Glu Ile Val Glu Val Leu Leu Lys Ala Gly Glu Asp Val Asn Ala Lys
    50                  55                  60

Asp His Lys Gly Arg Thr Pro Leu His Val Ala Ala Val Gly His
65                  70                  75                  80

Leu Glu Ile Val Glu Val Leu Leu Lys Ala Gly Ala Asp Val Asn Ala
                85                  90                  95

Lys Asp Gln Gln Gly Val Thr Pro Leu His Ile Ala Ala Ile Thr Gly
            100                 105                 110

His Leu Glu Ile Val Glu Val Leu Leu Lys Ala Gly Ala Asp Val Asn
            115                 120                 125

Ala Gln Asp Lys Ser Gly Lys Thr Pro Ala Asp Leu Ala Ala Arg Ala
        130                 135                 140

Gly His Gln Asp Ile Ala Glu Val Leu Gln Lys Ala Ala
145                 150                 155

<210> SEQ ID NO 50
<211> LENGTH: 159
<212> TYPE: PRT
<213> ORGANISM: Artificial Sequence
<220> FEATURE:
<223> OTHER INFORMATION: CD40 binding domain

<400> SEQUENCE: 50

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Thr Trp Gly Phe Thr Pro Leu His Ile Ala Ala Glu Ser Gly
        35                  40                  45

His Leu Glu Ile Val Glu Val Leu Leu Lys Ala Gly Ala Asp Val Asn
    50                  55                  60

Ala Lys Asp Val Gln Gly Arg Thr Pro Leu His Ile Ala Ala His Ser
65                  70                  75                  80

Gly His Leu Glu Ile Val Glu Val Leu Leu Lys Ala Gly Ala Asp Val
```

```
                    85                  90                  95
Asn Ala Lys Asp Phe Arg Gly Trp Thr Pro Leu His Leu Ala Ala Trp
            100                 105                 110

Ser Gly His Leu Glu Ile Val Glu Ile Leu Leu Lys Ala Gly Ala Asp
            115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155

<210> SEQ ID NO 51
<211> LENGTH: 277
<212> TYPE: PRT
<213> ORGANISM: Homo sapiens
<220> FEATURE:
<223> OTHER INFORMATION: Human CD40

<400> SEQUENCE: 51

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln Lys
65                  70                  75                  80

His Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
            275
```

<210> SEQ ID NO 52
<211> LENGTH: 760
<212> TYPE: PRT
<213> ORGANISM: Homo sapiens
<220> FEATURE:
<223> OTHER INFORMATION: Human FAP

<400> SEQUENCE: 52

```
Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asn Ser Glu Glu Asn Thr Met Arg Ala Leu Thr Leu Lys Asp Ile Leu
            35                  40                  45

Asn Gly Thr Phe Ser Tyr Lys Thr Phe Phe Pro Asn Trp Ile Ser Gly
        50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asn Gly Lys Phe Leu Ala Tyr Ala
210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
        275                 280                 285

Ser Asp Tyr Tyr Phe Ser Trp Leu Thr Trp Val Thr Asp Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
                325                 330                 335

Glu His Ile Glu Glu Ser Arg Thr Gly Trp Ala Gly Gly Phe Phe Val
            340                 345                 350

Ser Thr Pro Val Phe Ser Tyr Asp Ala Ile Ser Tyr Tyr Lys Ile Phe
        355                 360                 365

Ser Asp Lys Asp Gly Tyr Lys His Ile His Tyr Ile Lys Asp Thr Val
```

```
                370                 375                 380
Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
                405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
            435                 440                 445

Gln Tyr Tyr Thr Ala Ser Phe Ser Asp Tyr Ala Lys Tyr Tyr Ala Leu
        450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Ile Lys Lys Leu Glu
            500                 505                 510

Val Asp Glu Ile Thr Leu Trp Tyr Lys Met Ile Leu Pro Pro Gln Phe
            515                 520                 525

Asp Arg Ser Lys Lys Tyr Pro Leu Leu Ile Gln Val Tyr Gly Gly Pro
            530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Arg Lys Leu
            580                 585                 590

Gly Val Tyr Glu Val Glu Asp Gln Ile Thr Ala Val Arg Lys Phe Ile
        595                 600                 605

Glu Met Gly Phe Ile Asp Glu Lys Arg Ile Ala Ile Trp Gly Trp Ser
610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Val Tyr Thr Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
    690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
            740                 745                 750

Lys Gln Cys Phe Ser Leu Ser Asp
            755                 760

<210> SEQ ID NO 53
<211> LENGTH: 585
<212> TYPE: PRT
<213> ORGANISM: Homo sapiens
```

```
<220> FEATURE:
<223> OTHER INFORMATION: Human serum albumin

<400> SEQUENCE: 53

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400
```

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 54
<211> LENGTH: 173
<212> TYPE: PRT
<213> ORGANISM: Homo sapiens
<220> FEATURE:
<223> OTHER INFORMATION: Extracellular domain of human CD40

<400> SEQUENCE: 54

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170
```

-continued

```
<210> SEQ ID NO 55
<211> LENGTH: 735
<212> TYPE: PRT
<213> ORGANISM: Homo sapiens
<220> FEATURE:
<223> OTHER INFORMATION: Extracellular domain of human FAP

<400> SEQUENCE: 55

Leu Arg Pro Ser Arg Val His Asn Ser Glu Glu Asn Thr Met Arg Ala
1               5                   10                  15

Leu Thr Leu Lys Asp Ile Leu Asn Gly Thr Phe Ser Tyr Lys Thr Phe
            20                  25                  30

Phe Pro Asn Trp Ile Ser Gly Gln Glu Tyr Leu His Gln Ser Ala Asp
        35                  40                  45

Asn Asn Ile Val Leu Tyr Asn Ile Glu Thr Gly Gln Ser Tyr Thr Ile
    50                  55                  60

Leu Ser Asn Arg Thr Met Lys Ser Val Asn Ala Ser Asn Tyr Gly Leu
65                  70                  75                  80

Ser Pro Asp Arg Gln Phe Val Tyr Leu Glu Ser Asp Tyr Ser Lys Leu
                85                  90                  95

Trp Arg Tyr Ser Tyr Thr Ala Thr Tyr Tyr Ile Tyr Asp Leu Ser Asn
            100                 105                 110

Gly Glu Phe Val Arg Gly Asn Glu Leu Pro Arg Pro Ile Gln Tyr Leu
        115                 120                 125

Cys Trp Ser Pro Val Gly Ser Lys Leu Ala Tyr Val Tyr Gln Asn Asn
    130                 135                 140

Ile Tyr Leu Lys Gln Arg Pro Gly Asp Pro Pro Phe Gln Ile Thr Phe
145                 150                 155                 160

Asn Gly Arg Glu Asn Lys Ile Phe Asn Gly Ile Pro Asp Trp Val Tyr
                165                 170                 175

Glu Glu Glu Met Leu Ala Thr Lys Tyr Ala Leu Trp Trp Ser Pro Asn
            180                 185                 190

Gly Lys Phe Leu Ala Tyr Ala Glu Phe Asn Asp Thr Asp Ile Pro Val
        195                 200                 205

Ile Ala Tyr Ser Tyr Tyr Gly Asp Glu Gln Tyr Pro Arg Thr Ile Asn
    210                 215                 220

Ile Pro Tyr Pro Lys Ala Gly Ala Lys Asn Pro Val Val Arg Ile Phe
225                 230                 235                 240

Ile Ile Asp Thr Thr Tyr Pro Ala Tyr Val Gly Pro Gln Glu Val Pro
                245                 250                 255

Val Pro Ala Met Ile Ala Ser Ser Asp Tyr Tyr Phe Ser Trp Leu Thr
            260                 265                 270

Trp Val Thr Asp Glu Arg Val Cys Leu Gln Trp Leu Lys Arg Val Gln
        275                 280                 285

Asn Val Ser Val Leu Ser Ile Cys Asp Phe Arg Glu Asp Trp Gln Thr
    290                 295                 300

Trp Asp Cys Pro Lys Thr Gln Glu His Ile Glu Glu Ser Arg Thr Gly
305                 310                 315                 320

Trp Ala Gly Gly Phe Phe Val Ser Thr Pro Val Phe Ser Tyr Asp Ala
                325                 330                 335

Ile Ser Tyr Tyr Lys Ile Phe Ser Asp Lys Asp Gly Tyr Lys His Ile
            340                 345                 350

His Tyr Ile Lys Asp Thr Val Glu Asn Ala Ile Gln Ile Thr Ser Gly
        355                 360                 365
```

-continued

Lys Trp Glu Ala Ile Asn Ile Phe Arg Val Thr Gln Asp Ser Leu Phe
370                 375                 380

Tyr Ser Ser Asn Glu Phe Glu Tyr Pro Gly Arg Arg Asn Ile Tyr
385                 390                 395                 400

Arg Ile Ser Ile Gly Ser Tyr Pro Pro Ser Lys Lys Cys Val Thr Cys
                    405                 410                 415

His Leu Arg Lys Glu Arg Cys Gln Tyr Tyr Thr Ala Ser Phe Ser Asp
            420                 425                 430

Tyr Ala Lys Tyr Tyr Ala Leu Val Cys Tyr Gly Pro Gly Ile Pro Ile
            435                 440                 445

Ser Thr Leu His Asp Gly Arg Thr Asp Gln Glu Ile Lys Ile Leu Glu
        450                 455                 460

Glu Asn Lys Glu Leu Glu Asn Ala Leu Lys Asn Ile Gln Leu Pro Lys
465                 470                 475                 480

Glu Glu Ile Lys Lys Leu Glu Val Asp Glu Ile Thr Leu Trp Tyr Lys
                485                 490                 495

Met Ile Leu Pro Pro Gln Phe Asp Arg Ser Lys Lys Tyr Pro Leu Leu
            500                 505                 510

Ile Gln Val Tyr Gly Gly Pro Cys Ser Gln Ser Val Arg Ser Val Phe
        515                 520                 525

Ala Val Asn Trp Ile Ser Tyr Leu Ala Ser Lys Glu Gly Met Val Ile
530                 535                 540

Ala Leu Val Asp Gly Arg Gly Thr Ala Phe Gln Gly Asp Lys Leu Leu
545                 550                 555                 560

Tyr Ala Val Tyr Arg Lys Leu Gly Val Tyr Glu Val Glu Asp Gln Ile
                565                 570                 575

Thr Ala Val Arg Lys Phe Ile Glu Met Gly Phe Ile Asp Glu Lys Arg
            580                 585                 590

Ile Ala Ile Trp Gly Trp Ser Tyr Gly Gly Tyr Val Ser Ser Leu Ala
        595                 600                 605

Leu Ala Ser Gly Thr Gly Leu Phe Lys Cys Gly Ile Ala Val Ala Pro
610                 615                 620

Val Ser Ser Trp Glu Tyr Tyr Ala Ser Val Tyr Thr Glu Arg Phe Met
625                 630                 635                 640

Gly Leu Pro Thr Lys Asp Asp Asn Leu Glu His Tyr Lys Asn Ser Thr
                645                 650                 655

Val Met Ala Arg Ala Glu Tyr Phe Arg Asn Val Asp Tyr Leu Leu Ile
            660                 665                 670

His Gly Thr Ala Asp Asp Asn Val His Phe Gln Asn Ser Ala Gln Ile
        675                 680                 685

Ala Lys Ala Leu Val Asn Ala Gln Val Asp Phe Gln Ala Met Trp Tyr
690                 695                 700

Ser Asp Gln Asn His Gly Leu Ser Gly Leu Ser Thr Asn His Leu Tyr
705                 710                 715                 720

Thr His Met Thr His Phe Leu Lys Gln Cys Phe Ser Leu Ser Asp
                725                 730                 735

<210> SEQ ID NO 56
<211> LENGTH: 5
<212> TYPE: PRT
<213> ORGANISM: Artificial Sequence
<220> FEATURE:
<223> OTHER INFORMATION: Consensus GS linker
<220> FEATURE:
<221> NAME/KEY: VARIANT

```
<222> LOCATION: 1..5
<223> OTHER INFORMATION: [Gly-Gly-Gly-Gly-Ser]n, wherein n is 1, 2, 3,
      4, 5, or 6

<400> SEQUENCE: 56

Gly Gly Gly Gly Ser
1               5

<210> SEQ ID NO 57
<211> LENGTH: 10
<212> TYPE: PRT
<213> ORGANISM: Artificial Sequence
<220> FEATURE:
<223> OTHER INFORMATION: His-tag

<400> SEQUENCE: 57

Met Arg Gly Ser His His His His His His
1               5                   10

<210> SEQ ID NO 58
<211> LENGTH: 2010
<212> TYPE: DNA
<213> ORGANISM: Artificial Sequence
<220> FEATURE:
<223> OTHER INFORMATION: Nucleic acid encoding FAP/CD40 bispecific

<400> SEQUENCE: 58
atgggatccg atctgggtaa gaagctgctg gaagctgcga gagctggtca agacgatgaa      60
gtgcgcgagc tgttaaaagc gggtgccgac gtcaatgcca agactactt cagccacacg     120 cctctgcatc tggccgcacg caatggtcat ctgaagattg tggaggtgtt gctcaaagct    180
ggcgccgatg tcaatgctaa agatttcgcg ggtaaaacgc ctttgcacct ggcggctgca    240
gatggtcatt tggagattgt tgaagttctg ttgaaagcag gcgcggatgt aacgctcag    300 gacatctttg gcaagacccc agcggacatt gcggcggatg cgggccatga agatatcgcg    360
gaggttcttc agaaggcggc cggtagccca acgccaacgc tacgaccccc gactcctacg    420
cctactactc caactccgac tccaacgggt tccgatttgg gtaagaaact gttggaagcc    480
gcgcgcgctg ccaggatga cgaagttcgt atcttgcttg cggctggcgc agatgtcaac    540
gctaaggacg tgctgggttg accccgttg caccttgcag cattcgaagg tcatttagag    600
atcgttgagg ttctgctgaa ggcgggtgca gatgttaatg caaagacaa aaaaggctgg    660 actccactgc agttggcggc ccgcaccggt catctggaaa ttgtcgaggt tctcttgaag    720
gctggtgctg atgtaaatgc taaggaccac attggcgcga ccccttgca cttggcggca    780 tggcaaggtc atccggaaat cgtcgaagtc ctgttgaagg caggcgccga cgtgaatgcc    840
caagataaga gcggcaaaac cccggccgat ctggctgccg atgcaggcca cgaagatatt    900
gcagaggttc tgcagaaagc cgcgggcagc ccgaccccga cgccgactac cccaacgccg    960
actccgacga ctcctactcc gaccccaaca ggttccgacc tgggtaaaaa actgctgcaa   1020
gcagcacgtg caggtcagct ggatgaagtt cgtgaactgc tgaaagcagg cgccgatgtt   1080
aatgcaaaag ataccttggg cttcacccccg ctgcatattg ctgctgagtc tggtcacctg   1140
gaaattgttg aagttctgct gaaagccggt gcagatgtta tgcaaaaga tgtgcaaggc   1200 agaaccccgc tgcatatcgc tgctcactct ggtcacctgg aaattgttga agttctgctg   1260
aaagccggtg cagatgttaa tgcaaaagat ttcagaggct ggaccccgct gcatctggct   1320
gcttggtctg gtcaccctgga aattgttgaa attctgctga agccggtgc agatgttaac   1380 gcacaggata aaagcggtaa aaccccctgcc gatctggcag ctcgcgccgg tcatcaagat   1440
```

-continued

```
attgctgaag tgctgcagaa ggcagcaggc tcgccgactc cgaccccgac caccccaacg    1500
ccaacaccga ccaccccgac ccctacccca acaggttccg acctgggtaa aaaactgctg    1560
caagcagcac gtgcaggtca gctggatgaa gttcgtgaac tgctgaaagc aggcgccgat    1620
gttaatgcaa aagatacctg gggcttcacc ccgctgcata ttgctgctga gtctggtcac    1680
ctggaaattg ttgaagttct gctgaaagcc ggtgcagatg ttaatgcaaa agatgtgcaa    1740
ggcagaaccc cgctgcatat cgctgctcac tctggtcacc tggaaattgt tgaagttctg    1800
ctgaaagccg gtgcagatgt taatgcaaaa gatttcagag ctggaccccc gctgcatctg    1860
gctgcttggt ctggtcacct ggaaattgtt gaaattctgc tgaaagccgg tgcagatgtt    1920
aacgcacagg ataaaagcgg taaaacccct gccgatctgg cagctcgcgc cggtcatcaa    1980
gatattgcag aagtgctgca gaaggcagca                                      2010
```

<210> SEQ ID NO 59
<211> LENGTH: 307
<212> TYPE: PRT
<213> ORGANISM: Artificial Sequence
<220> FEATURE:
<223> OTHER INFORMATION: Binding protein

<400> SEQUENCE: 59

```
Gly Ser Asp Leu Gly Glu Lys Leu Leu Val Ala Ala Leu Tyr Gly Gln
1               5                   10                  15

Asp Asp Glu Val Arg Glu Leu Leu Lys Ala Gly Ala Asp Val Asn Ala
                20                  25                  30

Lys Asp Gln Trp Gly Leu Thr Pro Leu His Lys Ala Leu Gln Gly
            35                  40                  45

His Leu Glu Ile Val Glu Val Leu Leu Lys Ala Gly Ala Asp Val Asn
50                  55                  60

Ala Lys Asp Glu Arg Gly His Thr Pro Leu His Trp Ala Ala Arg Phe
65                  70                  75                  80

Gly His Leu Glu Ile Val Glu Val Leu Leu Lys Ala Gly Ala Asp Val
                85                  90                  95

Asn Ala Gln Asp Gln Lys Gly Tyr Thr Pro Ala Asp Leu Ala Ala Leu
                100                 105                 110

Trp Gly His Glu Asp Ile Ala Glu Val Leu Gln Lys Ala Ala Gly Ser
            115                 120                 125

Pro Thr Pro Thr Pro Thr Thr Pro Thr Pro Thr Pro Thr Thr Pro Thr
            130                 135                 140

Pro Thr Pro Thr Gly Ser Asp Leu Gly Lys Lys Leu Leu Gln Ala Ala
145                 150                 155                 160

Arg Ala Gly Gln Leu Asp Glu Val Arg Glu Leu Leu Lys Ala Gly Ala
                165                 170                 175

Asp Val Asn Ala Lys Asp Thr Trp Gly Phe Thr Pro Leu His Ile Ala
                180                 185                 190

Ala Glu Ser Gly His Leu Glu Ile Val Glu Val Leu Leu Lys Ala Gly
            195                 200                 205

Ala Asp Val Asn Ala Lys Asp Val Gln Gly Arg Thr Pro Leu His Ile
210                 215                 220

Ala Ala His Ser Gly His Leu Glu Ile Val Glu Val Leu Leu Lys Ala
225                 230                 235                 240

Gly Ala Asp Val Asn Ala Lys Asp Phe Arg Gly Trp Thr Pro Leu His
                245                 250                 255
```

```
Leu Ala Ala Trp Ser Gly His Leu Glu Ile Val Glu Ile Leu Leu Lys
            260                 265                 270

Ala Gly Ala Asp Val Asn Ala Gln Asp Lys Ser Gly Lys Thr Pro Ala
            275                 280                 285

Asp Leu Ala Ala Arg Ala Gly His Gln Asp Ile Ala Glu Val Leu Gln
            290                 295                 300

Lys Ala Ala
305

<210> SEQ ID NO 60
<211> LENGTH: 455
<212> TYPE: PRT
<213> ORGANISM: Artificial Sequence
<220> FEATURE:
<223> OTHER INFORMATION: Binding protein

<400> SEQUENCE: 60

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Ala Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Thr Pro Thr Thr Pro Thr
    130                 135                 140

Pro Thr Pro Thr Gly Ser Asp Leu Gly Glu Lys Leu Leu Val Ala Ala
145                 150                 155                 160

Leu Tyr Gly Gln Asp Asp Glu Val Arg Glu Leu Leu Lys Ala Gly Ala
                165                 170                 175

Asp Val Asn Ala Lys Asp Gln Trp Gly Leu Thr Pro Leu His Lys Ala
            180                 185                 190

Ala Leu Gln Gly His Leu Glu Ile Val Glu Val Leu Leu Lys Ala Gly
        195                 200                 205

Ala Asp Val Asn Ala Lys Asp Glu Arg Gly His Thr Pro Leu His Trp
    210                 215                 220

Ala Ala Arg Phe Gly His Leu Glu Ile Val Glu Val Leu Leu Lys Ala
225                 230                 235                 240

Gly Ala Asp Val Asn Ala Gln Asp Gln Lys Gly Tyr Thr Pro Ala Asp
                245                 250                 255

Leu Ala Ala Leu Trp Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300
```

-continued

```
Leu Gln Ala Ala Arg Ala Gly Gln Leu Asp Glu Val Arg Glu Leu Leu
305                 310                 315                 320

Lys Ala Gly Ala Asp Val Asn Ala Lys Asp Thr Trp Gly Phe Thr Pro
            325                 330                 335

Leu His Ile Ala Ala Glu Ser Gly His Leu Glu Ile Val Glu Val Leu
        340                 345                 350

Leu Lys Ala Gly Ala Asp Val Asn Ala Lys Asp Val Gln Gly Arg Thr
            355                 360                 365

Pro Leu His Ile Ala Ala His Ser Gly His Leu Glu Ile Val Glu Val
        370                 375                 380

Leu Leu Lys Ala Gly Ala Asp Val Asn Ala Lys Asp Phe Arg Gly Trp
385                 390                 395                 400

Thr Pro Leu His Leu Ala Ala Trp Ser Gly His Leu Glu Ile Val Glu
                405                 410                 415

Ile Leu Leu Lys Ala Gly Ala Asp Val Asn Ala Gln Asp Lys Ser Gly
                420                 425                 430

Lys Thr Pro Ala Asp Leu Ala Ala Arg Ala Gly His Gln Asp Ile Ala
            435                 440                 445

Glu Val Leu Gln Lys Ala Ala
        450                 455

<210> SEQ ID NO 61
<211> LENGTH: 603
<212> TYPE: PRT
<213> ORGANISM: Artificial Sequence
<220> FEATURE:
<223> OTHER INFORMATION: Binding protein

<400> SEQUENCE: 61

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Ala Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Thr Pro Thr Thr Pro
    130                 135                 140

Pro Thr Pro Thr Gly Ser Asp Leu Gly Glu Lys Leu Leu Val Ala Ala
145                 150                 155                 160

Leu Tyr Gly Gln Asp Asp Glu Val Arg Glu Leu Leu Lys Ala Gly Ala
                165                 170                 175

Asp Val Asn Ala Lys Asp Gln Trp Gly Leu Thr Pro Leu His Lys Ala
            180                 185                 190

Ala Leu Gln Gly His Leu Glu Ile Val Glu Val Leu Leu Lys Ala Gly
        195                 200                 205
```

-continued

Ala Asp Val Asn Ala Lys Asp Glu Arg Gly His Thr Pro Leu His Trp
210                 215                 220

Ala Ala Arg Phe Gly His Leu Glu Ile Val Glu Val Leu Leu Lys Ala
225                 230                 235                 240

Gly Ala Asp Val Asn Ala Gln Asp Gln Lys Gly Tyr Thr Pro Ala Asp
            245                 250                 255

Leu Ala Ala Leu Trp Gly His Glu Asp Ile Ala Glu Val Leu Gln Lys
            260                 265                 270

Ala Ala Gly Ser Pro Thr Pro Thr Pro Thr Thr Pro Thr Pro Thr Pro
            275                 280                 285

Thr Thr Pro Thr Pro Thr Pro Thr Gly Ser Asp Leu Gly Lys Lys Leu
290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Thr Trp Gly Phe Thr Pro
            325                 330                 335

Leu His Ile Ala Ala Glu Ser Gly His Leu Glu Ile Val Glu Val Leu
            340                 345                 350

Leu Lys Ala Gly Ala Asp Val Asn Ala Lys Asp Val Gln Gly Arg Thr
            355                 360                 365

Pro Leu His Ile Ala Ala His Ser Gly His Leu Glu Ile Val Glu Val
            370                 375                 380

Leu Leu Lys Ala Gly Ala Asp Val Asn Ala Lys Asp Phe Arg Gly Trp
385                 390                 395                 400

Thr Pro Leu His Leu Ala Ala Trp Ser Gly His Leu Glu Ile Val Glu
            405                 410                 415

Ile Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
            435                 440                 445

Glu Val Leu Gln Lys Ala Ala Gly Ser Pro Thr Pro Thr Pro Thr Thr
450                 455                 460

Pro Thr Pro Thr Pro Thr Thr Pro Thr Pro Thr Pro Thr Gly Ser Asp
465                 470                 475                 480

Leu Gly Lys Lys Leu Leu Glu Ala Ala Arg Ala Gly Gln Asp Asp Glu
            485                 490                 495

Val Arg Glu Leu Leu Lys Ala Gly Ala Asp Val Asn Ala Lys Asp Tyr
            500                 505                 510

Phe Ser His Thr Pro Leu His Leu Ala Ala Arg Asn Gly His Leu Lys
            515                 520                 525

Ile Val Glu Val Leu Leu Lys Ala Gly Ala Asp Val Asn Ala Lys Asp
            530                 535                 540

Phe Ala Gly Lys Thr Pro Leu His Leu Ala Ala Ala Asp Gly His Leu
545                 550                 555                 560

Glu Ile Val Glu Val Leu Leu Lys Ala Gly Ala Asp Val Asn Ala Gln
            565                 570                 575

Asp Ile Phe Gly Lys Thr Pro Ala Asp Ile Ala Ala Asp Ala Gly His
            580                 585                 590

Glu Asp Ile Ala Glu Val Leu Gln Lys Ala Ala
            595                 600

<210> SEQ ID NO 62
<211> LENGTH: 488
<212> TYPE: PRT

<213> ORGANISM: Artificial Sequence
<220> FEATURE:
<223> OTHER INFORMATION: Binding protein

<400> SEQUENCE: 62

Gly Ser Asp Leu Gly Glu Lys Leu Leu Val Ala Ala Leu Tyr Gly Gln
1               5                   10                  15

Asp Asp Glu Val Arg Glu Leu Leu Lys Ala Gly Ala Asp Val Asn Ala
            20                  25                  30

Lys Asp Gln Trp Gly Leu Thr Pro Leu His Lys Ala Ala Leu Gln Gly
        35                  40                  45

His Leu Glu Ile Val Glu Val Leu Leu Lys Ala Gly Ala Asp Val Asn
    50                  55                  60

Ala Lys Asp Glu Arg Gly His Thr Pro Leu His Trp Ala Ala Arg Phe
65                  70                  75                  80

Gly His Leu Glu Ile Val Glu Val Leu Leu Lys Ala Gly Ala Asp Val
                85                  90                  95

Asn Ala Gln Asp Gln Lys Gly Tyr Thr Pro Ala Asp Leu Ala Ala Leu
            100                 105                 110

Trp Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Gln Ala Ala
145                 150                 155                 160

Arg Ala Gly Gln Leu Asp Glu Val Arg Glu Leu Leu Lys Ala Gly Ala
                165                 170                 175

Asp Val Asn Ala Lys Asp Thr Trp Gly Phe Thr Pro Leu His Ile Ala
            180                 185                 190

Ala Glu Ser Gly His Leu Glu Ile Val Glu Val Leu Leu Lys Ala Gly
        195                 200                 205

Ala Asp Val Asn Ala Lys Asp Val Gln Gly Arg Thr Pro Leu His Ile
    210                 215                 220

Ala Ala His Ser Gly His Leu Glu Ile Val Glu Val Leu Leu Lys Ala
225                 230                 235                 240

Gly Ala Asp Val Asn Ala Lys Asp Phe Arg Gly Trp Thr Pro Leu His
                245                 250                 255

Leu Ala Ala Trp Ser Gly His Leu Glu Ile Val Glu Ile Leu Leu Lys
            260                 265                 270

Ala Gly Ala Asp Val Asn Ala Gln Asp Lys Ser Gly Lys Thr Pro Ala
        275                 280                 285

Asp Leu Ala Ala Arg Ala Gly His Gln Asp Ile Ala Glu Val Leu Gln
    290                 295                 300

Lys Ala Ala Gly Ser Pro Thr Pro Thr Pro Thr Thr Pro Thr Pro Thr
305                 310                 315                 320

Pro Thr Thr Pro Thr Pro Thr Pro Thr Gly Ser Asp Leu Gly Lys Lys
                325                 330                 335

Leu Leu Gln Ala Ala Arg Ala Gly Gln Leu Asp Glu Val Arg Glu Leu
            340                 345                 350

Leu Lys Ala Gly Ala Asp Val Asn Ala Lys Asp Thr Trp Gly Phe Thr
        355                 360                 365

Pro Leu His Ile Ala Ala Glu Ser Gly His Leu Glu Ile Val Glu Val
    370                 375                 380

Leu Leu Lys Ala Gly Ala Asp Val Asn Ala Lys Asp Val Gln Gly Arg

```
385             390             395             400
Thr Pro Leu His Ile Ala Ala His Ser Gly His Leu Glu Ile Val Glu
                405             410             415
Val Leu Leu Lys Ala Gly Ala Asp Val Asn Ala Lys Asp Phe Arg Gly
            420             425             430
Trp Thr Pro Leu His Leu Ala Ala Trp Ser Gly His Leu Glu Ile Val
                435             440             445
Glu Ile Leu Leu Lys Ala Gly Ala Asp Val Asn Ala Gln Asp Lys Ser
            450             455             460
Gly Lys Thr Pro Ala Asp Leu Ala Ala Arg Ala Gly His Gln Asp Ile
465             470             475             480
Ala Glu Val Leu Gln Lys Ala Ala
                485

<210> SEQ ID NO 63
<211> LENGTH: 636
<212> TYPE: PRT
<213> ORGANISM: Artificial Sequence
<220> FEATURE:
<223> OTHER INFORMATION: Binding protein

<400> SEQUENCE: 63

Gly Ser Asp Leu Gly Lys Lys Leu Leu Glu Ala Ala Arg Ala Gly Gln
1               5                   10                  15
Asp Asp Glu Val Arg Glu Leu Leu Lys Ala Gly Ala Asp Val Asn Ala
                20                  25                  30
Lys Asp Tyr Phe Ser His Thr Pro Leu His Leu Ala Ala Arg Asn Gly
            35                  40                  45
His Leu Lys Ile Val Glu Val Leu Leu Lys Ala Gly Ala Asp Val Asn
        50                  55                  60
Ala Lys Asp Phe Ala Gly Lys Thr Pro Leu His Leu Ala Ala Ala Asp
65              70                  75                  80
Gly His Leu Glu Ile Val Glu Val Leu Leu Lys Ala Gly Ala Asp Val
                85                  90                  95
Asn Ala Gln Asp Ile Phe Gly Lys Thr Pro Ala Asp Ile Ala Ala Asp
                100                 105                 110
Ala Gly His Glu Asp Ile Ala Glu Val Leu Gln Lys Ala Ala Gly Ser
            115                 120                 125
Pro Thr Pro Thr Pro Thr Pro Thr Pro Thr Pro Thr Thr Pro Thr
        130                 135                 140
Pro Thr Pro Thr Gly Ser Asp Leu Gly Glu Lys Leu Leu Val Ala Ala
145                 150                 155                 160
Leu Tyr Gly Gln Asp Asp Glu Val Arg Glu Leu Leu Lys Ala Gly Ala
                165                 170                 175
Asp Val Asn Ala Lys Asp Gln Trp Gly Leu Thr Pro Leu His Lys Ala
                180                 185                 190
Ala Leu Gln Gly His Leu Glu Ile Val Glu Val Leu Leu Lys Ala Gly
            195                 200                 205
Ala Asp Val Asn Ala Lys Asp Glu Arg Gly His Thr Pro Leu His Trp
        210                 215                 220
Ala Ala Arg Phe Gly His Leu Glu Ile Val Glu Val Leu Leu Lys Ala
225                 230                 235                 240
Gly Ala Asp Val Asn Ala Gln Asp Gln Lys Gly Tyr Thr Pro Ala Asp
                245                 250                 255
Leu Ala Ala Leu Trp Gly His Glu Asp Ile Ala Glu Val Leu Gln Lys
```

```
                260                 265                 270
Ala Ala Gly Ser Pro Thr Pro Thr Thr Pro Thr Thr Pro
            275                 280                 285
Thr Thr Pro Thr Pro Thr Pro Thr Gly Ser Asp Leu Gly Lys Lys Leu
        290                 295                 300
Leu Gln Ala Ala Arg Ala Gly Gln Leu Asp Glu Val Arg Glu Leu Leu
305                 310                 315                 320
Lys Ala Gly Ala Asp Val Asn Ala Lys Asp Thr Trp Gly Phe Thr Pro
                325                 330                 335
Leu His Ile Ala Ala Glu Ser Gly His Leu Glu Ile Val Glu Val Leu
                340                 345                 350
Leu Lys Ala Gly Ala Asp Val Asn Ala Lys Asp Val Gln Gly Arg Thr
            355                 360                 365
Pro Leu His Ile Ala Ala His Ser Gly His Leu Glu Ile Val Glu Val
        370                 375                 380
Leu Leu Lys Ala Gly Ala Asp Val Asn Ala Lys Asp Phe Arg Gly Trp
385                 390                 395                 400
Thr Pro Leu His Leu Ala Ala Trp Ser Gly His Leu Glu Ile Val Glu
                405                 410                 415
Ile Leu Leu Lys Ala Gly Ala Asp Val Asn Ala Gln Asp Lys Ser Gly
                420                 425                 430
Lys Thr Pro Ala Asp Leu Ala Ala Arg Ala Gly His Gln Asp Ile Ala
            435                 440                 445
Glu Val Leu Gln Lys Ala Ala Gly Ser Pro Thr Pro Thr Pro Thr Thr
        450                 455                 460
Pro Thr Pro Thr Pro Thr Thr Pro Thr Pro Thr Pro Thr Gly Ser Asp
465                 470                 475                 480
Leu Gly Lys Lys Leu Leu Gln Ala Ala Arg Ala Gly Gln Leu Asp Glu
                485                 490                 495
Val Arg Glu Leu Leu Lys Ala Gly Ala Asp Val Asn Ala Lys Asp Thr
                500                 505                 510
Trp Gly Phe Thr Pro Leu His Ile Ala Ala Glu Ser Gly His Leu Glu
            515                 520                 525
Ile Val Glu Val Leu Leu Lys Ala Gly Ala Asp Val Asn Ala Lys Asp
        530                 535                 540
Val Gln Gly Arg Thr Pro Leu His Ile Ala Ala His Ser Gly His Leu
545                 550                 555                 560
Glu Ile Val Glu Val Leu Leu Lys Ala Gly Ala Asp Val Asn Ala Lys
                565                 570                 575
Asp Phe Arg Gly Trp Thr Pro Leu His Leu Ala Ala Trp Ser Gly His
                580                 585                 590
Leu Glu Ile Val Glu Ile Leu Leu Lys Ala Gly Ala Asp Val Asn Ala
            595                 600                 605
Gln Asp Lys Ser Gly Lys Thr Pro Ala Asp Leu Ala Ala Arg Ala Gly
        610                 615                 620
His Gln Asp Ile Ala Glu Val Leu Gln Lys Ala Ala
625                 630                 635

<210> SEQ ID NO 64
<211> LENGTH: 784
<212> TYPE: PRT
<213> ORGANISM: Artificial Sequence
<220> FEATURE:
<223> OTHER INFORMATION: Binding protein
```

```
<400> SEQUENCE: 64

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
50                  55                  60

Ala Lys Asp Phe Ala Gly Lys Thr Pro Leu His Leu Ala Ala Ala Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Thr Pro Thr Thr Pro Thr
130                 135                 140

Pro Thr Pro Thr Gly Ser Asp Leu Gly Glu Lys Leu Leu Val Ala Ala
145                 150                 155                 160

Leu Tyr Gly Gln Asp Asp Glu Val Arg Glu Leu Leu Lys Ala Gly Ala
                165                 170                 175

Asp Val Asn Ala Lys Asp Gln Trp Gly Leu Thr Pro Leu His Lys Ala
            180                 185                 190

Ala Leu Gln Gly His Leu Glu Ile Val Glu Val Leu Leu Lys Ala Gly
        195                 200                 205

Ala Asp Val Asn Ala Lys Asp Glu Arg Gly His Thr Pro Leu His Trp
210                 215                 220

Ala Ala Arg Phe Gly His Leu Glu Ile Val Glu Val Leu Leu Lys Ala
225                 230                 235                 240

Gly Ala Asp Val Asn Ala Gln Asp Gln Lys Gly Tyr Thr Pro Ala Asp
                245                 250                 255

Leu Ala Ala Leu Trp Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Thr Trp Gly Phe Thr Pro
                325                 330                 335

Leu His Ile Ala Ala Glu Ser Gly His Leu Glu Ile Val Glu Val Leu
            340                 345                 350

Leu Lys Ala Gly Ala Asp Val Asn Ala Lys Asp Val Gln Gly Arg Thr
        355                 360                 365

Pro Leu His Ile Ala Ala His Ser Gly His Leu Glu Ile Val Glu Val
370                 375                 380

Leu Leu Lys Ala Gly Ala Asp Val Asn Ala Lys Asp Phe Arg Gly Trp
385                 390                 395                 400

Thr Pro Leu His Leu Ala Ala Trp Ser Gly His Leu Glu Ile Val Glu
                405                 410                 415
```

```
Ile Leu Leu Lys Ala Gly Ala Asp Val Asn Ala Gln Asp Lys Ser Gly
                420                 425                 430

Lys Thr Pro Ala Asp Leu Ala Ala Arg Ala Gly His Gln Asp Ile Ala
            435                 440                 445

Glu Val Leu Gln Lys Ala Ala Gly Ser Pro Thr Pro Thr Pro Thr Thr
450                 455                 460

Pro Thr Pro Thr Pro Thr Thr Pro Thr Pro Thr Pro Thr Gly Ser Asp
465                 470                 475                 480

Leu Gly Lys Lys Leu Leu Gln Ala Ala Arg Ala Gly Gln Leu Asp Glu
                485                 490                 495

Val Arg Glu Leu Leu Lys Ala Gly Ala Asp Val Asn Ala Lys Asp Thr
                500                 505                 510

Trp Gly Phe Thr Pro Leu His Ile Ala Ala Glu Ser Gly His Leu Glu
            515                 520                 525

Ile Val Glu Val Leu Leu Lys Ala Gly Ala Asp Val Asn Ala Lys Asp
530                 535                 540

Val Gln Gly Arg Thr Pro Leu His Ile Ala Ala His Ser Gly His Leu
545                 550                 555                 560

Glu Ile Val Glu Val Leu Leu Lys Ala Gly Ala Asp Val Asn Ala Lys
                565                 570                 575

Asp Phe Arg Gly Trp Thr Pro Leu His Leu Ala Ala Trp Ser Gly His
            580                 585                 590

Leu Glu Ile Val Glu Ile Leu Leu Lys Ala Gly Ala Asp Val Asn Ala
            595                 600                 605

Gln Asp Lys Ser Gly Lys Thr Pro Ala Asp Leu Ala Ala Arg Ala Gly
610                 615                 620

His Gln Asp Ile Ala Glu Val Leu Gln Lys Ala Ala Gly Ser Pro Thr
625                 630                 635                 640

Pro Thr Pro Thr Thr Pro Thr Pro Thr Pro Thr Thr Pro Thr Pro Thr
                645                 650                 655

Pro Thr Gly Ser Asp Leu Gly Lys Lys Leu Leu Glu Ala Ala Arg Ala
            660                 665                 670

Gly Gln Asp Asp Glu Val Arg Glu Leu Leu Lys Ala Gly Ala Asp Val
            675                 680                 685

Asn Ala Lys Asp Tyr Phe Ser His Thr Pro Leu His Leu Ala Ala Arg
690                 695                 700

Asn Gly His Leu Lys Ile Val Glu Val Leu Leu Lys Ala Gly Ala Asp
705                 710                 715                 720

Val Asn Ala Lys Asp Phe Ala Gly Lys Thr Pro Leu His Leu Ala Ala
                725                 730                 735

Ala Asp Gly His Leu Glu Ile Val Glu Val Leu Leu Lys Ala Gly Ala
            740                 745                 750

Asp Val Asn Ala Gln Asp Ile Phe Gly Lys Thr Pro Ala Asp Ile Ala
            755                 760                 765

Ala Asp Ala Gly His Glu Asp Ile Ala Glu Val Leu Gln Lys Ala Ala
770                 775                 780
```

<210> SEQ ID NO 65
<211> LENGTH: 784
<212> TYPE: PRT
<213> ORGANISM: Artificial Sequence
<220> FEATURE:
<223> OTHER INFORMATION: Binding protein

<400> SEQUENCE: 65

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
                20                  25                  30

Lys Asp Tyr Phe Ser His Thr Pro Leu His Leu Ala Ala Arg Asn Gly
            35                  40                  45

His Leu Lys Ile Val Glu Val Leu Leu Lys Ala Gly Ala Asp Val Asn
50                      55                  60

Ala Lys Asp Phe Ala Gly Lys Thr Pro Leu His Leu Ala Ala Ala Asp
65                      70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala Gly Ser
            115                 120                 125

Pro Thr Pro Thr Pro Thr Thr Pro Thr Pro Thr Thr Pro Thr Thr Pro Thr
130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
                180                 185                 190

Ala Arg Asn Gly His Leu Lys Ile Val Glu Val Leu Leu Lys Ala Gly
            195                 200                 205

Ala Asp Val Asn Ala Lys Asp Phe Ala Gly Lys Thr Pro Leu His Leu
210                 215                 220

Ala Ala Ala Asp Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
                260                 265                 270

Ala Ala Gly Ser Pro Thr Pro Thr Pro Thr Thr Pro Thr Pro Thr Pro
            275                 280                 285

Thr Thr Pro Thr Pro Thr Pro Thr Gly Ser Asp Leu Gly Glu Lys Leu
            290                 295                 300

Leu Val Ala Ala Leu Tyr Gly Gln Asp Asp Glu Val Arg Glu Leu Leu
305                 310                 315                 320

Lys Ala Gly Ala Asp Val Asn Ala Lys Asp Gln Trp Gly Leu Thr Pro
                325                 330                 335

Leu His Lys Ala Ala Leu Gln Gly His Leu Glu Ile Val Glu Val Leu
            340                 345                 350

Leu Lys Ala Gly Ala Asp Val Asn Ala Lys Asp Glu Arg Gly His Thr
                355                 360                 365

Pro Leu His Trp Ala Ala Arg Phe Gly His Leu Glu Ile Val Glu Val
            370                 375                 380

Leu Leu Lys Ala Gly Ala Asp Val Asn Ala Gln Asp Gln Lys Gly Tyr
385                 390                 395                 400

Thr Pro Ala Asp Leu Ala Ala Leu Trp Gly His Glu Asp Ile Ala Glu
                405                 410                 415
```

Val Leu Gln Lys Ala Ala Gly Ser Pro Thr Pro Thr Pro Thr Pro
                420                 425                 430

Thr Pro Thr Pro Thr Thr Pro Thr Pro Thr Pro Thr Gly Ser Asp Leu
            435                 440                 445

Gly Lys Lys Leu Leu Gln Ala Ala Arg Ala Gly Gln Leu Asp Glu Val
        450                 455                 460

Arg Glu Leu Leu Lys Ala Gly Ala Asp Val Asn Ala Lys Asp Thr Trp
465                 470                 475                 480

Gly Phe Thr Pro Leu His Ile Ala Ala Glu Ser Gly His Leu Glu Ile
                485                 490                 495

Val Glu Val Leu Leu Lys Ala Gly Ala Asp Val Asn Ala Lys Asp Val
            500                 505                 510

Gln Gly Arg Thr Pro Leu His Ile Ala Ala His Ser Gly His Leu Glu
        515                 520                 525

Ile Val Glu Val Leu Leu Lys Ala Gly Ala Asp Val Asn Ala Lys Asp
            530                 535                 540

Phe Arg Gly Trp Thr Pro Leu His Leu Ala Ala Trp Ser Gly His Leu
545                 550                 555                 560

Glu Ile Val Glu Ile Leu Leu Lys Ala Gly Ala Asp Val Asn Ala Gln
                565                 570                 575

Asp Lys Ser Gly Lys Thr Pro Ala Asp Leu Ala Ala Arg Ala Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Thr Trp Gly Phe Thr Pro Leu His Ile Ala Ala Glu Ser
            660                 665                 670

Gly His Leu Glu Ile Val Glu Val Leu Leu Lys Ala Gly Ala Asp Val
        675                 680                 685

Asn Ala Lys Asp Val Gln Gly Arg Thr Pro Leu His Ile Ala Ala His
        690                 695                 700

Ser Gly His Leu Glu Ile Val Glu Val Leu Leu Lys Ala Gly Ala Asp
705                 710                 715                 720

Val Asn Ala Lys Asp Phe Arg Gly Trp Thr Pro Leu His Leu Ala Ala
                725                 730                 735

Trp Ser Gly His Leu Glu Ile Val Glu Ile Leu Leu Lys Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
    770                 775                 780

<210> SEQ ID NO 66
<211> LENGTH: 669
<212> TYPE: PRT
<213> ORGANISM: Artificial Sequence
<220> FEATURE:
<223> OTHER INFORMATION: Binding protein

<400> SEQUENCE: 66

```
Gly Ser Asp Leu Gly Glu Lys Leu Leu Val Ala Ala Leu Tyr Gly Gln
1               5                   10                  15

Asp Asp Glu Val Arg Glu Leu Leu Lys Ala Gly Ala Asp Val Asn Ala
            20                  25                  30

Lys Asp Gln Trp Gly Leu Thr Pro Leu His Lys Ala Ala Leu Gln Gly
            35                  40                  45

His Leu Glu Ile Val Glu Val Leu Leu Lys Ala Gly Ala Asp Val Asn
        50                  55                  60

Ala Lys Asp Glu Arg Gly His Thr Pro Leu His Trp Ala Ala Arg Phe
65                  70                  75                  80

Gly His Leu Glu Ile Val Glu Val Leu Leu Lys Ala Gly Ala Asp Val
                85                  90                  95

Asn Ala Gln Asp Gln Lys Gly Tyr Thr Pro Ala Asp Leu Ala Ala Leu
                100                 105                 110

Trp Gly His Glu Asp Ile Ala Glu Val Leu Gln Lys Ala Ala Gly Ser
            115                 120                 125

Pro Thr Pro Thr Pro Thr Thr Pro Thr Pro Thr Pro Thr Thr Pro Thr
            130                 135                 140

Pro Thr Pro Thr Gly Ser Asp Leu Gly Lys Lys Leu Leu Gln Ala Ala
145                 150                 155                 160

Arg Ala Gly Gln Leu Asp Glu Val Arg Glu Leu Leu Lys Ala Gly Ala
                165                 170                 175

Asp Val Asn Ala Lys Asp Thr Trp Gly Phe Thr Pro Leu His Ile Ala
                180                 185                 190

Ala Glu Ser Gly His Leu Glu Ile Val Glu Val Leu Leu Lys Ala Gly
            195                 200                 205

Ala Asp Val Asn Ala Lys Asp Val Gln Gly Arg Thr Pro Leu His Ile
            210                 215                 220

Ala Ala His Ser Gly His Leu Glu Ile Val Glu Val Leu Leu Lys Ala
225                 230                 235                 240

Gly Ala Asp Val Asn Ala Lys Asp Phe Arg Gly Trp Thr Pro Leu His
                245                 250                 255

Leu Ala Ala Trp Ser Gly His Leu Glu Ile Val Glu Ile Leu Leu Lys
            260                 265                 270

Ala Gly Ala Asp Val Asn Ala Gln Asp Lys Ser Gly Lys Thr Pro Ala
            275                 280                 285

Asp Leu Ala Ala Arg Ala Gly His Gln Asp Ile Ala Glu Val Leu Gln
            290                 295                 300

Lys Ala Ala Gly Ser Pro Thr Pro Thr Pro Thr Thr Pro Thr Pro Thr
305                 310                 315                 320

Pro Thr Thr Pro Thr Pro Thr Pro Thr Gly Ser Asp Leu Gly Lys Lys
                325                 330                 335

Leu Leu Gln Ala Ala Arg Ala Gly Gln Leu Asp Glu Val Arg Glu Leu
            340                 345                 350

Leu Lys Ala Gly Ala Asp Val Asn Ala Lys Asp Thr Trp Gly Phe Thr
            355                 360                 365

Pro Leu His Ile Ala Ala Glu Ser Gly His Leu Glu Ile Val Glu Val
            370                 375                 380

Leu Leu Lys Ala Gly Ala Asp Val Asn Ala Lys Asp Val Gln Gly Arg
385                 390                 395                 400

Thr Pro Leu His Ile Ala Ala His Ser Gly His Leu Glu Ile Val Glu
                405                 410                 415

Val Leu Leu Lys Ala Gly Ala Asp Val Asn Ala Lys Asp Phe Arg Gly
```

```
                   420                 425                 430
Trp Thr Pro Leu His Leu Ala Ala Trp Ser Gly His Leu Glu Ile Val
            435                 440                 445
Glu Ile Leu Leu Lys Ala Gly Ala Asp Val Asn Ala Gln Asp Lys Ser
        450                 455                 460
Gly Lys Thr Pro Ala Asp Leu Ala Ala Arg Ala Gly His Gln Asp Ile
465                 470                 475                 480
Ala Glu Val Leu Gln Lys Ala Ala Gly Ser Pro Thr Pro Thr Pro Thr
                485                 490                 495
Thr Pro Thr Pro Thr Pro Thr Thr Pro Thr Pro Thr Pro Thr Gly Ser
            500                 505                 510
Asp Leu Gly Lys Lys Leu Leu Gln Ala Ala Arg Ala Gly Gln Leu Asp
        515                 520                 525
Glu Val Arg Glu Leu Leu Lys Ala Gly Ala Asp Val Asn Ala Lys Asp
    530                 535                 540
Thr Trp Gly Phe Thr Pro Leu His Ile Ala Ala Glu Ser Gly His Leu
545                 550                 555                 560
Glu Ile Val Glu Val Leu Leu Lys Ala Gly Ala Asp Val Asn Ala Lys
                565                 570                 575
Asp Val Gln Gly Arg Thr Pro Leu His Ile Ala Ala His Ser Gly His
            580                 585                 590
Leu Glu Ile Val Glu Val Leu Leu Lys Ala Gly Ala Asp Val Asn Ala
        595                 600                 605
Lys Asp Phe Arg Gly Trp Thr Pro Leu His Leu Ala Ala Trp Ser Gly
    610                 615                 620
His Leu Glu Ile Val Glu Ile Leu Leu Lys Ala Gly Ala Asp Val Asn
625                 630                 635                 640
Ala Gln Asp Lys Ser Gly Lys Thr Pro Ala Asp Leu Ala Ala Arg Ala
                645                 650                 655
Gly His Gln Asp Ile Ala Glu Val Leu Gln Lys Ala Ala
            660                 665

<210> SEQ ID NO 67
<211> LENGTH: 636
<212> TYPE: PRT
<213> ORGANISM: Artificial Sequence
<220> FEATURE:
<223> OTHER INFORMATION: Binding protein

<400> SEQUENCE: 67

Gly Ser Asp Leu Gly Lys Lys Leu Leu Glu Ala Ala Arg Ala Gly Gln
1               5                   10                  15
Asp Asp Glu Val Arg Glu Leu Leu Lys Ala Gly Ala Asp Val Asn Ala
            20                  25                  30
Lys Asp Tyr Phe Ser His Thr Pro Leu His Leu Ala Ala Arg Asn Gly
        35                  40                  45
His Leu Lys Ile Val Glu Val Leu Leu Lys Ala Gly Ala Asp Val Asn
    50                  55                  60
Ala Lys Asp Phe Ala Gly Lys Thr Pro Leu His Leu Ala Ala Ala Asp
65                  70                  75                  80
Gly His Leu Glu Ile Val Glu Val Leu Leu Lys Ala Gly Ala Asp Val
                85                  90                  95
Asn Ala Gln Asp Ile Phe Gly Lys Thr Pro Ala Asp Ile Ala Ala Asp
            100                 105                 110
Ala Gly His Glu Asp Ile Ala Glu Val Leu Gln Lys Ala Ala Gly Ser
```

-continued

```
                115                 120                 125
Pro Thr Pro Thr Pro Thr Thr Pro Thr Pro Thr Thr Pro Thr
        130                 135                 140
Pro Thr Pro Thr Gly Ser Asp Leu Gly Lys Lys Leu Leu Glu Ala Ala
145                 150                 155                 160
Arg Ala Gly Gln Asp Glu Val Arg Glu Leu Leu Lys Ala Gly Ala
                165                 170                 175
Asp Val Asn Ala Lys Asp Lys Asp Gly Tyr Thr Pro Leu His Leu Ala
                180                 185                 190
Ala Arg Glu Gly His Leu Glu Ile Val Glu Val Leu Leu Lys Ala Gly
                195                 200                 205
Ala Asp Val Asn Ala Lys Asp Lys Asp Gly Tyr Thr Pro Leu His Leu
        210                 215                 220
Ala Ala Arg Glu Gly His Leu Glu Ile Val Glu Val Leu Leu Lys Ala
225                 230                 235                 240
Gly Ala Asp Val Asn Ala Gln Asp Lys Ser Gly Lys Thr Pro Ala Asp
                245                 250                 255
Leu Ala Ala Asp Ala Gly His Glu Asp Ile Ala Glu Val Leu Gln Lys
                260                 265                 270
Ala Ala Gly Ser Pro Thr Pro Thr Pro Thr Thr Pro Thr Pro Thr Pro
                275                 280                 285
Thr Thr Pro Thr Pro Thr Pro Thr Gly Ser Asp Leu Gly Lys Lys Leu
        290                 295                 300
Leu Gln Ala Ala Arg Ala Gly Gln Leu Asp Glu Val Arg Glu Leu Leu
305                 310                 315                 320
Lys Ala Gly Ala Asp Val Asn Ala Lys Asp Thr Leu Gly Ser Thr Pro
                325                 330                 335
Leu His Leu Ala Ala Trp Glu Gly His Leu Glu Ile Val Glu Val Leu
                340                 345                 350
Leu Lys Ala Gly Ala Asp Val Asn Ala Lys Asp Ile Glu Gly Arg Thr
                355                 360                 365
Pro Leu His Leu Ala Ala Arg Val Gly His Leu Glu Ile Val Glu Val
        370                 375                 380
Leu Leu Lys Ala Gly Ala Asp Val Asn Ala Lys Asp Ala Tyr Gly Phe
385                 390                 395                 400
Thr Pro Leu His Leu Ala Ala Glu Ser Gly His Leu Glu Ile Val Glu
                405                 410                 415
Val Leu Leu Lys Ala Gly Ala Asp Val Asn Ala Gln Asp Lys Ser Gly
                420                 425                 430
Lys Thr Pro Ala Asp Leu Ala Ala Arg Ala Gly His Gln Asp Ile Ala
                435                 440                 445
Glu Val Leu Gln Lys Ala Ala Gly Ser Pro Thr Pro Thr Pro Thr Thr
        450                 455                 460
Pro Thr Pro Thr Pro Thr Thr Pro Thr Pro Thr Pro Thr Gly Ser Asp
465                 470                 475                 480
Leu Gly Lys Lys Leu Leu Gln Ala Ala Arg Ala Gly Gln Leu Asp Glu
                485                 490                 495
Val Arg Glu Leu Leu Lys Ala Gly Ala Asp Val Asn Ala Lys Asp Thr
                500                 505                 510
Leu Gly Ser Thr Pro Leu His Leu Ala Ala Trp Glu Gly His Leu Glu
                515                 520                 525
Ile Val Glu Val Leu Leu Lys Ala Gly Ala Asp Val Asn Ala Lys Asp
                530                 535                 540
```

```
Ile Glu Gly Arg Thr Pro Leu His Leu Ala Ala Arg Val Gly His Leu
545                 550                 555                 560

Glu Ile Val Glu Val Leu Leu Lys Ala Gly Ala Asp Val Asn Ala Lys
                565                 570                 575

Asp Ala Tyr Gly Phe Thr Pro Leu His Leu Ala Ala Glu Ser Gly His
            580                 585                 590

Leu Glu Ile Val Glu Val Leu Leu Lys Ala Gly Ala Asp Val Asn Ala
        595                 600                 605

Gln Asp Lys Ser Gly Lys Thr Pro Ala Asp Leu Ala Ala Arg Ala Gly
    610                 615                 620

His Gln Asp Ile Ala Glu Val Leu Gln Lys Ala Ala
625                 630                 635
```